US011053314B2

(12) United States Patent
Roberts et al.

(10) Patent No.: US 11,053,314 B2
(45) Date of Patent: Jul. 6, 2021

(54) METHODS TO ELIMINATE CANCER STEM CELLS BY TARGETING CD47

(71) Applicant: The U.S.A, as represented by the Secretary, Department of Health and Human Services, Bethesda, MD (US)

(72) Inventors: David D. Roberts, Bethesda, MD (US); Sukhbir Kaur, Bethesda, MD (US); Chengyu Liu, Boyds, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/517,345

(22) PCT Filed: Oct. 9, 2015

(86) PCT No.: PCT/US2015/055029
§ 371 (c)(1),
(2) Date: Apr. 6, 2017

(87) PCT Pub. No.: WO2016/057980
PCT Pub. Date: Apr. 14, 2016

(65) Prior Publication Data
US 2018/0355032 A1    Dec. 13, 2018

Related U.S. Application Data

(60) Provisional application No. 62/062,675, filed on Oct. 10, 2014.

(51) Int. Cl.
| | |
|---|---|
| *C07K 16/28* | (2006.01) |
| *C07K 16/30* | (2006.01) |
| *A61K 38/18* | (2006.01) |
| *A61K 39/00* | (2006.01) |
| *A61K 39/395* | (2006.01) |

(52) U.S. Cl.
CPC .......... *C07K 16/2803* (2013.01); *A61K 38/18* (2013.01); *A61K 39/00* (2013.01); *A61K 39/395* (2013.01); *C07K 16/2863* (2013.01); *C07K 16/30* (2013.01); *C07K 16/3015* (2013.01); *A61K 2039/505* (2013.01); *A61K 2039/507* (2013.01); *C07K 16/28* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 9,518,117 B2* | 12/2016 | Frazier | C07K 16/2803 |
| 2014/0303354 A1* | 10/2014 | Masternak | C07K 16/2803 |
| | | | 530/387.3 |

FOREIGN PATENT DOCUMENTS

| | | |
|---|---|---|
| WO | WO 2011/034969 | 3/2011 |
| WO | WO 2011/143624 | 11/2011 |
| WO | WO 2013/155109 | 10/2013 |
| WO | WO 2014/005089 A2 | 1/2014 |
| WO | WO 2014/093678 | 6/2014 |

OTHER PUBLICATIONS

Dalerba P, et al. (2007) Phenotypic characterization of human colorectal cancer stem cells. Proc Natl Acad Sci USA 104:10158-10163.*
GeneChip Human Genome U133 Plus 2.0 Array—Thermo Fisher Scientific p. 1 of 4; down loaded Feb. 1, 2019.*
Naujokat et al., Apr. 24, 2014 Immunotherapy, vol. 6, No. 3 | Review pp. 291-308.*
Zhao et al PNAS Oct. 16, 2012 109 (42) E2843 On the mechanism of CD47 targeting in cancer.*
Majeti et al CD47 Is an Adverse Prognostic Factor and Therapeutic Antibody Target on Human Acute Myeloid Leukemia Stem Cells ; Cell 138, 286-299, Jul. 24, 2009.*
Baccelli et al., "Co-expression of MET and CD47 is a novel prognosticator for survival of luminal-type breast cancer patients," *Oncotarget* 5(18):8147-8160, 2014.
Chao et al., "Therapeutic Antibody Targeting of CD47 Eliminates Human Acute Lymphoblastic Leukemia," *Cancer Res* 71(4):1374-1384, 2011.
Charafe-Jauffret et al., "ALDH1-Positive Cancer Stem Cells Predict Engraftment of Primary Breast Tumors and Are Governed by a Common Stem Cell Program," *Cancer Res* 73:7290-7300, 2013.
Cioffi et al., Inhibition of CD47 Effectively Targets Pancreatic Cancer Stem Cells via Dual Mechanisms, *Clin Cancer Res* 21(10):2325-2337, 2015.
Edris et al., "Antibody therapy targeting the CD47 protein is effective in a model of aggressive metastatic leiomyosarcoma," *Proc Natl Acad Sci USA* 109(17):6656-6661, 2012.
Fillmore and Kuperwasser, "Human breast cancer stem cell markers CD44 and CD24: enriching for cells with functional properties in mice or in man?" *Breast Cancer Res* 9:303, 2007.
Giancotti, "Mechanisms Governing Metastatic Dormancy and Reactivation," *Cell* 155:750-764, 2013.
Gudjonsson et al., "Isolation, immortalization, and characterization of a human breast epithelial cell line with stem cell properties," *Genes Dev* 16:696-706, 2002.
Ince et al., "Transformation of Different Human Breast Epithelial Cell Types Leads to Distinct Tumor Phenotypes," *Cancer Cell* 12:160-170, 2007.

(Continued)

*Primary Examiner* — Maria G Leavitt
(74) *Attorney, Agent, or Firm* — Klarquist Sparkman, LLP

(57) ABSTRACT

Described herein is the discovery that cancer stem cells (CSCs) can be induced to differentiate by altering CD47 signaling. Provided herein are methods and compositions for inducing differentiation of cancer stem cells, for instance irreversible differentiation, including methods of treating subjects with cancer such as breast cancer, colon cancer, lung cancer, ovarian cancer, or melanoma, and including metastatic as well as primary cancer. Also provided are methods for treating subjects with triple negative breast cancers involving forcing differentiation of bCSCs of the subjects through targeting of CD47.

8 Claims, 48 Drawing Sheets
Specification includes a Sequence Listing.

(56) References Cited

OTHER PUBLICATIONS

Kaur et al., "Thrombospondin-1 Signaling through CD47 Inhibits Self-renewal by Regulating c-Myc and Other Stem Cell Transcription Factors," *Sci Rep* 3:1673, 2013.
Naujokat, Cord, "Monoclonal antibodies against human cancer stems cells," *Immunotherapy* 6(3):290-308, 2014.
Pettersen et al., "CD47 Signals T Cell Death," *J Immunol* 162:7031-7040, 1999.
Rosen et al.,"Pathological Prognostic Factors in Stage I ($T_1N_0M_0$) and Stage II ($T_1N_1M_0$) Breast Carcinoma: A Study of 644 Patients With Median Follow-Up of 18 Years," *J Clin Oncol* 7:1239-1251, 1989.
Singh et al., "Identification of human brain tumour initiating cells," *Nature* 432:396-401, 2004.
Sun et al., "High Susceptibility of a Human Breast Epithelial Cell Type with Stem Cell Characteristics to Telomerase Activation and Immortalization," *Cancer Res* 59:6118-6123, 1999.
Villadsen et al., "Evidence for a stem cell hierarchy in the adult human breast," *J Cell Biol* 177(1):87-101, 2007.
Willingham et al., "The CD47-signal regulatory protein alpha (SIRPa) interaction is a therapeutic target for human solid tumors," *Proc Natl Acad Sci USA* 109(17):6662-6667, 2012.
Yoshida et al., "CD47 is an adverse prognostic factor and a therapeutic target in gastric cancer," *Cancer Medicine* 4(9):1322-1333, 2015.
Zhao et al., "CD47-signal regulatory protein-α (SIRPα) interactions form a barrier for antibody-mediated tumor cell destruction," *Proc Natl Acad Sci USA* 108(45):18342-18347, 2011.
Zhao et al., "On the mechanism of CD47 targeting in cancer," *Proc Natl Acad Sci USA* 109(42):E2843. 2012.
Zhao et al., "To the editor: Is targeting of CD47-SIRPα enough for treating hematopoietic malignancy?" *Blood* 119(18):4333-4334, 2012.
Manna et al., "CD47 Mediates Killing of Breast Tumor Cells via Gi-Dependent Inhibition of Protein Kinase a," *Cancer Research*, vol. 64, pp. 1026-1036, 2004.

\* cited by examiner

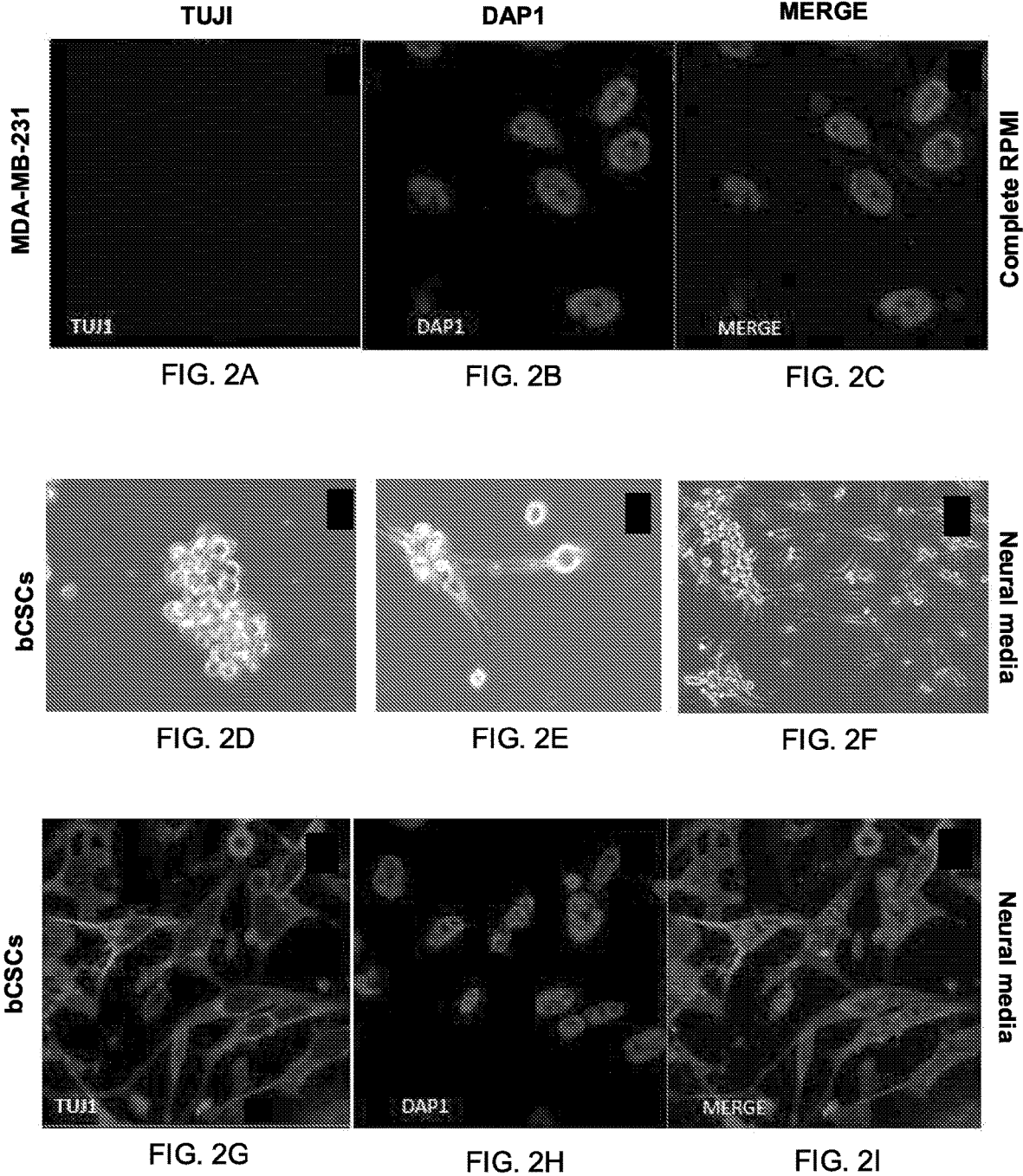

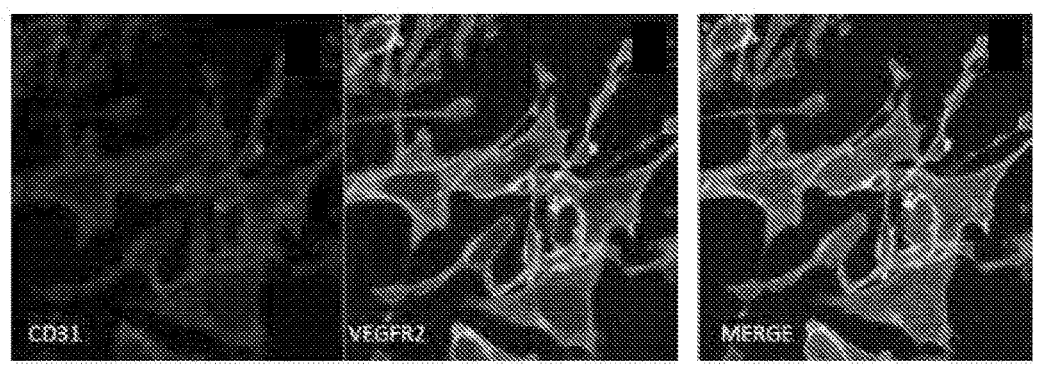
FIG. 3A  FIG. 3B  FIG. 3C
FIG. 3D  FIG. 3E  FIG. 3F
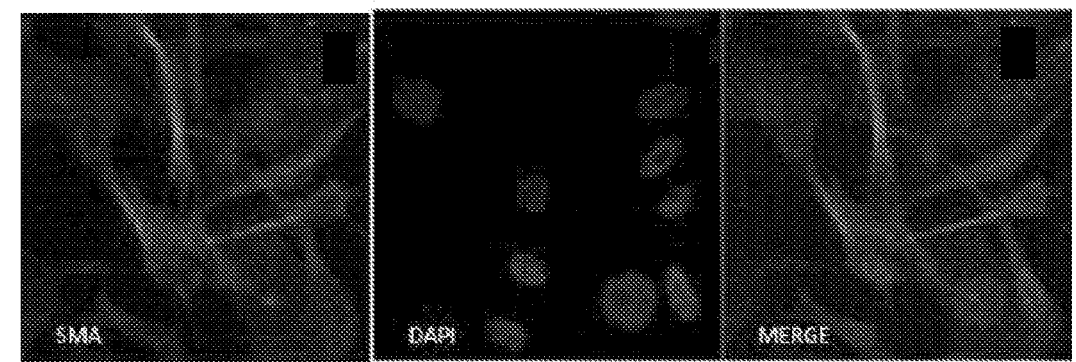
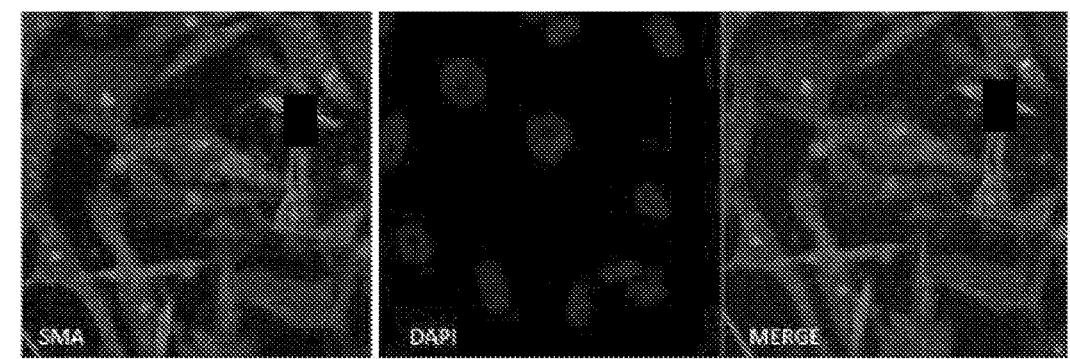
FIG. 4A  FIG. 4B  FIG. 4C
FIG. 4D  FIG. 4E  FIG. 4F

| | B2M | VEGF | Oct4 | Nanog | Sox2 | Nestin | Ptbp1 | CD44 | CD24 |
|---|---|---|---|---|---|---|---|---|---|
| FIG. 5A MDA-MB-231 | 20.56597 | 19.41295 | 21.45108 | 22.00939 | 26.09301 | 21.63852 | 28.04824 | 25.36813 | 23.19235 |
| | 20.27897 | 19.83395 | 21.28975 | 21.95306 | 26.52046 | 21.43096 | 27.86551 | 25.39445 | 23.34318 |
| FIG. 5B bCSC | 20.16075 | 18.05089 | 20.24509 | 21.89715 | 22.22748 | 16.11204 | 15.93916 | 17.04986 | 24.84856 |
| | 20.33394 | 17.81972 | 20.09437 | 21.43437 | 24.82614 | 15.99497 | 16.47788 | 17.34328 | 25.42249 |
| FIG. 5C bCSC-replating | 22.95268 | 20.40965 | 21.99848 | 24.21067 | 27.44107 | | | | |
| | 22.93922 | 21.00079 | 22.91329 | 23.37882 | 27.69665 | | | | |
| FIG. 5D bCSCs cultured in EGM2 media | 18.58069 | 22.20645 | 21.5929 | 21.98934 | 24.36762 | 23.42293 | 26.82679 | 26.38155 | 22.53205 |
| | 18.58949 | 22.00183 | 21.6627 | 21.80455 | 24.52121 | 23.19079 | 27.01294 | 26.31778 | 22.69279 |
| FIG. 5E bCSCs cultured in neural media | 18.81483 | 20.00318 | 19.4826 | 20.52555 | 23.15275 | 19.9185 | 21.16671 | 21.62547 | 23.40676 |
| | 18.80083 | 20.70061 | 19.72538 | 20.89371 | 23.19893 | 19.63731 | 20.91347 | 22.04533 | 22.91572 |

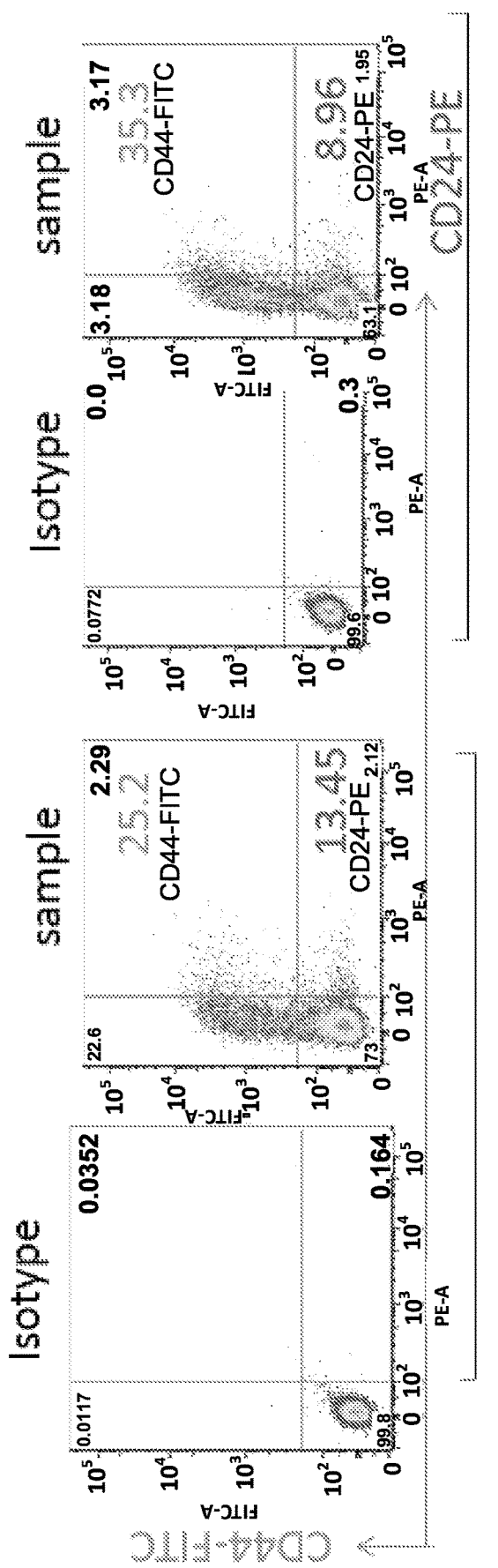

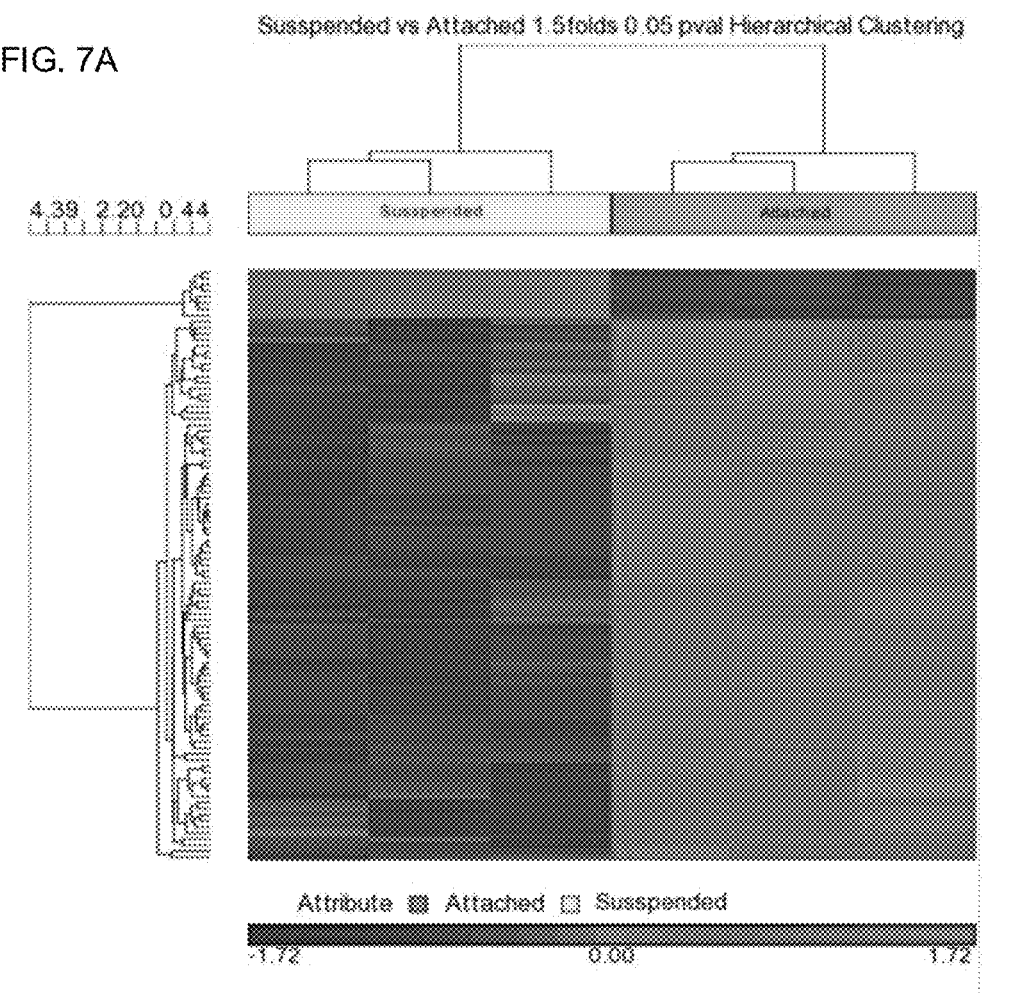

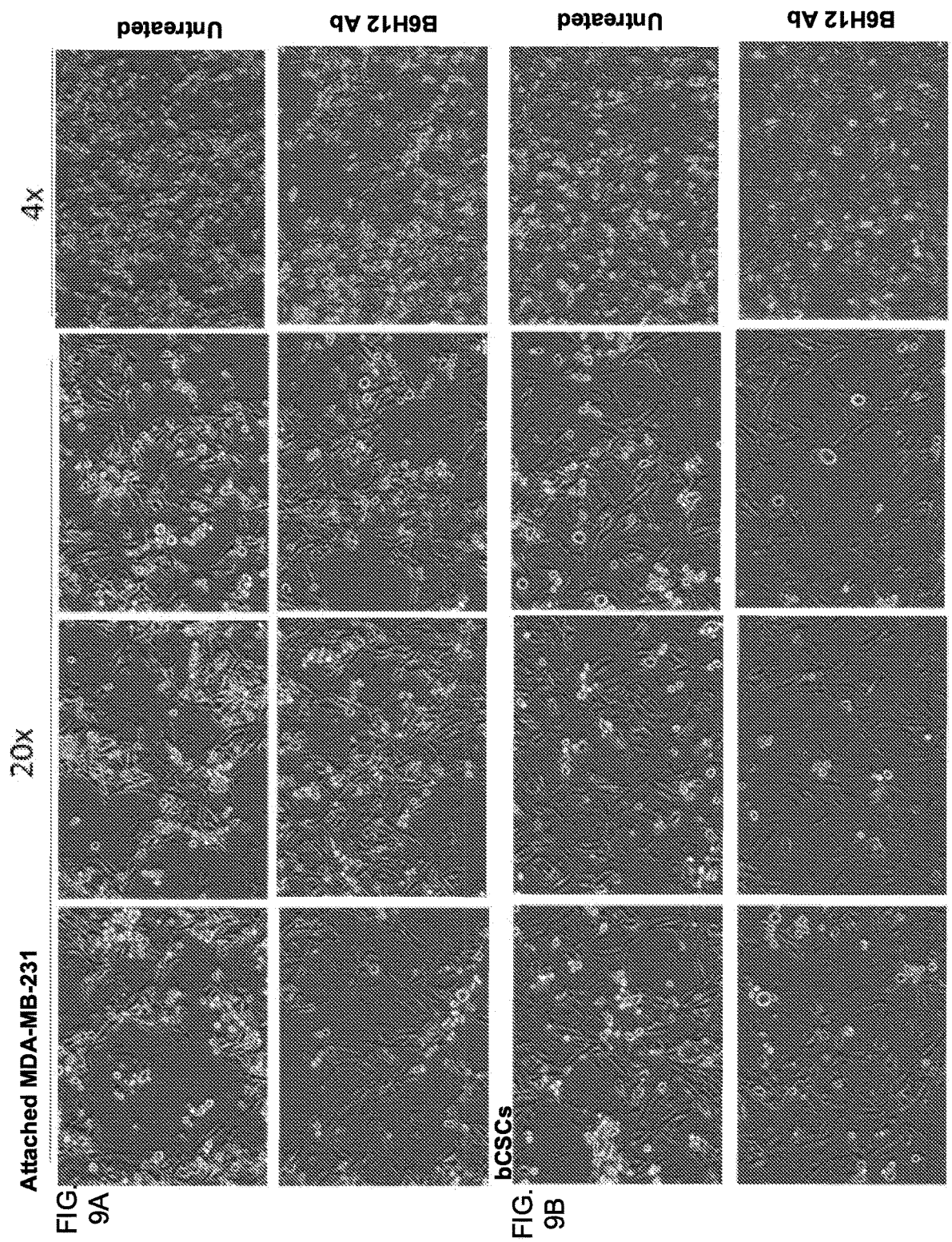

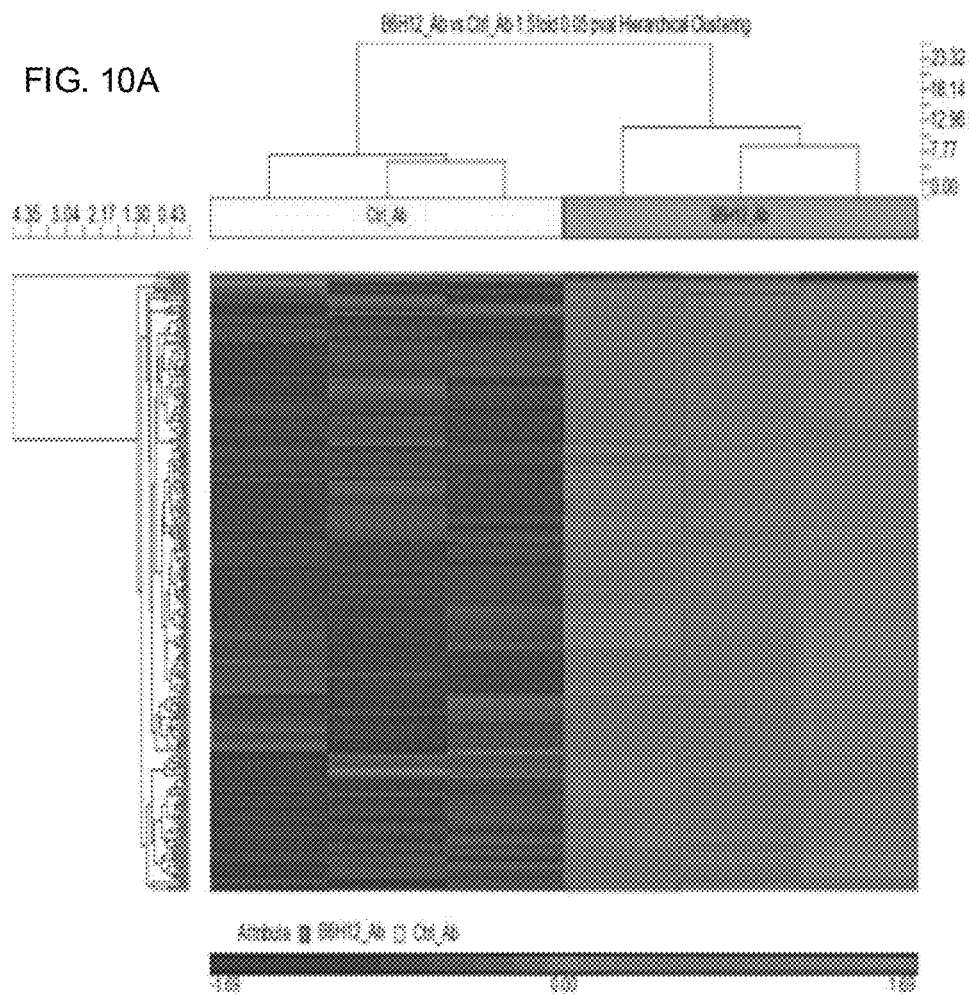

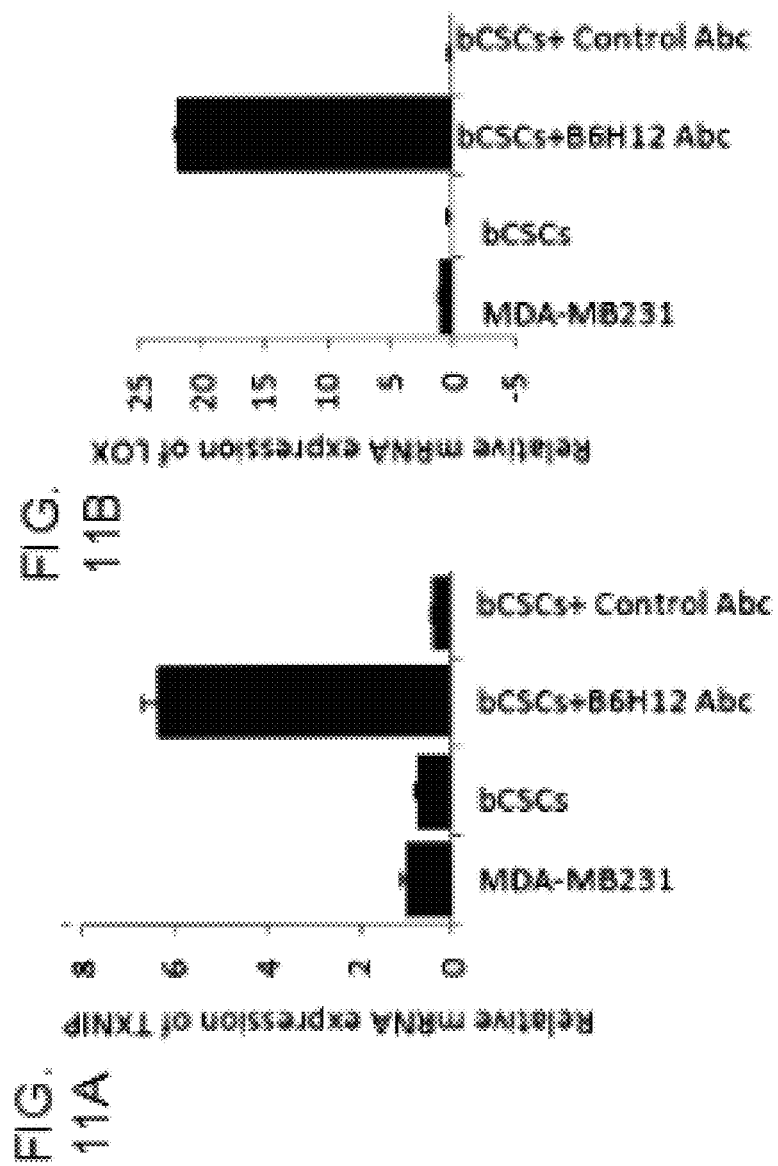

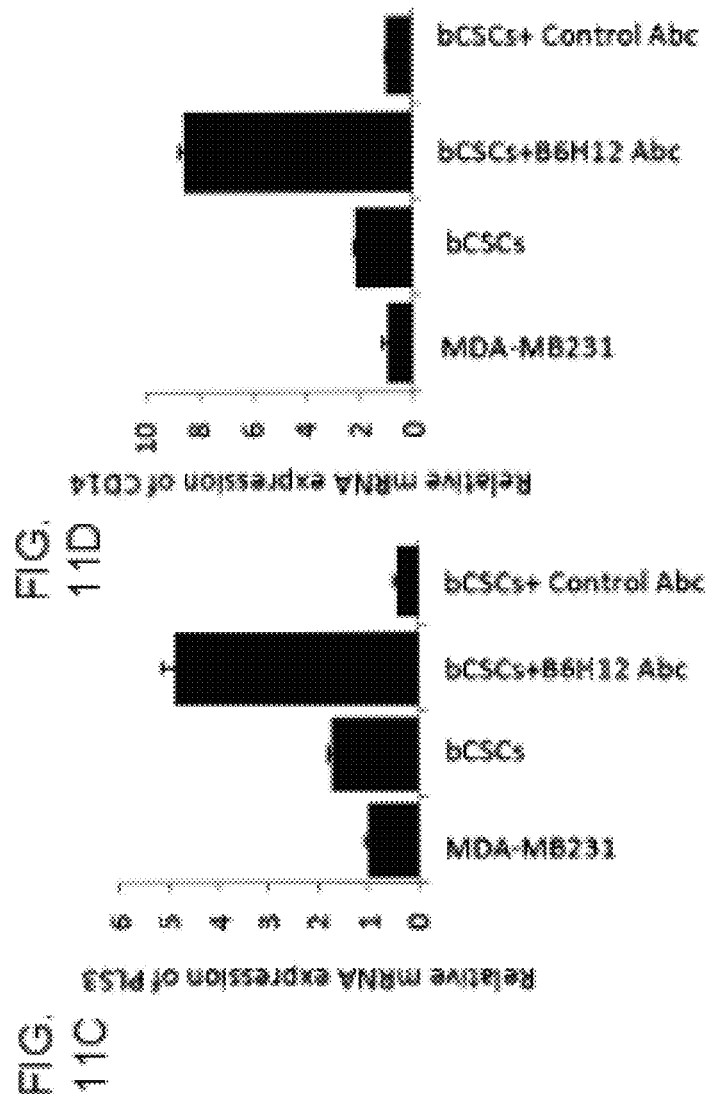

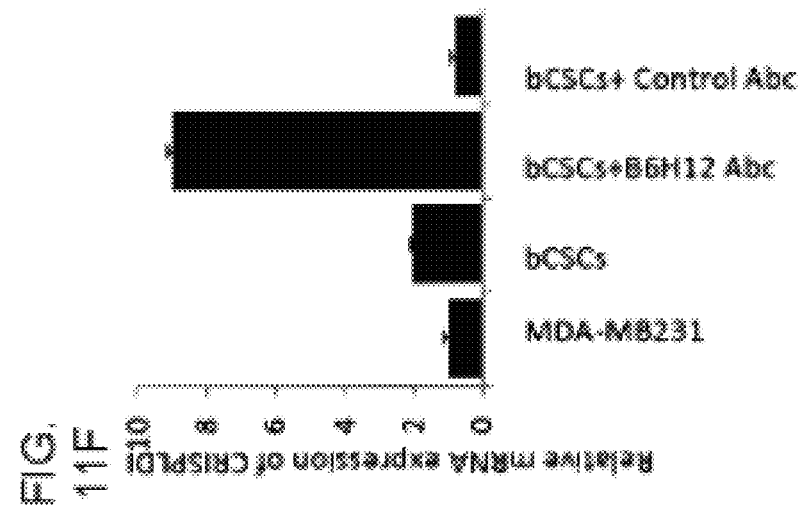
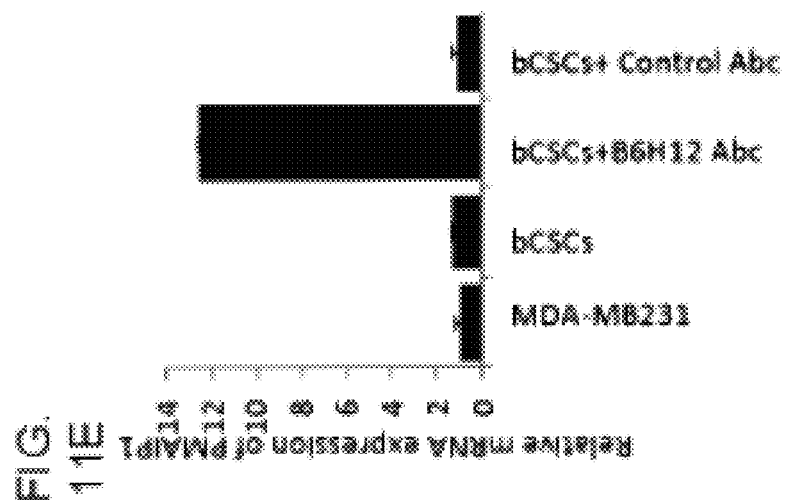

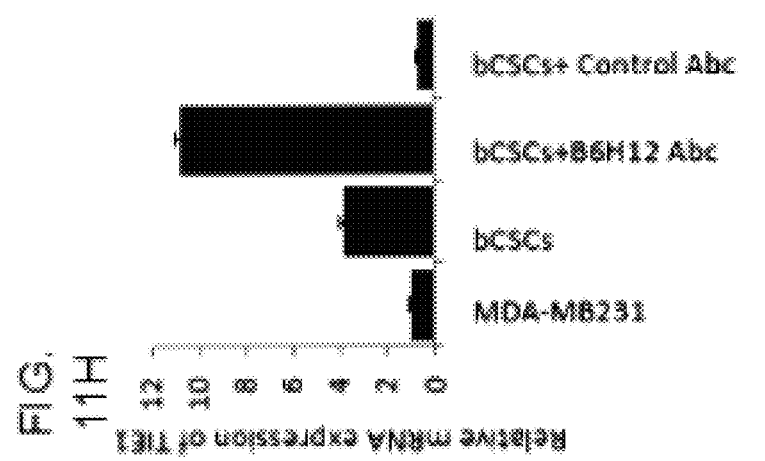
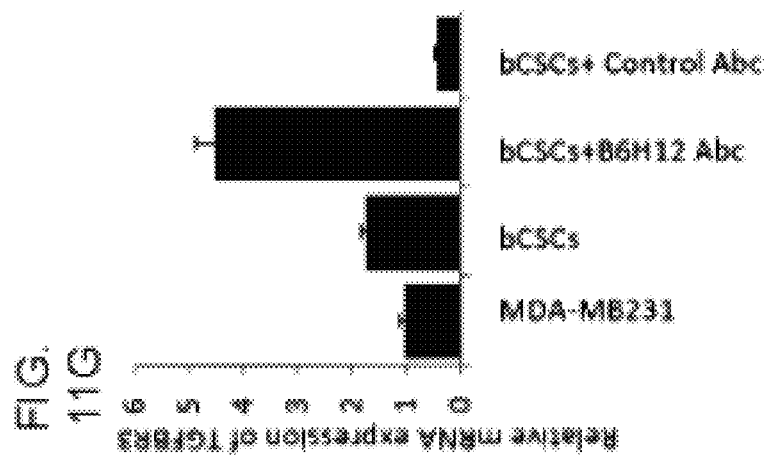

B6H12 Ab inhibit asymmetric cell division

FIG. 12E
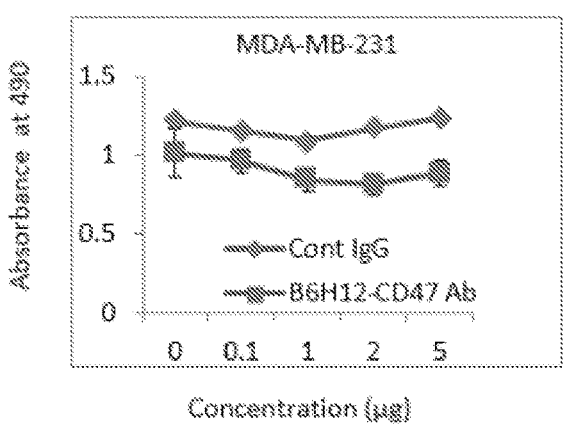
FIG. 12F
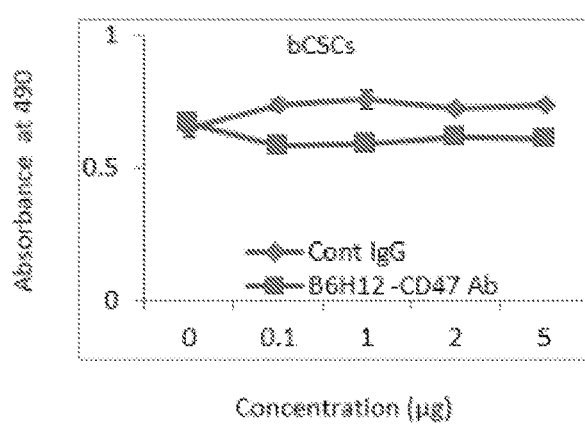
FIG. 13A
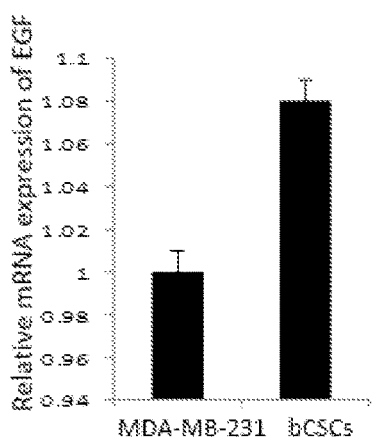
FIG. 13B
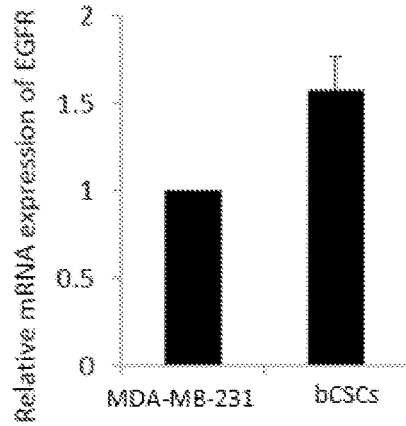
FIG. 13C
|  | 18 S RNA | EGF | EGFR |
|---|---|---|---|
| UT | 19.13744 | 30.99029 | 24.76555 |
|  | 18.48919 | 31.44832 | 24.51606 |
| B6H12 Ab | 22.29072 | None | 35.64032 |
|  | 22.25605 | None | 36.04201 |
| B6H12 Ab+EGF | 22.05395 | None | None |
|  | 22.01361 | None | None |
| EGF | 17.89758 | 31.78809 | 25.30861 |
|  | 17.40071 | 32.25872 | 27.10437 |
| EGF+ Cont IgG | 17.58061 | 31.60415 | 26.52253 |
|  | 17.6107 | 30.36993 | 24.33233 |
| Cont IgG | 17.45655 | 30.10047 | 24.48624 |
|  | 17.40909 | 30.08806 | 24.57056 |
bCSCs FIG. 16A  MCF7
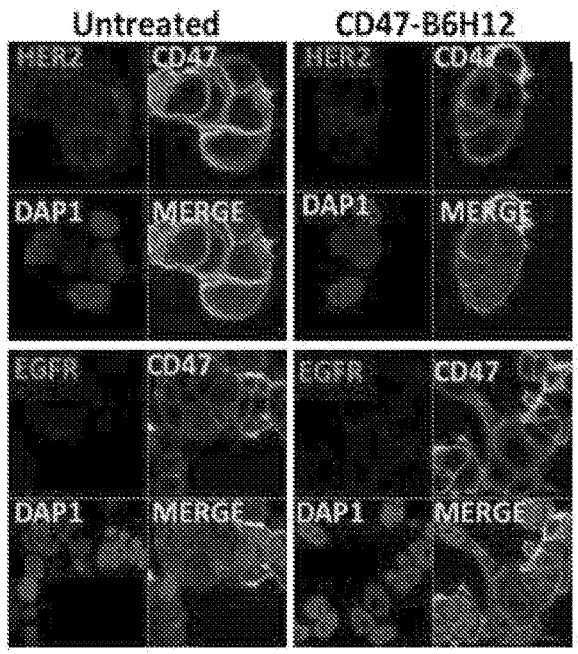
FIG. 16B  T47D1
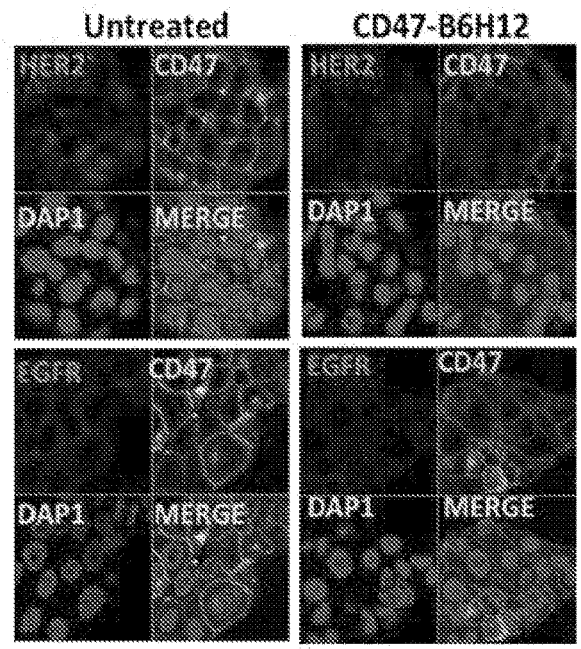
FIG. 16C  bCSCs
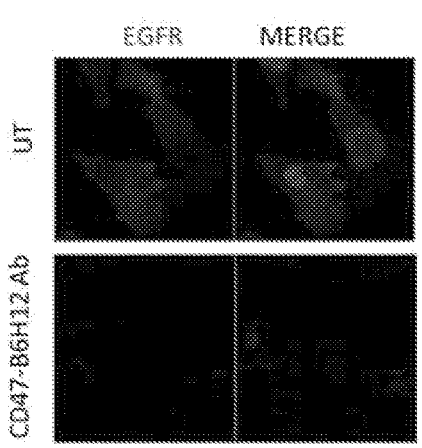
FIG. 16E
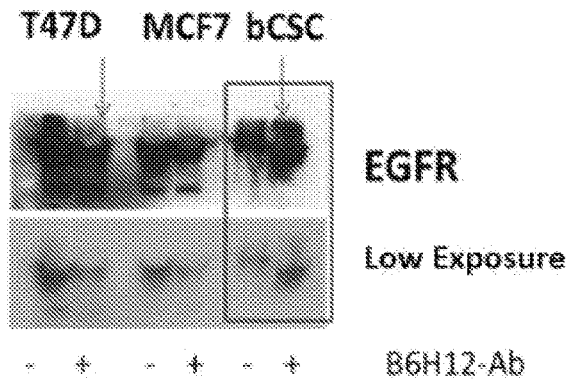
FIG. 16D
bCSCs
IP : anti-CD47-biotin
WB:EGFR
−   +   B6H12 Ab
FIG. 16F
MCF7   T47D1
IP:EGFR
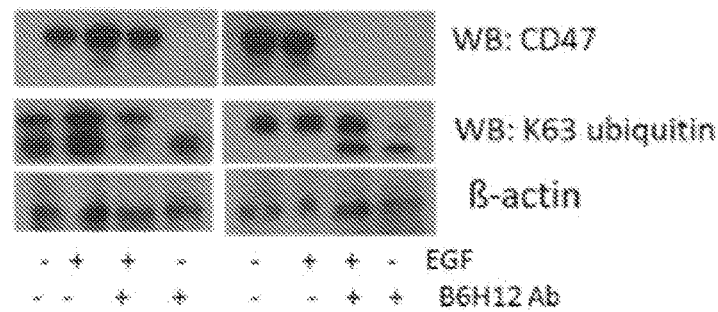

FIG. 17A

|        | Ct       | Avg      |
|--------|----------|----------|
| UT     | 36.74282 | 37.07896 |
|        | 37.4151  |          |
| B6H12  | 36.63909 | 36.64373 |
|        | 36.64837 |          |
| EGF    | 36.3102  | 36.92098 |
|        | 37.53175 |          |
| EGF+B6H| 37.18789 | 36.6726  |
|        | 36.15731 |          |
| TSP1   | 36.26373 | 36.24651 |
|        | 36.22929 |          |
| TSP1+EG| 36.1519  | 36.35335 |
|        | 36.55479 |          |

SIRP α

FIG. 17B

|         | SIRP BETA |          |
|---------|-----------|----------|
|         | Ct        | Avg      |
| UT      | 34.75369  | 34.76792 |
|         | 34.78215  |          |
| B6H12   | 35.28682  | 35.13938 |
|         | 34.99194  |          |
| EGF     | 34.42692  | 34.67926 |
|         | 34.9316   |          |
| EGF+B6H1| 35.85501  | 36.12333 |
|         | 36.39164  |          |
| TSP1    | 34.5186   | 35.01785 |
|         | 35.51709  |          |
| TSP1+EGF| 34.63617  | 34.62561 |
|         | 34.61504  |          |

SIRP β

FIG. 17C

|         | SIRP GAMMA |          |
|---------|------------|----------|
|         | Ct         | Avg      |
| UT      | 34.5826    | 34.93205 |
|         | 35.2815    |          |
| B6H12   | 35.17374   | 35.62366 |
|         | 36.07357   |          |
| EGF     | 35.92498   | 35.68063 |
|         | 35.43628   |          |
| EGF+B6H1| 36.31258   | 36.59248 |
|         | 36.87237   |          |
| TSP1    | 35.36719   | 35.06987 |
|         | 34.77254   |          |
| TSP1+EGF| 35.01999   | 34.57284 |
|         | 34.12569   |          |

SIRP γ

PC200.Hcd47.g3a-CRISPR design bCSCs-10d at 37° C

FIG. 24D

Total gene =98 bCSCs vs Differentiated (up 8)

| Gene Symbol | Gene Title | Fold Change (Suspended vs. Attached) |
|---|---|---|
| AKR1C3 | aldo-keto reductase family 1, member C3 (3-alpha hydroxysteroid dehydrogenase, type II) | 1.8188 |
| AKR1C2 | aldo-keto reductase family 1, member C2 (dihydrodiol dehydrogenase 2; bile acid binding) | 1.6718 |
| AKR1C1 | aldo-keto reductase family 1, member C1 (dihydrodiol dehydrogenase 1; 20-alpha (3-alpha... | 1.6018 |
| TRIM16 | tripartite motif containing 16 | 1.5183 |
| HLA-DRA | major histocompatibility complex, class II, DR alpha | 1.5188 | bCSCs vs Differentiated (down 90)

| Gene Symbol | Gene Title | Fold Change (MDA231_Suspended vs. MDA231_Attached) |
|---|---|---|
| TFF1 | trefoil factor 1 | -4.8504 |
| ATRX | alpha thalassemia/mental retardation syndrome X-linked | -2.4673 |
| ANKRD36B | ankyrin repeat domain 36B | -2.3548 |
| SORBS2 | sorbin and SH3 domain containing 2 | -2.3364 |
| TOP3 | topoisomerase (DNA) 3 | -2.330 |
| NCF2 | neutrophil cytosolic factor 2 | -2.1861 |
| TNFSF10 | tumor necrosis factor (ligand) superfamily, member 10 | -2.1661 |
| INHBA | inhibin, beta A | -2.1074 |
| CDC42BPA | CDC42 binding protein kinase alpha (DMPK-like) | -2.0608 |
| CCDC88A | coiled-coil domain containing 88A | -2.0716 |
| MALAT1 | metastasis associated lung adenocarcinoma transcript 1 (non-protein coding) | -2.0548 |
| SPAG9 | sperm associated antigen 9 | -2.0522 |
| INHBA | inhibin, beta A | -2.0481 |
| KIAA1199 | KIAA1199 | -2.0466 |
| SIF1 | SIF1 interacting factor homolog (yeast) | -2.0133 |
| CD34 | CD34 molecule | -1.9893 |

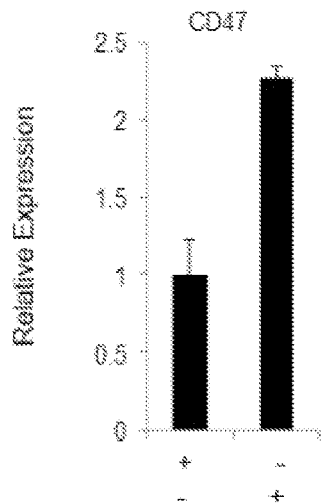
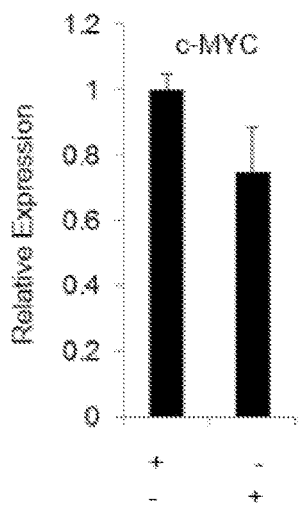
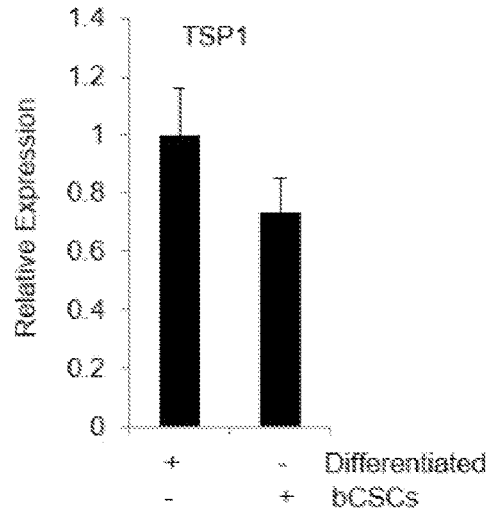
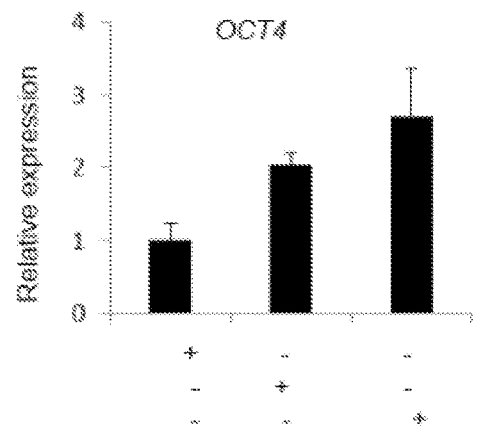
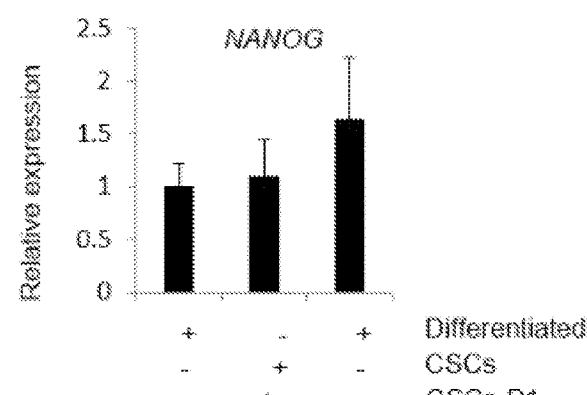
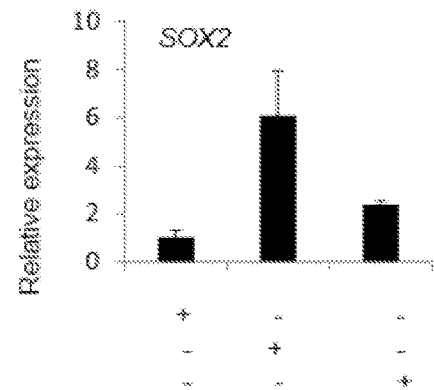
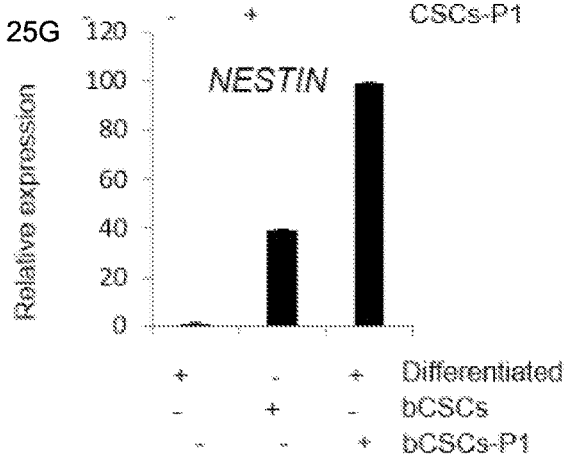

FIG. 27A

B6H12_Ab down vs Ctrl_Ab (1)

| Gene Symbol | Gene Title | Fold-change (B6H12_Ab vs. Ctrl_Ab) |
|---|---|---|
| EGFR | epidermal growth factor receptor | -1.9058 |
| --- | --- | -1.55596 |

B6H12_Ab up vs Ctrl_Ab (224)

| Gene Symbol | Gene Title | Fold-Change (B6H12_Ab vs. Ctrl_Ab) |
|---|---|---|
| NIPBL | Nipped-B homolog (Drosophila) | 2.92333 |
| ASPM | asp (abnormal spindle) homolog, microcephaly associated (Drosophila) | 2.83547 |
| WASL | Wiskott-Aldrich syndrome-like | 2.82213 |
| NASP | Nuclear autoantigenic sperm protein (histone-binding) | 2.75136 |
| IQGAP1 | IQ motif containing GTPase activating protein 1 | 2.68542 |
| TPR | translocated promoter region, nuclear basket protein | 2.62456 |
| TPR | translocated promoter region, nuclear basket protein | 2.56223 |
| RIF1 | RAP1 interacting factor homolog (yeast) | 2.46908 |
| WASF2 | WAS protein family, member 2 | 2.36071 |
| ATRX | alpha thalassemia/mental retardation syndrome X-linked | 2.31098 |
| TOP1 | topoisomerase (DNA) I | 2.13487 |
| DICER1 | dicer 1, ribonuclease type III | 1.5686 |

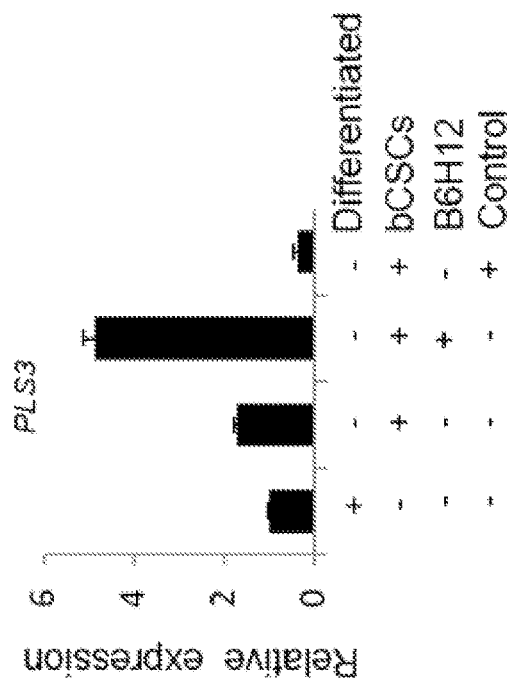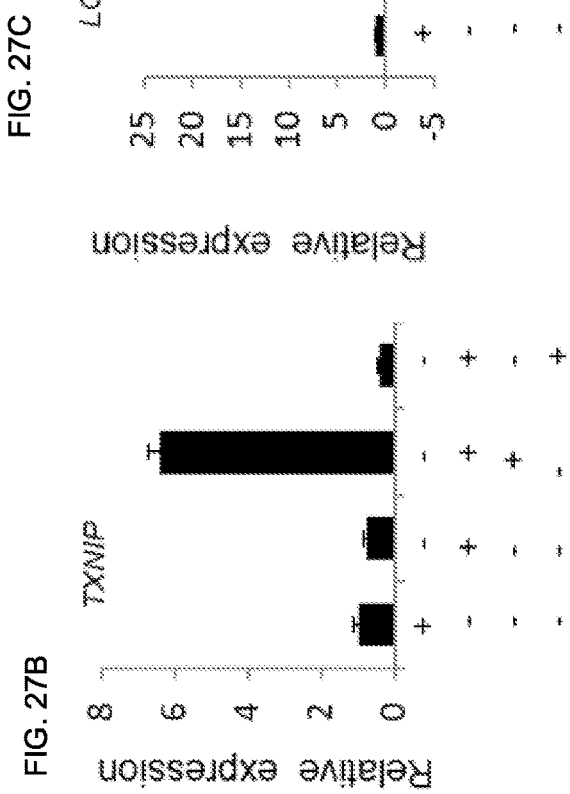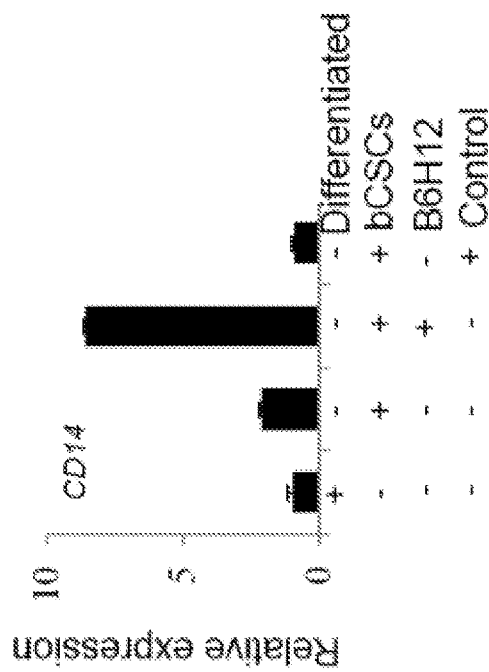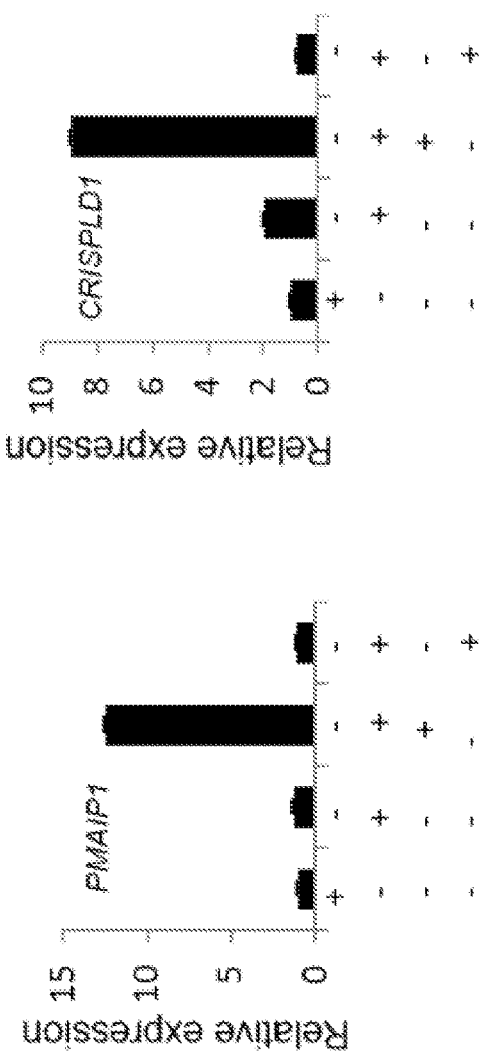
FIG. 27B  FIG. 27C  FIG. 27D
FIG. 27E  FIG. 27F  FIG. 27G

MDA-MB-231
CD44+/CD24-

MDA-MB-231 cells bCSCs

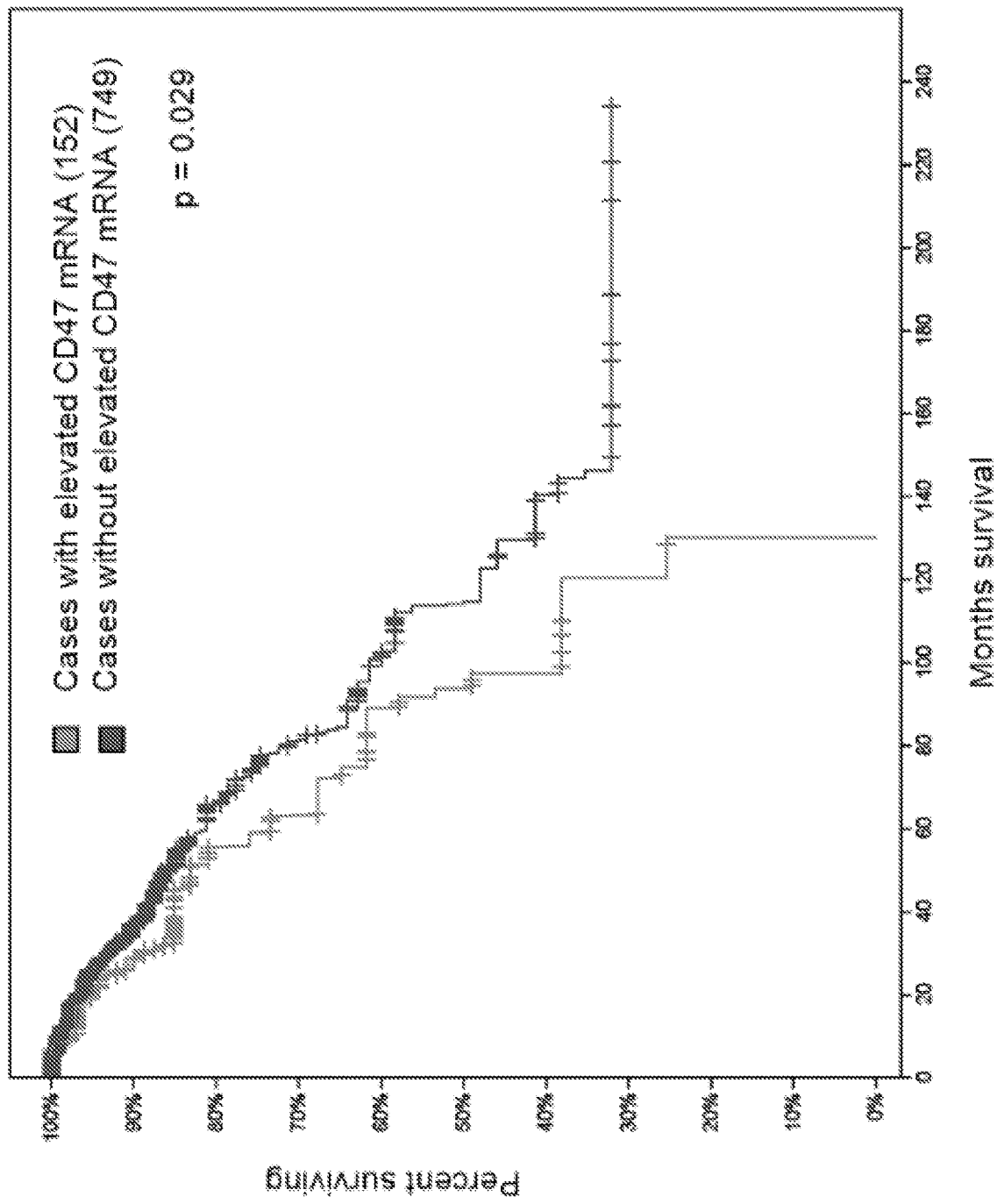

SEQUENCE LISTING

<160> NUMBER OF SEQ ID NOS: 52

<210> SEQ ID NO 1
<211> LENGTH: 11
<212> TYPE: PRT
<213> ORGANISM: artificial sequence
<220> FEATURE:
<223> OTHER INFORMATION: Peptide

```
<400> SEQUENCE: 1

Phe Ile Arg Val Val Met Tyr Glu Gly Lys Lys
1               5                   10

<210> SEQ ID NO 2
<211> LENGTH: 22
<212> TYPE: DNA
<213> ORGANISM: artificial sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n is a, c, g, or t

<400> SEQUENCE: 2
ctactgaagt atacgtaagn gg                                          22

<210> SEQ ID NO 3
<211> LENGTH: 21
<212> TYPE: DNA
<213> ORGANISM: artificial sequence
<220> FEATURE:
<223> OTHER INFORMATION: Primer

<400> SEQUENCE: 3
tggttccttc tgtgtcaatc c                                           21

<210> SEQ ID NO 4
<211> LENGTH: 20
<212> TYPE: DNA
<213> ORGANISM: artificial sequence
<220> FEATURE:
<223> OTHER INFORMATION: Primer

<400> SEQUENCE: 4
gtactctcgc aggaaatggg                                             20

<210> SEQ ID NO 5
<211> LENGTH: 20
<212> TYPE: DNA
<213> ORGANISM: artificial sequence
<220> FEATURE:
<223> OTHER INFORMATION: Primer

<400> SEQUENCE: 5
tcctctggag gctgagaaaa                                             20

<210> SEQ ID NO 6
<211> LENGTH: 20
<212> TYPE: DNA
<213> ORGANISM: artificial sequence
<220> FEATURE:
<223> OTHER INFORMATION: Primer

<400> SEQUENCE: 6
gggctctgga ggaaaagaaa                                             20

<210> SEQ ID NO 7
<211> LENGTH: 24
<212> TYPE: DNA
<213> ORGANISM: artificial sequence
<220> FEATURE:
<223> OTHER INFORMATION: Primer

<400> SEQUENCE: 7
```

```
aggaccgcgg ttctattttg ttgg                                              24

<210> SEQ ID NO 8
<211> LENGTH: 19
<212> TYPE: DNA
<213> ORGANISM: artificial sequence
<220> FEATURE:
<223> OTHER INFORMATION: Primer

<400> SEQUENCE: 8
cccccggccg tccctctta                                                    19

<210> SEQ ID NO 9
<211> LENGTH: 24
<212> TYPE: DNA
<213> ORGANISM: artificial sequence
<220> FEATURE:
<223> OTHER INFORMATION: Primer

<400> SEQUENCE: 9
cgtccaagca gaggagcaaa agct                                              24

<210> SEQ ID NO 10
<211> LENGTH: 21
<212> TYPE: DNA
<213> ORGANISM: artificial sequence
<220> FEATURE:
<223> OTHER INFORMATION: Primer

<400> SEQUENCE: 10
cgcacaagag ttccgtagct g                                                 21

<210> SEQ ID NO 11
<211> LENGTH: 24
<212> TYPE: DNA
<213> ORGANISM: artificial sequence
<220> FEATURE:
<223> OTHER INFORMATION: Primer

<400> SEQUENCE: 11
tcctgaattg ctatgtgtct gggt                                              24

<210> SEQ ID NO 12
<211> LENGTH: 22
<212> TYPE: DNA
<213> ORGANISM: artificial sequence
<220> FEATURE:
<223> OTHER INFORMATION: Primer

<400> SEQUENCE: 12
gatagaaaga ccagtccttg ct                                                22

<210> SEQ ID NO 13
<211> LENGTH: 20
<212> TYPE: DNA
<213> ORGANISM: artificial sequence
<220> FEATURE:
<223> OTHER INFORMATION: Primer

<400> SEQUENCE: 13
aggaagctca aagccgaact                                                   20

<210> SEQ ID NO 14
<211> LENGTH: 20
<212> TYPE: DNA
<213> ORGANISM: artificial sequence
```

```
<220> FEATURE:
<223> OTHER INFORMATION: Primer

<400> SEQUENCE: 14
acgcttcttc tggaagacca                                               20

<210> SEQ ID NO 15
<211> LENGTH: 20
<212> TYPE: DNA
<213> ORGANISM: artificial sequence
<220> FEATURE:
<223> OTHER INFORMATION: Primer

<400> SEQUENCE: 15
aagtttctgc cggaagttca                                               20

<210> SEQ ID NO 16
<211> LENGTH: 19
<212> TYPE: DNA
<213> ORGANISM: artificial sequence
<220> FEATURE:
<223> OTHER INFORMATION: Primer

<400> SEQUENCE: 16
gcaagaacgc tcaaccgag                                                19

<210> SEQ ID NO 17
<211> LENGTH: 20
<212> TYPE: DNA
<213> ORGANISM: artificial sequence
<220> FEATURE:
<223> OTHER INFORMATION: Primer

<400> SEQUENCE: 17
ttgcaaaggc ctctttgagt                                               20

<210> SEQ ID NO 18
<211> LENGTH: 20
<212> TYPE: DNA
<213> ORGANISM: artificial sequence
<220> FEATURE:
<223> OTHER INFORMATION: Primer

<400> SEQUENCE: 18
cccaggactc tgcgacttta                                               20

<210> SEQ ID NO 19
<211> LENGTH: 20
<212> TYPE: DNA
<213> ORGANISM: artificial sequence
<220> FEATURE:
<223> OTHER INFORMATION: Primer

<400> SEQUENCE: 19
atggatgact gcattccaca                                               20

<210> SEQ ID NO 20
<211> LENGTH: 20
<212> TYPE: DNA
<213> ORGANISM: artificial sequence
<220> FEATURE:
<223> OTHER INFORMATION: Primer

<400> SEQUENCE: 20
gagaaaccag cccaaaatga                                               20
```

<210> SEQ ID NO 21
<211> LENGTH: 20
<212> TYPE: DNA
<213> ORGANISM: artificial sequence
<220> FEATURE:
<223> OTHER INFORMATION: Primer

<400> SEQUENCE: 21
tggcagtcta tgtctgcacc                                                20

<210> SEQ ID NO 22
<211> LENGTH: 20
<212> TYPE: DNA
<213> ORGANISM: artificial sequence
<220> FEATURE:
<223> OTHER INFORMATION: Primer

<400> SEQUENCE: 22
ctatggctac cacaggcgat                                                20

<210> SEQ ID NO 23
<211> LENGTH: 20
<212> TYPE: DNA
<213> ORGANISM: artificial sequence
<220> FEATURE:
<223> OTHER INFORMATION: Primer

<400> SEQUENCE: 23
ccatgttccc acaagcaact                                                20

<210> SEQ ID NO 24
<211> LENGTH: 21
<212> TYPE: DNA
<213> ORGANISM: artificial sequence
<220> FEATURE:
<223> OTHER INFORMATION: Primer

<400> SEQUENCE: 24
tcaggtgtat ccaacagcct c                                              21

<210> SEQ ID NO 25
<211> LENGTH: 19
<212> TYPE: DNA
<213> ORGANISM: artificial sequence
<220> FEATURE:
<223> OTHER INFORMATION: Primer

<400> SEQUENCE: 25
ctcacaaggt tctggcgtg                                                 19

<210> SEQ ID NO 26
<211> LENGTH: 20
<212> TYPE: DNA
<213> ORGANISM: artificial sequence
<220> FEATURE:
<223> OTHER INFORMATION: Primer

<400> SEQUENCE: 26
tgagctcaga ggttcggaag                                                20

<210> SEQ ID NO 27
<211> LENGTH: 17
<212> TYPE: DNA
<213> ORGANISM: artificial sequence
<220> FEATURE:
<223> OTHER INFORMATION: Primer

```
<400> SEQUENCE: 27
ctcgcttcgg cagcaca                                                  17

<210> SEQ ID NO 28
<211> LENGTH: 20
<212> TYPE: DNA
<213> ORGANISM: artificial sequence
<220> FEATURE:
<223> OTHER INFORMATION: Primer

<400> SEQUENCE: 28
aacgcttcac gaatttgcgt                                               20

<210> SEQ ID NO 29
<211> LENGTH: 22
<212> TYPE: DNA
<213> ORGANISM: artificial sequence
<220> FEATURE:
<223> OTHER INFORMATION: Primer

<400> SEQUENCE: 29
taggctgtgg gaaaggacca ag                                            22

<210> SEQ ID NO 30
<211> LENGTH: 22
<212> TYPE: DNA
<213> ORGANISM: artificial sequence
<220> FEATURE:
<223> OTHER INFORMATION: Primer

<400> SEQUENCE: 30
gttcgatgaa ccgcttctga tg                                            22

<210> SEQ ID NO 31
<211> LENGTH: 22
<212> TYPE: DNA
<213> ORGANISM: artificial sequence
<220> FEATURE:
<223> OTHER INFORMATION: Primer

<400> SEQUENCE: 31
caagcaggag acatcggaca ag                                            22

<210> SEQ ID NO 32
<211> LENGTH: 22
<212> TYPE: DNA
<213> ORGANISM: artificial sequence
<220> FEATURE:
<223> OTHER INFORMATION: Primer

<400> SEQUENCE: 32
cacaatggac atcttgggct tc                                            22

<210> SEQ ID NO 33
<211> LENGTH: 20
<212> TYPE: DNA
<213> ORGANISM: artificial sequence
<220> FEATURE:
<223> OTHER INFORMATION: Primer

<400> SEQUENCE: 33
tgaagtgtga cgtggacatc                                               20

<210> SEQ ID NO 34
```

```
<210> SEQ ID NO 34
<211> LENGTH: 20
<212> TYPE: DNA
<213> ORGANISM: artificial sequence
<220> FEATURE:
<223> OTHER INFORMATION: Primer

<400> SEQUENCE: 34
ggaggagcaa tgatcttgat                                              20

<210> SEQ ID NO 35
<211> LENGTH: 20
<212> TYPE: DNA
<213> ORGANISM: artificial sequence
<220> FEATURE:
<223> OTHER INFORMATION: Primer

<400> SEQUENCE: 35
cgtagagtca accgggaagt                                              20

<210> SEQ ID NO 36
<211> LENGTH: 19
<212> TYPE: DNA
<213> ORGANISM: artificial sequence
<220> FEATURE:
<223> OTHER INFORMATION: Primer

<400> SEQUENCE: 36
cctcaaagtc gacccgttc                                               19

<210> SEQ ID NO 37
<211> LENGTH: 19
<212> TYPE: DNA
<213> ORGANISM: artificial sequence
<220> FEATURE:
<223> OTHER INFORMATION: Primer

<400> SEQUENCE: 37
tgcaggcgtt acacgatgc                                               19

<210> SEQ ID NO 38
<211> LENGTH: 21
<212> TYPE: DNA
<213> ORGANISM: artificial sequence
<220> FEATURE:
<223> OTHER INFORMATION: Primer

<400> SEQUENCE: 38
tacctcatgg atggcaagtg c                                            21

<210> SEQ ID NO 39
<211> LENGTH: 24
<212> TYPE: DNA
<213> ORGANISM: artificial sequence
<220> FEATURE:
<223> OTHER INFORMATION: Primer

<400> SEQUENCE: 39
caggtatact tctcagccat gtga                                         24

<210> SEQ ID NO 40
<211> LENGTH: 23
<212> TYPE: DNA
<213> ORGANISM: artificial sequence
<220> FEATURE:
<223> OTHER INFORMATION: Primer

<400> SEQUENCE: 40
```
gcccacttct gtcagtaaat ggt					23

<210> SEQ ID NO 41
<211> LENGTH: 23
<212> TYPE: DNA
<213> ORGANISM: artificial sequence
<220> FEATURE:
<223> OTHER INFORMATION: Primer

<400> SEQUENCE: 41
caacgtaagt gaatgaaaat ggt					23

<210> SEQ ID NO 42
<211> LENGTH: 23
<212> TYPE: DNA
<213> ORGANISM: artificial sequence
<220> FEATURE:
<223> OTHER INFORMATION: Primer

<400> SEQUENCE: 42
taaattaatt tatttccagg cca					23

<210> SEQ ID NO 43
<211> LENGTH: 24
<212> TYPE: DNA
<213> ORGANISM: artificial sequence
<220> FEATURE:
<223> OTHER INFORMATION: Primer

<400> SEQUENCE: 43
gaaaatacag catgggtaca agga					24

<210> SEQ ID NO 44
<211> LENGTH: 25
<212> TYPE: DNA
<213> ORGANISM: artificial sequence
<220> FEATURE:
<223> OTHER INFORMATION: Primer

<400> SEQUENCE: 44
ttaagaaatg gtagttttcc agcca					25

<210> SEQ ID NO 45
<211> LENGTH: 19
<212> TYPE: DNA
<213> ORGANISM: artificial sequence
<220> FEATURE:
<223> OTHER INFORMATION: Primer

<400> SEQUENCE: 45
agaatccctg tgcccttgg					19

<210> SEQ ID NO 46
<211> LENGTH: 21
<212> TYPE: DNA
<213> ORGANISM: artificial sequence
<220> FEATURE:
<223> OTHER INFORMATION: Primer

<400> SEQUENCE: 46
ggcacctagg cctgtcagac t					21

<210> SEQ ID NO 47
<211> LENGTH: 23
<212> TYPE: DNA

```
<213> ORGANISM: artificial sequence
<220> FEATURE:
<223> OTHER INFORMATION: Primer

<400> SEQUENCE: 47
caggttaatt tgaagtgcat ctg                                              23

<210> SEQ ID NO 48
<211> LENGTH: 22
<212> TYPE: DNA
<213> ORGANISM: artificial sequence
<220> FEATURE:
<223> OTHER INFORMATION: Primer

<400> SEQUENCE: 48
agcaccatgc tgcagtttat aa                                               22

<210> SEQ ID NO 49
<211> LENGTH: 19
<212> TYPE: DNA
<213> ORGANISM: artificial sequence
<220> FEATURE:
<223> OTHER INFORMATION: Primer

<400> SEQUENCE: 49
ggggaaacct tttgcttct                                                   19

<210> SEQ ID NO 50
<211> LENGTH: 22
<212> TYPE: DNA
<213> ORGANISM: artificial sequence
<220> FEATURE:
<223> OTHER INFORMATION: Primer

<400> SEQUENCE: 50
ctgtgcctac tgtacttgaa ca                                               22

<210> SEQ ID NO 51
<211> LENGTH: 23
<212> TYPE: DNA
<213> ORGANISM: artificial sequence
<220> FEATURE:
<223> OTHER INFORMATION: Primer

<400> SEQUENCE: 51
tacatgaaca tgctgtttca gag                                              23

<210> SEQ ID NO 52
<211> LENGTH: 24
<212> TYPE: DNA
<213> ORGANISM: artificial sequence
<220> FEATURE:
<223> OTHER INFORMATION: Primer

<400> SEQUENCE: 52
catctaagtc aaatgactcc actg                                             24
```

METHODS TO ELIMINATE CANCER STEM CELLS BY TARGETING CD47

CROSS REFERENCE TO RELATED APPLICATIONS

This application is the § 371 U.S. National Stage of International Application No. PCT/US2015/055029, filed Oct. 9, 2015, published in English under PCT Article 21(2), which claims the benefit of the earlier filing date of U.S. Provisional Application No. 62/062,675, filed Oct. 10, 2014; that earlier application is incorporated herein in its entirety.

FIELD

This disclosure relates to methods and compositions for selectively eliminating cancer stem cells, particularly through perturbing CD47 signaling.

BACKGROUND

Cancer stem cells (CSC) can be defined by three general properties: 1) their capability for self-renewal, 2) asymmetric cell division, and 3) capability to divide and differentiate (Sugiarto et al., *Cancer Cell.* 20(3):328-340, 2011). Initially the concept of cancer stem cells was introduced based on the properties of $CD34^+$ and $CD38^-$ leukemia cells isolated from patients (Lapidot et al., *Nature.* 367:645-648, 1994). Subsequently, cancer stem cells have been isolated from many types of solid tumors including brain and breast tumors (Visvader & Lindeman, *Nat Rev Cancer.* 8:755-768, 2008). Studies using cancer cells fractioned for stem cell markers demonstrate that CSC isolated from various cancer cell lines have the ability to initiate tumor formation in rodent models, but the same cell lines depleted of CSC are unable to initiate tumor formation. Consequently, CSC are also referred to as tumor initiating cells. Cancer stem cells may originate from malignant transformation of normal stem cells or tissue-resident committed progenitor cells. The growing research interest in cancer stem cells is based on evidence that current cancer therapies selectively kill fast growing differentiated tumor cells but are unable to kill tumor initiating cancer stem cells (Dean et al., *Nat Rev Cancer.* 5:275-284, 2005). These refractory tumor cells can be responsible for recurrence of tumors following treatment. Cancer stem cells may also migrate to distal sites and be responsible for initiating cancer metastasis.

Targeting new cancer therapies to cancer stem cells is very challenging because many of the tumor suppressor and polycomb genes (Hedgehog and WNT signaling pathway) that are important for normal stem cell regulation are dysregulated during carcinogenesis (Karamboulas & Ailles, *Biochim Biophys Acta.* 1830(2):2481-2495, 2013). The ubiquitous cell surface protein CD47 is up-regulated in many cancers, especially during metastasis, and high expression is a negative prognostic indicator for several cancers. Additional studies have indicated that CD47 expression is elevated in leukemic cancer stem cells. The current conventional wisdom is that the function of this elevated CD47 expression on CSC is to serve as a "don't eat me" signal that protects the CSC from phagocytic clearance by macrophages (reported online at news.sciencemag.org/health/2012/03/one-drug-shrink-all-tumors). Consequently, antibody and ligand therapeutics that engage CD47 have been developed to stimulate the destruction of CSC by macrophages, and these are now entering human clinical trials. The CD47 antibody B6H12 is known to block the recognition of CD47 by its counter-receptor SIRPα on macrophages. Human tumor xenografts grown in immunodeficient mice that express a mutant form of SIRPα that is capable of binding human CD47 (Nod-SCID) have been used to test the ability of B6H12 to enhance macrophage-mediated clearance of human tumor xenografts. Inhibition of tumor growth by B6H12 in these models provided evidence to support the humanization of such CD47 antibodies for treating human cancer patients.

SUMMARY

However, CD47 is more than a passive SIRPα counter-receptor, and B6H12 has effects on CD47 signaling that are independent of blocking SIRPα binding. Signal transduction through CD47 regulates important cell functions and gene expression. Described herein is the discovery of an unanticipated activity of B6H12 and other agents that perturb CD47 signaling in cancer stem cells (CSCs), and methods of using this to inhibit or treat cancer, or prevent or reduce metastasis, by inducing differentiation of CSCs.

Provided herein are methods for inducing differentiation (for instance, irreversible differentiation) of a cancer stem cell, involving contacting the cancer stem cell with an agent that alters CD47 signaling to induce cancer stem cell (CSC) differentiation. Optionally, the CSC may be in a subject. The agent used in the method comprises, in various embodiments, an anti-CD47 antibody or binding fragment thereof, peptide 7N3, or a CD47-targeted CRISPR construct. Where the agent comprises an antibody or fragment thereof, it is specifically contemplated that the agent can be the monoclonal antibody B6H12, humanized B6H12, a binding fragment of B6H12 or humanized B6H12, or a monoclonal antibody that binds competitively with B6H12.

Also provided herein are methods of treating a subject by inducing differentiation of a cancer stem cell in the subject. It is contemplated that the subject may have a tumor, such as a primary tumor, has a tumor in regression, has or is suspected of having a metastatic tumor, or a combination thereof. Such treatment methods involve administering to the subject a therapeutically effective amount of agent that alters CD47 signaling to induce cancer stem cell (CSC) differentiation, thereby treating the subject with the tumor.

Also provided are treatment methods which further involve administering a therapeutically effective amount of an anti-cancer treatment to the subject. This can occur before, concurrent with, or after treatment with the agent that alters CD47 signaling to induce cancer stem cell (CSC) differentiation. In particular examples, the anti-cancer treatment is administered first, followed (for instance 1-4 days, or 1-7 days later) by administration with the agent that alters CD47 signaling.

Also provided herein are methods for inducing differentiation (such as irreversible differentiation) of cancer stem cells, substantially as described herein.

The foregoing and other objects, features, and advantages of the invention will become more apparent from the following detailed description, which proceeds with reference to the accompanying figures.

BRIEF DESCRIPTION OF THE DRAWINGS

At least some of the figures submitted herewith contain color.

1A) MDA-MB-231 cells were cultured using RPMI media with 10% FBS+P/S+ Glutamine at 37 C°. Inset showing the presence of bCSCs in the form of small round suspension cells. FIG. 1B) With gentle agitation of the flask, loosely bound bCSCs were separated from adherent MDA-MB-231 cells. FIG. 1C) bCSCs form loose aggregates after incubation at 37° C. FIG. 1D) MDA-MB-231 bCSCs exhibit high asymmetric cell division. Adherent MDA-MB-231 and enriched bCSCs cells were labeled with BrdU for 10 days and then chased in BrdU free media for 3-4 days and followed by 2 µM Cytochalasin. The cells were immunostained using BrdU antibody and mounted with Vectashield DAPI. The confocal images were taken using a Zeiss 780 microscope at 63×. FIG. 1E) Quantification of asymmetric cell division ratio between cells negative for BrdU and positive for DAPI counted manually at 20×.

FIG. 2A-2I illustrates differentiation of bCSCs into neural cells. MDA-MB-231 bCSCs induced to form embryoid bodies can differentiate along a neural lineage. MDA-MB-231 cells were cultured in complete RPMI media, and bCSCs were cultured with neural media containing EBM medium supplemented with FGF2 and EGF (~5-20 ng/ml), heparin and gentamycin sulfate for 36 h. FIG. 2A-2C) MDA-MB-231 cells were immunostained with Tuj 1, Neuron-specific class III beta-tubulin. FIG. 2D) Loosely formed embryoid body-like cluster of bCSCs. FIGS. 2E & 2F) Differentiation of bCSC clusters into neuron like cells.

FIG. 2G-2I) Neuron like differentiated cells from bCSCs were immunostained with Tuj 1. The images were captured using a Zeiss 780 confocal microscope.

FIG. 3A-3F illustrate differentiation of MDA-MB-231 bCSCs into endothelial-mimic cells using endothelial growth medium (EGM2). FIG. 3A-3C) Control adherent MDA-MB-231 cells were cultured in complete RPMI medium for 36 h and were immunostained for expression of the endothelial markers CD31 and VEGFR2. FIG. 3D-3F) Immunostaining of differentiated bCSC cells cultured in EGM2 media for expression of CD31 and VEGFR2.

FIG. 4A-4F illustrate differentiation of MDA-MB-231 bCSCs into smooth muscle cells using Smooth Muscle Basal Medium (Lonza) supplemented with PDGF (10 ng/ml) and TGF-β1 (5 ng/ml). FIG. 4A-4C) Control MDA-MB-231 cells were cultured in complete RPMI media for 36 h and were immunostained with smooth muscle actin (SMA) antibody. FIG. 4D-4F) SMA Immunostaining of smooth muscle cells differentiated from bCSC cells.

FIG. 5A-5E is a table showing the Ct values of real time PCR of MDA-MB-231 and bCSCs. MDA-MB-231 bCSCs have up-regulated mRNA expression of a subset of embryonic and cancer stem cell markers. FIGS. 5A & 5B) MDA-MB-231 and bCSCs cells were separated, and total RNA was extracted for real time PCR (q-PCR) analysis using the indicated primers for VEGF, OCT4, Nanog, Sox2, Nestin, PTPBP1, CD44 and CD24 with B2M control. FIG. 5C) Real time Ct value of gene expression of above listed genes after Re-plating of bCSCs. FIGS. 5D & 5E) Real time Ct value of differentiated using EGM2 and Neural media.

FIG. 6A-6B show that bCSCs have high cell surface expression of CD44 and low CD24 than MDA-MB-231 cells. FIGS. 6A & 6B) bCSCs have higher cell surface expression of CD44 and lower CD24 expression than control MDA-MB-231 cells. Representative flow cytometry analysis is shown.

FIG. 7A-7B show global analysis of differential gene expression in MDA-MB-231 bCSC versus unfractionated MDA-MB-231 cells. FIG. 7A) Hierarchical clustering of differentially expressed genes based on microarray analysis of MDA-MB-231 and bCSCs. FIG. 7B) List of differential expression of genes between MDA-MB-231 and bCSCs.

FIG. 9A-9B shows that the CD47 blocking antibody (B6H12 Ab) exhibits morphological change only in bCSCs not in MDA-MB-231. FIGS. 9A & 9B) MDA-MB-231 and bCSCs are treated in the presence or absence of 1 ug/ml of B6H12 for 72 h. The images of live cells were captured using Olympus microscope at 20× and 4×.

FIG. 10A-10B show that B6H12 Ab alters gene expression of bCSCs. FIG. 10A) Microarray analysis clustering of bCSCs treated with Control IgG antibody or B6H12 Ab for 36 h. FIG. 10B) List of Differential expression of genes between Control antibody vs B6H12 Ab. Microarray analysis of CD47 Blocking antibody Treated Cancer Stem Cells.

FIG. 11A-11H show that CD47 blocking antibody increase mRNA expression of tumor suppressor and apoptotic genes. Validation of microarray gene expression results of differentially expressed genes between bCSCs treated with control IgG antibody or B6H12 Ab for 36 h. Up-regulation of tumor suppressor (TXNIP in FIG. 11A, LOX in FIG. 11B and PLS3 in FIG. 11C), activation of apoptotic and caspases genes (PMAIP1 in FIG. 11E and CRISPLDI in FIG. 11F) and cell surface markers such as CD14 (FIG. 11D), TIE1 (FIG. 11H) and TGFBR3 (FIG. 11G) was demonstrated.

FIG. 12A-12F shows that CD47 blocking antibody globally and predominantly targets mitochondrial energetics, asymmetric cell division and cell proliferation in bCSCs. The control MDA-MB-231 and bCSCs were plated using XF24 well plates for 1-4 days. Mitochondrial energetics was measured using extracellular flux assay kits. FIG. 12A) B6H12 (1 µg/ml) alters mitochondrial energetics in bCSCs but not in control MDA-MB-231 cells. FIGS. 12B & 12C) Long term treatment of bCSC with B6H12 (1 µg/ml) leads to decrease in basal oxygen consumption rate (OCR) due to decreased ATP associated OCR and decreases reserve mitochondrial metabolic capacity. The CD47 ligand TSP1 (1 µg/ml) modestly changes mitochondrial energetics but stays consistent from 1-4 days. FIG. 12D) B6H12 Ab shows decreased in asymmetric cell division of bCSCs cells. bCSCs were labeled with BrdU for 10 days, and then chased, treated with Control Ab (1 µg/ml) or B6H12 Ab (1 µg/ml) in BrdU-free medium for 3-4 days and followed by 2 µM Cytochalasin. The cells were immunostained using BrdU antibody and mounted with Vectashield DAPI. The confocal images were taken using a Zeiss 710 microscope at 63×. FIGS. 12E & 12F) Control MDA-MB-231 cells and bCSCs were treated with control or B6H12 Ab at 0.1, 1, 2 and 5 (1 µg/ml) for 72 h. The cell proliferation was measured using CellTiter 96® Aqueous Non-Radioactive Cell Proliferation Assay (MTS) according to manufacturers' instructions.

FIG. 13A-13C illustrate that EGF and EGFR mRNA expression is up-regulated in bCSCs, and B6H12-antibody down-regulates mRNA expression of EGF and EGFR. FIGS. 13A & 13B) Total RNA was extracted from bCSCs and the gene expression of EGF and EGFR2 was measured using real time PCR. FIG. 13C) bCSCs were treated with B6H12 or control Ab (1 µg/ml) in the presence or absence of EGF (30 ng/ml) for 36 h. EGF and EGFR mRNA expressions were undetectable in bCSCs treated with B6H12 Ab (1 µg/ml) however control Ab (1 µg/ml) does not show any effect on bCSCs.

FIG. 14A) Unfractionated MDA-MB-231 cells were treated with B6H12 Ab (1 µg/ml) for 20 minutes and further stimulated with EGF (30 ng/ml) for 5 minutes. The cells were fixed immediately using PFA and immunostained with CD47 and EGFR antibody. The green fluorescence indicates protein expression of CD47 and red fluorescence shows protein expression of EGFR. FIG. 14B) bCSCs were pretreated with B6H12 Ab (1 µg/ml) for 15 minutes followed by EGF (30 ng/ml) for 5 minutes. The total lysates were made using NP-40 lysis buffer and immunoprecipitation was performed using phospho-Tyrosine antibody. Global tyrosine phosphorylation of proteins was analyzed by SDS-PAGE performed using Bis-Tris gels 4-12% and stained with Coomassie blue. FIG. 14C) Control MDA-MB-231 and bCSCs were treated with B6H12 (1 µg/ml) and EGF (5 ng/ml) as above, and IP-western blot was performed using phospho-EGFR antibodies. B6H12 Ab down regulated EGFR $Y^{1068}$ phosphorylation only in bCSCs. FIG. 14D) bCSCs were further sorted to isolate $CD44^{high}$ and $CD24^{low}$ cells using FACS. The IP-western blot of EGFR was performed using similar conditions as above. B6H12 Ab (1 µg/ml) treatment reduces EGFR $Y^{1068}$ phosphorylation.

FIGS. 15A & 15B) MCF7 and T47D1 cells were pretreated with B6H12 Ab (1 µg/ml) for 15 minutes followed by EGF (5 ng/ml) for 5 minutes. The total lysates were made using NP-40 lysis buffer and immunoprecipitation was performed using HER2 antibody. IP-western blots were performed using phospho-HER2 antibodies. FIGS. 15C & 15D) MCF7 and T47D1 cells were labeled with BrdU for 24 h. BrdU treated cells were further treated with B6H12 Ab (1 µg/ml) for 24 h. The BrdU incorporation was measured using a BrdU cell proliferation assay kit according to manufactures' instructions.

FIG. 16A-16F illustrate that B6H12-Ab decreases cell surface expression of EGFR via release of Exosomes and K63 Ubiquitination. FIGS. 16A, 16B and 16C) MCF7, T47D1 and bCSCs were pretreated with B6H12 Ab (1 µg/ml) for 15 minutes and immediately fixed with 4% PFA. Immunostaining of HER2 and EGFR was performed and images were captured using a Zeiss 780 microscope at 63×. FIG. 16D) B6H12-Ab Disrupts the Interaction between CD47 and EGFR in bCSCs. FIG. 16E) B6H12-Ab (1 µg/ml) blocks the release of Exosomes in T47D1 and MCF7 Cells but not in bCSCs. FIG. 16F) B6H12-Ab (1 µg/ml) disrupts the Interaction between CD47 and EGFR by Inducing K63 Ubiquitination of EGFR FIG. 17A-17C illustrate that B6H12 Ab signal may be independent of SIRP ligand. FIGS. 17A, 17B & 17C) B6H12-Ab (1 µg/ml) does not affect mRNA expression of SIRPα, β and γ in bCSCs FIG. 18A) MDA-MB-231 cells were cultured in complete RPMI media, and bCSCs were cultured with neural media containing EBM medium supplemented with FGF2 and EGF (~5-20 ng/ml), heparin and gentamycin sulfate for 36 h. The total RNA was extracted and global Microarray was performed. The differential gene expression of neural linage cancer cells were compared to MDA-MB-231 derived differentiated and cancer stem cells. FIG. 18B) Gene enrichment analysis (GSEA) of differentiated neural lineage MDA-MB231 cells with parental MDA-MB-231 cells and seeder cells (MDA-231-S1a and S1b). FIGS. 18C & 18D) GSEA of mammospheres and EMT formation.

FIG. 19A) Gene enrichment analysis (GSEA) of B6H12 antibody treated cells vs. differentiated neural lineage MDA-MB-231 cells and parental MDA-MB-231 cells. FIG. 19B) Principal component analysis of B6H12 treated cells.

FIG. 20A) B6H12 antibody Inhibits Cell Proliferation in $CD44^+CD24$ breast cancer stem cells (bCSCs) isolated from the triple negative breast cancer MDA-MB-231 cell line.

FIG. 20B) B6H12-Ab inhibits cell proliferation of T47D1 breast carcinoma cells, and bCSCs derived from parental T47D1 cells. FIGS. 20C & 20D) B6H12-Ab does not inhibit cell proliferation of normal mammary epithelial cells (MCF10A) or the ER+ breast carcinoma cell line MCF7 cells.

FIG. 21B) A2058 (Human Melanoma cancer cell line) was treated with B6H12 Ab (1 µg/ml) in the presence or absence of EGF (30 ng/ml) for 48 h. A2058 cells were labeled with BrdU for 4 h, and BrdU incorporation was measured using a BrdU cell proliferation assay kit according to manufacturer's instructions. FIG. 21C) SW480 (human colon adenocarcinoma cell line) and SW620 (colon carcinoma; derived from metastatic site) was treated with B6H12 Ab (1 µg/ml) for 48 h. SW480 and 620 cell lines were labeled and BrdU incorporation is measured using above indicated method (FIG. 21B). FIG. 21D) SW480 and 620 cells were plated overnight using L-15 media. After 24 h, cells were pretreated with B6H12 Ab (1 µg/ml) for 15 minutes followed by EGF (5 ng/ml) for 5 minutes. The total lysates were made using NP-40 lysis buffer and immunoprecipitation was performed using EGF antibody. IP-western blots were performed using phospho-EGFR Y1068 antibody. B6H12-Ab does not inhibit cell proliferation of SW480 and SW602 cells. B6H12-Ab inhibits EGFR phosphorylation only in SW620 cells but not in SW480.

FIG. 24A-24F illustrates characterization of breast cancer stem cells (bCSCs) derived from suspension cell-enriched MDA-MB-231 triple negative breast carcinoma cells. (FIG. 1A) Routinely cultured MDA-MB-231 cells. Inset showing loosely attached small round cells. (FIG. 1B) With gentle agitation, loosely bound bCSCs were separated from adherent MDA-MB-231 cells. (FIG. 24a) bCSCs form loose aggregates after incubation at 37° C. for 10 days. (FIG. 6A, 6B) Cell surface protein expression of CD44 and CD24 determined by flow, (FIG. 24B, FIG. 24C) Replated bCSCs have higher CD44 and lower CD24 mRNA expression than control MDA-MB-231 cells. Real time Ct values for the indicated genes and reference B2M are listed. (FIG. 7A) Hierarchical clustering of differentially expressed genes based on microarray analysis of MDA-MB-231 bCSCs versus unfractionated MDA-MB-231 cells. (FIG. 24D) Top differentially expressed genes between MDA-MB-231 and bCSCs. (FIG. 24E) Representative image showing asymmetric division of BrdU-labeled MDA-MB-231 bCSCs after chasing with unlabeled BrdU and counterstaining with DAPI. (FIG. 24F) Microscopic quantification of asymmetric cell division ratios for bCSCs and differentiated MDA-MB-231 cells (*p<0.05).

FIG. 25A-25G is a series of bar graphs showing the relative level of expression of the noted proteins between differentiated and bCSCs. FIG. 25A-25C shows relative expression of CD47, c-MYC and TSP1 in Differentiated and bCSCs isolated from the MDA-MB-231 cell line. FIG. 25D-25G show relative Expression of OCT4, NANOG, SOX2 and NESTIN in Differentiated and bCSCs.

FIGS. 9A & 9B) MDA-MB-231 and bCSCs were treated in the presence or absence of 1 μg/ml of B6H12 for 72 h. The images of live cells were captured using an Olympus microscope at 20× and 4×. (FIG. 26A). bCSCs were treated with control or 1 μg/ml of B6H12 for 10 days using cancer stem cell media form aggregates. FIGS. 26B & 26C are graphs showing quantification of mammosphere size FIG. 27A-27G illustrates that B6H12 alters gene expression of bCSCs. FIG. 10A) Hierarchical clustering of microarray data comparing bCSCs treated with control IgG or B6H12 for 36 h. FIG. 27A) List of top differentially expressed genes between control antibody and B6H12 treatments. Principal component analysis of parental MDA-MB-231, bCSCs, neural differentiated bCSCs, bCSCs treated with anti-CD47 B6H12 and control IgG is shown in FIG. 19B. FIG. 27B-27G are a series of graphs showing Real time PCR validation of differentially expressed genes between bCSCs treated with control IgG or B6H12 for 36 h.

(FIG. 28A & FIG. 28B) EGF and EGFR mRNA expressions were undetectable in bCSCs treated with B6H12 Ab however control Ab does not show any effect on bCSCs for 3 days. (FIG. 28C & FIG. 28D) The differentiated and bCSCs cells were treated with B6H12 Ab for 24 h. The total miRNA was extracted and let-7 family miRNAs were analyzed using real time PCR. Relative expression of let-7a-2miRNA in differentiated and bCSCs cells was determined using U6 as control. (FIG. 28E) EGFR mRNA expression on EVs derived from MDA-MB-231, bCSCs, T47D1 and MCF7 cells. The cells were treated with control or B6H12 antibody for 6 h using AB serum media. (FIG. 28F) Protein expression of EGFR in the presence or absence of B6H12 for 24 h using FACS sorted CD44+/CD24-bCSCs from MDA-MB-231, T47D1 and MCF7 cell lines. FIG. 28G) Relative expression of let-7a-2miRNA from EVs. FIG. 28H) Amplification and expression of let-7a-3 miRNA from EV (I don't see a FIG. 28H).

FIG. 14A is an image of a blot, illustrating that B6H12 does not inhibit EGHFR$^{Y992}$ B6H12. FIGS. 30A & 30B are graphs showing quantification of EGFRY1068 using Image J program with respect to total Tubulin and EGFR control. (n=2)

FIG. 31A) EGFR-Immunoprecipitation followed by western blotting shows that B6H12 treatment for 15 min disrupts the association between EGFR and CD47 and inhibits EGFRY1068 phosphorylation. FIG. 31B) CD47-immunoprecipitation showed that small fraction of EGFR co-immunoprecipitates with EGFR. B6H12 treatment for 15 min leads to further reduced interaction between CD47 and EGFR in MDA-MB-231 cells. FIGS. 31C & 31D) MDA-MB-231 were pretreated with B6H12 for 15 minutes followed by EGF for 5 minutes, and IP-western blot was performed using phospho-EGFR antibody (FIG. 31D) quantification and t-test used for spastically significant value. FIG. 31E) Differentiated and bCSCs were separated EGFR Immunoprecipitation was performed using FIG. 31A conditions. One representative of 3 independent experiments is shown (FIG. 31D). FIG. 31F) IP-western blot of EGFR was performed using CD44$^{high}$ and CD24$^{low}$ sorted cells under similar conditions as above.

FIG. 32A) The B6H12-Ab and control antibody treated cells were immunostained using BrdU antibody (Red) and mounted with Vectashield DAPI at 63×, and the asymmetric cell division ratio was calculated (*p<0.05). FIG. 32B) MDA-MB-231 and bCSCs cells were treated with B6H12 or isotype control antibody for 24 h and immunostained using KLF4 antibody. Total mean intensity of KLF4 positive cells was calculated, and t-test was performed. FIG. 32C) Flow cytometry analysis of KLF4. FIG. 32D) Quantification of BrdU staining using MFI of BrdU positive cells. FIG. 32E) CD44$^{high}$/CD24$^{low}$ sorted bCSCs derived from MDA-MB-231 were labeled with BrdU for 24 h and further treated with B6H12 (1 μg/ml) for 24 h. BrdU incorporation was measured using a BrdU cell proliferation assay kit. FIG. 32F) Flow cytometry analysis of caspase 7. FIG. 32G) B6H12 increases caspase 7 expression in MDA-MB-231 cells.

FIG. 34A and FIG. 34B). MDAMB-231 cells and bCSCs were plated on LabTek 8 well chamber slides using medium containing 2% FBS for 24 h at 37° C. The cells were pre-treated with B6H12 for 24 h. The cells were immunostained with KLF4 antibody, and images were captured using a Zeiss 710 confocal microscope. FIG. 34C) Total intensity of KLF4 positive cells was calculated and t-test was performed.

(FIG. 35A) MCF10A (FIG. 35B) MCF7 (FIG. 35C) T47D1 and (FIG. 35D) bCSCs sorted for CD44$^{high}$/CD24$^{low}$ sorted bCSCs derived from T47D1 FIG. 35C). The cells were labeled with BrdU for 24 hours. BrdU treated cells were further treated with B6H12 Ab (1 μg/ml) for 24 h. The BrdU incorporation was measured using a BrdU cell proliferation assay kit. (FIG. 35E) MDA-MB-231 cells have a higher percentage of CD44$^{high}$/CD24$^{low}$ cells than MCF7 and T47D1 cells.

FIG. 36A-36E is a series of images illustrating: FIG. 36A is a chart of TCGA Kaplan-Meier survival curves for breast invasive carcinoma patients comparing those with CD47 mRNA expression determined by RNAseq>1 SD higher than the mean (16% of cases, lower line) and those without increased CD47 expression (upper line). FIG. 36B-36E are series of plots showing TCGA expression data for the indicated proteins in breast tumors determined by reverse phase protein arrays (RPPA) stratified by CD47 mRNA expression. Caspase 7 activation was detected using an antibody specific for the $D^{198}$ cleavage. P-values in panels FIG. 36B-36E were based on 2-sided 2 sample t-tests.

FIG. 37A) Reverse phase protein array for breast invasive carcinomas comparing cKit protein expression in those with CD47 mRNA expression determined by RNAseq>1 SD higher than the mean (16% of cases, altered) and those without increased CD47 expression (unaltered). FIG. 37B) TCGA expression data for PDK1 phosphorylation at serine-241 in breast tumors determined by reverse phase protein arrays (RPPA) stratified by CD47 mRNA expression. P-values in panels FIG. 37A-37B were based on 2-sided 2 sample t-tests. FIG. 37C) Scatter plot for TCGA data comparing PATZ1 mRNA expression and CD47 mRNA expression in beast carcinomas.

SEQUENCE LISTING

Figure 1A:
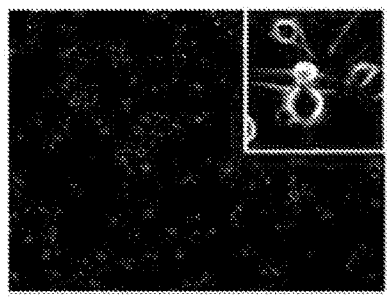
FIG. 1A-1E illustrates characterization of breast cancer stem cells (bCSCs) derived from suspension cell-enriched MDA-MB-231 triple negative breast carcinoma cells. FIG.
Figure 1B:
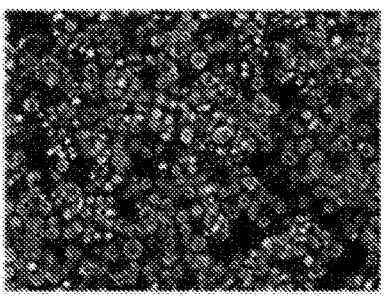
Figure 1C:
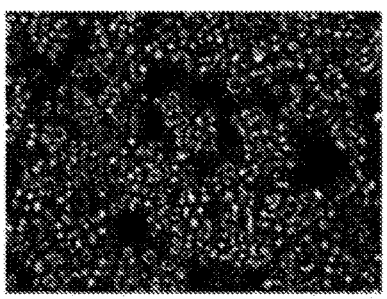
Figure 1D:
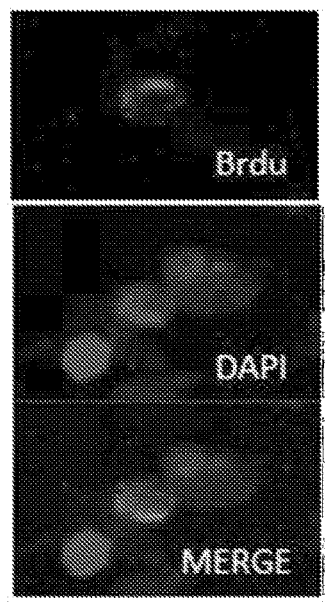
Figure 1E:
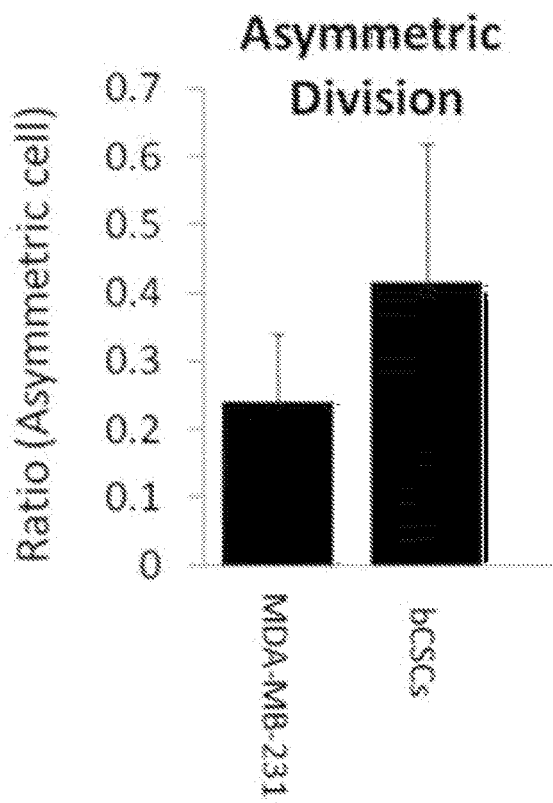

The nucleic and amino acid sequences listed in the accompanying sequence listing are shown using standard letter abbreviations for nucleic acid bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Apr. 4, 2017, 9.55 KB, which is incorporated by reference herein.

SEQ ID NO: 1 is the peptide p7N3 (FIRVVMYEGKK).

SEQ ID NO: 2 is gRNA PC200.Hcd47.g3a (CTACT-GAAGTATACGTAAG ngg), a targeting sequence for CRISPR knockout of CD47.

SEQ ID NOs: 3-52 are primers used as controls to normalize mRNA expression.

SEQ ID NOs: 53-69 are additional targeting sequences for CRISPR knockout of CD47.

DETAILED DESCRIPTION

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Animal: Living multi-cellular vertebrate organisms, a category that includes, for example, mammals and birds. The term mammal includes both human and non-human mammals. Similarly, the term subject includes both human and veterinary subjects, for example, humans, non-human primates, rodents, dogs, cats, horses, and cows.

Alters CD47 signaling: CD47 is a cell surface receptor that can impact cellular signal transduction through several known and undefined mechanisms, and consequently CD47 signaling can be altered through several signal transduction pathways. One mechanism involves the lateral association of CD47 with other well characterized signaling receptors belonging to the integrin family, with CD14, with VEGF receptor-2, or with Fas. Agents that decrease the expression of CD47 and pharmacological agents that directly bind to CD47 or inhibit the binding of thrombospondin-1 (TSP1) or SIRPs to CD47 may disrupt the association of CD47 with these receptors and/or induce conformation changes in the respective receptors that activate or inactivate their signaling. In addition, CD47 associates with cytoplasmic proteins including PLIC1, BNIP3, and some heterotrimeric G proteins.

Agents that change the expression of CD47 or the binding of natural or pharmacological ligands to CD47 can also alter CD47 signaling. The specific pathways involved are cell type-specific and depend on which CD47 binding partners are expressed in a given cell. These upstream perturbations of CD47 signaling lead to cell-specific alterations in cyclic nucleotide signaling, calcium signaling, and patterns of gene expression. One of the ultimate effects of altering CD47 signaling is regulation of stem cell self-renewal. In non-transformed differentiated cells, blocking CD47 signaling increases their self-renewal and stem cell characteristics (see, e.g., International Patent Publication No. WO 2013/155109, incorporated herein by reference), whereas in cancer cell lines or isolated cancer stem cells (as described herein) blockade decreases their stem cell markers and results in differentiation.

Altered expression: Expression of a biological molecule (for example, mRNA or protein) in a subject or biological sample from a subject that deviates from expression if the same biological molecule in a subject or biological sample from a subject having normal or unaltered characteristics for the biological condition associated with the molecule. Normal expression can be found in a control, a standard for a population, etc. Altered expression of a biological molecule may be associated with a disease. The term associated with, in this context, includes an increased risk of developing the disease as well as the disease itself. Expression may be altered in such a manner as to be increased or decreased. The directed alteration in expression of mRNA or protein may be associated with therapeutic benefits.

Altered protein expression refers to expression of a protein that is in some manner different from expression of the protein in a normal (wild type) situation. This includes but is not necessarily limited to any one or more of: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of an decreased amount of the protein, compared to a control or standard amount; (6) alteration of the sub-cellular localization or targeting of the protein; (7) alteration of the temporally regulated expression of the protein (such that the protein is expressed when it normally would not be, or alternatively is not expressed when it normally would be); and (8) alteration of the localized (for example, organ or tissue specific) expression of the protein (such that the protein is not expressed where it would normally be expressed or is expressed where it normally would not be expressed), each compared to a control or standard.

Controls or standards appropriate for comparison to a sample, for the determination of altered expression, include samples believed to express normally as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (The Science and Practice of Pharmacology, 19th Edition (1995), chapter 28). A derivative is a biologically active molecule derived from the base structure. A mimetic is a molecule that mimics the activity of another molecule, such as a biologically active molecule. Biologically active molecules can include chemical structures that mimic the biological activities of a compound. It is acknowledged that these terms may overlap in some circumstances.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce F(ab)'$_2$, a dimer of Fab which itself is a light chain joined to $V_H$-$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, Fundamental Immunology, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (Antibodies, *A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antisense, Sense, and Antigene: Double-stranded DNA (dsDNA) has two strands, a 5'→3' strand, referred to as the plus strand, and a 3'→5' strand (the reverse complement), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or plus strand DNA. Sense molecules are molecules that are specifically hybridizable or specifically complementary to the minus strand of DNA. Antigene molecules are either antisense or sense molecules complimentary to a dsDNA target. In one embodiment, an antisense molecule specifically hybridizes to a target mRNA and inhibits transcription of the target mRNA.

Aptamer: A single-stranded nucleic acid molecule (such as DNA or RNA) that assumes a specific, sequence-dependent shape and binds to a target protein with high affinity and specificity. Aptamers generally comprise fewer than 100 nucleotides, fewer than 75 nucleotides, or fewer than 50 nucleotides. Mirror-image aptamer(s) (also called Spiegelmers™) are high-affinity L-enantiomeric nucleic acids (for example, L-ribose or L-2'-deoxyribose units) that display high resistance to enzymatic degradation compared with D-oligonucleotides (such as aptamers). The target binding properties of mirror-image aptamers are designed by an in vitro-selection process starting from a random pool of oligonucleotides, as described for example, in Wlotzka et al., *Proc. Natl. Acad. Sci.* 99(13):8898-8902, 2002. Applying this method, high affinity mirror-image aptamers specific for a polypeptide can be generated.

Binding affinity: A term that refers to the strength of binding of one molecule to another at a site on the molecule. If a particular molecule will bind to or specifically associate with another particular molecule, these two molecules are said to exhibit binding affinity for each other. Binding affinity is related to the association constant and dissociation constant for a pair of molecules, but it is not critical to the methods herein that these constants be measured or determined. Rather, affinities as used herein to describe interactions between molecules of the described methods are generally apparent affinities (unless otherwise specified) observed in empirical studies, which can be used to compare the relative strength with which one molecule (e.g., an antibody or other specific binding partner) will bind two other molecules (e.g., two versions or variants of a peptide). The concepts of binding affinity, association constant, and dissociation constant are well known.

Binding domain: The molecular structure associated with that portion of a receptor that binds ligand. More particularly, the binding domain may refer to a polypeptide, natural or synthetic, or nucleic acid encoding such a polypeptide, the amino acid sequence of which represents a specific region (binding domain) of a protein, which either alone or in combination with other domains, exhibits binding characteristics. Neither the specific sequences nor the specific boundaries of such domains are critical, so long as binding activity is exhibited. Likewise, used in this context, binding characteristics necessarily includes a range of affinities, avidities and specificities, and combinations thereof, so long as binding activity is exhibited.

Binding partner: Any molecule or composition capable of recognizing and binding to a specific structural aspect of another molecule or composition. Examples of such binding partners and corresponding molecule or composition include antigen/antibody, hapten/antibody, lectin/carbohydrate, apoprotein/cofactor and biotin/(strept)avidin.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Breast carcinomas lose the typical histology and architecture of normal breast glands. Generally, carcinoma cells overgrow the normal cells and lose their ability to differentiate into glandular like structures. The degree of loss of differentiation in general is related to the aggressiveness of the tumor. For example, "in situ" carcinoma by definition retains the basement membrane intact, whereas as it progresses to "invasive", the tumor shows breakout of basement membranes. Thus one would not expect to see, within breast carcinomas, staining of a discrete layer of basal cells as seen in normal breast tissue. For a discussion of the physiology and histology of normal breast and breast carcinoma, see Ronnov-Jessen (*Physiol Rev* 76, 69-125, 1996).

Breast cancers can be divided into groups based on their expression profiles. Basal-type carcinomas usually are negative for expression of estrogen receptor (ER) and negative for expression of HER2 (erbB2) and progesterone receptor (PR), and thus are referred to as "triple-negative breast cancers" or "TNBC." This type of breast cancer is also denoted $ER^-/HER2^-/PR^-$ and represents about 15-20% of all breast cancer, and generally cannot be treated using Her2 targeted or estrogen targeted therapies. It is believed that the aggressive nature of this cancer is correlated with an enrichment for cancer stem cells (CSC) with a $CD44^+CD24^{-/lo}$ phenotype. In some embodiments, basal carcinomas are negative for expression of progesterone receptor (PR), positive for expression of epidermal growth factor receptor (EGFR), and positive for expression of cytokeratin 5 (CK5). This phenotype is denoted as follows: $ER^-/PR^-/HER2^-/CK5^+/EGFR^+$.

A breast cancer sample is a sample that includes tissue or cells from a breast tumor. In some examples, a breast cancer sample is a breast tumor biopsy, lymph node tissue from a subject with breast cancer, or a metastasis from a breast tumor.

Cancer: A malignant neoplasm that has undergone characteristic anaplasia with loss of differentiation, increase rate of growth, invasion of surrounding tissue, and is capable of metastasis. For example, thyroid cancer is a malignant neoplasm that arises in or from thyroid tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived. Cancer includes, but is not limited to, solid tumors.

Cancer Stem Cells (CSCs): The cancer stem cell hypothesis suggests that tumors contain a small subpopulation of cells which are exclusively responsible for cancer initiation and maintenance and contribute to therapeutic failure, called cancer stem cells (CSC). Although, CSC were first identified in hematologic malignancies, recent studies have suggested the presence of CSC in solid tumors of various organs including breast, brain, pancreas, colon, and liver. CSC have been identified using non-specific markers such as CD133, CD24, CD44, CD90, although these markers are present on other cells. The ability to efflux the Hoechst dye, defined as the "side-population," has also been used to identify CSC. Collectively, these methods resulted in heterogenic populations enriched with putative CSC. However, cells identified using these methods generally were not able to initiate tumors with less than 100 cells. Cancer cells found within solid tumors or hematological cancers that possess characteristics associated with normal stem cells, specifically the ability to give rise to all cell types found in a particular cancer, and also have the ability to self-renew. Cancer stem cells are tumorigenic (tumor-forming). CSCs can generate tumors through the stem cell processes of self-renewal and differentiation into multiple cell types. Such cells are proposed to persist in tumors as a distinct population and cause relapse and metastasis by giving rise to new tumors at distant sites. CSCs have recently been identified in several solid tumors, including cancers of the brain, breast, colon, ovary, pancreas and prostate, as well as in hematologic cancers. A standard for testing CSC is xenogeneic transplantation into immunosuppressed mice. It tests CSC capacity to initiate tumors in a non-human-environment.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from messenger RNA extracted from cells.

Cell Culture: Cell culture or culturing cells refers to placing cells in a dish, flask, or other container with an appropriate medium (such as a growth medium or differentiation medium) for the type of cells utilized (such as a medium including glucose, essential amino acids, vitamins, trace elements, salts, a buffer to maintain pH, and/or other components for particular applications).

Chemotherapy; chemotherapeutic agents: As used herein, these terms include any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating neoplasms such as solid tumors. In one embodiment, a chemotherapeutic agent is radioactive molecule. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., © 2000 Churchill Livingstone, Inc.; Baltzer L., Berkery R. (eds): Oncology Pocket Guide to Chemotherapy, 2nd ed. St. Louis, Mosby-Year Book, 1995; Fischer D S, Knobf M F, Durivage H J (eds): *The Cancer Chemotherapy Handbook,* 4th ed. St. Louis, Mosby-Year Book, 1993). Chemotherapeutic agents include those known by those skilled in the art, including but not limited to: 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol. Rapamycin has also been used as a chemotherapeutic. Additional chemotherapeutic agents are described herein, and are known in the art.

Colon cancer: Colorectal cancer, also called large bowel cancer, includes cancerous growths in the colon, rectum and appendix. With 655,000 deaths worldwide per year, it is the third most common form of cancer and the second leading cause of cancer-related death in the Western world. Many colorectal cancers are thought to arise from adenomatous polyps in the colon. These mushroom-like growths are usually benign, but some may develop into cancer over time. The majority of the time, the diagnosis of localized colon cancer is through colonoscopy. Therapy is usually through surgery, which in many cases is followed by chemotherapy. The first symptoms of colon cancer are usually vague, such as bleeding, weight loss, and fatigue (tiredness). Local (bowel) symptoms are rare until the tumor has grown to a large size. Generally, the nearer the tumor is to the anus, the more bowel symptoms there will be.

Control or control sample: Samples believed to be normal (in that they are not altered for the desired characteristic, for example non-tumor cell or tissue) as well as laboratory values, even though possibly arbitrarily set, keeping in mind that such values can vary from laboratory to laboratory. In one example, a control sample is non-tumor cell or tissue from an individual without a particular cancer, such as without breast cancer. In another example, a control sample is non-tumor cell or tissue from an individual with cancer.

Conjugated (Linked): Two entities are conjugated when under physiological conditions of pH, ionic strength and osmotic potential, the majority of the entities are associated with each other at equilibrium, such as due to the presence of a covalent bond. Covalent linkage may be by any of a variety of chemical linking and cross-linking agents including, for example, homobifunctional or heterobifunctional crosslinking reagents, many of which are commercially available (see, e.g., Pierce Chemical Co. or Sigma Chemical Co.). Linking or crosslinking can be achieved by any of a variety of chemistries well known in the art including, for example, activated polyethylene glycols, aldehydes, isocyanates, maleimides and the like. Linking or cross-linking can also be achieved using physical methods, such as irradiation, for example gamma irradiation or ultraviolet (UV) irradiation.

DNA (deoxyribonucleic acid): A long chain polymer that comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA (which may be as short as a single nucleotide), the regions on either side being joined together.

Encode: A polynucleotide is said to encode a polypeptide if, in its native state or when manipulated by methods known to those skilled in the art, it can be transcribed and/or translated to produce the mRNA for and/or the polypeptide or a fragment thereof.

Epitope: An antigenic determinant. These are particular chemical groups or peptide sequences on a molecule that are antigenic, for instance, that elicit a specific immune response. An antibody binds a particular antigenic epitope, based on a 3D structure of the antibody and the matching or cognate epitope. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion," or "expanded." Typically, during an expansion phase, the cells do not differentiate to form mature cells, but divide to form more cells.

Fluorescence Activated Cell Sorting (FACS): A technique for counting, examining and separating microscopic particles, such as cells and chromosomes, by suspending them in a stream of fluid and passing them by an electronic detection apparatus. It allows simultaneous multiparametric analysis of the physical and/or chemical characteristics of up to thousands of particles per second. Flow cytometry is routinely used in the diagnosis of cancer and the isolation of populations of lymphocytes, but has many other applications in both research and clinical practice.

A beam of light (usually laser light) of a single wavelength is directed onto a hydrodynamically-focused stream of fluid. A number of detectors are aimed at the point where the stream passes through the light beam: one in line with the light beam (Forward Scatter or FSC) and several perpendicular to it (Side Scatter (SSC) and one or more fluorescent detectors). Each suspended particle from 0.2 to 150 micrometers passing through the beam scatters the light in some way, and fluorescent chemicals found in the particle or attached to the particle may be excited into emitting light at a longer wavelength than the light source. This combination of scattered and fluorescent light is picked up by the detectors, and, by analyzing fluctuations in brightness at each detector (one for each fluorescent emission peak), it is then possible to derive various types of information about the physical and chemical structure of each individual particle.

A flow cytometer generally has several main components: (1) a flow cell—liquid stream (sheath fluid), which carries and aligns the cells so that they pass single file through the light beam for sensing; (2) a measuring system, such as those that allow measurement of impedance (or conductivity) and optical systems—lamps (mercury, xenon); high-power water-cooled lasers (argon, krypton, dye laser); low-power air-cooled lasers (argon (488 nm), red-HeNe (633 nm), green-HeNe, HeCd (UV)); diode lasers (blue, green, red, violet) resulting in light signals; (3) a detector and Analogue-to-Digital Conversion (ADC) system which generates FSC and SSC as well as fluorescence signals from light into electrical signals that can be processed by a computer; (4) an amplification system (either linear or logarithmic); and (5) a computer for analysis of the signals. FACS instruments usually have multiple lasers and fluorescence detectors (such as up to 4 lasers and 18 fluorescence detectors). Increasing the number of lasers and detectors allows for multiple antibody labeling, and can more precisely identify a target population by their phenotypic markers.

Using fluorescent activated cell sorting (FACS), a heterogeneous mixture of biological cells can be separated into two or more containers, one cell at a time, based upon the specific light scattering and fluorescent characteristics of each cell. The cell suspension is entrained in the center of a narrow, rapidly flowing stream of liquid. The flow is arranged so that there is a large separation between cells relative to their diameter. A vibrating mechanism causes the stream of cells to break into individual droplets. The system is adjusted so that there is a low probability of more than one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately-prior fluorescence intensity measurement, and the opposite charge is trapped on the droplet as it breaks from the stream. The charged droplets then fall through an electrostatic deflection system that diverts droplets into containers based upon their charge. In some systems, the charge is applied directly to the stream, and the droplet breaking off retains a charge of the same sign as the stream. The stream is then returned to neutral after the droplet breaks off. FACS can be used to identify and isolate cancer stem cells, as described herein.

Gating: The data generated by FACS can be plotted in a single dimension, to produce a histogram, or in two-dimensional dot plots or even in three dimensions. The regions on these plots can be sequentially separated, based on fluorescence intensity, by creating a series of subset extractions, termed "gates." Specific gating protocols exist for diagnostic and clinical purposes especially in relation to hematology and the identification of stem cells.

The plots are often made on logarithmic scales. Because different fluorescent dyes' emission spectra overlap, signals at the detectors have to be compensated electronically as well as computationally. Data accumulated using the flow cytometer can be analyzed using software, e.g., FLOJO™, or CELLQUEST PRO™.

Gene expression: The process by which the coded information of a nucleic acid transcriptional unit (including, for example, genomic DNA or cDNA) is converted into an operational, non-operational, or structural part of a cell, often including the synthesis of a protein. Gene expression can be influenced by external signals; for instance, exposure of a subject to an agent that inhibits gene expression. Expression of a gene also may be regulated anywhere in the pathway from DNA to RNA to protein. Regulation of gene expression occurs, for instance, through controls acting on transcription, translation, RNA transport and processing, degradation of intermediary molecules such as mRNA, or through activation, inactivation, compartmentalization or degradation of specific protein molecules after they have been made, or by combinations thereof. Gene expression may be measured at the RNA level or the protein level and by any method known in the art, including Northern blot, RT-PCR, Western blot, or in vitro, in situ, or in vivo protein activity assay(s).

The expression of a nucleic acid may be modulated compared to a control state, such as at a control time (for example, prior to administration of a substance or agent that affects regulation of the nucleic acid under observation) or in a control cell or subject, or as compared to another nucleic acid. Such modulation includes but is not necessarily limited to overexpression, underexpression, or suppression of expression. In addition, it is understood that modulation of nucleic acid expression may be associated with, and in fact may result in, a modulation in the expression of an encoded protein or even a protein that is not encoded by that nucleic acid.

Interfering with or inhibiting gene expression refers to the ability of an agent to measurably reduce the expression of a target gene. Expression of a target gene may be measured by any method known to those of ordinary skill in the art, including for example measuring mRNA or protein levels. It is understood that interfering with or inhibiting gene expression is relative, and does not require absolute suppression of the gene. Thus, in certain embodiments, interfering with or inhibiting gene expression of a target gene requires that, following application of an agent, the gene is expressed at least 5% less than prior to application, at least 10% less, at least 15% less, at least 20% less, at least 25% less, or even more reduced. Thus, in some particular embodiments, application of an agent reduces expression of the target gene by about 30%, about 40%, about 50%, about 60%, or more. In specific examples, where the agent is particularly effective, expression is reduced by 70%, 80%, 85%, 90%, 95%, or even more. Gene expression is substantially eliminated when expression of the gene is reduced by 90%, 95%, 98%, 99% or even 100%.

Growth factor: A substance that promotes cell growth, survival, and/or differentiation. Growth factors include molecules that function as growth stimulators (mitogens), factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are a fibroblast growth factor (such as FGF-2), epidermal growth factor (EGF), cilliary neurotrophic factor (CNTF), nerve growth factor (NGF), activin-A, and insulin.

Heterologous: A type of sequence (nucleic acid or protein) that is not normally (for example, in the wild-type sequence) found adjacent to a second sequence. In one embodiment, the sequence is from a different genetic source, such as a virus or other organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Inhibiting protein activity: To decrease, limit, or block an action, function, association, or expression of a protein. The phrase "inhibit protein activity" is not intended to be an absolute term. Instead, the phrase is intended to convey a wide range of inhibitory effects that various agents may have on the normal (for example, uninhibited or control) protein activity. Inhibition of protein activity may, but need not, result in a change (increase or decrease) in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

A signaling protein (such as CD47) may control several activities in parallel, and inhibition may occur when one or more downstream indicators is altered while downstream indicators of other signaling responses controlled by the same protein remain unchanged. Conversely, a given inhibitor may alter additional downstream indicators that are irrelevant to a specific application of that protein inhibitor.

Inhibition of protein activity may also be effected, for example, by inhibiting expression of the gene encoding the protein or by decreasing the half-life of the mRNA encoding the protein.

Injectable composition: A pharmaceutically acceptable fluid composition comprising at least one active ingredient, for example, a protein, peptide, or antibody. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Isolated: An isolated biological component (such as a nucleic acid, peptide or protein) has been substantially separated, produced apart from, or purified away from other biological components in the cell of the organism in which the component naturally occurs, for instance, other chromosomal and extrachromosomal DNA and RNA, and proteins. Nucleic acids, peptides and proteins that have been isolated thus include nucleic acids and proteins purified by standard purification methods. The term also embraces nucleic acids, peptides and proteins prepared by recombinant expression in a host cell as well as chemically synthesized nucleic acids. The terms isolated and purified do not require absolute purity; rather, it is intended as a relative term. Thus, for example, an isolated peptide preparation is one in which the peptide or protein is more enriched than the peptide or protein is in its natural environment within a cell. In certain embodiments, a preparation is purified such that the protein or peptide represents at least 50% of the total peptide or protein content of the preparation.

Label: An agent capable of detection, for example by ELISA, spectrophotometry, flow cytometry, or microscopy. In some instances, the detectable compound or composition is conjugated directly or indirectly to another molecule to facilitate detection of that molecule. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, fluorescent tags, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (*In Current Protocols in Molecular Biology*, John Wiley & Sons, New York, 1998).

Lung cancer: The main type of lung cancer is carcinoma of the lung, which includes small cell lung carcinoma and non-small cell lung carcinoma. Non-small cell lung carcinoma (NSCLC) is sometimes treated with surgery, while small cell lung carcinoma (SCLC) usually responds to chemotherapy and radiation. The most common cause of lung cancer is long-term exposure to tobacco smoke.

The non-small cell lung carcinomas are grouped together because their prognosis and management are similar. There are three main sub-types: squamous cell lung carcinoma, adenocarcinoma, and large cell lung carcinoma. Squamous cell lung carcinoma usually starts near a central bronchus. Cavitation and necrosis within the center of the cancer is a common finding. Well-differentiated squamous cell lung cancers often grow more slowly than other cancer types. Adenocarcinoma accounts for 29.4% of lung cancers. It usually originates in peripheral lung tissue. Most cases of adenocarcinoma are associated with smoking; however, among people who have never smoked, adenocarcinoma is the most common form of lung cancer. A subtype of adenocarcinoma, the bronchioalveolar carcinoma, is more common in females.

Small cell lung cancers (SCLC, also called "oat cell carcinoma") is less common. It tends to arise in the larger airways (primary and secondary bronchi) and grows rapidly, becoming quite large. The "oat" cell contains dense neurosecretory granules (vesicles containing neuroendocrine hormones), which give this an endocrine/paraneoplastic syndrome association. While initially more sensitive to chemotherapy, it ultimately carries a worse prognosis and is often metastatic at presentation. Small cell lung cancers are divided into limited stage and extensive stage disease. This type of lung cancer also is strongly associated with smoking.

Lymphoma: A cancer that begins in the lymphocytes and presents as a solid tumor of lymphoid cells. Lymphomas are generally treatable with chemotherapy, and in some cases radiotherapy and/or bone marrow transplantation, and can be curable, depending on the histology, type, and stage of the disease. The WHO classification is a generally accepted system for the classification of lymphoma and is based upon the foundations laid within the "Revised European-American Lymphoma classification" (REAL). This system attempts to group lymphomas by cell type (i.e. the normal cell type that most resembles the tumor) and defining phenotypic, molecular or cytogenetic characteristics. There are three large groups of lymphoma: the B cell, T cell, and natural killer cell tumors. Hodgkin's lymphoma, although considered separately within the WHO classification, is now recognized as being a tumor of lymphocytes of the mature B cell lineage.

Lymphomas include mature B cell lymphomas such as chronic lymphocytic leukemia/Small lymphocytic lymphoma, B-cell prolymphocytic leukemia, lymphoplasmacytic lymphoma (such as Waldenström macroglobulinemia), splenic marginal zone lymphoma, plasma cell neoplasms: plasma cell myeloma, plasmacytoma, monoclonal immunoglobulin deposition diseases, heavy chain diseases extranodal marginal zone B cell lymphoma, nodal marginal zone B cell lymphoma (NMZL), follicular lymphoma, mantle cell lymphoma, diffuse large B cell lymphoma, mediastinal (thymic) large B cell lymphoma, intravascular large B cell lymphoma, primary effusion lymphoma, and Burkitt lymphoma/leukemia. Lymphomas also include mature T cell and natural killer cell neoplasms, such as T cell prolymphocytic leukemia, T cell large granular lymphocytic leukemia, aggressive NK cell leukemia, adult T cell leukemia/lymphoma, extranodal NK/T cell lymphoma (nasal type), enteropathy-type T cell lymphoma, hepatosplenic T cell lymphoma, blastic NK cell lymphoma, mycosis fungoides/Sezary syndrome, primary cutaneous CD30-positive T cell lymphoproliferative disorders, primary cutaneous anaplastic large cell lymphoma, lymphomatoid papulosis, angioimmunoblastic T cell lymphoma, peripheral T cell lymphoma, and anaplastic large cell lymphoma.

Modulator: An agent that increases or decreases (modulates) the activity of a protein or other bio-active compound, as measured by the change in an experimentally measured biological parameter. A modulator can be essentially any compound or mixture (for example, two or more proteins or a protein and another compound), such as an antibody molecule or other polypeptide, a hormone, a nucleic acid, a sugar, a lipid and the like.

Morpholino: A morpholino oligo is structurally different from natural nucleic acids, with morpholino rings replacing the ribose or deoxyribose sugar moieties and non-ionic phosphorodiamidate linkages replacing the anionic phosphates of DNA and RNA. Each morpholino ring suitably positions one of the standard bases (A, G, C, T/U), so that a 25-base morpholino oligo strongly and specifically binds to its complementary 25-base target site in a strand of RNA via Watson-Crick pairing. Because the backbone of the morpholino oligo is not recognized by cellular enzymes of signaling proteins, it is stable to nucleases and does not trigger an innate immune response through the toll-like receptors. This avoids loss of oligo, inflammation or interferon induction. Morpholinos can be delivered by a number of techniques, including direct injection to tissues or via infusion pump and intravenous bolus. A morpholino is one example of a stabilized nucleic acid molecule.

Neoplasm: An abnormal cellular proliferation, which includes benign and malignant tumors, as well as other proliferative disorders.

Non-viable cells: Cells that are in the process of dying or are dead. These cells do not divide. Non-viable cells include necrotic and apoptotic cells.

Nucleic acid molecule: A polymeric form of nucleotides, which may include both sense and antisense strands of RNA, cDNA, genomic DNA, and synthetic forms and mixed polymers thereof. A nucleotide refers to a ribonucleotide, deoxynucleotide or a modified form of either type of nucleotide. A nucleic acid molecule as used herein is synonymous with nucleic acid and polynucleotide. A nucleic acid molecule is usually at least 10 bases in length, unless otherwise specified. The term includes single- and double-stranded forms. A polynucleotide may include either or both naturally occurring and modified nucleotides linked together by naturally occurring and/or non-naturally occurring nucleotide linkages.

Nucleic acid molecules may be modified chemically or biochemically or may contain non-natural or derivatized nucleotide bases, as will be readily appreciated by those of ordinary skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and modified linkages (for example, alpha anomeric nucleic acids, etc.). The term nucleic acid molecule also includes any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless specified otherwise, the left hand end of a polynucleotide sequence written in the sense orientation is the 5' end and the right hand end of the sequence is the 3' end. In addition, the left hand direction of a polynucleotide sequence written in the sense orientation is referred to as the 5' direction, while the right hand direction of the polynucleotide sequence is referred to as the 3' direction. Further, unless otherwise indicated, each nucleotide sequence is set forth herein as a sequence of deoxyribonucleotides. It is intended, however, that the given sequence be interpreted as would be appropriate to the polynucleotide composition: for example, if the isolated nucleic acid is composed of RNA, the given sequence intends ribonucleotides, with uridine substituted for thymidine.

An antisense nucleic acid is a nucleic acid (such as, an RNA or DNA oligonucleotide) that has a sequence complementary to a second nucleic acid molecule (for example, an mRNA molecule). An antisense nucleic acid will specifically bind with high affinity to the second nucleic acid sequence. If the second nucleic acid sequence is an mRNA molecule, for example, the specific binding of an antisense nucleic acid to the mRNA molecule can prevent or reduce translation of the mRNA into the encoded protein or decrease the half-life of the mRNA, and thereby inhibit the expression of the encoded protein.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include stabilized oligonucleotides, such as peptide nucleic acid (PNA) molecules and morpholinos.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Ortholog: Two nucleic acid or amino acid sequences are orthologs of each other if they share a common ancestral sequence and diverged when a species carrying that ancestral sequence split into two species. Orthologous sequences are also homologous sequences.

Parenteral: Administered outside of the intestine, for example, not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., $21^{st}$ Edition (2005), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or drug: A chemical compound or composition capable of inducing a desired therapeutic or prophylactic effect when properly administered to a subject. Incubating includes exposing a target to an agent for a sufficient period of time for the agent to interact with a cell. Contacting includes incubating an agent in solid or in liquid form with a cell. Pharmaceutical agents include, but are not limited to, chemotherapeutic agents and anti-infective agents.

Polypeptide: A polymer in which the monomers are amino acid residues that are joined together through amide bonds. When the amino acids are alpha-amino acids, either the L-optical isomer or the D-optical isomer can be used, the L-isomers usually being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity are well known, and representative programs and algorithms can be found at the NCBI website.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates at least one sign or symptom of a disease or pathological condition, or interferes with a pathophysiological process after it has begun to develop. Treatment includes inhibiting or preventing the partial or full development or progression of a disease, for example in a person who is known to have a predisposition to a disease.

Primary cells: Cells directly obtained or isolated from tissue. Primary cells are not transformed and are not immortalized. These cells generally do not proliferate indefinitely when placed in cell culture unless they undergo spontaneous immortalization or malignant transformation. Primary cells obtained from a tissue may include a population of multiple cell types, including multiple types of differentiated cells, lineage-committed cells, and/or stem cells (such as adult stem cells, for example hematopoietic stem cells, mesenchymal stem cells, or neural stem cells). Primary cells obtained from a tissue may also include primarily a single cell type (or a single cell type may be isolated or selected from a population of primary cells), such as human umbilical vein endothelial cells (HUVEC).

Purified: In a more pure form than is found in nature. The term purified does not require absolute purity; rather, it is intended as a relative term. Thus, for example, a purified protein preparation is one in which the protein referred to is more pure than the protein in its natural environment within a cell.

The term substantially purified as used herein refers to a molecule (for example, a nucleic acid, polypeptide, oligonucleotide, etc.) that is substantially free of other proteins, lipids, carbohydrates, or other materials with which it is naturally associated. In one embodiment, a substantially purified molecule is a polypeptide that is at least 50% free of other proteins, lipids, carbohydrates, or other materials with which it is naturally associated. In another embodiment, the polypeptide is at least at least 80% free of other proteins, lipids, carbohydrates, or other materials with which it is naturally associated. In yet other embodiments, the polypeptide is at least 90% or at least 95% free of other proteins, lipids, carbohydrates, or other materials with which it is naturally associated.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques.

RNA interference (RNA silencing; RNAi): A gene-silencing mechanism whereby specific double-stranded RNA (dsRNA) trigger the degradation of homologous mRNA (also called target RNA). Double-stranded RNA is processed into small interfering RNAs (siRNA), which serve as a guide for cleavage of the homologous mRNA in the RNA-induced silencing complex (RISC). The remnants of the target RNA may then also act as siRNA; thus resulting in a cascade effect.

Senescence: The biological process(es) of aging and showing the effects of increased age. In one embodiment, a senescent cell does not divide and/or has a reduced capacity to divide.

Separating: In reference to the separation of a stem cell, such as a cancer stem cell, from other cells, such as a non-cancerous stem cell. More generally, the term refers to the purification of one cell type from another cell type, as used herein, refers to spatially segregating cells of the different cell types from each other so as to yield a fraction that is relatively enriched in a first cell type, with respect to a second cell type, and another fraction that is relatively enriched in a second cell type, with respect to a first cell type. In certain embodiments, cell types (e.g., cancer stem cells and/or progenitor cells and non-cancerous stem cells and/or progenitor cells) can be separated from each other such that the segregated fractions of the respective cell types are enriched in the desired cells by at least a factor of about 5, in some embodiments by at least a factor of about 10, in some embodiments by at least a factor of about 100, in some embodiments by at least a factor of about 1000, in some embodiments by at least a factor of about $10^4$, in some embodiments by at least a factor of about $10^5$, in some embodiments by at least a factor of about $10^6$, and in yet other embodiments the desired cells in the segregated fraction are free of cells of the undesired type.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.* 2: 482, 1981); Needleman and Wunsch (*J. Mol. Biol.* 48: 443, 1970); Pearson and Lipman (*PNAS. USA* 85: 2444, 1988); Higgins and Sharp (*Gene*, 73: 237-244, 1988); Higgins and Sharp (*CABIOS* 5: 151-153, 1989); Corpet et al. (*Nuc. Acids Res.* 16: 10881-10890, 1988); Huang et al. (*Comp. Appls Biosci.* 8: 155-165, 1992); and Pearson et al. (*Meth. Mol. Biol.* 24: 307-31, 1994). Altschul et al. (*Nature Genet.*, 6: 119-129, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., *J. Mol. Biol.* 215:403-410, 1990; Gish. & States, *Nature Genet.* 3:266-272, 1993; Madden et al. *Meth. Enzymol.* 266:131-141, 1996; Altschul et al., *Nucleic Acids Res.* 25:3389-3402, 1997; and Zhang & Madden, *Genome Res.* 7:649-656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (*In Molecular Cloning: A Laboratory Manual*, Cold Spring Harbor, N.Y., 1989) and Tijssen (*Laboratory Techniques in Biochemistry and Molecular Biology Part I, Ch.* 2, Elsevier, New York, 1993).

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na+ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference. The following is an exemplary set of hybridization conditions:

Very High Stringency (Detects Sequences that Share 90% Identity)
  Hybridization: 5×SSC at 65° C. for 16 hours
  Wash twice: 2×SSC at room temperature (RT) for 15 minutes each
  Wash twice: 0.5×SSC at 65° C. for 20 minutes each
High Stringency (Detects Sequences that Share 80% Identity or Greater)
  Hybridization: 5×-6×SSC at 65° C.-70° C. for 16-20 hours
  Wash twice: 2×SSC at RT for 5-20 minutes each
  Wash twice: 1×SSC at 55° C.-70° C. for 30 minutes each
Low Stringency (Detects Sequences that Share Greater than 50% Identity)
  Hybridization: 6×SSC at RT to 55° C. for 16-20 hours
  Wash at least twice: 2×-3×SSC at RT to 55° C. for 20-30 minutes each.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Specifically hybridizable and specifically complementary are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of 0- to about 5-nucleotides, wherein the sequence of the double stranded RNAs is essentially identical to a portion of a coding region of the target gene for which interference or inhibition of expression is desired. The double stranded RNAs can be formed from complementary ssRNAs or from a single stranded RNA that forms a hairpin or from expression from a DNA vector.

Small molecule inhibitor: A molecule, typically with a molecular weight less than 1000, or in some embodiments, less than about 500 Daltons, wherein the molecule is capable of inhibiting, to some measurable extent, an activity of some target molecule.

Stabilized nucleic acid molecules: A variety of synthetic nucleic acid derivatives with increased stability as compared to native (e.g., non-modified) nucleic acids. Stabilized nucleic acid molecules include nucleic acids where the labile phosphodiester bonds in nucleic acids are replaced with more stable phosphoramidates or peptide amide backbones, or oligonucleotides including one or more such nucleic acid derivatives. Also included are nucleic acids having a substitution of the deoxyribosyl moiety with a more stable morpholine derivative (e.g., morpholinos) or oligonucleotides including one or more morpholino nucleic acids. In other examples, stabilized nucleic acid molecules include "locked" nucleic acids where the ribose moiety is modified with a bridge connecting the 2' oxygen and the 4' carbon, or oligonucleotides including one or more locked nucleic acid.

Stem cell: A cell that can generate a fully differentiated functional cell of a more than one given cell type. The role of stem cells in vivo is to replace cells that are destroyed during the normal life of an animal. Generally, stem cells can divide asymmetrically without limit and may be lineage-committed, totipotent, or pluripotent. After division, the stem cell may remain as a stem cell, become a precursor cell, or proceed to terminal differentiation. A nervous system stem cell is, for example, a cell of the central nervous system that can self-renew and can generate astrocytes, neurons and oligodendrocytes.

A "somatic precursor cell" is a cell that can generate a fully differentiated functional cell of at least one given cell type from the body of an animal, such as a human. A neuronal precursor cell can generate of fully differentiated neuronal cell, such as, but not limited to, and adrenergic or a cholinergic neuron. A glial precursor cell can generate fully differentiated glial cells, such as but not limited to astrocytes, microglia and oligodendroglia. Generally, precursor cells can divide and are pluripotent. After division, a precursor cell can remain a precursor cell, or may proceed to terminal differentiation. A neuronal precursor cell can give rise to one or more types of neurons, such as dopaminergic, adrenergic, or serotonergic cells, but is more limited in its ability to differentiate than a stem cell. In one example, a neuronal stem cell gives rise to all of the types of neuronal cells (such as dopaminergic, adrenergic, and serotonergic neurons) but does not give rise to other cells, such as glial cells.

Suspension of cells; Cellular suspension: A mixture of cells suspended in a carrier liquid. The carrier liquid may be naturally part of the biological sample from which the cells derive, for example blood is a suspension of blood cells suspended in plasma, or, for cells which are not normally present in a suspension, the carrier liquid can be any suitable diluent or medium. A cellular suspension can include a plurality of stem cells of one or more specific and desired types, for example cancer stem cells, lympho-hematopoietic stem cells. For example, for such an embodiment in the context of cancer treatment, diagnostics, or research, the methods described herein can be used to generate cellular suspension including a plurality of cancer stem cells.

Target sequence: A target sequence is a portion of ssDNA, dsDNA, or RNA that, upon hybridization to a therapeutically effective oligonucleotide or oligonucleotide analog (e.g., a morpholino), results in the inhibition of expression of the target. Either an antisense or a sense molecule can be used to target a portion of dsDNA, as both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, oligonucleotide, or antibody) in blood (in vivo) or a buffer (in vitro) that produces an effect. The effective amount of the compound usually will be dependent on the compound applied, the subject being treated, the severity and type of the affliction, and the manner of administration of the compound.

Treating a disease: Includes inhibiting or preventing the partial or full development or progression of a disease, for example in a person who is known to have a predisposition to a disease. Furthermore, treating a disease refers to a therapeutic intervention that ameliorates at least one sign or symptom of a disease or pathological condition, or interferes with a pathophysiological process, after the disease or pathological condition has begun to develop.

Tumor: An abnormal growth of cells, which can be benign or malignant. Cancer is a malignant tumor, which is characterized by abnormal or uncontrolled cell growth. Other features often associated with malignancy include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Tumors of the same tissue type may be divided into tumor of different sub-types (a classic example being bronchogenic carcinomas (lung tumors) which can be an adenocarcinoma, small cell, squamous cell, or large cell tumor). Breast cancers can be divided histologically into scirrhous, infiltrative, papillary, ductal, medullary and lobular.

Tumors include original (primary) tumors, recurrent tumors, and metastases (secondary) tumors. A tumor recurrence is the return of a tumor, at the same site as the original (primary) tumor, after the tumor has been removed surgically, by drug or other treatment, or has otherwise disappeared. A metastasis is the spread of a tumor from one part of the body to another. Tumors formed from cells that have spread are called secondary tumors and contain cells that are like those in the original (primary) tumor. There can be a recurrence of either a primary tumor or a metastasis.

The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as 11q23-positive acute leukemia, acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non- Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (including basal breast carcinoma, ductal carcinoma and lobular breast carcinoma), lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyrgioma, ependymoma, pinealoma, hemangioblastoma, acoustic neuroma, oligodendroglioma, meningioma, melanoma, neuroblastoma and retinoblastoma). In several examples, a tumor is melanoma, lung cancer, lymphoma breast cancer or colon cancer.

Under conditions sufficient for: A phrase that is used to describe any environment that permits the desired activity. In one example, includes administering a therapeutically effective amount of a composition that includes a peptide, antibody, or oligonucleotide (e.g., morpholino), sufficient to enable the desired activity.

Unless otherwise explained, all technical and scientific terms used herein have the same meaning as commonly understood by one of ordinary skill in the art to which this invention belongs.

The singular terms "a," "an," and "the" include plural referents unless context clearly indicates otherwise. Similarly, the word or is intended to include and unless the context clearly indicates otherwise. Hence "comprising A or B" means "including A, or including B, or including A and B." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety.

In case of conflict, the present specification, including explanations of terms, will control. In addition, the materials, methods, and examples are illustrative only and not intended to be limiting.

II. Overview of Several Embodiments

Provided herein in a first embodiment is a method for inducing differentiation of a cancer stem cell, wherein the method includes contacting the cancer stem cell with an agent that alters CD47 signaling to induce cancer stem cell (CSC) differentiation, thereby inducing differentiation of CSCs. In examples of this embodiment, the induced differentiation is irreversible. Optionally, the agent used in the method comprises an anti-CD47 antibody or binding fragment thereof, peptide 7N3, or a CD47-targeted CRISPR construct. By way of example, the agent is the monoclonal antibody B6H12, humanized B6H12, a binding fragment of B6H12 or humanized B6H12, or a monoclonal antibody that binds competitively with B6H12.

In embodiments of the disclosed methods, the CSC comprises a breast cancer stem cell, a lung cancer stem cell, a prostate cancer stem cell, a colon carcinoma stem cell, or a melanoma stem cell.

By way of examples, in embodiment of the disclosed methods for inducing differentiation of CSCs, the agent that alters CD47 signalling induces in the CSC down-regulation of EGFR and up-regulation of one or more of the molecules listed in Table 1 as having increased expression.

It is contemplated herein that the methods of inducing cancer stem cell (CSC) differentiation disclosed herein can be practiced on CSCs that are in a subject. In examples of such treatment methods, the subject has a primary tumor, has a tumor in regression, has or is suspected of having a metastatic tumor, or a combination thereof Also provided herein are methods of treating a subject with a tumor, which methods involve administering a therapeutically effective amount of agent that alters CD47 signaling to induce cancer stem cell (CSC) differentiation to the subject, thereby treating the subject with the tumor. In examples of this method, the agent comprises an anti-CD47 antibody or binding fragment thereof, peptide 7N3, or a CD47-targeted CRISPR construct. By way of example, the agent is the monoclonal antibody B6H12, humanized B6H12, a binding fragment of B6H12 or humanized B6H12, or a monoclonal antibody that binds competitively with B6H12.

Also provided are treatment methods which further involve administering a therapeutically effective amount of an anti-cancer treatment to the subject. This can occur before, concurrent with, or after treatment with the agent that alters CD47 signaling to induce cancer stem cell (CSC) differentiation. In particular examples, the anti-cancer treatment is administered first, followed (for instance 1-4 days, or 1-7 days later) by administration with the agent that alters CD47 signaling.

In embodiments of treatment methods, the subject has a primary tumor, has a tumor in regression, has or is suspected of having a metastatic tumor, or a combination thereof.

Also provided herein are methods for inducing differentiation (such as irreversible differentiation) of cancer stem cells, substantially as described herein.

III. Methods to Eliminate Cancer Stem Cells by Targeting CD47

CD47 is a ubiquitously expressed cell surface receptor for thrombospondin-1 and the counter-receptor for signal-regulatory protein-α (SIRPα). High expression of CD47 on several types of cancer cells has been identified as a 'don't eat me signal' that inhibits their killing by macrophages or NK cells. Conversely, the CD47 antibody B6H12 that blocks SIRPα binding enhances macrophage-dependent clearance of tumors in several mouse models, although others have shown that such clearance can be independent of SIRPα signaling. We recently found that the absence of CD47 enhances stem cells in vitro and in vivo by increasing expression of four stem cell transcription factors (see, e.g., International Patent Publication WO 2013/155109, incorporated herein by reference in its entirety).

Stem cells also play an important role in the pathogenesis of cancer. Cancer stem cells have been reported to express elevated CD47 levels, but the role of CD47 in cancer stem cell function, apart from protecting CSC from phagocytosis by engaging SIRPα on macrophages, has not been examined. Breast cancer stem cells (bCSCs) isolated from the triple negative MDA-MB-231 cell line have up-regulation of embryonic as well as cancer stem cell markers and exhibit high asymmetric cell division as compared to differentiated MDA-MB-231 cells. bCSCs can form mammospheres and can differentiate into endothelial, smooth muscle, and neural phenotypes, but they preserve the gene expression patterns of differentiated MDA-MB-231 cells. Relative to differentiated MDA-MB-231 cells, bCSCs have low expression of genes associated with tumor suppression, the RNAi silencing complex, and metabolism.

Global analysis of gene expression of bCSCs treated with B6H12 antibody showed up-regulation of tumor suppressor genes (TXNIP, LOX and PLS3), the RNAi silencing gene DICER 1, and TOP1, but decreased expression of epidermal growth factor receptor (EGFR). We further found that CD47 and EGFR are co-localized and interact with each other in MDA-MB-231 breast cancer cells. Treatment with B6H12 antibody inhibits EGF-induced EGFR-tyrosine phosphorylation and cell proliferation. Data presented herein show that B6H12 specifically targets bCSCs but not differentiated cancer cells, and this CD47 signaling is independent of SIRPα. Treatment of the estrogen receptor-positive breast cancer cell line MCF7 with B6H12 antibody did not alter expression of the above indicated genes. This suggests that therapeutic antibodies targeting CD47 may selectively benefit patients with triple negative breast cancers that are associated with high rates of metastasis by forcing differentiation of bCSCs.

Breast epithelial stem cells are important for tissue self renewal (Villadsen et al., *J Cell Biol.* 177:87 101, 2007). The presences of breast progenitor cells has been reported and characterized in normal adults (Stingl et al., *Breast Canc Res Treat.* 67:93 109, 2001). Normal stem and progenitor cells play active role in cyclic changes that takes place during pregnancy and ovulation in women (Petersen & Polyak, *CSH Persps in Biol.* 2: a003160, 2010). Human breast epithelial cells with stem cell like phenotype showing increased telomerase activity and led to immortalization (Gudjonsson et al., *Genes & Deve.* 16:693 706, 2002; Ince et al., *Cancer Cell.* 12:160 170, 2007; Sun et al., *Cancer Res.* 59:6118 6123, 1999). This suggested that breast cancer initiation might involve cells having stem cell like properties and defined as cancer stem cells. These cancer stem cells have distinct properties from differentiated tumor cells. It is thought that restoration, progression and resistance of cancer to therapy is due to small pool of cancer stem cells. These may account for the frequency of breast cancer recurrence in 5 7 years (Rosen et al., *J Clin Oncol* 7:1239 1251, 1989). It has been speculated that cancer stem cells are in a dormant stage and become active during epithelial mesenchymal transition (Giancotti, *Cell.* 155:750 764, 2013).

Reports have shown that cancer stem cells are lin⁻ and express the CD133⁺ marker. CD133⁺ expressing cells are tumorigenic in Nod SCID mice, but CD133 engrafted cells do not form tumors (Singh et al., *Nature.* 432:396 401, 2004). Other flow cytometric analysis has shown that a CD44⁺(high) and CD24 low population represents cancer stem cells (Fillmore & Kuperwasser, *Breast Cancer Res: BCR.* 9:303, 2007). ALD1, a metabolic dehydrogenase, has been associated with cancer stem cells (Charafe Jauffret et al., *Cancer Res.* 73:7290 7300, 2013).

CD47 is also known as hematopoietic stem cell marker that inhibits phagocytosis via SIRP alpha (SIRP-α) (Jaiswal et al., *Cell.* 138(2):271-285-2009). Inhibition of CD47 using the antibody B6H12 has been in pre-clinical trials where human tumor xenografts are implanted into Nod-SCID mice that express a mutant form of mouse SIRPα that can recognize human CD47 (Majeti, *Cell.* 2009 Jul. 23; 138(2): 286-99; Chan et al., *Proc Natl Acad Sci USA.* 2009 Aug. 18; 106(33):14016-21; Chao et al., *Cell.* 2010 Sep. 3; 142(5): 699-713; *Cancer Res.* 2011 Feb. 15; 71(4):1374-84; Chao et al., *Blood.* 2011 Nov. 3; 118(18):4890-901). In these mice, B6H12 inhibits the interaction between human CD47 on the tumor cells and SIRPα on mouse macrophages and thereby enhances clearance of the tumor xenograft by the mouse innate immune system. Humanized CD47 antibodies are potential candidates for treating many cancers (Willingham et al., *PNAS USA.* 109:6662 6667, 2012). Many labs have argued that data in the above publications is not fully supportive of the CD47-SIRP-α hypothesis (Zhao et al., *Blood.* 119:4333 4334; author reply 4334 4335, 2012; Zhao et al., *PNAS USA.* 109: E2843; author reply E2844 2845, 2012; Soto-Pantoja et al., *Proc Natl Acad Sci USA.* 109 (42): E2842, 2012; author reply E2844-5). However, none of these publications has identified a cancer cell-autonomous function of CD47 that is blocked by B6H12 and could lead to tumor ablation. On the contrary, previous publications that have identified other CD47 antibodies that directly induce death of certain leukemic and breast cancer cell lines, but B6H12 was generally used as a negative control in those studies. The CD47 antibody Ad22 induced apoptosis of Jurkat cells and CD3epsilon-stimulated PBMC, but the CD47 mAbs 2D3 and B6H12 were inactive (Pettersen et al., *J Immunol.* 162(12):7031-40, 1999) Another study reported that immobilized but not soluble B6H12 induced caspase-independent cell death of human B cell chronic lymphocytic leukemia cells (Mateo et al., *Nat Med.* 5(11):1277-84, 1999; Mateo et al., *Blood.* 100(8):2882-90, 2002). However, in the same study CD34⁺ hematopoietic progenitor stem cells were not killed by immobilized B6H12, despite their high level of CD47 expression.

Recently we discovered that CD47 null primary cells derived from mouse lungs exhibit enhanced self renewal, which is mediated by up-regulation of the four stem cell transcription factors c-MYC, KLF4, OCT4 and SOX2. Global transcriptome analysis confirmed a close resemblance with ES and iPS cells (Kaur et al., *Scientific Rep.* 3:1673, 2013).

Breast cancer stem cells (bCSCs) isolated from the triple negative MDA-MB-231 cell line have up regulation of embryonic as well as cancer stem cell markers and exhibit high asymmetric cell division as compared to differentiated MDA-MB-231 cells. These bCSCs can form mammospheres and can differentiate into endothelial, smooth muscle, and neural phenotypes, but they preserve the gene expression patterns of differentiated MDA-MB-231 cells. Relative to differentiated MDA-MB-231 cells, the bCSCs have low expression of genes associated with tumor suppression, the RNAi silencing complex, and metabolism. Remarkably, treating the bCSCs with the CD47 function-blocking antibody B6H12 induces irreversible differentiation of the bCSC and inhibits their proliferation. Global analysis of gene expression of bCSCs treated with B6H12 showed up-regulation of tumor suppressor genes (TXNIP, LOX and PLS3), the RNAi silencing gene DICER 1, and TOP1, but decreased expression of EGFR.

Further, CD47 and EGFR are co-localized and interact with each other in MDA-MB-231 breast cancer cells. Treatment with B6H12 antibody inhibits EGF induced EGFR tyrosine phosphorylation and cell proliferation. Our preliminary data show that B6H12 specifically targets bCSCs but not differentiated cancer cells, and this CD47 signaling is independent of SIRP-α. Treatment of estrogen receptor positive breast cancer cell lines with B6H12 antibody did not alter expression of the above indicated genes. This suggests that therapeutic antibodies targeting CD47 may selectively benefit patients with triple negative breast cancers that are associated with high rates of metastasis by forcing differentiation of bCSCs. These experiments reveal an unexpected direct activity of CD47 blockade to target breast cancer by suppressing bCSC (by inducing terminal differentiation, thereby eliminating the cancer stem cells). This challenges the current dogma that CD47 antibodies have therapeutic benefit exclusively through blocking clearance of tumor cells by macrophage phagocytosis.

Though exemplified herein with cancer stem cells (including particularly triple negative breast cancer), it is to be understood that the methods provided herein are application in other cancer types, including but not limited to colon cancer, lung cancer, kidney cancer, bone cancer, brain cancer, leukemia, lymphoma, prostate cancer, bladder cancer, or pancreatic cancer.

Evidence is emerging that CSC also play a major role in the metastatic spread of cancer, which is the major cause of treatment failure and death from malignancies (Li et al., *Cell Res.* 17(1):3-14, 2007; Baccelli and Trumpp, *J Cell Biol.* 198(3):281-93, 2012; Shiozawa et al., *Pharmacol Ther.* 2013 May; 138(2):285-93). Metastatic cells share many molecular features with CSC, and in common with CSC: the cells that initiate distant metastases have a self-renewal capability and can give rise to various differentiated tumor cell types in any given metastasis. Elevated expression of CD47 is emerging as another characteristic shared between CSC and metastatic cancer cells. Luminal-type breast cancers with the highest expression of CD47 were associated with lymph node metastasis and poor survival (Baccelli et al., *Oncotarget.* 2014 Sep. 2. [Epub ahead of print]). Circulating cancer cells in these patients also had elevated CD47 expression. In mouse xenograft studies, circulating tumor cells selected for high expression of CD47 and other CSC markers, but not bulk circulating tumor cells efficiently gave rise to bone, lung and liver metastases in mice (Baccelli et al., *Nat Biotechnol.* 31(6):539-44, 2013). Elevated CD47 expression was also reported on circulating colorectal cancer cells (Steinert et al., *Cancer Res.* 74(6):1694-704, 2014). In the context of the present findings, these studies indicate that the high CD47 expression on circulating tumor cells serves not merely to prevent their clearance by phagocytes, but rather is important for maintaining their stem cell character. Conversely, one application of the agents and methods described herein as useful to alter CD47 signaling in CSC is to differentiate circulating tumor cells and cancer cells in nascent micrometastases, thereby preventing the establishment and growth of metastatic lesions.

IV. Production of Antibodies

Examples of the therapeutic methods described herein employ an anti-CD47 antibody or derivative thereof; one specific example is the monoclonal antibody B6H12. However, additional antibodies can be used in these methods, including for instance humanized versions of B6H12, binding fragments of B6H12, and monoclonal antibodies that bind competitively with B6H12. Additional specific antibodies include BRIC 126, 6H9, Clkm1, OVTL16, OX101, mIAP410, or mIAP301. Some of these antibodies, e.g. B6H12, are known to inhibit both TSP1 and SIRPα binding to CD47. mIAP301 blocks binding of murine CD47 to murine SIRPα. Given the large size of antibodies, some CD47 antibodies may bind to epitopes distinct from the SIRP or TSP1 binding sites but still be capable of sterically blocking the binding of one or both of these ligands. Evidence provided herein suggests that the activity of B6H12 to differentiate CSC is independent of blocking SIRP binding. Blocking of EGFR or TSP1 binding may be important, but B6H12 and related CD47 antibodies may induce CSC differentiation without inhibiting EGFR association or TSP1 binding to CD47. Thus some CD47 antibodies that do not inhibit SIRP or TSP1 binding but similarly alter the conformation of CD47 would be expected to share the ability to differentiate CSC. Tests are provided herein for evaluating the usefulness of any particular antibody for inducing differentiation of CSCs.

Optimally, antibodies raised against a target protein (such as CD47) would specifically detect that peptide/protein, and optimally would inhibit the functional interaction between CD47 and a protein with which it normally interacts, such as EGFR or TSP1 or SIRPα. Antibodies that specifically detect a target protein would recognize and bind that protein (and peptides derived therefrom) and would not substantially recognize or bind to other proteins or peptides found in a biological sample. The determination that an antibody specifically detects its target protein is made by any one of a number of standard immunoassay methods; for instance, the Western blotting technique (Sambrook et al., In *Molecular Cloning: A Laboratory Manual, CSHL*, New York, 1989). Antibodies that do not inhibit binding of these ligands but similarly alter the conformation of CD47 or its lateral associations in the cell membrane are another preferred embodiment.

To determine by Western blotting that a given antibody preparation (such as one produced in a mouse or rabbit) specifically detects the target peptide, the peptide of interest is synthesized and transferred to a membrane (for example, nitrocellulose) by Western blotting, and the test antibody preparation is incubated with the membrane. After washing the membrane to remove non-specifically bound antibodies, the presence of specifically bound antibodies is detected by the use of an anti-mouse or anti-rabbit antibody conjugated to an enzyme such as alkaline phosphatase.

Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the target peptide will, by this technique, be shown to bind to the target peptide band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-target peptide binding.

The determination that an antibody inhibits the association between CD47 and EGFR, or induces differentiation of CSCs through blockade of CD47, may be made, for example, using any one of the assays described herein. For instance, the determination that an antibody inhibits EGFR association with purified or recombinant CD47 can be made by comparing the binding (or functional) activity alone with the binding (or functional activity in the presence of the antibody using a solid phase ligand binding assay.

A. Monoclonal Antibody Production by Hybridoma Fusion

Monoclonal antibody to epitopes of a target peptide (e.g., from CD47) can be prepared from murine hybridomas according to the classical method of Kohler and Milstein (*Nature* 256:495, 1975) or derivative methods thereof. Briefly, a mouse is repetitively inoculated with a few micrograms of the selected protein over a period of a few weeks. The mouse is then sacrificed, and the antibody-producing cells of the spleen are isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Enzymol.* 70:419, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against a target peptide is to use synthetic peptides synthesized on a commercially available peptide synthesizer based upon the amino acid sequence of the native protein (e.g., CD47).

By way of example only, polyclonal antibodies to a CD47 peptide can be generated through well-known techniques by injecting rabbits or another mammal with chemically synthesized peptide.

D. Antibodies Raised by Injection of a Peptide-Encoding Sequence

Antibodies may be raised against a target peptide by subcutaneous injection of a DNA vector that expresses that peptide into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the desired peptide-encoding sequence under the transcriptional control of either the human β-actin promoter or the cytomegalovirus (CMV) promoter.

E. Humanized Antibodies

Also contemplated are humanized antibodies, for instance humanized equivalents of the described murine monoclonal antibodies. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgM or an IgG, including but not limited to, $IgG_1$, $IgG_2$, $IgG_3$ and $IgG_4$.

Humanized monoclonal antibodies can be produced by transferring donor complementarity determining regions (CDRs) from heavy and light variable chains of the donor mouse (or other animal) immunoglobulin. The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds a cell surface antigen of pancreatic cells (such as endocrine, exocrine or ductal cells) and immunoglobulin and heavy and light chain variable region frameworks from human acceptor immunoglobulin heavy and light chain frameworks. Generally, the humanized immunoglobulin specifically binds to the cell surface antigen (or cells expressing the antigen) with an affinity constant of at least $10^7$ M$^{-1}$, such as at least $10^8$ M$^{-1}$ at least $5\times10^8$ M$^{-1}$ or at least $10^9$ M$^{-1}$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 95%, or at least about 99% identical to the sequence of the donor murine immunoglobulin heavy chain variable region framework. Human framework regions, and mutations that can be made in a humanized antibody framework regions, are known in the art (see, for example, U.S. Pat. No. 5,585,089, which is incorporated herein by reference). One of skill in the art can readily select a human framework region of use.

Also contemplated are fully human antibodies. Mice have been generated that express only human immunoglobulin genes, instead of mouse genes. These mice are immunized with the antigen, such as CD47, and resultant antibodies that are raised are selected for the activity desired. In the current instance, it is contemplated that this technique can be used to generate antibodies (including monoclonal antibodies) useful for blocking CD47 interactions. These procedures are substantially similar just those used to select a mouse anti-human Ab, but result in a fully human antibody since the mouse only has human Ig genes.

V. Peptides and Peptide Variants

The peptides useful in methods disclosed herein (e.g., peptide p7N3, FIRVVMYEGKK; SEQ ID NO: 1) can be chemically synthesized by standard methods, or can be produced recombinantly. The synthesis of the presently disclosed peptide compounds can be accomplished using standard chemical reactions known to be useful for preparing a variety of analogous compounds. Indeed, exemplary techniques known to those of ordinary skill in the art of peptide synthesis are taught by Bodanszky & Bodanszky (The Practice of Peptide Synthesis; Springer Verlag, New York, 1994) and by Jones (Amino Acid and Peptide Synthesis; 2nd ed.; Oxford University Press, 2002), both of which are incorporated herein by reference. The Bodanszky and Jones references detail the parameters and techniques for activating and coupling amino acids and amino acid derivatives. Moreover, the references teach how to select, use and remove various useful protecting groups. An exemplary specific process for (poly)peptide production is described in Lu et al. (*Fed. Europ Biochem Societies Lett.* 429:31-35, 1998).

Polynucleotides encoding the peptides disclosed herein are also provided. These polynucleotides include DNA, cDNA and RNA sequences that encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3$^{rd}$ Edition, W.H. 5 Freeman and Co., NY).

A nucleic acid encoding a peptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the peptide (or a longer polypeptide, such as an expression fusion polypeptide, containing the peptide) can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

The polynucleotides encoding a peptide (e.g., a peptide from or derived from TSP1 or CD47) include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane H$^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PH05 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the peptides disclosed herein. Myriad viral vectors have been constructed and are known to those of skill in the art, including but not limited to polyoma, SV40 (Madzak et al., *J. Gen. Virol.* 73:1533-1536, 1992), adenovirus (Berkner, *Cur. Top. Microbiol. Immunol.*, 158:39-36, 1992; Berliner et al., *BioTechniques,* 6:616-629, 1988; Gorziglia et al., *J. Virol.* 66:4407-4412, 1992; Quantin et al., *Proc. Nad. Acad. Sci. USA* 89:2581-2584, 1992; Rosenfeld et al., *Cell,* 68:143-155, 1992; Wilkinson et al., *Nucl. Acids Res.* 20:2233-2239, 1992; Stratford-Perricaudet et al., *Hum. Gene Ther.,* 1:241-256), vaccinia virus (Mackett et al., *Biotechnology,* 24:495-499, 1992), adeno-associated virus (Muzyczka, *Curr. Top. Microbiol. Immunol.* 158:91-123, 1992; On et al., 1990, *Gene,* 89:279-282), herpes viruses including HSV and EBV (Margolskee, *Curr. Top. Microbiol. Immunol.,* 158:67-90, 1992; Johnson et al., *J. Virol.* 66:2952-2965, 1992; Fink et al., *Hum. Gene Ther.* 3:11-19, 1992; Breakfield et al., *Mol. Neurobiol.,* 1:337-371, 1987; Fresse et al., *Biochem. Pharmacol.* 40:2189-2199, 1990), Sindbis viruses (Herweijer et al., *Human Gene Therapy* 6:1161-1167, 1995; U.S. Pat. No. 5,091,309), alphaviruses (Schlesinger, *Trends Biotechnol.* 11:18-22, 1993; Frolov et al., *Proc. Natl. Acad. Sci. USA* 93:11371-11377, 1996) and retroviruses of avian (Brandyopadhyay et al., *Mol. Cell Biol.* 4:749-754, 1984; Petropouplos et al., *J. Virol.* 66:3391-3397, 1992), murine (Miller, *Curr. Top. Microbiol. Immunol.,* 158:1-24, 1992; Miller et al., 1985, *Mol. Cell Biol.,* 5:431-437; Sorge et al., *Mol. Cell Biol.* 4:1730-1737, 1984; Mann et al., *J. Virol.* 54:401-407, 1985), and human origin (Page et al., *J. Virol.* 64:5370-5276, 1990; Buchschalcher et al., *J. Virol.* 66:2731-2739, 1992). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

The characteristics of the peptides disclosed herein lie not in their precise and entire amino acid sequence, but rather in the three-dimensional structure inherent in the amino acid sequences encoded by the DNA sequences. It is possible to recreate the binding characteristics of any of these peptides, for instance the binding characteristics of any one of the specific peptides described herein, by recreating the three-dimensional structure, without necessarily recreating the exact amino acid sequence. Production of variations is enabled particularly in view of the guidance provided for the tolerance of variations at various positions within the core peptide. Such modifications and variations can be achieved for instance by designing a nucleic acid sequence that encodes for the three-dimensional structure, but which differs, for instance by reason of the redundancy of the genetic code or the substitution of one or more specific amino acids. Similarly, the DNA sequence may also be varied, while still producing a functional peptide.

Variant therapeutic peptides include peptides that differ in amino acid sequence from the disclosed sequence, but that share structurally significant sequence homology with any of the provided peptides. Such variants may be produced by manipulating the nucleotide sequence of the encoding sequence, using standard procedures, including site-directed mutagenesis or PCR. The simplest modifications involve the substitution of one or more amino acids for amino acids having similar biochemical properties. These so-called conservative substitutions are likely to have minimal impact on the activity of the resultant peptide, especially when made outside of the binding site of the peptide. One of ordinary skill in the art will be able to predict or empirically determine (particularly in view of the provided teachings) amino acids that may be substituted for an original amino acid in a peptide.

More substantial changes in peptide structure may be obtained by selecting amino acid substitutions that are less conservative. Such changes include changing residues that differ more significantly in their effect on maintaining polypeptide backbone structure (for example, sheet or helical conformation) near the substitution, charge or hydrophobicity of the molecule at the target site, or bulk of a specific side chain. The following substitutions are generally expected to produce the greatest changes in protein properties: (a) a hydrophilic residue (for example, seryl or threonyl) is substituted for (or by) a hydrophobic residue (for example, leucyl, isoleucyl, phenylalanyl, valyl or alanyl); (b) a cysteine or proline is substituted for (or by) any other residue; (c) a residue having an electropositive side chain (for example, lysyl, arginyl, or histadyl) is substituted for (or by) an electronegative residue (for example, glutamyl or aspartyl); or (d) a residue having a bulky side chain (for example, phenylalanine) is substituted for (or by) one lacking a side chain (for example, glycine).

Variant peptide-encoding sequences may be produced by standard DNA mutagenesis techniques, for example, M13 primer mutagenesis. Details of these techniques are provided in Sambrook (In Molecular Cloning: A Laboratory Manual, Cold Spring Harbor, N.Y., 1989), Ch. 15. By the use of such techniques, variants may be created which differ in minor ways from the angiogenic and anti-angiogenic-encoding sequences disclosed. DNA molecules and nucleotide sequences which are derivatives of those specifically disclosed herein and that differ from those disclosed by the deletion, addition, or substitution of nucleotides while still encoding a peptide that promotes or inhibits angiogenesis, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a peptide having an amino acid sequence substantially similar to the disclosed peptide sequences. For example, one nucleotide codon triplet GCT encodes alanine. Because of the degeneracy of the genetic code, three other nucleotide codon triplets—(GCG, GCC and GCA)—also code for alanine. Thus, a nucleotide sequence containing GCT for alanine could be changed at the same position to any of the three alternative codons without affecting the amino acid composition or characteristics of the encoded peptide. Based upon the degeneracy of the genetic code, variant DNA molecules may be derived from the cDNA and gene sequences disclosed herein using standard DNA mutagenesis techniques as described above, or by synthesis of DNA sequences. Thus, this disclosure also encompasses nucleic acid sequences which encode the subject peptides, but which vary from the disclosed nucleic acid sequences by virtue of the degeneracy of the genetic code.

The present disclosure includes biologically active molecules that mimic the action of the inhibitor/blockade peptides of the present disclosure. The peptides of the disclosure include synthetic embodiments of naturally-occurring peptides described herein, as well as analogues (non-peptide organic molecules), derivatives (chemically functionalized protein molecules obtained starting with the disclosed peptide sequences) and variants (homologs) of these peptides that specifically bind CD47, or that block one or more signalling functions of CD47. Each peptide of the disclosure is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the peptides, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptides, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains in the described inhibitor peptides, resulting in such peptido- and organomimetics of the peptides of this disclosure having measurable or enhanced angiogenic or anti-angiogenic activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, Computer-Assisted Modeling of Drugs, in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques that produce angiogenic or anti-angiogenic peptides.

VI. Compositions and Methods for Inducing CSC Differentiation

The disclosed methods include inhibiting or blocking CD47 signaling, for example to induce differentiation of cancer stem cells, and particularly to induce irreversible differentiation of cancer stem cells. In various embodiments, inhibiting CD47 signaling includes one or more of inhibiting the expression of CD47, or blockading or inhibiting the interaction between CD47 and EGFR.

Agents that alter CD47 signaling to increase or induce CSC differentiation include but are not limited to peptides, antibodies, antisense oligonucleotides, morpholinos, or small molecule inhibitors. The agents include, in various embodiments, synthetic peptides having specific binding affinity for CD47; oligonucleotide comprising at least about 15 contiguous bases and that hybridizes to the mature or unprocessed nuclear mRNA of CD47 under high stringency conditions; isolated or recombinant CD47 molecules or soluble fragments thereof, or molecule that binds thereto; agents that decrease the expression of CD47; agents that enhance the proteolysis of CD47; agents that enhance removal of CD47 from the cell surface; CD47 antagonists; antibodies that specifically bind CD47; or a mixture of two or more thereof. Exemplary agents that influence CD47 signaling include those described in U.S. Pat. No. 8,236,313 and International Pat. Publ. No. WO 2010/017332, both of which are incorporated herein by reference in their entirety.

A. Suppression of Protein Expression

In some embodiments, inhibition or blockade of CD47 signaling is achieved by reducing or suppressing CD47 protein expression, for example in methods of inducing differentiation (such as irreversible differentiation) of cancer stem cells, such as exemplified herein.

Although the mechanism by which antisense RNA molecules interfere with gene expression has not been fully elucidated, it is believed that antisense RNA molecules (or fragments thereof) bind to the endogenous mRNA molecules and thereby inhibit translation of the endogenous mRNA, splicing of the nuclear mRNA precursor, or result in its degradation. A reduction of protein expression in a cell may be obtained by introducing into cells an antisense construct based on CD47 encoding sequences, including the human (or other mammalian) CD47 cDNA or gene sequence or flanking regions thereof. For antisense suppression, a nucleotide sequence from a CD47-encoding sequence, for example all or a portion of a CD47 cDNA or gene, is arranged in reverse orientation relative to the promoter sequence in the transformation vector. One of ordinary skill in the art will understand how other aspects of the vector may be chosen.

The introduced sequence need not be the full length of the cDNA or gene, or reverse complement thereof, and need not be exactly homologous to the equivalent sequence found in the cell type to be transformed. Generally, however, where the introduced sequence is of shorter length, a higher degree of homology to the native target sequence will be needed for effective antisense suppression. The introduced antisense sequence in the vector may be at least 15 nucleotides in length, and improved antisense suppression will typically be observed as the length of the antisense sequence increases. The length of the antisense sequence in the vector advantageously may be greater than about 20 nucleotides, greater than about 30 nucleotides, or greater than about 100 nucleotides. For suppression of the CD47 gene itself, transcription of an antisense construct results in the production of RNA molecules that are the reverse complement of mRNA molecules transcribed from the endogenous CD47 gene in the cell.

Suppression of CD47 expression can also be achieved using ribozymes. Ribozymes are synthetic molecules that possess highly specific endoribonuclease activity. The production and use of ribozymes are disclosed in U.S. Pat. Nos. 4,987,071 and 5,543,508. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Suppression can also be achieved using RNA interference, using known and previously disclosed methods. Several models have been put forward to explain RNAi, in particular the mechanisms by which the cleavage derived small dsRNAs or siRNAs interact with the target mRNA and thus facilitate its degradation (Hamilton et al., *Science* 286:950, 1999; Zamore et al., *Cell* 101:25, 2000; Hammond et al., *Nature* 404:293, 2000; Yang et al., *Curr. Biol.* 10:1191, 2000; Elbashir et al., *Genes Dev.* 15:188, 2001; Bass *Cell* 101:235, 2000). It has been proposed that the cleavage derived small dsRNAs or siRNAs act as a guide for the enzymatic complex required for the sequence specific cleavage of the target mRNA. Evidence for this includes cleavage of the target mRNA at regular intervals of about 21-23 nucleotides in the region corresponding to the input dsRNA (Zamore et al., Cell 101, 25, 2000), with the exact cleavage sites corresponding to the middle of sequences covered by individual 21 or 22 nucleotide small dsRNAs or siRNAs (Elbashir et al., *Genes Dev.* 15:188, 2001). Although mammals and lower organisms appear to share dsRNA-triggered responses that involve a related intermediate (small dsRNAs), it is likely that there will be differences as well as similarities in the underlying mechanism. dsRNAs can be formed from RNA oligomers produced synthetically (for technical details see material from the companies Xeragon and Dharmacon, both available on the internet). Small dsRNAs and siRNAs can also be manufactured using standard methods of in vitro RNA production. In addition, the Silencer™ siRNA Construction kit (and components thereof) available from Ambion (Catalog #1620; Austin, Tex.), which employs a T7 promoter and other well-known genetic engineering techniques to produce dsRNAs. Double stranded RNA triggers could also be expressed from DNA based vector systems.

Inhibition also can be accomplished using morpholino oligonucleotides, for instance as described herein. The morpholino can be delivered directly to cells (for example, in vitro) or can be administered to a subject as herein described. In particular embodiments, the morpholino is an antisense morpholino oligonucleotide complementary to CD47 (such as human and/or murine CD47). Example CD47 morpholino are provided, for instance, in International Patent Publication No. WO 2008/060785, which is incorporated herein by reference in its entirety for all that it teaches.

The nucleic acids and nucleic acid analogs that are used to suppress CD47 expression may be modified chemically or biochemically or may contain one or more non-natural or derivatized nucleotide bases, as will be readily appreciated by those of ordinary skill in the art. Such modifications include, for example, labels, methylation, substitution of one or more of the naturally occurring nucleotides with an analog, internucleotide modifications, such as uncharged linkages (for example, methyl phosphonates, phosphotriesters, phosphoramidates, carbamates, etc.), charged linkages (for example, phosphorothioates, phosphorodithioates, etc.), pendent moieties (for example, polypeptides), intercalators (for example, acridine, psoralen, etc.), chelators, alkylators, and/or modified linkages (for example, alpha anomeric nucleic acids, etc.). The term nucleic acid molecule also includes any topological conformation, including single-stranded, double-stranded, partially duplexed, triplexed, hair-pinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Additionally, although particular exemplary sequences are disclosed herein, one of ordinary skill in the art will appreciate that the present methods also encompass sequence alterations of the disclosed agents that yield the same results as described herein. Such sequence alterations can include, but are not limited to, deletions, base modifications, mutations, labeling, and insertions.

Suppression of protein expression may also be achieved through agents that enhance proteolysis of CD47 (Allen et al., *Endocrinology* 150:1321-1329, 2009). In other particular examples, the suppression of CD47 expression involves an agent that enhances the removal of CD47 from the cell surface or decreases the transcription, mRNA processing, or translation of CD47.

It is also contemplated that suppression of expression can be achieved through the engineered, directed editing of the genomic sequence encoding CD47, for instance through the clustered, regularly interspaced, short palindronic repeat (CRISPR) technology (Sander & Joung. Nature *Biotechnol* 32:347-355, 2014, doi: 10.1038/nbt.2842, which is incorporated by reference herein in its entirety); this approach generates RNA-guided nucleases, such as Cas9, with customizable specificities. CRISPRs are DNA loci containing short repetitions of base sequences. Each repetition is followed by short segments of "spacer DNA" from previous exposures to a virus (Marraffini & Sontheimer. Nature Rev Genetics 11:181-190, 2010, doi: 10.1038/nrg2749, which is incorporated by reference herein in its entirety). CRISPRs are often associated with Cas genes that code for proteins related to CRISPRs. The CRISPR/Cas system is a prokaryotic immune system that confers resistance and acquired immunity against invading foreign genetic elements such as plasmids and via RNA-guided DNA cleavage (Wiedenheft et al., *Nature* 482:331-338, 2012, which is incorporated by reference herein in its entirety). In the type II CRISPR/Cas system, short segments of foreign DNA, termed 'spacers' are integrated within the CRISPR genomic loci and transcribed and processed into short CRISPR RNA (crRNA). These crRNAs anneal to transactivating crRNAs (tracrRNAs) and direct sequence-specific cleavage and silencing of pathogenic DNA by Cas proteins. Target recognition by the Cas9 protein requires a 'seed' sequence within the crRNA and a conserved dinucleotide-containing protospacer adjacent motif (PAM) sequence upstream of the crRNAbinding region (Jinek et al. *Science* 337:816-821, 2012, which is incorporated by reference herein in its entirety). The CRISPR/Cas system can thereby be retargeted to cleave virtually any DNA sequence by redesigning the crRNA. Significantly, the CRISPR/Cas system has been shown to be directly portable to human cells by co-delivery of plasmids expressing the Cas9 endonuclease and the necessary crRNA components (Cho et al., *Nature Biotechnol* 31:230-232, 2013; Cong et al., *Science* 339:819-823, 2013; Mali et al., *Science* 339:823-826, 2013, each of which is incorporated by reference herein in its entirety). These programmable RNA-guided DNA endonucleases have demonstrated multiplexed gene disruption capabilities (Cong et al., *Science* 339:819-823, 2013, which is incorporated by reference herein in its entirety) and targeted integration in iPS cells (Mali et al., *Science* 339:823-826, 2013, which is incorporated by reference herein in its entirety). Cas9 endonucleases have also been converted into nickases (Cong et al., *Science* 339:819-823, 2013, which is incorporated by reference herein in its entirety), enabling an additional level of control over the mechanism of DNA repair. The CRISPR/Cas system can be used for gene editing (adding, disrupting or changing the sequence of specific genes) and gene regulation in species throughout the tree of life (Mali et al., *Nature Methods* 10:957-963, 2013; doi: 10.1038/nmeth.2649, which is incorporated by reference herein in its entirety). By delivering the Cas9 protein and appropriate guide RNAs into a cell, the organism's genome can be cut at any desired location. It may be possible to use CRISPR to build RNA-guided gene drives capable of altering the genomes of entire populations (Esvelt et al., *eLife* doi: 10.7554/eLife.03401, which is incorporated by reference herein in its entirety).

The following table lists representative gRNA sequences useful for CRISPR disruption of CD47:

| SEQ ID NO: | Name | gRNA |
|---|---|---|
| 53 | hCD47.g1 | TCCATGCTTTGTTACTAATANGG |
| 54 | hCD47.g10 | ATCGAGCTAAAATATCGTGTNGG |
| 55 | hCD47.g11 | GATGATCGTTTCACCTTCTCNGG |
| 56 | hCD47.g12 | ACTCTTATCCATCTTCAAAGNGG |
| 57 | hCD47.g13 | TTTTGCACTACTAAAGTCAGNGG |
| 58 | hCD47.g14 | TTTGCACTACTAAAGTCAGTNGG |
| 59 | hCD47.g15 | TTGCACTACTAAAGTCAGTGNGG |
| 60 | hCD47.g16 | ACTAAAGTCAGTGGGGACAGNGG |
| 61 | hCD47.g17 | CTTGTTTAGAGCTCCATCAANGG |
| 62 | hCD47.g18 | TCCATATTAGTAACAAAGCANGG |
| 63 | hCD47.g2 | ATGCTTTGTTACTAATATGGNGG |
| 2 | hCD47.g3 | CTACTGAAGTATACGTAAAGNGG |
| 64 | hCD47.g4 | TACGTAAAGTGGAAATTTAANGG |
| 65 | hCD47.g5 | AGAGATATTTACACCTTTGANGG |
| 66 | hCD47.g6 | GAAGTCTCACAATTACTAAANGG |
| 67 | hCD47.g7 | AGGAGATGCCTCTTTGAAGANGG |
| 68 | hCD47.g8 | AGTGATGCTGTCTCACACACNGG |
| 69 | hCD47.g9 | GTAACAGAATTAACCAGAGANGG |

There is provided herein an example CRISPR-mediated disruption of CD47 expression. One of ordinary skill will recognize that there are hundreds of possible CRISPR binding sites in the CD47 gene (for instance, most cites with a "GG" or CC" sequence can be used to target Cas9-mediated gene inactivation), and thus the example provided herein is intended to be illustrative rather than limiting. Likewise, CRISPR is not the only art-recognized way to knock out or knock down expression of a garget gene, such as CD47. In addition to the many CRISPR systems (including systems that use Cpf1) that have been harnessed for use in the laboratory, Zinc Finger Nucleases (ZFN) and TALEN are alternative methods for knocking out the CD47 gene. Other art-recognized methods and systems are also contemplated.

B. Suppression of Protein Activity

In some embodiments, inhibition or blockade of CD47 signaling is achieved by reducing or suppressing CD47 protein activity, for example in methods of inducing differentiation of cancer stem cells, such as exemplified herein.

In some examples, an inhibitor of CD47 signaling includes an agent that decreases or blocks binding of a ligand (such as EGFR or TSP1) to CD47. The determination that an agent (such as an antibody or a peptide) inhibits an association with or functional signalling from CD47 may be made, for example, using assays known to one of ordinary skill in the art. For instance, the determination that an agent inhibits EGFR binding to purified or recombinant CD47 can be made by comparing the binding activity alone with the binding activity in the presence of the agent using a solid phase ligand binding assay, an EGFR tyrosine phosphorylation assay, or an assay of a known downstream signaling target of EGFR. An agent that inhibits a signaling pathway through CD47 on cells may reduce the activity of a cGMP-dependent reporter in a suitable transfected cell assay by a certain amount, for example, by 20%, 30%, 40%, 50%, 60%, 70%, 80%, 90%, or even by 100%. In addition, an agent that inhibits the activity or CD47 can be identified using any one of the assays described herein, including, but not limited to, determining TXNIP expression in a cell, or the change in expression of any of the other genes listed in Table 1 (where an agent useful in methods described herein will influence the gene expression level in a manner similar to that seen with the antibody B6H12). For instance, an agent that inhibits CD47 signaling (such that the agent will induce differentiation of CSCs) will increase TXNIP expression (such as an increase in TXNIP mRNA or TXNIP protein) in a cell or population of cells by a certain amount, for example by 20%, 30%, 40%, 50%, 60%, 70%, 80%, 90%, 100%, 150%, 200%, 250%, or more as compared to a suitable control. Altered expression of genes that are known markers of CSC such as CD24 can also be measured by changes in mRNA expression or in surface expression by flow cytometry.

Thus, in various embodiments an agent that alters CD47 signaling to induce CSC differentiations includes antibodies (such as monoclonal antibodies or humanized antibodies) that specifically bind to CD47. In some examples, an antibody that specifically binds CD47 is of use in the methods disclosed herein. Antibodies that specifically bind to CD47 include polyclonal antibodies, monoclonal antibodies, or humanized monoclonal antibodies, or fragments thereof. Methods of constructing such antibodies are known in the art (see, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: *Current Protocols in Immunology*, section 2.4.1, 1992; Kohler & Milstein, *Nature* 256:495, 1975; Coligan et al., sections 2.5.1-2.6.7; and Harlow et al. in: *Antibodies: a Laboratory Manual*, page 726, Cold Spring Harbor Pub., 1988). In addition, such antibodies may be commercially available.

In some examples, an agent that alters CD47 signaling includes an anti-CD47 antibody, such as anti-CD47 antibodies B6H12, 1F7, BRIC 126, 6H9, Clkm1, OVTL16, OX101, mIAP410, or mIAP301 (also referred to as ab301), a binding fragment of any one of these, or a humanized version of any one of these, or an antibody or fragment thereof that competes with B6H12, BRIC 126, 6H9, Clkm1, OVTL16, OX101, mIAP410, or mIAP301 for binding. It is to be understood that agents that alter CD47 signaling for use in the present disclosure also include novel CD47 antibodies developed in the future.

In other embodiments, an inhibitor of CD47 signaling includes a peptide or recombinant protein derived from TSP1 that specifically binds to CD47. In some examples an inhibitor of CD47 signaling is a CD47-binding peptide, such as a TSP1-derived CD47-binding peptide. An exemplary CD47-binding peptides is 7N3 (FIRVVMYEGKK; SEQ ID NO: 1). Additional CD47-binding peptides include those described in U.S. Pat. No. 8,236,313, which is incorporated herein by reference in its entirety. It is to be understood that CD47 signaling inhibitors for use in the present disclosure also include novel CD47 binding peptides developed in the future.

In additional embodiments, an inhibitor of CD47 signaling includes a small molecule (such as a small organic molecule). Some small molecule inhibitors may inhibit CD47 expression or activity. It is to be understood that CD47 signaling inhibitors for use in the present disclosure also include novel CD47 small molecule inhibitors developed in the future.

VII. Administration of Compounds that Induce Differentiation of CSCs

The disclosed methods include selectively inducing terminal and irreversible differentiation of cancer stem cells by administering to a CSC, or to CSCs in a subject in need of treatment for cancer, a compound that alters CD47 signaling. In particular examples, the subject in need of treatment has a cancer such as colon cancer, breast cancer (including particularly triple negative breast cancer), lung cancer, kidney cancer, bone cancer, or brain cancer. In additional examples, the subject in need of treatment may have a leukemia, lymphoma, prostate cancer, bladder cancer, or pancreatic cancer.

Agents that influence CD47 signalling are administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure. The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

In some embodiments, the CD47 blocking agent is administered to a subject in a single dose. In other embodiments, the CD47 blocking agent is administered to a subject in multiple doses. When administered in multiple doses, the time period between each administration can vary and will depend in part on the subject being treated and the type of cancer being treated. In some examples, an agent that alters CD47 signaling to increase CSC differentiation is administered daily, bi-weekly, weekly, bi-monthly or monthly. When administered in multiple doses, the time period between each administration can vary and will depend in part on the subject being treated and the type of cancer being treated. One of skill in the art can determine an appropriate dosing schedule for each subject.

It is particularly contemplated that an agent that alters CD47 signaling to increase CSC differentiation can be administered in conjunction with standard of care chemotherapy or radiation therapy. Dosing with the agent (such as B6H12) 1-4 days before administering chemotherapy or radiation is expected to sensitize the CSC to respond to these therapies, thereby making the otherwise conventional therapy more effective.

In one example, administration of an agent that alters CD47 signaling to increase CSC differentiation decreases the volume of a tumor or a metastatic tumor, or both, or initiation of metastatic tumor(s). Decreasing the volume of a tumor or a metastatic tumor does not require a 100% reduction in the volume, and in some examples includes decreasing the volume by at least 10%, for example by at least 20% or more as compared to a volume in the absence of the therapeutic agent. In one example, such administration enhances apoptosis of the cancer cells, or metastatic tumor cells, or both. Increasing the apoptosis of cancer cells, or metastatic tumor cells, does not require a 100% apoptosis, and in some examples includes increasing the apoptosis by at least 10%, for example by at least 20% or more as compared to an amount of apoptosis in the absence of the therapeutic agent. In addition, the disclosed methods can result in a decrease in the symptoms associated with a tumor or a metastatic tumor.

In further embodiments, the methods include administering a second anti-cancer therapeutic to the subject in addition to the CD47 blocking agent, such as a cell-cycle checkpoint inhibitor. Anti-cancer therapeutics include, but are not limited to, chemotherapeutic drug treatment, radiation, gene therapy, hormonal manipulation, immunotherapy and antisense oligonucleotide therapy. Chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and bbr3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as podophyllum (for example, etoposide, and teniposide), taxane (for example, docetaxel and paclitaxel), vinca (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, hydroxyurea, and mitomycin; topoisomerase inhibitors, such as topotecan and irinotecan; monoclonal antibodies, such as alemtuzumab, bevacizumab, cetuximab, gemtuzumab, rituximab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, bexarotene, bortezomib, celecoxib, denileukin diftitox, erlotinib, estramustine, gefitinib, hydroxycarbamide, imatinib, pentostatin, masoprocol, mitotane, pegaspargase, and tretinoin.

Co-administration of the disclosed agents with radiation therapy is also contemplated. Methods for treating cancers using radiation therapy are well known in the art. In addition, methods of radioprotection are taught, for instance, in International Patent Publication No. WO 2010/017332, which is incorporated herein by reference.

The CD47 blocking agent and the second anti-cancer therapeutic can be delivered at the same time (such as part of the same composition or as separate compositions), or can be administered at different times. When administered at different times, the second anti-cancer therapeutic can either be administered before the agent that alters CD47 signaling to induce cancer stem cell (CSC) differentiation or after that agent. The time between administration of the CD47 blocking agent and the second anti-cancer therapeutic can vary and will depend on the type of second anti-cancer therapy selected, the cancer being treated and the subject being treated. Similarly, the second anti-cancer therapeutic can be administered in a single dose or in multiple doses. One of skill in the art can determine an appropriate dosing schedule for each subject.

Administration to cells of inhibitors of CD47 signaling (such as the monoclonal antibody B6H12, a humanized version of B6H12, a binding fragment of B6H12, or a monoclonal antibody that binds competitively with B6H12) can be local or systemic. Examples of local administration include, but are not limited to, topical administration, subcutaneous administration, transdermal administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration intended to distribute an active compound or composition widely throughout the body, for example, via the circulatory system. Thus, systemic administration includes, but is not limited to, intra-arterial and intravenous administration. Systemic administration also includes, but is not limited to, topical administration, subcutaneous administration, transdermal administration, intramuscular administration, or administration by inhalation, when such administration is directed at absorption and distribution throughout the body by the circulatory system. Systemic administration also includes oral administration, in some examples.

In other embodiments, the methods include administering an agent that alters CD47 signaling to induce CSC differentiation to a subject, for example, to induce differentiation of CSCs in vivo In some embodiments, an agent that alters CD47 signaling to induce CSC differentiation (such as a peptide, antibody or antibody fragment, nucleic acid, or inhibitory oligonucleotide (e.g., morpholino)) is administered locally to an affected area, for example by direct administration to a tumor, or is incorporated into an implant device and placed directly at an affected area, such as at or near a tumor, or in contact with bone marrow. In some embodiments, administration is, for example, by direct topical administration, or by intra-arterial, intravenous, subcutaneous, or intramuscular injection into the affected area. Efficacy of the treatment is shown, for example, by a regression of symptoms, for example reduction of tumor size, reduction of metastasis, reduction of recurrence of cancer, or any other measurable return to or towards a system more characteristic of health (for instance, changes in gene expression to be more like a healthy profile and less like a cancerous profile).

Liposomes containing a therapeutic compound, including cationic and anionic liposomes, can be made using standard procedures as known to one skilled in the art. Liposomes can be applied topically, either in the form of drops or as an aqueous based cream, or can be injected intraocularly. The cells or an agent that alters CD47 signaling to induce CSC differentiation can also be included in a delivery system that can be implanted at various sites, depending on the size, shape and formulation of the implant, and the type of transplant procedure. The delivery system is then introduced into the subject, for instance at or near a tumor or the site from which a tumor has been removed.

An effective amount of an agent that alters CD47 signaling to induce CSC differentiation (such as a peptide, antibody, inhibitor peptide-encoding DNA, or oligonucleotide (e.g., morpholino)) can be administered in a single dose, or in multiple doses, for example daily, weekly, every two weeks, or monthly during a course of treatment. Additionally, the therapeutic agents may be incorporated into or on implantable constructs or devices, such as vascular stents, for sustained regional or local release.

In some examples, the methods include identifying or selecting a subject for administration of an agent that alters CD47 signaling to induce CSC differentiation. For example, the methods include selecting a subject with cancer. In some instances, the method involves selecting a subject at risk for metastasis, or already showing evidence of metastatic disease.

VIII. Pharmaceutical Compositions

The therapeutic compounds described herein may be formulated in a variety of ways depending on the location and type of disease to be treated or prevented in the subject. Pharmaceutical compositions are thus provided for both local use at or near an affected area and for systemic use (in which the agent is administered in a manner that is widely disseminated via the cardiovascular system).

Pharmaceutical compositions that include at least one peptide or other inhibitor or therapeutic compound as described herein as an active ingredient, or that include both a therapeutic peptide or inhibitor/blockade agent and an additional agent as active ingredients, or that include both an ischemia-influencing peptide or inhibitor and an additional therapeutic agent, may be formulated with an appropriate solid or liquid carrier, depending upon the particular mode of administration chosen. Additional active ingredients include, for example, nitric oxide donors, nitrovasodilators, activators of the enzyme soluble guanylyl cyclase, or cGMP phosphodiesterase inhibitors.

A suitable administration format may best be determined by a medical practitioner for each subject individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.*, 10 (Supp. 42): 2S, 1988.

The dosage form of the pharmaceutical composition will be determined by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intra-articular injection or infusion, or by sublingual, oral, topical, intra-nasal, ophthalmic, or transmucosal administration, or by pulmonary inhalation. When the active compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or depot slow release preparation may be used so that therapeutically effective amounts of the preparation are delivered into the bloodstream over many hours or days following transdermal injection or delivery.

Active compounds (e.g., peptides, proteins, antibodies or fragments thereof, oligos, and so forth) are also suitably administered by sustained-release systems. Suitable examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of the therapeutic agent(s) (e.g., peptides, antibodies, oligonucleotides or other compounds that block CD47 and/or TSP1 activity or interaction). For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, therapeutic agent(s) are delivered by way of a pump (see Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution may also be employed. The key factor in selecting an appropriate dose is the result obtained, as measured by increases or decreases in angiogenesis, or by other criteria for measuring control or prevention of disease, as are deemed appropriate by the practitioner. Other controlled release systems are discussed in the review by Langer (Science 249:1527-1533, 1990).

In another aspect of the disclosure, therapeutic agent(s) are delivered by way of an implanted pump, described, for example, in U.S. Pat. Nos. 6,436,091; 5,939,380; and 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with therapeutic agent(s) at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

The therapeutic agents may also be delivered passively and in sustained fashion as part of and incorporated into implantable devices, such as vascular stents which can be placed directly into diseased blood vessels through several standard approaches, including direct surgical insertion or percutaneoulsy with angiographic control.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds can be, for example, mixed with a liquid delivery agent for administration locally. The agents used therapeutically (such as peptides, antibodies and morpholinos) are readily soluble or suspendable in water and saline, and as such these would be useful for delivery since water or saline do not cause adverse biological tissue effects. This allows sufficiently high doses to be administered locally or systemically, without secondary toxicity from the delivery vehicle.

By way of example, in the treatment of burns agents can be given by direct injection into the wound bed or topically dissolved in saline as a spray to the burn area, to skin grafts and/or to graft wound beds. They may also be mixed directly into antibiotic creams used to treat burns, such as bacitracin or silver sulfadine, or incorporated in a manner allowing release into dressing and bandaging materials applied to wounds, grafts or burns.

Pharmaceutical compositions that comprise at least one therapeutic agent as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, therapeutic agent(s) can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the therapeutic agent(s) each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise at least one therapeutic agent, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of therapeutic agent, such as a peptide, antibody, or oligonucleotide (e.g., morpholino or other antisense molecule) will be dependent on the peptide or inhibitor utilized, the subject being treated, the severity and type of the affliction, and the manner of administration. The exact dose is readily determined by one of skill in the art based on the potency of the specific compound, the age, weight, sex and physiological condition of the subject.

The peptides/proteins of the present disclosure (for example, CD47 or TSP1 peptides, or a peptide that inhibits or alters binding between TSP1 and CD47) also can be administered as naked DNA encoding the peptide. To simplify the manipulation and handling of the nucleic acid encoding the peptide, the nucleic acid is generally inserted into a cassette, where it is operably linked to a promoter. Preferably, the promoter is capable of driving expression of the protein in cells of the desired target tissue. The selection of appropriate promoters can readily be accomplished. Preferably, the promoter is a high expression promoter, for example the 763-base-pair cytomegalovirus (CMV) promoter, the Rous sarcoma virus (RSV) promoter (Davis et al., *Hum. Gene. Ther.* 4:151, 1993), or the MMT promoter.

Other elements that enhance expression also can be included, such as an enhancer or a system that results in high levels of expression, such as a tat gene or tar element. This cassette is inserted into a vector, for example, a plasmid vector such as pUC 118, pBR322, or other known plasmid vector, that includes, for example, an *E. coli* origin of replication. See, Sambrook, et al., *Molecular Cloning: A Laboratory Manual*, Cold Spring Harbor Laboratory Press (1989). The plasmid vector may also include a selectable marker such as the 1-lactamase gene for ampicillin resistance, provided that the marker polypeptide does not adversely affect the metabolism of the organism being treated. The cassette also can be bound to a nucleic acid binding moiety in a synthetic delivery system, such as the system disclosed in PCT publication WO 95/22618.

Optionally, the DNA may be used with a microdelivery vehicle such as cationic liposomes and adenoviral vectors. (For a review of the procedures for liposome preparation, targeting and delivery of contents, see Mannino & Gould-Fogerite, *BioTechniques,* 6:682, 1988; Feigner & Holm, *Bethesda Res. Lab. Focus,* 11(2):21, 1989); and Maurer, *Bethesda Res. Lab. Focus,* 11(2):25, 1989.) Replication-defective recombinant adenoviral vectors can be produced in accordance with known techniques. (See Quantin et al., *Proc. Natl. Acad. Sci. USA,* 89:2581-2584, 1992; Stratford-Perricadet et al., *J. Clin. Invest.,* 90:626-630, 1992; and Rosenfeld et al., *Cell,* 68:143-155, 1992).

In order to facilitate injection, the nucleic acid is formulated with a pharmaceutically acceptable carrier. Examples of suitable carriers include, but are not limited to, saline, albumin, dextrose and sterile water. The nucleic acid is injected into the ischemic tissue using standard injection techniques by use of, for example, a hypodermic needle, for example a hypodermic needle size between No. 29 and No. 16. The nucleic acid also may be injected by an externally applied local injection apparatus, such as that used to inject antigens for allergy testing; or a transcutaneous patch capable of delivery to subcutaneous muscle. The nucleic acid is injected at one site, or at multiple sites throughout the ischemic tissue.

Once injected, the nucleic acid capable of expressing the desired angiogenic protein is taken up and expressed by the cells of the tissue. Because the vectors containing the nucleic acid of interest are not normally incorporated into the genome of the cells, expression of the protein of interest takes place for only a limited time. Typically, the angiogenic protein is only expressed in therapeutic levels for about two days to several weeks, preferably for about one to two weeks. Reinjection of the DNA can be utilized to provide additional periods of expression of the angiogenic protein. If desired, use of a retrovirus vector to incorporate the heterologous DNA into the genome of the cells will increase the length of time during which the therapeutic polypeptide is expressed, from several weeks to indefinitely.

The therapeutic agents can also be administered directly as part of a surgical procedure, or at the bedside by a treating physician. Drug quality product (e.g., peptide, antibody or morpholino) can be diluted for instance in sterile saline and given by injection using sterile 1 cc syringes and small bore needles (25 gauge and less) to ischemic soft tissue units. Alternatively, a wound bed can be irrigated for instance with a saline or other therapeutically effective solution containing a known concentration (dosage) of drug or compound, or a combination thereof. Precise control and localization of therapeutic effects can thus be obtained.

Controlled release parenteral formulations can be made as implants, oily injections, or as particulate systems. For a broad overview of protein delivery systems, see Banga, *Therapeutic Peptides and Proteins: Formulation, Processing, and Delivery Systems,* Technomic Publishing Company, Inc., Lancaster, Pa., 1995. Particulate systems include microspheres, microparticles, microcapsules, nanocapsules, nanospheres, and nanoparticles. Microcapsules contain the therapeutic peptide as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems,* J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc. New York, N.Y., pp. 315-339, 1992).

Also contemplated is the use of nanoparticles as delivery agents, which can be targeted to specific cells, tissues or organ for instance by incorporation on their surface ligands of receptors specific in their expression to the targeted cells, tissues or organs, The targeting entity can be the same or different than the therapeutically active agent carried by the nanoparticle. Further, distribution of nanoparticles to certain tissues spaces (e.g. the blood versus the central nervous system protected by the blood-brain barrier) can be determined by altering the size of the nanoparticles thereby allowing or preventing their transit of such barriers between tissue compartments.

Polymers can be used for ion-controlled release. Various degradable and non-degradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of lipid-capsulated compounds (Betageri et al., *Liposome Drug Delivery Systems,* Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

IX. Kits

Also disclosed herein are kits that can be used to induce differentiation in CSCs in vivo or in cells in culture. In some embodiments, the kit includes one or more agent that alters CD47 signaling to induce CSC differentiation, such as one or more of an anti-CD47 antibody or fragment thereof, a CD47-binding peptide, a CD47 antisense oligonucleotide, a CD47 morpholino. In other embodiments, the kit includes a small molecule capable of binding to CD47.

In another example, the kit includes an anti-CD47 antibody or fragment thereof, such as monoclonal antibody B6H12 or a humanized B6H12. By way of example, humanized versions of B6H12 are taught in International Patent Publication No. WO 2011/143624, which is incorporated by reference in its entirety.

The kits may further include additional components such as instructional materials and additional reagents, for example cell culture medium (such as growth medium or differentiation medium) for one or more cell types. The kits may also include additional components to facilitate the particular application for which the kit is designed (for example tissue culture plates). The instructional materials may be written, in an electronic form (such as a computer diskette or compact disk), or may be visual (such as video files).

The following examples are provided to illustrate certain particular features and/or embodiments. These examples should not be construed to limit the invention to the particular features or embodiments described.

EXAMPLES

Example 1: Characterization of bCSC Phenotype

This example illustrates characterization of the stem cell phenotype of breast cancer stem cells (bCSC) isolated from cultures of the human triple negative breast carcinoma cell line MDA-MB-231.

The bCSC are enriched in nonadherent fractions of parental MDA-MB-231 cells and were further purified for some experiments by flow sorting for CD44hi/CD24lo cells. The bCSC exhibit increased asymmetric cell division characteristic of stem cells (FIG. 1). The bCSCs also exhibit abilities to differentiate along several lineages including neuronal and vascular (FIGS. 2, 3 and 4).

Figure 8:
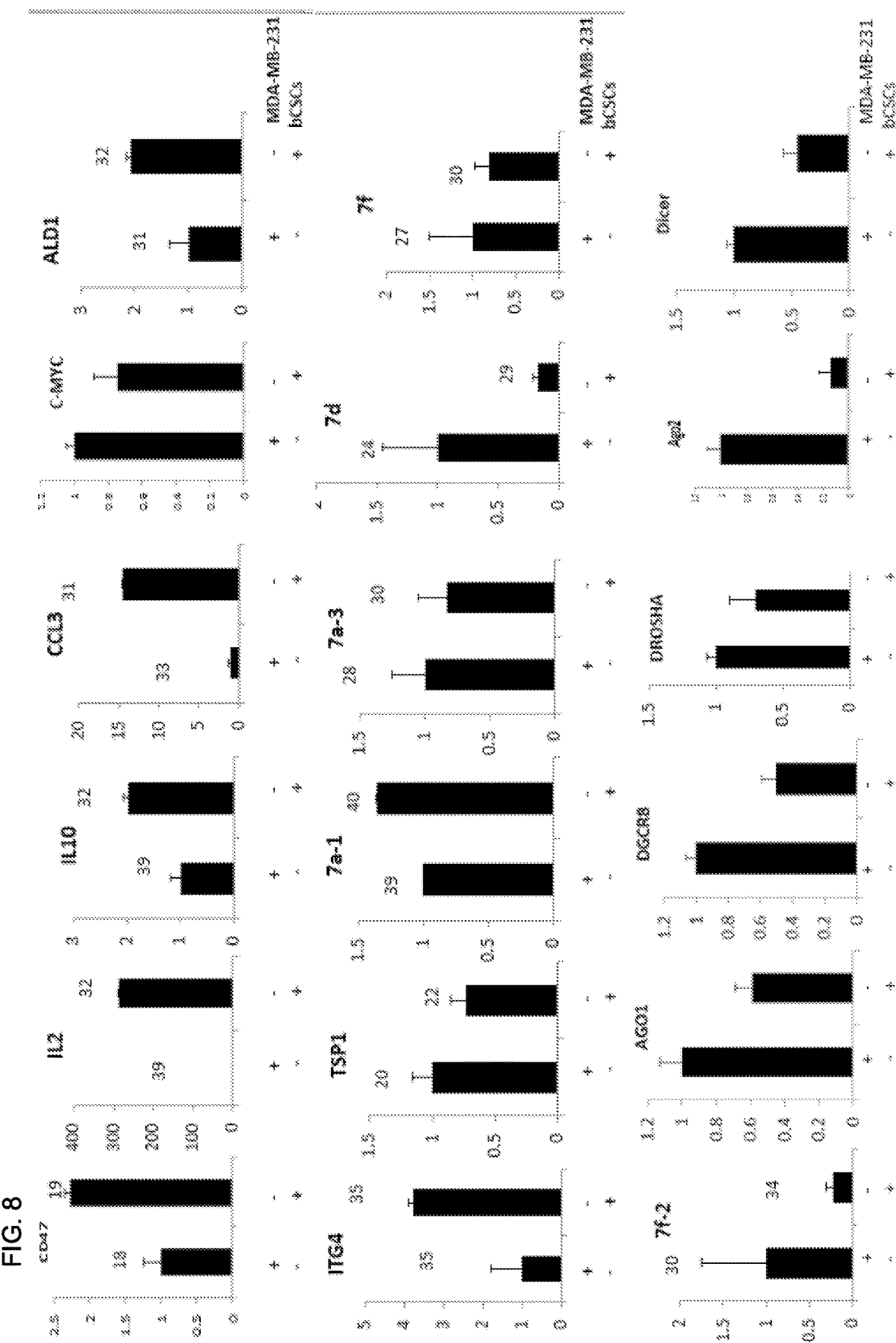
FIG. 8. Relative gene expression between CD47, IL2, IL10, CCL3, c-MYC, ALDI, ITG4, TSP1, 7a-1, 7a-3, 7d, 7f, 7f-2, AGO1, DGCR8, DROSHA, AGO2, DICER were analyzed using control actin primer. The Ct value of actin for MDA-MB-231 (12) and for bCSCs (14) respectively.

The bCSC exhibit elevated mRNA and protein expression of the bCSC marker CD44 and characteristic decreased expression of CD24 (FIGS. 5, 6). They also exhibit elevated expression of the stem cell transcription factor Sox2 and the stem cell markers nestin and PTP-BP1 (FIG. 5), but not the pluripotency marker Nanog. Upon addition of differentiating growth factors, the elevated stem cell marker expression is reversed. Global transcriptome analysis and qRT-PCR confirmed altered CD24 expression and identified additional changes in gene expression in MDA-MB-231 bCSC (FIGS. 7, 8). CD47 expression is elevated in the bCSC, consistent with published reports of elevated CD47 expression in other CSC, but expression of the CD47 ligand thrombospondin-1 (TSP1) is decreased.

Example 2: Differentiation of bCSCs Through CD47 Blockade Using B6H12

The CD47-blocking antibody B6H12 is known to inhibit binding of CD47 to its counter-receptor SIRPα on phagocytic cells, including macrophages. Consequently, this blocking antibody is known to increase in vitro killing of tumor cells by macrophages or NK cells. Based on these observations, others have proposed that the ability of B6H12 to inhibit the growth of various human tumor xenografts grown in Nod.SCID mice, which express a mutant murine SIRPα that can recognize human CD47, results from blocking the "don't eat me" signal of the human tumor cell CD47 engaging Nod.SIRPα on the mouse macrophages. However, we have discovered a potent cell-autonomous activity of the same CD47 antibody that directly suppresses the viability of human breast cancer stem cells.

Treatment of unfractionated MDA-MB-231 cells with B6H12 results in rapid loss of rounded non-adherent cells from the culture (FIG. 6A). Isolated bCSC from the same cell line also rapidly adopt a flattened morphology and stop proliferating when treated with B6H1, but not with an isotype-matched control antibody (FIG. 6B). Microarray analysis and qRT-PCR demonstrated reversal by B6H12 of many of the gene expression changes in bCSCs but not by the control antibody (FIGS. 10, 11).

Figure 12A:
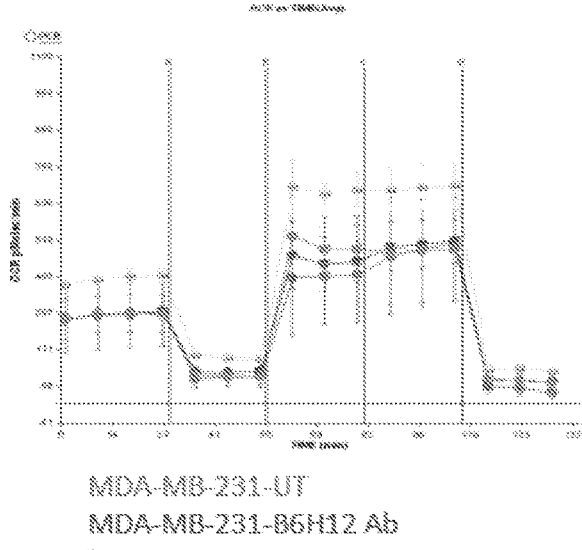
Figure 12B:
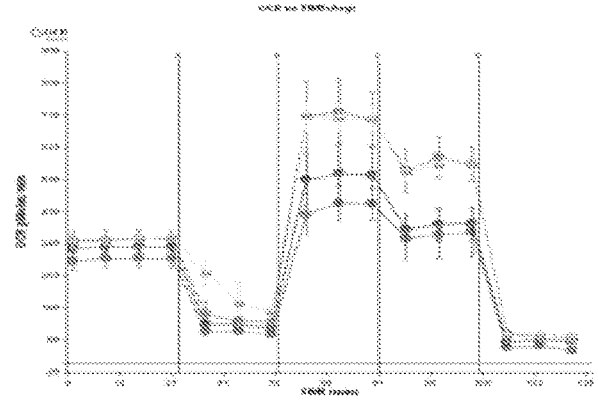
Figure 12C:
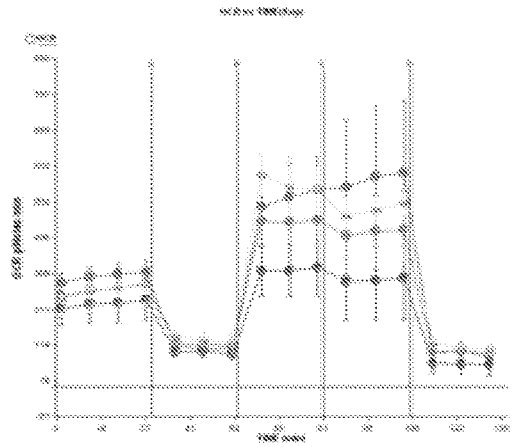
Figure 12D:
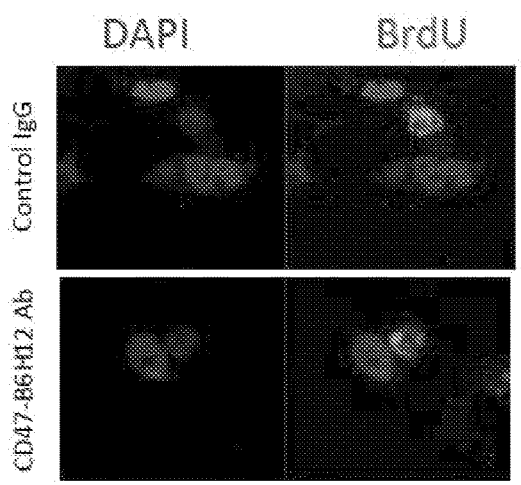

To define the mechanism by which the CD47 antibody B6H12 directly inhibits bCSC, we examined effects on energy metabolism using the Seahorse Analyzer (FIGS. 12A-12C). B6H12 increased the basal oxygen consumption rate (OCR) at day 1 and day 3 but this was lost at day 4, when both the basal and spare metabolic capacity were decreased. The CD47 ligand TSP1 had less effect than the CD47 antibody. B6H12 decreased asymmetric division and proliferation measured by the MTS assay (FIGS. 12D-12F).

Figure 14A:
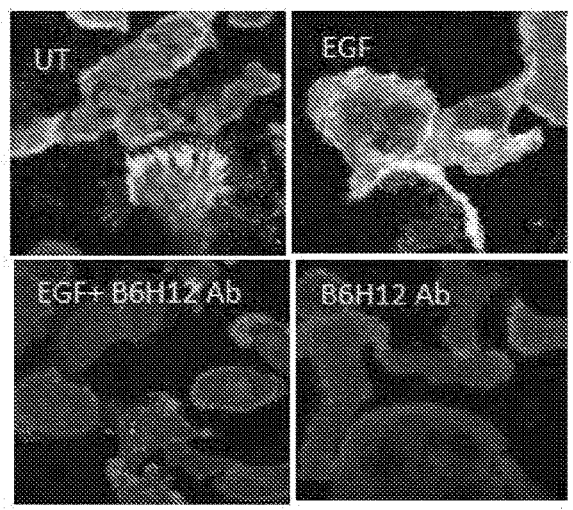
FIG. 14A-14D show that B6H12-antibody disrupts the association between EGFR and CD47 and inhibits EGFR phosphorylation at $Y^{1068}$ in bCSCs.
Figure 14B:
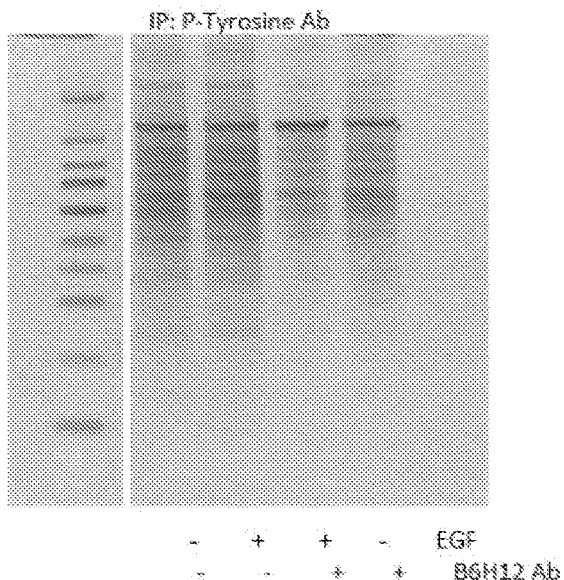
Figure 14C:
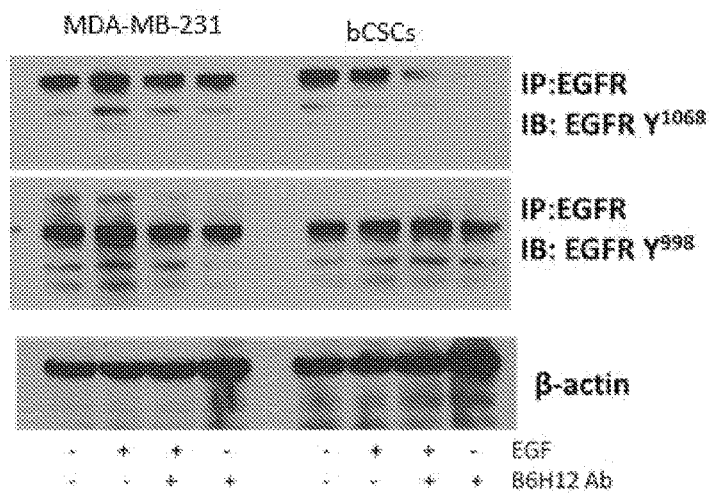
Figure 14D:
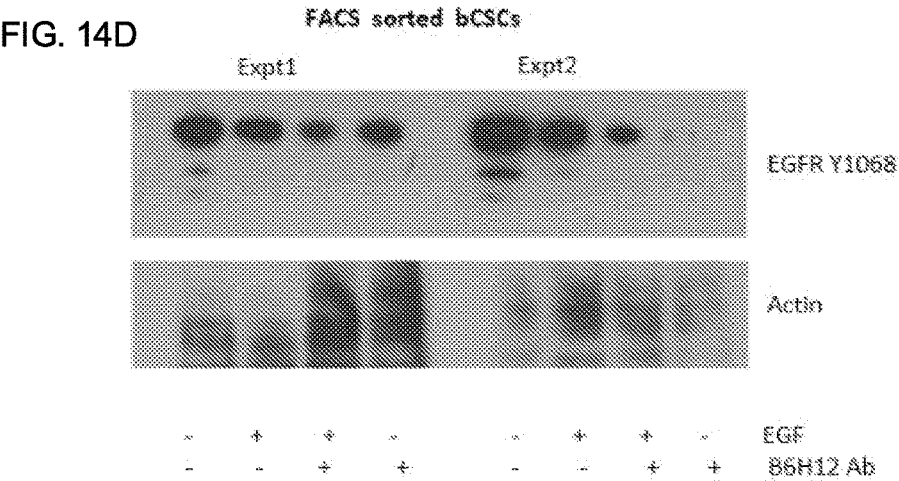
Figure 15A:
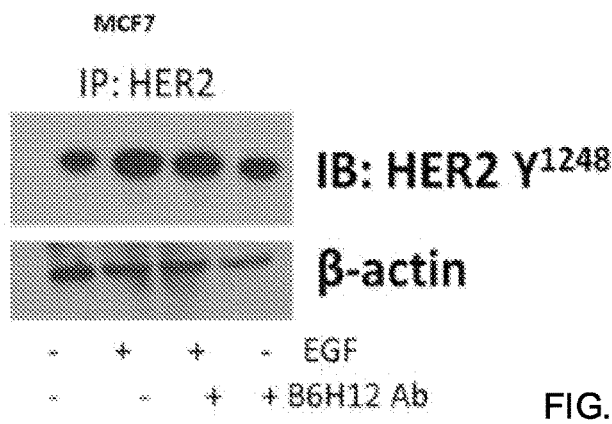
FIG. 15A-15D show that B6H12-Ab inhibits cell proliferation but not HER2 phosphorylation in ER+ breast cancer cells.
Figure 15B:
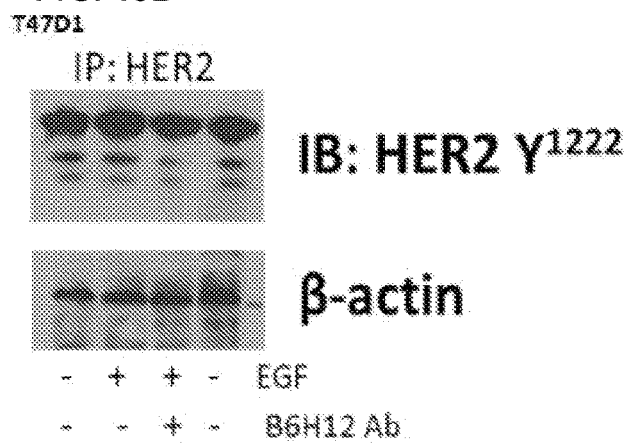
Figure 15C:
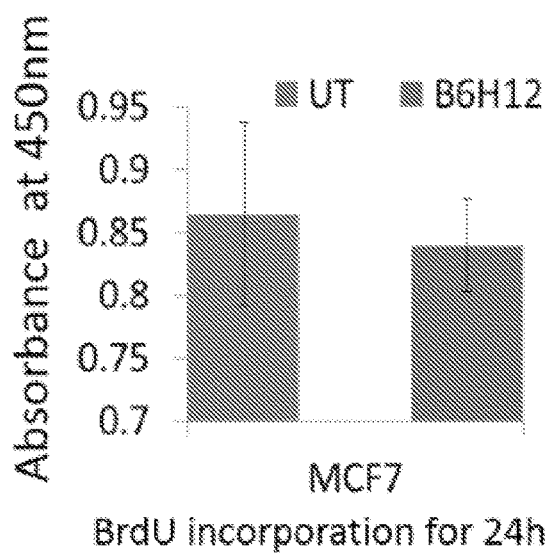
Figure 15D:
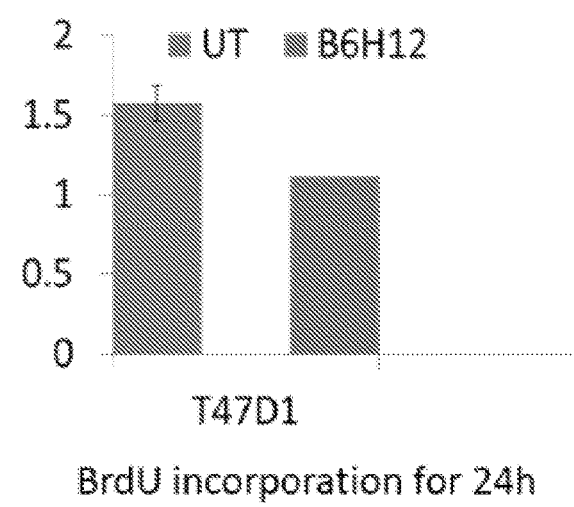

Based on our recently published discovery that CD47 associates with and regulates the tyrosine kinase receptor VEGFR2 in endothelial cells and T lymphocytes, and our previously published finding that TSP1 synergized with EGF to inhibit growth of small cell lung carcinoma cells, we considered the possibility that CD47 may also regulate EGFR signaling in bCSC, and this could be a mechanism through which the CD47 antibody B6H12 inhibits bCSC. EGF and EGFR both showed moderately elevated mRNA expression in bCSC relative to control MDA-MB-231 cells (FIGS. 13A, 13B). Remarkably, treatment of the bCSC with B6H12 alone or in the presence of EGF dramatically reduced expression of both EGF and EGFR (FIG. 13C). The control IgG was inactive, and B6H12 did not alter the same mRNAs on differentiated MDA-MB-231 cells or in the ER+ breast carcinoma cell lines MCF7 or T47D (FIG. 17). At the protein level, B6H12 suppressed global tyrosine phosphorylation of proteins either in the absence or presence of RGF (FIG. 14B) and preferentially inhibited EGFR phosphorylation at Y1068 but not Y998 in bCSC but not in control MDA-MB-231 cells (FIG. 14C, 14D).

The EGFR family member HER2 is not expressed well in the triple negative cell line MDA-MB-231, so we used the Her2+ cell lines MCF7 and T47D to examine the specificity of B6H12 effects on EGFR signaling (FIG. 15). B6H12 also inhibited proliferation of these cell lines, but this was not accompanied by inhibition of HER2 phosphorylation. Unlike EGFR, Her2 showed no colocalization with CD47 in these cell lines (FIG. 16). In the MDA-MB-231 bCSCs, CD47 co-immunoprecipitated with EGFR, and preincubation with B6H12 decreased the cell surface expression of EGFR (FIG. 16D). Reduced expression of EGFR after B6H12 treatment is associated with exosome shedding of EGFR (FIG. 16E) and K63 ubiquitinylation of EGFR (FIG. 16F).

In contrast to the SIRPα-dependent role of CD47 in tumor innate immunity, the three SIRP genes are poorly expressed in breast cancer cells, and B6H12 did not affect their expression (FIG. 17).

Based on these data, we propose a novel mechanism of anti-tumor action for certain CD47 antibodies, including those based on B6H12 that have been recently humanized and are expected to soon enter clinical trials for treating cancer patients (Edris et al., Proc Natl Acad Sci USA. 109(17):6656-6661, 2012). Our data demonstrates that these antibodies directly act on human breast cancer cells to suppress bCSC, and our preliminary results suggest that this finding will generalize to other cancers that express elevated levels of CD47. Because elevated CD47 expression is a negative prognostic factor for many major human cancers, certain CD47 antibodies may generally exhibit direct tumor suppressive activity independent of the proposed indirect macrophage-dependent mechanism. This discovery is an extension of but not predictable from our recent discovery that CD47 regulates stem cell self-renewal and reprogramming in healthy tissues (see, e.g., PCT publication WO 2013/155109, incorporated herein by reference in its entirety). We demonstrate here a direct signaling function of CD47 on CSC that sustains their stem cell properties. This contrasts with the signaling by CD47 in normal stem cells, where it limits their self-renewal. More importantly, we demonstrate that ligation of CD47 with antibodies has the potential to suppress CSC and thereby stop cancer growth.

Example 3: Differentiation of Additional CSCs Through CD47 Blockade

Targeting new cancer therapies to cancer stem cells is very challenging because many of the tumor suppressor and polycomb genes (Hedgehog and WNT signaling pathway) that are important for normal stem cell regulation are dysregulated during carcinogenesis. The ubiquitous cell surface protein CD47 is up-regulated in many cancers, especially during metastasis, and high expression is a negative prognostic indicator for several cancers. Additional studies have indicated that CD47 expression is elevated in leukemic cancer stem cells. The conventional wisdom has been that the function of this elevated CD47 expression on CSC is to serve as a "don't eat me" signal that protects the CSC from phagocytic clearance by macrophages (reported online at news.sciencemag.org/health/2012/03/one-drug-shrink-all-tumors). Consequently, antibody and ligand therapeutics that engage CD47 have been developed to stimulate the destruction of CSC by macrophages, and these are now entering human clinical trials.

The CD47 antibody B6H12 is known to block the recognition of CD47 by its counter-receptor SIRPα on macrophages. Human tumor xenografts grown in immunodeficient mice that express a mutant form of SIRPα that is capable of binding human CD47 (Nod-SCID) have been used to test the ability of B6H12 to enhance macrophage-mediated clearance of human tumor xenografts. Inhibition of tumor growth by B6H12 in these models provided evidence to support the humanization of such CD47 antibodies for treating human cancer patients.

The central assumption for developing such antibody-based therapies is that CD47 is a passive cell surface protein that serves only to protect CSC from host innate immune surveillance. However, our recent work has revealed that expression of CD47 in non-transformed cells plays a critical role in regulating stem cell homeostasis. Specifically, CD47 signaling inhibits the expression of the Yamanaka transcription factors cMyc, Sox2, Oct3/4 and Klf4. Decreasing CD47 in non-transformed cells increases their self-renewal, asymmetric division and ability to reprogram into other differentiated cell types.

Figure 18A:
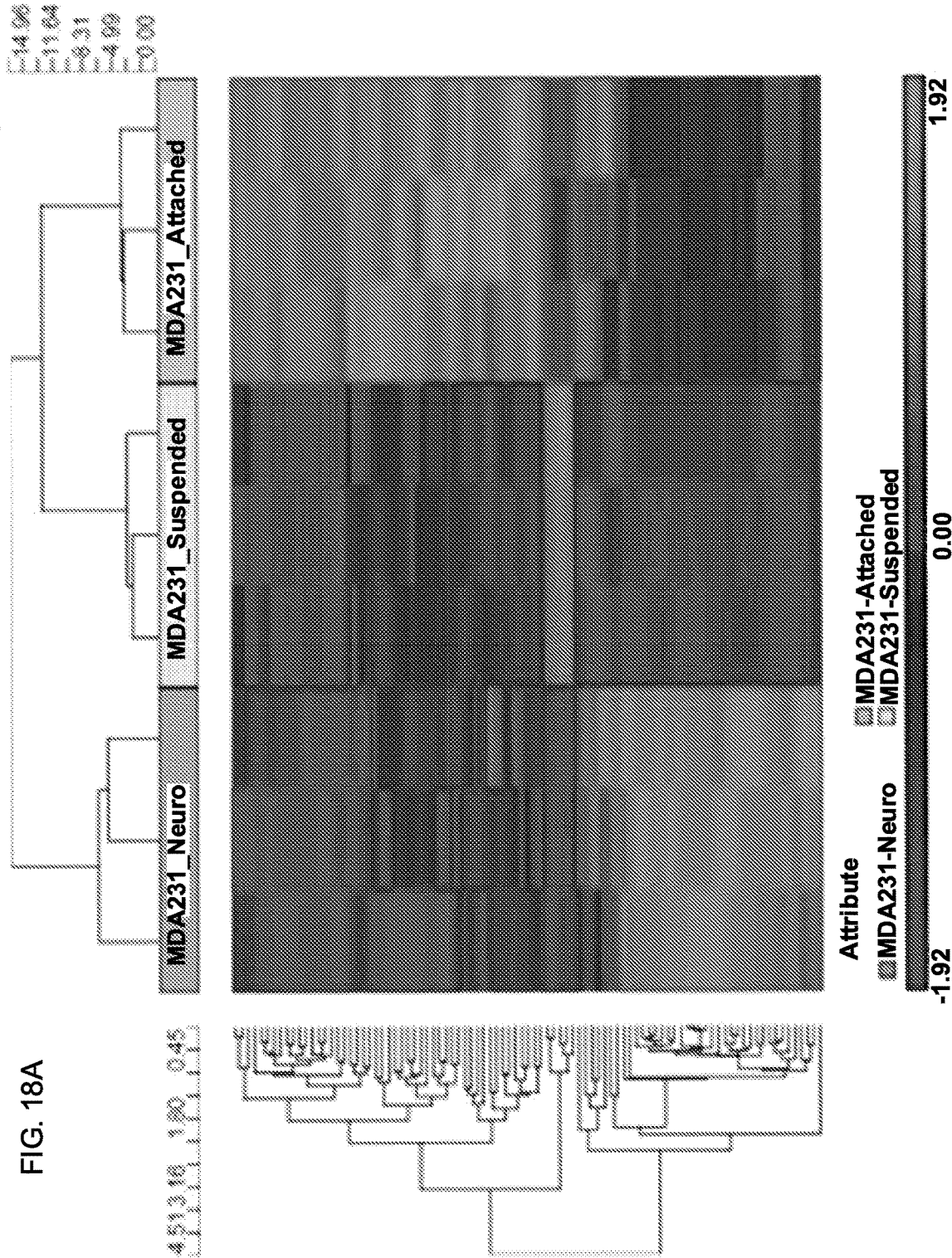
FIG. 18A-18D show that bCSCs differentiated into neural linage exhibit mammospheres and EMT gene enrichment.
Figure 18B:
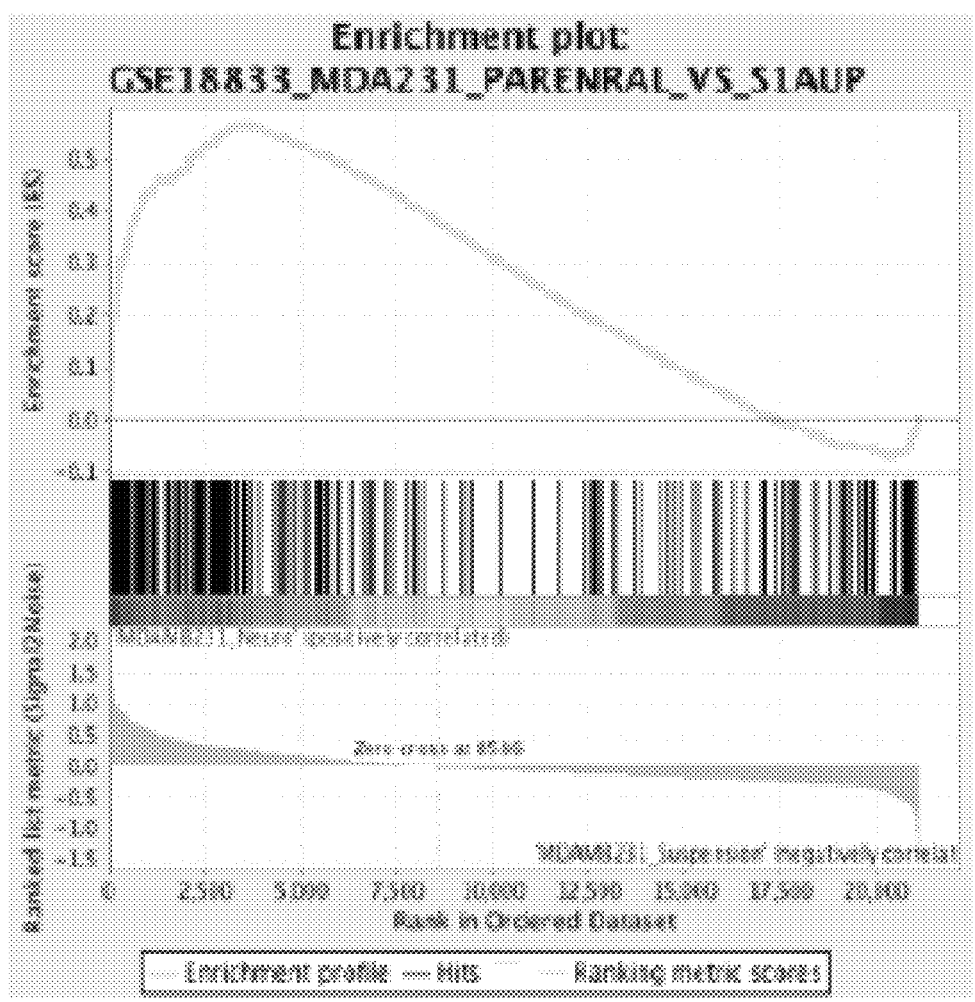
Figure 18C:
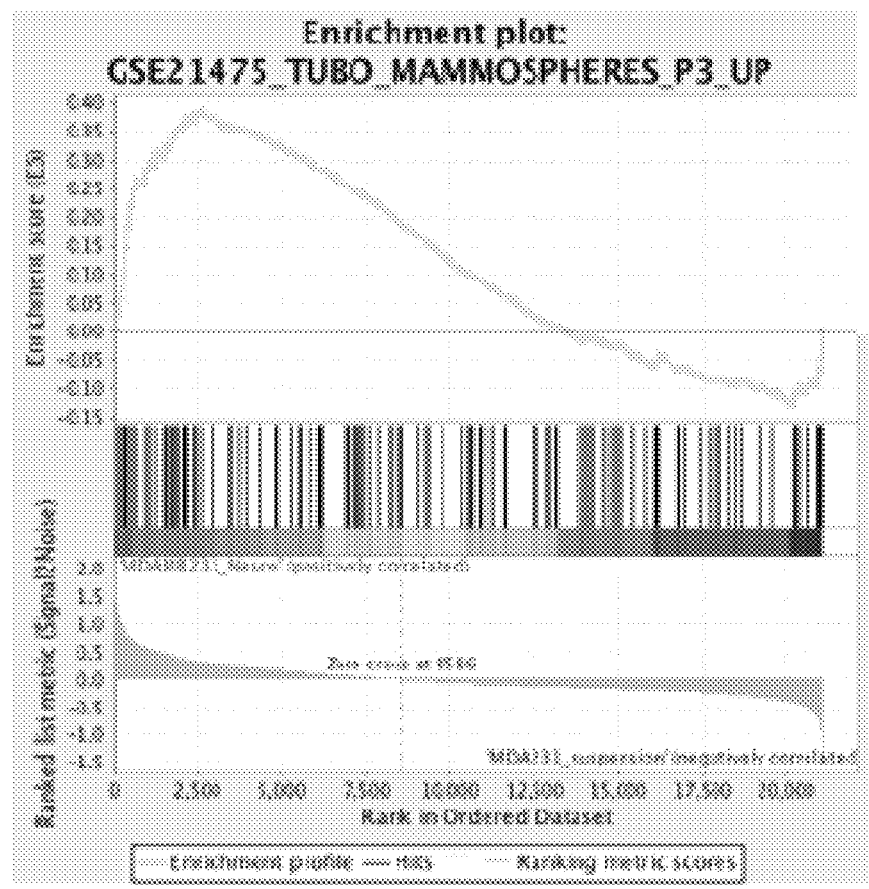
Figure 18D:
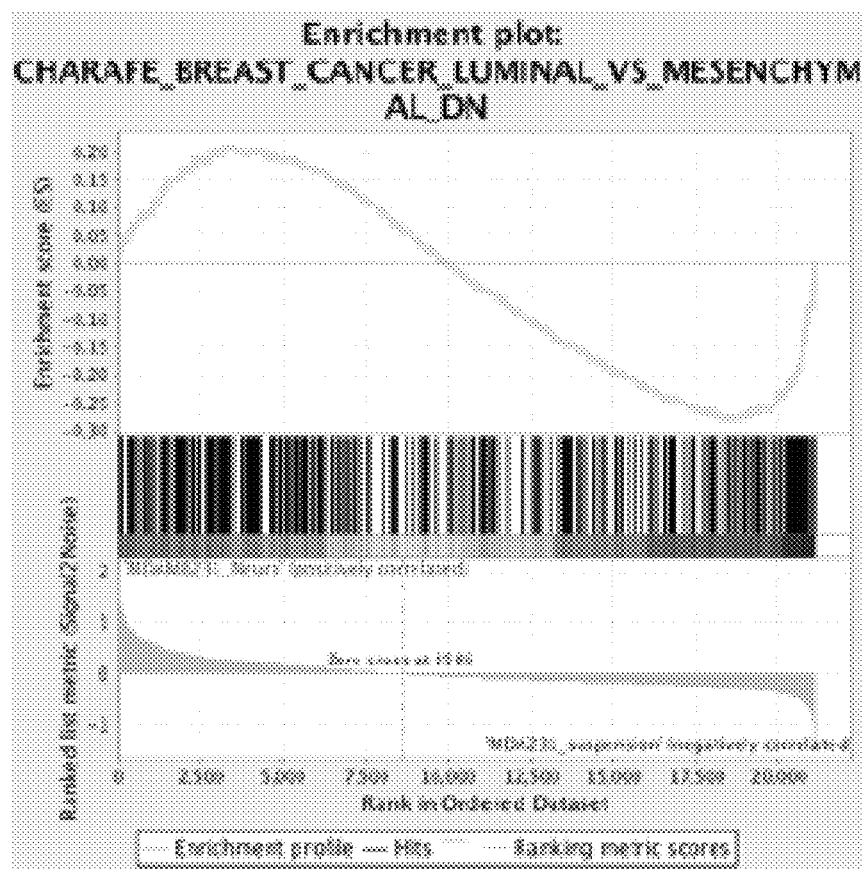

Because high CD47 expression limits the stem cell character of non-transformed cells, the high expression of CD47 on cancer stem cells seemed paradoxical. This suggested that the CD47 expressed on CSC may lack the signaling activity to control stem cell self-renewal, either due to alterations in the CD47 or inactivation of genes that mediate its signaling in CSC. However, to date the signaling function of CD47 in CSC has not been examined. Therefore, we isolated CSC and cells depleted of CSC from the triple-negative breast carcinoma cell line MDA-MB-231 and examined the effects of ligating CD47 on these cells when treated with the CD47 antibody B6H12.

bCSCs were isolated and differentiated similar to FIG. 2D-F. bCSCs were cultured using neural differentiation media for 36 h. Total RNA was extracted using TriZol method and global microarray analysis was performed. FIG. 18A shows comparison between differentiated neural lineage bCSCs vs. differentiated MDA-MB-231 or bCSCs; FIG. 18B-18D show gene enrichment of bCSCs differentiated into neural lineage using published Geo sets data's (GSE21475_TUBO_MAMMOSPHERES; GSE18833_MDA231_PARENRAL_VS_S1) and CHARAFE_BREAST_CANCER_LUMINAL_VS_BASAL_DN (Charafe-Jauffret et al., *Oncogene.* 25(15):2273-2284, 2006). These molecular characteristics analyses of differentiated neural lineage cancer cells showed enrichment of genes related with mammosphere formation, epithelial mesenchymal transition and tumorigenesis. We further compared gene enrichment analysis to committed neural lineage or neural cells or parts of brain region, none of these markers show any enrichment of neural biomarkers. This indicates that bCSCs derived from neural linage differentiated MDA-MB-231 cells are tumorigenic and cancerous cells.

Figure 19A:
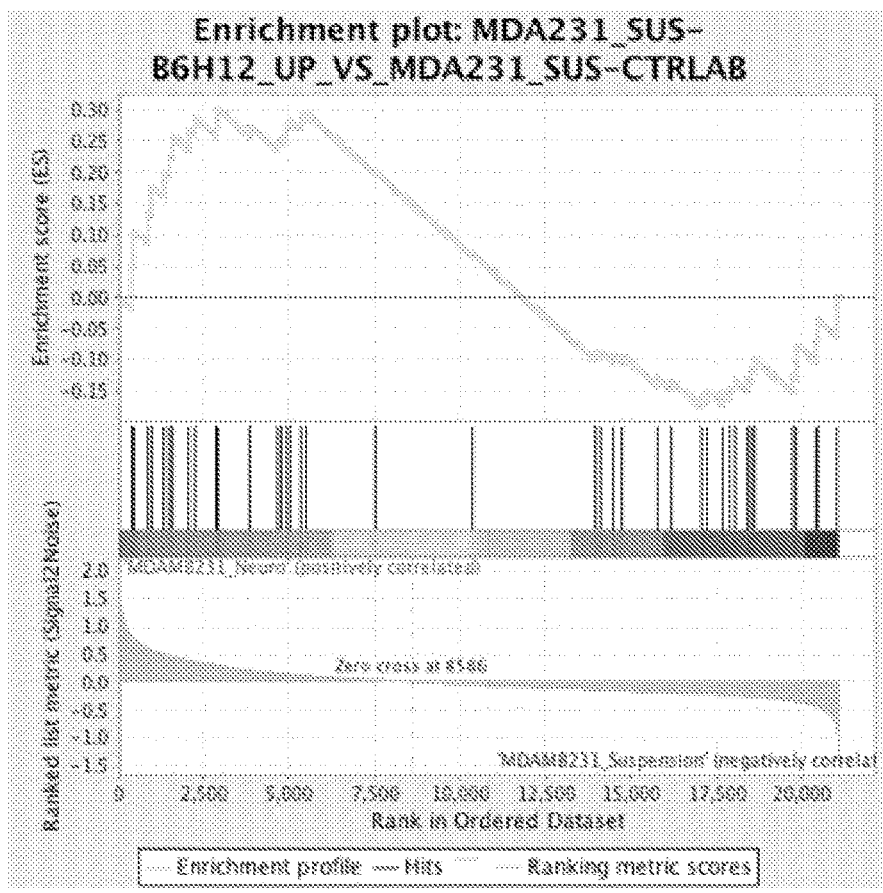
FIG. 19A-19B illustrates that CD47-B6H12 antibody does not show similar enrichment to MDA231 differentiated or cancer stem cells.

Microarray global expression data showed that treating CSC isolated from the MDA-MB-231 cell line with the CD47 blocking antibody B6H12 down regulated EGFR and up regulated Dicer 1 and many more genes (Table 1). In Table 1, a blank gene (---) symbol indicates that gene has not been annotated in genome/gene bank but the probe sequences are hybridizing to an expressed sequence tag (EST). Dicer 1 cleaves double stranded and pre-micro RNA into short stranded RNA and miRNA. Decreased dicer level correlates with advanced tumor stages and poor survival and outcomes. In addition to this, B6H12 up regulated CDC14 (cell division cycle 14 homolog B, *S. cerevisiae*), which regulates CDK1 activity at the G2/M transition. The CD47 blocking antibody also up-regulated MOB kinase activator 1A, which is known as a tumor suppressor that controls cell proliferation and apoptosis. Our gene enrichment analysis (FIG. 19A) also suggested that CD47-B6H12 blocking antibody does not enrich the expression of genes related with tumorigenesis. These studies clearly establish that CD47 is functional signaling receptor in breast CSC and suggested that B6H12 may directly inhibit the tumorigenic potential of breast CSC.

Figure 20A:
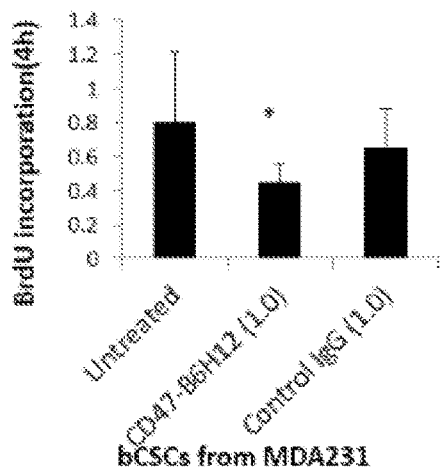
FIG. 20A-20D illustrates that the anti-CD47 antibody B6H12 inhibits cell proliferation of certain types of breast cancer cell lines.
Figure 22A:
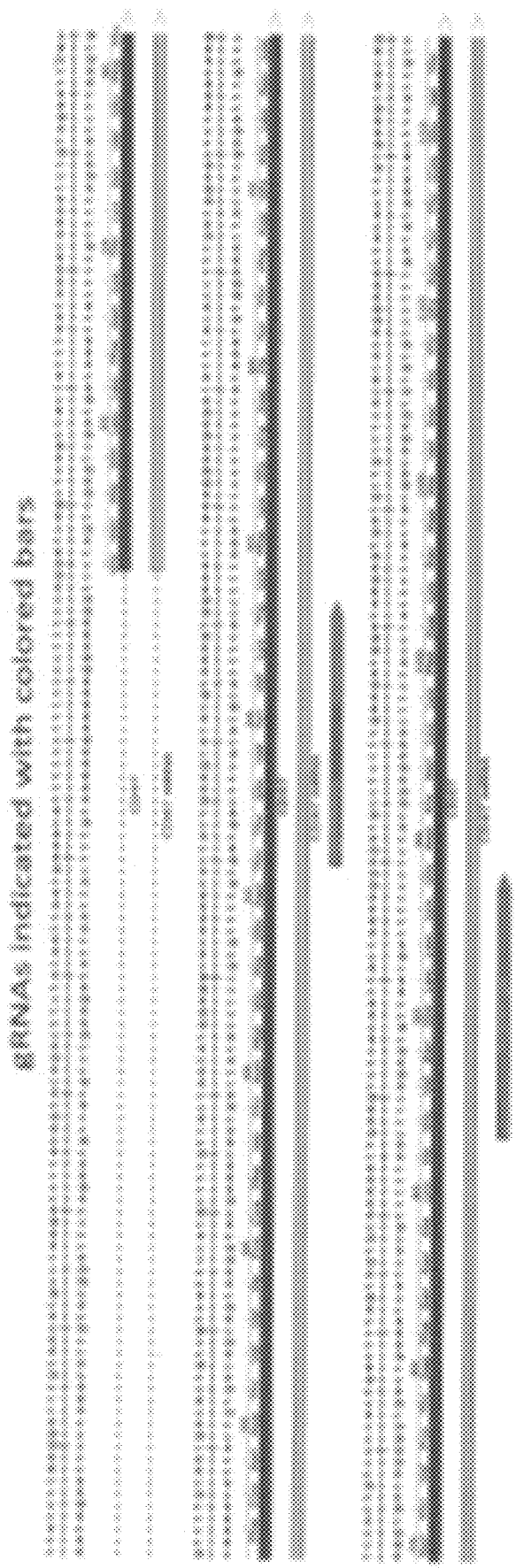
FIG. 22A-22C illustrates that CD47 targeted CRISPR inhibits cell proliferation of bCSCs derived from MDA-MB-231.
Figure 22B:
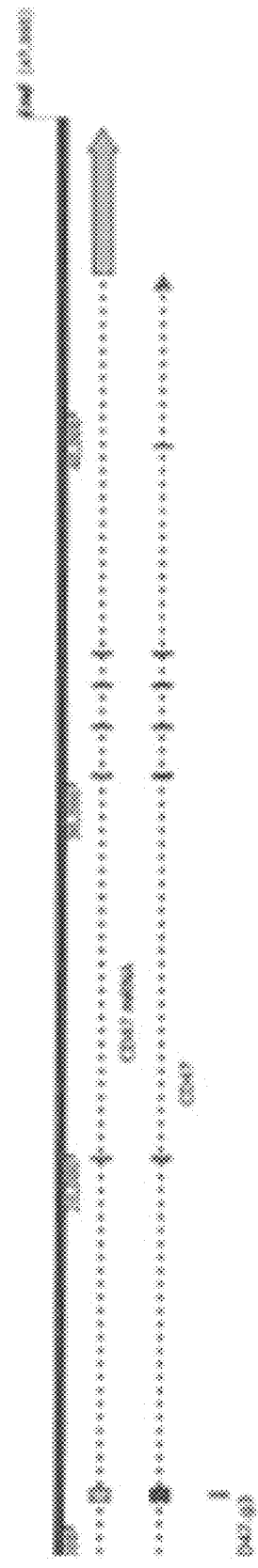
Figure 22C:
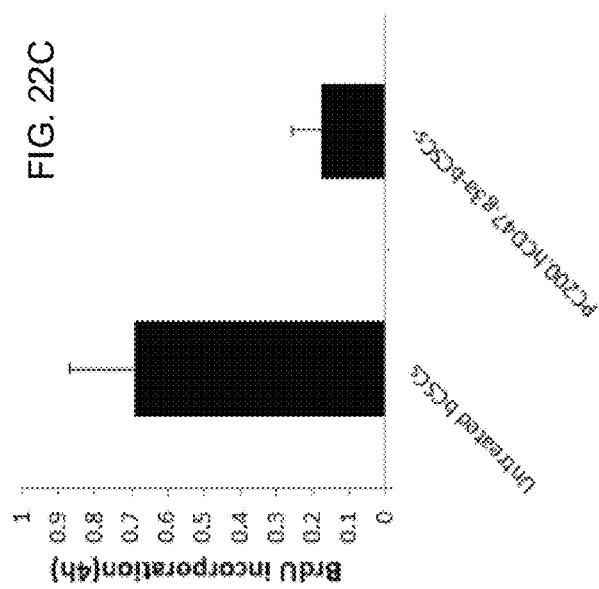
Figure 23:
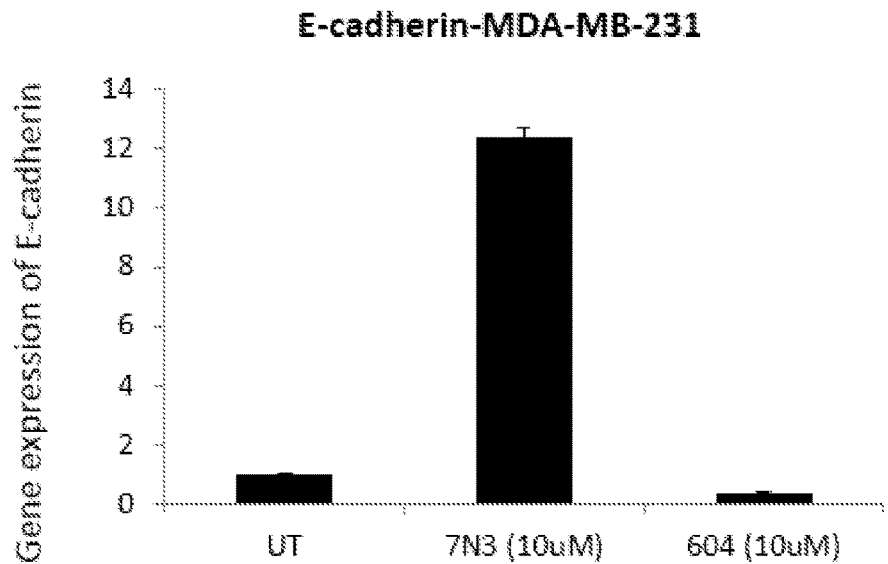
FIG. 23 is a bar graph showing that 7N3 peptide increase mRNA expression of E-cadherin.

To assess the effect of B6H12 on CSC proliferation, bCSC from MDA-MB-231 cells were treated with B6H12 or an isotype-matched control antibody, and proliferation was assessed by bromodeoxyuridine (BrdU) incorporation (FIG. 20A). B6H12 significantly inhibited DNA synthesis, but the control antibody was inactive. This indicated that ligation of CD47 by B6H12 initiates an anti-proliferative signal in bCSC, but it remained unclear whether CD47 expression on bCSC positively regulates their growth or, as we demonstrated on non-transformed stem cells, is a negative regulator of stem cell function. We addressed this question by using a CRISPR vector (based on pX330-U6-Chimeric_BB-CBh-hSpCas9; Cong et al., *Science.* 339(6121):819-23, 2013, PMID: 23287718; sequence and other information available online at addgene.org/42230/) designed to specifically disrupt the CD47 gene in MDA-MB-231 cells (FIGS. 22A and 22B), using the following gRNA targeting sequence: 5' CTACTGAAGTATACGTAAG ngg 3' (PC200.Hcd47.g3a; SEQ ID NO: 2). PC200.Hcd47.g3a was transfected into bCSCs derived from MDA-MB-231 using a NUCLEOFEC-TOR™ kit (Lonza, Switzerland). CD47 negative cells were sorted using FACS analysis. $CD47^{neg}$ bCSCs cells were expanded in culture and cell proliferation was measured using BrdU cell proliferation kit (EMD Millipore). CD47 targeted clone showed diminished BrdU incorporation, indicating that CD47 has the opposite effect on bCSC proliferation as what we reported in normal tissue stem cells (FIG. 22C).

Figure 20B:
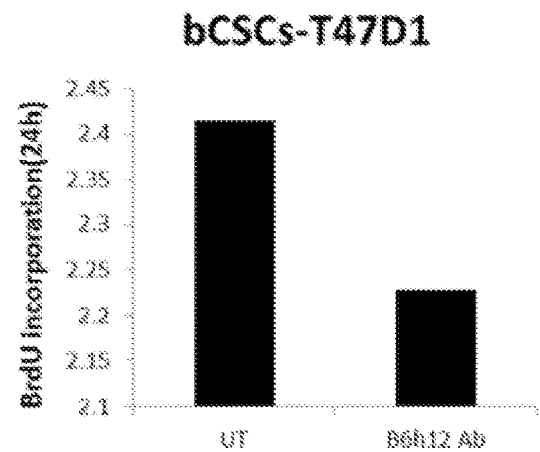
Figure 20C:
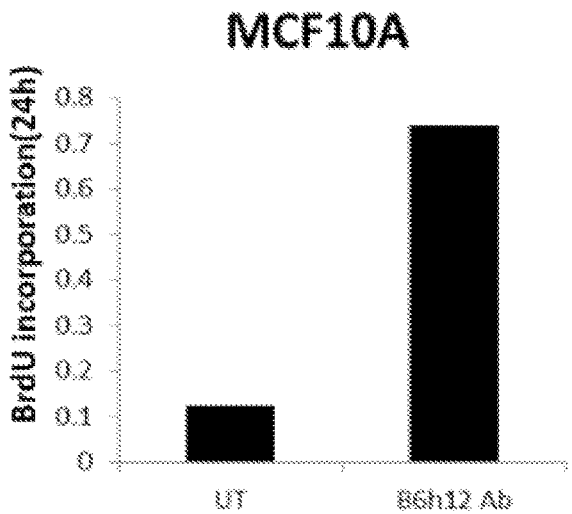
Figure 20D:
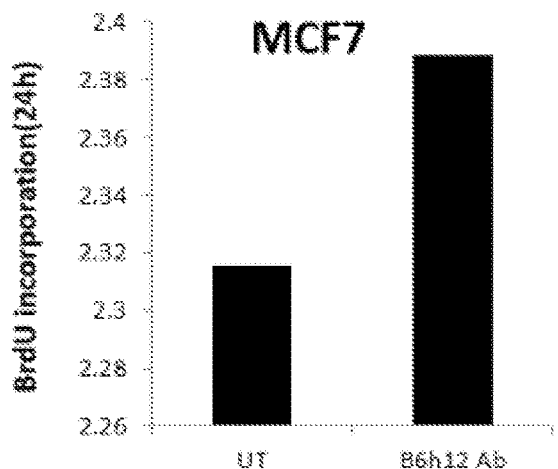

We next examined whether other breast cancer cell lines (MCF-7 and T47D) and a normal immortalized breast epithelial cell line (MCF10A) showed similar responses to B6H12 (FIG. 20B-20D). Consistent with our published studies using lung epithelial cells and T cells, the CD47 blocking antibody B6H12 increased DNA synthesis in MCF10A cells (FIG. 20C). MCF7 is an ER+ well-differentiated breast carcinoma cell line with limited malignant potential and also exhibited a positive response to B6H12 (FIG. 20D). However, the T47D breast carcinoma cell line showed a similar inhibition of proliferation by B6H12 as we found for MDA-MB-231 cells (FIGS. 20A & B).

To determine whether the inhibitory effects of B6H12 were limited to breast cancer cells, we examined proliferation in cell lines from other major human cancers (FIG. 21). The classic small cell lung carcinoma (SCLC) cell line OH-1 showed inhibition by b6H12, and the variant SCLC cell line showed greater inhibition of proliferation assessed by the MTS assay (FIG. 21A). Proliferation of the prostate carcinoma cell line PC-3 was also inhibited by B6H12. Proliferation of the human melanoma cell line A2058 was also inhibited by B6H12, but consistent with the regulation of EGF pathway genes we observed in bCSC, combining B6H12 with EGF reversed the inhibitor effects of both agents (FIG. 21B).

Figure 21A:
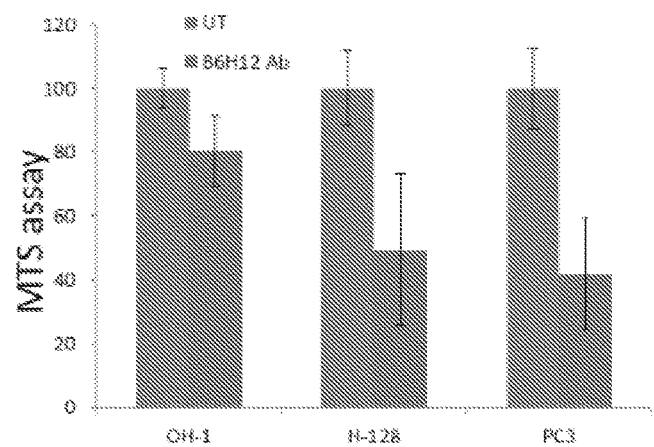
FIG. 21A-21D FIG. 21A) OH-1 (small cell lung cancer cells), H-128 (small cell lung cancer carcinoma) and PC3 (Prostatic adenocarcinoma) cells were plated for 0-72 h. The cell proliferation was performed using CellTiter 96® AQueous Non-Radioactive Cell Proliferation kit from Promega after 72 h.
Figure 21B:
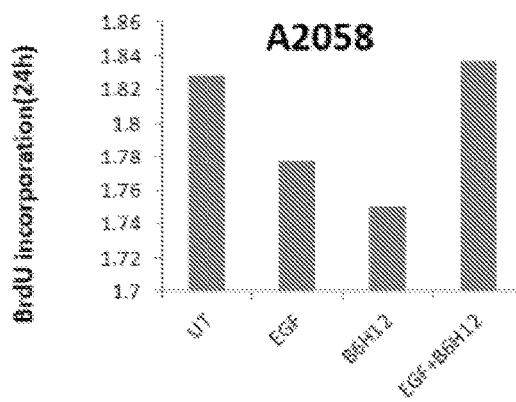
Figure 21C:
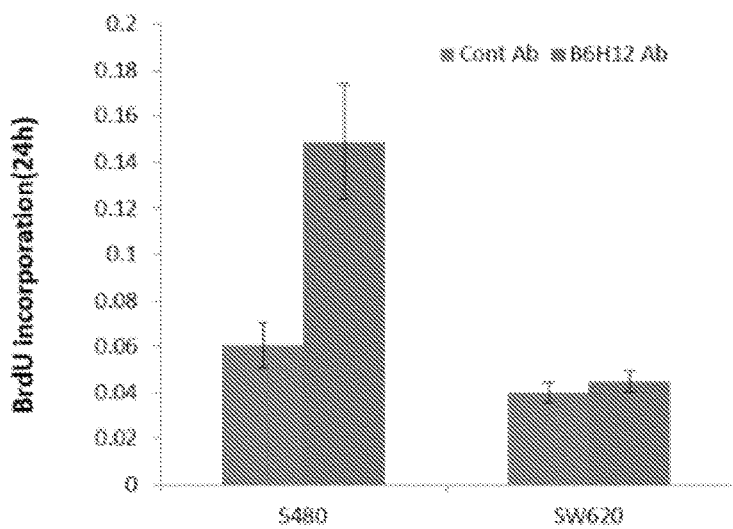
Figure 21D:
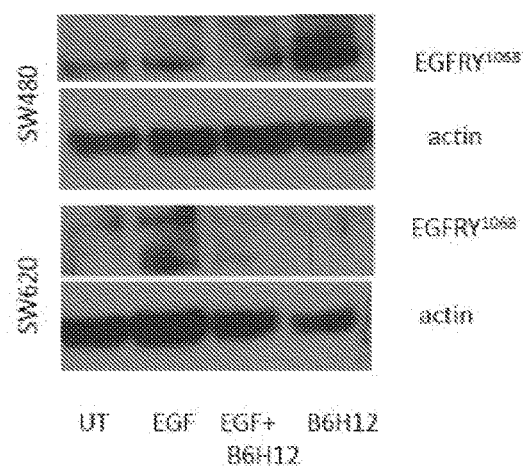

We compared the proliferative responses of metastatic (SW620) and non-metastatic variants of a human colon carcinoma (SW480) to B6H12 (FIG. 21C). B6H12 had a positive effect on SW480 cells but not on SW620. Correspondingly, EGFR phosphorylation in SW480 cells was increased following B6H12 treatment, but EGFR phosphorylation in SW620 cells was inhibited (FIG. 21D). This suggests that binding of B6H12 to CD47 elicits a signal that inhibits EGF signaling only in the more metastatic cell line.

In summary, these data demonstrate that CD47 is an active signaling receptor in multiple human cancer types including breast, lung, prostate, and colon carcinomas and human melanoma. B6H12 antibody does not inhibit cell growth in a subset of the cancer cell lines we have tested, but stimulation of proliferation was also observed in some cell lines with lower malignant potential, which is consistent with known CD47 signaling in non-transformed cells. Our cell proliferation and EGFR phosphorylation data indicates that B6H12 antibody predominantly inhibits proliferation of aggressive cancer cells as compared to less malignant tumor cell lines.

Example 4: Inducing Differentiation of CSCs in an In Vivo Model

This example describes representative methods to assess the efficacy of a compound to selectively induce differentiation of cancer stem cells or prevent tumor growth or metastasis in an in vivo model.

Mice having a human cancer xenograft(s) can be generated using the method of Forsberg et al. (*British J. Cancer* 85:129-36, 2001). Briefly, the xenograph is established in immune-deficient mice (such as SCID or Balb/c nu/nu mice). The xenograft can be allowed to grow for a period of time prior to administration of the compound (such as 5-20 days). Alternatively, the compound can be administered at the same time as the cancer cells (and optionally administration can continue for a period of time after administration of the cancer cells), and growth of the xenograft monitored in the absence of further administration of the compound (to determine if xenograft growth can be prevented). The development of the xenograft can be compared to mice which are administered vehicle or a control compound.

Tumor metastasis can also be measured by intravenously injecting tumor cells in the tail vein of athymic nude mice. Gross tumor number in a site such as lung tissue is assessed by gross observation at necroscopy 21 days after transplantation.

Administration of a compound that inhibits CD47 functional interaction with EGFR and induces differentiation of cancer stem cells should reduce tumor size, tumor cell volume, or number of tumor metastases or prevent tumor growth or metastasis to a greater extent than the control tumors (e.g., in untreated or control treated animals).

It is believed that administration of CD47 blocking agents will be useful for selectively inducing differentiation and senescence of cancer, such as breast tumors (e.g., including triple negative breast cancer) as well as other cancers.

By way of example, athymic Nude mice BALB/c can be used for animal study in vivo. ~$1*10^6$/0.2 ml WT and CD47-CRISPR transfected bCSCs derived from MDA-MB-231 cells are injected into subaxillary mammary fat pads at both sites of 4-6 week-old female BALB/c nude mice.

Tumor size is monitored weekly after inoculation; a tumor with a diameter 100 $mm^3$ will be further treated with B6H12 Ab, or a test agent being evaluated for activity in the methods claimed herein.

To measure spontaneous metastasis (using same experimental conditions as above described), when the mean tumor diameter reaches 1.0 cm, the primary tumor is surgically removed. Mice are then maintained for an additional 2 months to allow further growth of lung metastasis. To produce lung metastasis; ~$1*10^6$/0.2 ml WT and CD47-CRISPR transfected bCSCs derived from MDA-MB-231 cells are injected into lateral tail veins of female athymic nude mice using a restraint box. The bCSCs cells are treated with B6H12 Ab after the growth of tumor (100 $mm^3$). After 4 weeks, the mice are euthanized and the lung metastases examined.

Example 5: Antibody-Induced CD47 Signaling Suppresses Stem Cells in Triple-Negative Breast Cancer CD47 is a signaling receptor for thrombospondin-1 and the counter-receptor for signal-regulatory protein-α (SIRPα). By inducing inhibitory SIRPα signaling, elevated CD47 expression by some cancers prevents phagocytosis by macrophages. In preclinical studies the CD47 blocking antibody B6H12 inhibited tumor growth in several xenograft models, presumably by preventing SIRPα engagement. Evidence that CD47 signaling in non-transformed and some malignant cells regulates self-renewal suggested that B6H12 and related therapeutic antibodies may have a second mechanism of action involving cancer stem cells (CSC).

This example provides data illustrating that breast CSC isolated from the triple negative MDA-MB-231 cell line showed up-regulation of CD47 and CSC markers and more frequent asymmetric cell division than differentiated MDA-MB-231 cells. Gene expression analysis in breast CSCs treated with B6H12 showed up-regulation of tumor suppressor genes and decreased expression of epidermal growth factor receptor (EGFR) and the stem cell transcription factor KLF4. B6H12 treatment also inhibited co-immunoprecipitation of EGFR with CD47. EGFR and CD47 co-immunoprecipitation analysis revealed that very small fraction of CD47 and EGFR co-immunoprecipitate, and pretreatment with B6H12 antibody disrupted this interaction. EGF-induced EGFR tyrosine phosphorylation, asymmetric cell division, and cell proliferation and up-regulated caspase 3/7 activity. Similarly, B6H12 inhibited proliferation of T47D CSCs but not of MCF7 breast carcinoma or MCF10A breast epithelial cells. Caspase-7 cleavage and EGFR expression in human breast cancers correlated with CD47 expression, suggesting that this CD47 signaling pathway is functional in vivo.

These data reveal a novel SIRPα-independent mechanism by which therapeutic CD47 antibodies can control tumor growth by directly forcing differentiation of CSC. Therefore, therapeutic CD47 antibodies intended to enhance macrophage-mediated tumor cell clearance may also benefit triple negative breast cancer patients by directly suppressing CSCs.

The subject matter of this Example overlaps at least in part with that of Examples 2 and 3.

INTRODUCTION

Breast progenitor cells play an active role in the cyclic changes that take place during pregnancy and ovulation in women (Stingl et al., *Breast Cancer Res Treat,* 67(2):93-109, 2001; Petersen & Polyak, "Stem cells in the human breast." *Cold Spring Harb Perspect Biol,* 2 (5): a003160, 2010). A minor subset of tumor cells have the capacity to initiate a new tumor upon transplantation into a healthy host. These tumor initiating cells have stem cell-like properties and are also known as cancer stem cells (CSC). In contrast to CSCs, the bulk tumor cells have limited proliferative capacity and cannot form new tumors.

Despite advances in the diagnosis and treatment of breast cancer, these cancers frequently recur with a relapse time of 5-7 years (Rosen et al., *J Clin Oncol,* 7(9):1239-51, 1989). One proposed mechanism is that CSCs are more resistant to chemoradiation therapies and persist in a dormant state during therapy but later reinitiate tumor regrowth. As few as 100 $CD133^+$-expressing brain and breast cancer cells were sufficient to establish a new cancer in non-obese diabetic, severe combined immunodeficient (NOD-SCID) mice. In contrast, engrafted $CD133^-$ cells did not form any tumor (Singh et al., *Nature,* 432(7015):396-401, 2004; Wright et al., *Breast Cancer Res,* 10 (1): R10, 2008). Flow cytometric analysis has shown that a $CD44^{high}$ and $CD24^{low}$ population is enriched in CSCs (Sheridan et al., *Breast Cancer Res,* 8 (5): R59, 2006). However, most existing therapies to treat solid tumors do not efficiently target cancer stem cells.

Breast cancers comprise four major molecular subtypes: luminal A, luminal B, triple negative/basal-like, and HER2 type (Sorlie, *Eur J Cancer,* 40(18):2667-75, 2004). Triple negative breast cancers (TNBC) represent approximately 20% of cases and are defined by their lack of expression of estrogen receptor (ER), progesterone receptor, and human epidermal growth factor receptor-2 (HER2). TNBC highly express epidermal growth factor receptor-1 (EGFR) and are highly proliferative, aggressive and resistant to systemic chemotherapies. Consequently, outcome for these patients is poor compared to $ER^+$ and $HER2^+$ cancers. Approximately 30-40% of deaths are caused by recurrence and metastasis of TNBC. Even though EGFR inhibitors have shown some promise for treating TNBC (Al-Ejeh et al., *J Nucl Med,* 54(6):913-21, 2013), no FDA approved therapies have improved patient outcome for TNBC. Thus, there is urgency to identify signaling pathways required for TNBC and develop therapies targeting these pathways.

The ubiquitous cell surface protein CD47 is up-regulated in many cancers, especially during metastasis, and high expression is a negative prognostic indicator for several cancers including invasive breast cancer (Zhao et al., *Proc Natl Acad Sci USA,* 108(45):18342-7, 2011; Willingham et al., *Proc Natl Acad Sci USA,* 109(17):6662-7, 2012). One proposed function of elevated CD47 expression on CSC is to serve as a "don't eat me" signal that protects the CSC from phagocytic clearance by macrophages (Jaiswal et al., *Trends Immunol,* 31(6):212-9, 2010). Consequently, antibody and recombinant protein therapeutics that engage CD47 and block SIRPα binding have been developed to stimulate the destruction of CSC by macrophages. The CD47 antibody B6H12 blocks the recognition of CD47 by its counter-receptor SIRPα on macrophages. Human tumors grown in immunodeficient NOD-SCID mice that express a mutant form of SIRPα capable of binding human CD47 have been used to test the ability of B6H12 to enhance macrophage-mediated clearance of human tumor xenografts (Willingham et al., *Proc Natl Acad Sci USA,* 109(17):6662-7, 2012).

Inhibition of tumor growth by B6H12 in these models provided evidence to support the humanization of related CD47 antibodies for treating human cancer patients, which humanized antibodies have now entered human clinical trials (NCT02216409, NCT02367196, NCT02096770). Based in part on evidence that B6H12 has effects on CD47 signaling that are independent of blocking SIRPα binding (Soto-Pantoja et al., *Cancer Res,* 74(23):6771-83, 2014; Soto-Pantoja et al., *Proc Natl Acad Sci USA,* 109(42): E2842; author reply E2844-5, 2012; Zhao et al., *Proc Natl Acad Sci USA,* 108(45):18342-7, 2011), however, others have concluded that the CD47/SIRPα hypothesis is not sufficient to explain the antitumor activity of CD47 blockade and have reported that CD47 is more than a passive SIRPα counter-receptor.

In this Example, we present evidence for an unanticipated activity of B6H12 and other agents that perturb CD47 signaling in CSC. We demonstrate a signaling role of the prototypical CD47 blocking antibody B6H12 on breast CSC but not differentiated cancer cells from the MDA-MB-231 cell line. These data provide evidence that this blocking antibody can function independently of its known ligands TSP1 and SIRPα and should be considered a pharmacological agonist of CD47 signaling.

Material and Methods

Asymmetric Cell Division

MDA-MB-231 cells (ATCC) were labeled with 5-bromo-2'-deoxyuridine (BrdU) for two weeks. The cells were then grown in BrdU-free medium for at least two consecutive cell divisions. The numbers of asymmetric cells were quantified as described (Kaur et al., *Sci Rep,* 3:1673, 2013; Pine et al., *Proc Natl Acad Sci USA,* 107(5):2195-200, 2010).

RNA Extraction and Real-Time PCR

CSC-depleted MDA-MB-231 and bCSCs were plated at $1\times10^6$ cells in 6-well plates and were-treated with B6H12 or Isotype control antibody (1 μg/ml) for 36 h. Total RNA was extracted using TriPure (Roche). One μg of total RNA was used for first strand cDNA synthesis using a Maxima kit (2-Step RT PCR, Thermo Scientific) according to the manufacturer's instructions. Real time PCR was performed using SYBR Green (Roche) on an MJ Research Opticon I instrument (Bio-Rad) with the amplification program as described in (Kaur et al., *Matrix Biol,* 37:49-59, 2014). β2-microglobulin (B2M), HPRT1 or 18S rRNA primers were used as control to normalize mRNA expression (Table 2).

TABLE 2

| SEQ ID NO: | Gene Name | Primer Sequence |
|---|---|---|
| 3 | EGF-F | TGG TTC CTT CTG TGT CAA TCC |
| 4 | EGF-R | GTA CTC TCG CAG GAA ATG GG |
| 5 | EGFR-F | TCC TCT GGA GGC TGA GAA AA |
| 6 | EGFR-R | GGG CTC TGG AGG AAA AGA AA |
| 7 | 18S r RNA-F | AGG ACC GCG GTT CTA TTT TGT TGG |
| 8 | 18S rRNA-R | CCC CCG GCC GTC CCT CTT A |
| 9 | hMYC-F | CGT CCA AGC AGA GGA GCA AAA GCT |
| 10 | hMYC-R | CGC ACA AGA GTT CCG TAG CTG |
| 11 | B2M-F | TCC TGA ATT GCT ATG TGT CTG GGT |
| 12 | B2M-R | GAT AGA AAG ACC AGT CCT TGC T |
| 13 | TXNIP-F | AGG AAG CTC AAA GCC GAA CT |
| 14 | TXNIP-R | ACG CTT CTT CTG GAA GAC CA |
| 15 | PMAIP1-F | AAG TTT CTG CCG GAA GTT CA |
| 16 | PMAIP1-R | GCA AGA ACG CTC AAC CGA G |
| 17 | PLS3-F | TTG CAA AGG CCT CTT TGA GT |
| 18 | PLS3-R | CCC AGG ACT CTG CGA CTT TA |
| 19 | NRIP1-F | ATG GAT GAC TGC ATT CCA CA |
| 20 | NRIP1-R | GAG AAA CCA GCC AAA ATG A |
| 21 | LOX-F | TGG CAG TCT ATG TCT GCA CC |
| 22 | LOX-R | CTA TGG CTA CCA CAG GCG AT |
| 23 | CRISPLD1-F | CCA TGT TCC CAC AAG CAA CT |
| 24 | CRISPLD1-R | TCA GGT GTA TCC AAC AGC CTC |
| 25 | CD14-F | CTC ACA AGG TTC TGG CGT G |
| 26 | CD14-R | TGA GCT CAG AGG TTC GGA AG |
| 27 | U 6-Forward: | CTCGCTTCGGCAGCACA |
| 28 | u 6-Reverse: | AACGCTTCACGAATTTGCGT |
| 29 | Drosha forward | TAGGCTGTGGGAAAGGACCAAG |
| 30 | Drosha reverse | GTTCGATGAACCGCTTCTGATG |
| 31 | DGCR8 forward | CAAGCAGGAGACATCGGACAAG |
| 32 | DGCR8 reverse | CACAATGGACATCTTGGGCTTC |

TABLE 2-continued

| SEQ ID NO: | Gene Name | Primer Sequence |
|---|---|---|
| 33 | Actin forward | TGAAGTGTGACGTGGACATC |
| 34 | Actin reverse | GGAGGAGCAATGATCTTGAT |
| 35 | Ago1 forward | CGTAGAGTCAACCGGGAAGT |
| 36 | Ago1 reverse | CCTCAAAGTCGACCCGTTC |
| 37 | Ago2 forward | TGCAGGCGTTACACGATGC |
| 38 | Ago2 reverse | TACCTCATGGATGGCAAGTGC |
| 39 | Dicer forward | CAGGTATACTTCTCAGCCATGTGA |
| 40 | Dicer reverse | GCCCACTTCTGTCAGTAAATGGT |
| 41 | let 7a-1-F | CAA CGT AAG TGA ATG AAA ATG GT |
| 42 | let 7a-1-R | TAA ATT AAT TTA TTT CCA GGC CA |
| 43 | let 7a-2-F | GAA AAT ACA GCA TGG GTA CAA GGA |
| 44 | let 7a-2-R | TTA AGA AAT GGT AGT TTT CCA GCC A |
| 45 | let 7a-3-F | AGA ATC CCT GTG CCC TTG G |
| 46 | let 7a-3-R | GGC ACC TAG GCC TGT CAG ACT |
| 47 | let 7d-F | CAG GTT AAT TTG AAG TGC ATC TG |
| 48 | let 7d-R | AGC ACC ATG CTG CAG TTT ATA A |
| 49 | let 7f-1-F | GGG GAA ACC TTT TGC TTC T |
| 50 | let 7f-1-R | CTG TGC CTA CTG TAC TTG AAC A |
| 51 | let 7f-2-F | TAC ATG AAC ATG CTG TTT CAG AG |
| 52 | let 7f-2-R | CAT CTA AGT CAA ATG ACT CCA CTG |

BrdU Cell Proliferation Assay

Approximately 8,000 cells were plated per well on 96-well plates and incubated overnight at 37° C. The cells were treated with B6H12 or isotype control antibody (1 μg/ml) for 24 h. BrdU was added for 4 or 24 h as indicated in the figures, and BrdU incorporation was quantified using a BrdU Cell Proliferation Kit according to the manufacturer's instructions (EMD Millipore). For flow analysis, MDA-MB-231 cells were labeled with BrdU, and unlabeled cells were used as a negative control.

Microarray Processing and Analysis

Samples were prepared according to Affymetrix protocols (Affymetrix, Santa Clara, Calif.). RNA quality and quantity was ensured using the Bioanalyzer (Agilent, Santa Clara, Calif.) and NanoDrop (Thermo Scientific, Waltham, Mass.)

respectively. Per RNA labeling, 500 nanograms of total RNA was used in conjunction with the Affymetrix recommended protocol for the HG_U133_Plus 2.0 chips. The hybridization cocktail containing the fragmented and labeled cDNAs was hybridized to the Affymetrix Human HG_U133_Plus 2.0 GeneChip. The chips were washed and stained by the Affymetrix Fluidics Station using the standard format and protocols as described by Affymetrix and the Affymetrix Gene Chip Scanner 3000 was used to scan the probe arrays. Gene expression intensities were extracted using Affymetrix AGCC software. Partek Genomic Suite was used to RMA normalize (Robust Multichip Analysis), summarize, log 2 transform the data and run the ANOVA analysis. The raw data is deposited in NCBI Gene Expression Omnibus (GEO): GSE67966.

Cell Culture and Reagents

The breast carcinoma cell lines MDA-MB-231, MCF7, MCF10A and T47D1 cells were purchased from ATCC (Manassas, Va.) and cultured at 37° C. in 5% $CO_2$ using Gibco RPMI 1640 medium with 10% FBS, Penicillin Streptomycin and Glutamine (Life Technologies, Grand Island, N.Y.). The bCSCs were cultured using cancer stem cell media from (ProMab, Richmond, Calif.). APC-conjugated antibodies for EGF and human KLF4 were obtained from R&D Systems. Antibodies specific for EGFR and phospho-$Tyr^{1175}$ EGFR, actin, nanog, OCT4, and SOX2 were obtained from Cell Signaling (Danvers, Mass.), CD47 antibody B6H12 (Abcam, Cambridge, Mass.), Human CD47-FITC (BD Biosciences). Functional grade purified anti-human CD47-B6H12 and isotype-matched control antibody were from eBioscience, (San Diego, Calif.), Anti-BrdU APC, EGFR-PE, CD44-FITC, CD24-PE conjugated and Isotype control antibodies were obtained from Bio Legend. Cytoclasin D and anti-tubulin were purchased from Sigma Aldrich. For functional studies B6H12 and its isotype-matched control antibody were used at 1 µg/ml for all experiment analysis throughout the manuscript using RPMI medium containing 2% FBS.

Immunoprecipitation and Western Blots bCSC-depleted MDA-MB-231 cells and bCSCs were plated at $1\times10^6$ cells in 6-well plates. The cells were serum-starved for 2 hours using serum-free RPMI medium. The cells were pre-treated with B6H12 (1 µg/ml) for 20 min. Cell lysates were made using immunoprecipitation buffer (50 mM Tris-HCl, 150 mM NaCl, and 1% Nonidet P-40) along with 1× Complete Mini-protease inhibitor mixture (Roche Applied Science). Cell lysates were centrifuged at 13,000 rpm for 15 min. A BCA assay (Thermo scientific) was used to quantify total protein. DYNABEADS® magnetic separation beads (Invitrogen) were used for Immunoprecipitation. The DYNABEADS® magnetic separation beads were washed three times with activation buffer. The cell lysates were incubated in DYNABEADS®-protein G along with anti-EGFR and CD47 antibodies (1:500) and incubated for 24 hours at 4° C. on a shaker. The beads were washed three times with lysate buffer and heated at 95° C. for 5 min. The immunoprecipitated cell lysates were loaded on 4-12% NuPAGE gels (Life Technologies), and Western blotting was performed. For immunoprecipitation, primary antibody against phospho-EGFR (1:1000) was used. Normalization of protein lysates used for Western blotting was performed by reprobing with anti-β-actin (1:3000) or tubulin or EGFR antibodies.

CD47 and EGFR Immunoprecipitation

MDA-MB-231 cells were pretreated with B6H12 (1 µg/ml) for 15 min. The cells were further treated with EGF for 7 min and total Lysate were performed using NP-40 lysis buffer as described above. CD47 and EGFR immunoprecipitation was performed using DYNABEADS® Protein G Immunoprecipitation Kit (Life technologies) according to manufacturer's instructions with slight modifications in incubation time (3 h) for EGFR and CD47 antibodies with Dyna beads. The immunoprecipitated cell lysates were loaded on 4-12% NuPAGE gels (Life Technologies) and transferred using IBLOT®—Western Blotting System (Life Technologies). The membrane was blocked with 3% milk with addition of Complete, mini, Pellet protease inhibitor mix (Roche Life Sciences) for 20 minutes. IP-western blots were performed using –$EGFR^{Y1068}$, EGFR and CD47 antibodies (1:1000) overnight at 4° C. The membrane was washed two times with TBST for 10 minutes. Secondary HRP (Amersham), IRDye 800 or 680 (LI-COR) 1:3000 were used for 1 h at RT. The membranes were further washed 3 times for 10 minutes interval. The images were captured by using WesternSure PREMIUM Chemiluminescent Substrate with ODYSSEY® Fc (LI-COR). The membranes were immunoblotted with EGFR and CD47 for total IP-input.

Transfection

MDA-MB-231 cells were plated overnight using Lab-Tek Chambers. EGFR-GFP (Addgene) was transfected using Fugene 6. Cells were treated with B6H12 and immunostaining performed as above described section.

Exosomes Secretion

MDA-MB-231, bCSCs, T47D1 and MCF7 cells were treated with B6H12 for 6 hours and condition media was harvested. The exosomes were isolated using ExoQuick Kit (SBI-System Biosciences) as previously described (Kaur et al., *Matrix Biol,* 37:49-59, 2014).

Flow Cytometry

MDA-MB-231 and bCSCs cells were stained with either isotype control antibody or anti-CD44-FITC and anti-CD24-PE antibodies for 30 min. at room temperature. bCSCs cells treated with control antibody or EGF or B6H12 antibodies alone or in combinations were incubated at 4° C. or 37° C. for 2 hours and stained with anti-CD47-FITC and anti-EGFR-PE antibodies for 30 min. at room temperature. For caspase 3/7 staining bCSCs cells treated with either control antibody or B6H12 antibody were stained using CellEvent™ Caspase-3/7 Green READYPROBES® Reagent. For intracellular staining, bCSCs cells were stimulated with Leukocyte Activation Cocktail, with GOLGIPLUS™ reagent (BD Pharmingen) for 6 hours at 37° C. before being stained with anti-KLF4 using Foxp3 staining buffer set kit (eBiosciences). Cells were analyzed using a LSR II System flow cytometer (BD Biosciences), and the data were subsequently analyzed and presented using FlowJO software (TreeStar).

Extended Asymmetric Cell Division

With gentle agitation of the flask, loosely bound bCSCs were separated from adherent MDA-MB-231 cells. bCSCs form loose aggregates after incubation at 37° C. Adherent MDA-MB-231 and enriched bCSCs cells were labeled with BrdU for 10 days and then chased in BrdU free medium for 3-4 days and followed by 2 µM Cytochalasin. The cells were immunostained using BrdU antibody and mounted with Vectashield DAPI. The confocal images were taken using a Zeiss 780 microscope at 63× quantification of asymmetric cell division ratio between cells negative for BrdU and positive for DAPI counted manually (Kaur et al., *Sci Rep,* 3:1673, 2013; Pine et al., *Proc Natl Acad Sci USA,* 107(5): 2195-200, 2010; Sunderaraman et al., *Circ Res,* 110(9): 1169-73, 2012).

The MDA-MB-231 cells were labeled with BrdU for two weeks. The cells were grown in BrdU free media at least to two consecutive cell divisions. BrdU free media at 0 h and rest of them split into two plates and treated with antiB6H12 or Isotype control antibody (1 µg/ml) for 5 days. BrdU staining was performed using BrdU Cell Proliferation Kit 2752 from EMD Millipore. BrdU negative and positive for DAPI for DNA segregation was counted manually. The total numbers of DAPI were divided by BrdU negative cells. The untreated or control asymmetric cells were normalized to 1. The ratio of B6H12 was determined as compared to 1 (control).

Mammosphere Formation Medium

Cultured MDA-MB-231 cells were washed with IXPBS and Suspension cells (bCSCs) were harvested with gentle agitation from flask. Mammosphere formation medium with slight modification according to Cioce et al. (*Cell Cycle*, 9(14):2878-87, 2010) for FIGS. 1B and 24A only. bCSCs were seeded using Petri dishes (Corning) in DMEM/F-12 (1:1) Invitrogen media) containing 5 µg/ml insulin, 0.5 µg/ml hydrocortisone, 25 ng/ml EGF, 25 ng/ml bFGF, 4 µg/ml heparin and gentamycin sulfate. In other experiments the bCSCs was cultured using cancer stem cell medium from ProMab.

TCGA Invasive Breast Carcinoma Patient Tumor Data mRNA (RNA Seq V2 RSEM) and protein expression data from the TCGA Breast Invasive Carcinoma raw data at the NCI was analyzed using cBioPortal tools (Gao et al., *Sci Signal*, 6(269): p11, 2013; Cerami et al., *Cancer Discov*, 2(5):401-404, 2012).

Statistical Analysis

The p-values for asymmetric cell division, cell proliferation, cell imaging intensity and flow MFI were measured using the t-test for two samples assuming equal variances. The p-value less than ≤0.05 were used as statistically significant. *,  and * corresponding to ≤0.05, 0.05 and 0.005 respectively.

Results

Figure 24A:
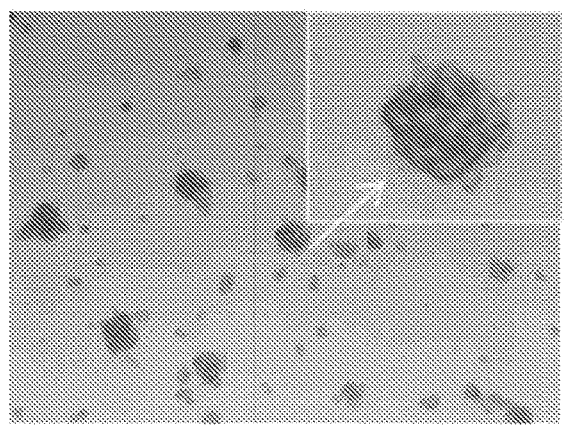
Figure 24B:
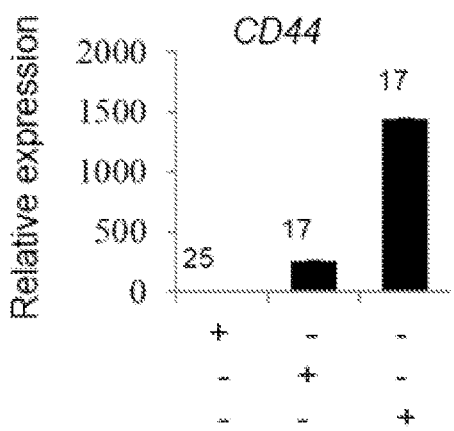
Figure 24C:
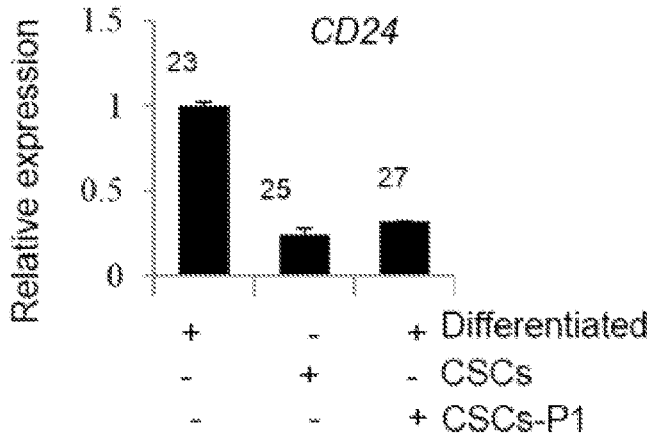

Characterization of Breast CSCs Derived from Suspension Cell-Enriched MDA-MB-231 Cells Routinely cultured MDA-MB-231 cells displayed abundant loosely attached round cells as well as firmly attached spread cells (FIG. 1A and inset). The loosely attached cells could be harvested by gentle shaking (FIG. 1B) and formed aggregates within 10 days at 37° C. in cancer stem cell medium (FIG. 24A). The presence of $CD44^{high}$ and $CD24^{low}$ cancer stem/progenitor cells is a hallmark of aggressive metastatic TNBC (Idowu et al., *Hum Pathol*, 43(3):364-73, 2012). Based on flow cytometry the loosely attached cells expressed more surface CD44 than the firmly attached MDA-MB-231 cells (FIGS. 6A & 6B). Gene expression analysis of CD44 and CD24 mRNA in suspension and attached cells indicated that the suspension cells have 257-fold up-regulation of CD44 as compared to attached cells, and re-plating the suspension cells in stem cell media further increased CD44 gene expression (FIG. 24B). On the other hand, the suspension cells expressed 8-fold less CD24 than attached cells, which did not further change after re-plating. Global microarray gene expression analysis of these two subsets indicated that loosely bound MDA-MB-231 cells differentially express many genes characteristic of CSC (FIG. 7A). Among them, 8 transcripts were significantly upregulated (P=0.005), and 90 transcripts were down regulated in suspension cells including four CD24 transcripts. (FIG. 24D and Table 3). Based on these characteristics, we hereafter refer to the suspension cells as bCSC and to the firmly attached cells as differentiated MDA-MB-231 cells.

Interestingly, CD47 showed 2.3-fold higher expressions in bCSCs, whereas TSP1 and c-Myc showed decreased expression in bCSCs (FIG. 25A-25C).

Figure 24E:
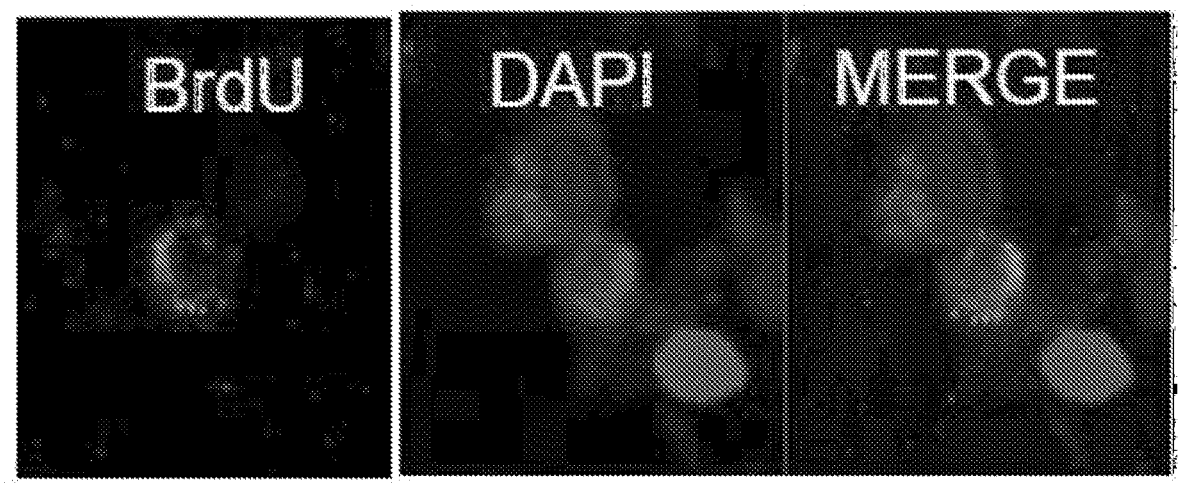
Figure 24F:
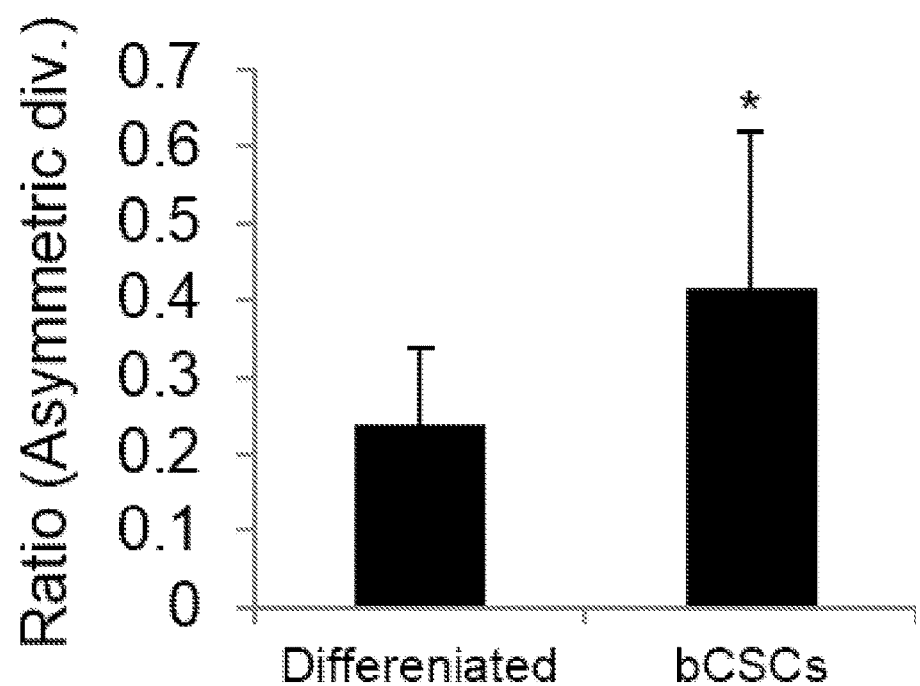

CSCs share some characteristics with embryonic stem cells. Correspondingly, real time PCR analysis of bCSCs revealed up-regulation of OCT4, Nanog, SOX2, and nestin relative to attached cells (FIG. 25D-25G). Another defining characteristic of stem cells is asymmetrical division. MDA-MB-231 cells have been reported to divide asymmetrically for self-renewal (Liu et al., *Mol Cancer*, 12(1):139, 2013), and asymmetric division is correlated with the $CD44^{high}/CD24^{low}$ phenotype (Ghiabi et al., *PLoS One*, 9(11): e112424, 2014). We chased BrdU-labeled bCSCs with unlabeled BrdU to quantify asymmetric DNA template strand segregation (Pine et al., *Proc Natl Acad Sci USA*, 107(5): 2195-200, 2010). Differentiated MDA-MB-231 cells and bCSCs were labeled with BrdU for two weeks and chased for 2 divisions in BrdU-free complete RPMI medium. The cells were treated with cytochalasin D, and symmetric versus asymmetric DNA segregation was counted microscopically. bCSCs enriched for $CD44^{high}CD24^{low}$ showed an increase in asymmetric cell division (FIG. 24E-24F).

CD47 Blocking Antibody B6H12 Specifically Targets bCSCs

Figure 19B:
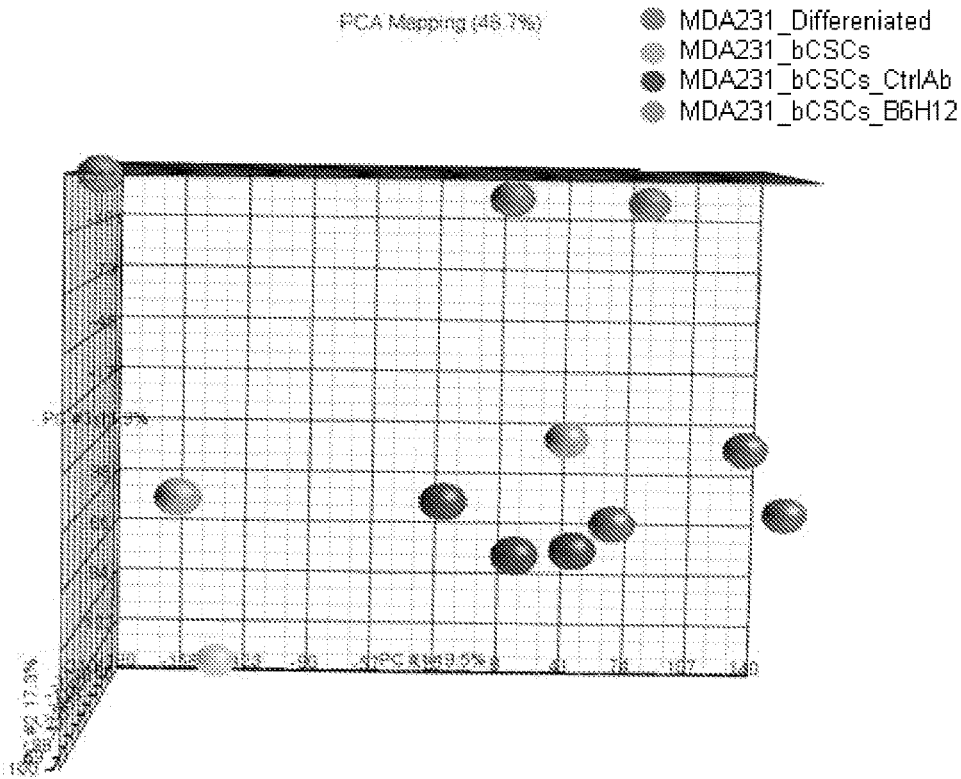
Figure 26A:
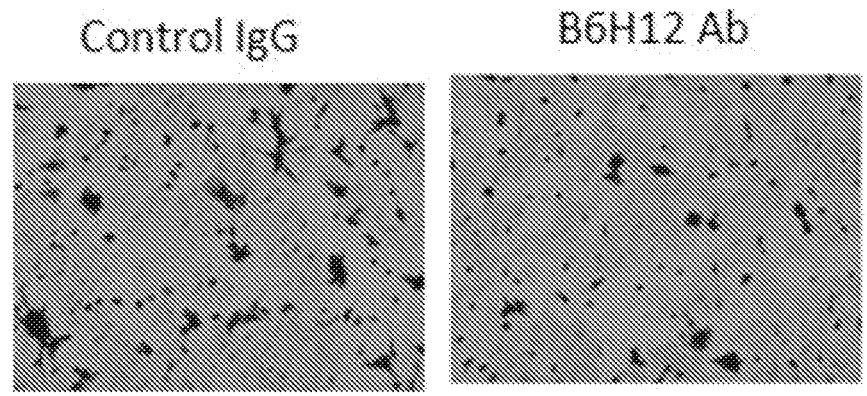
FIG. 26A-26C is a series of images illustrating that CD47 blocking antibody (B6H12) induces morphological change and reduce number of aggregates only in bCSCs but not in CSC-depleted MDA-MB-231 cells.
Figure 26B:
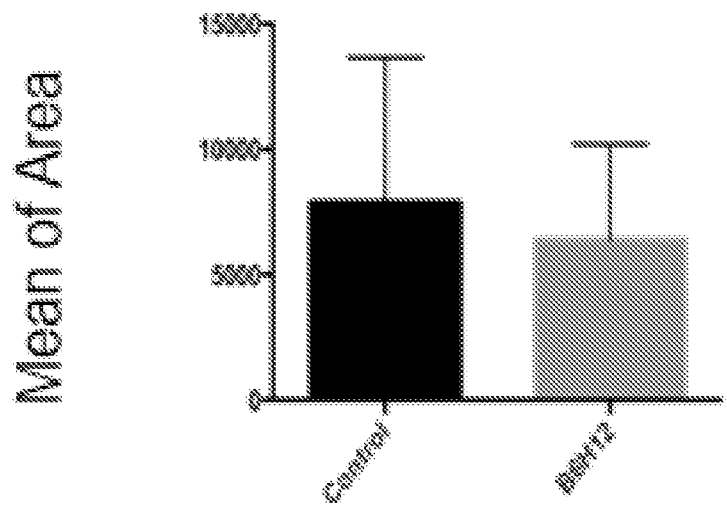
Figure 26C:
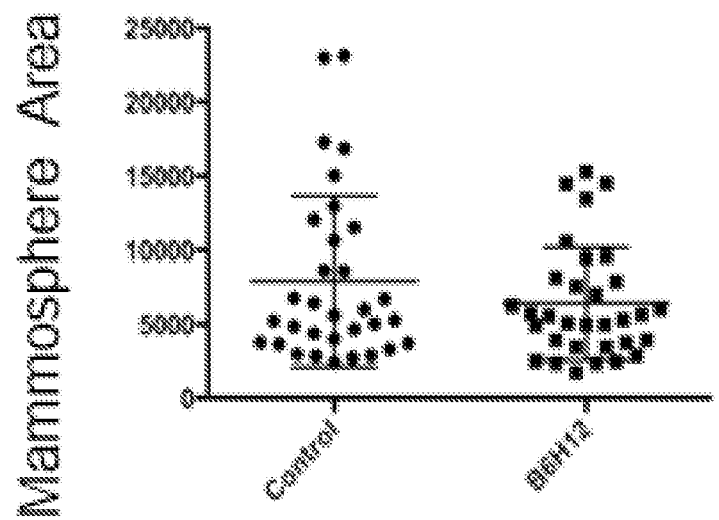

To investigate if the CD47 blocking antibody B6H12 has direct effects on bCSCs cells, we cultured differentiated MDA-MB-231 cells and bCSCs in the presence of B6H12 or an isotype-matched control IgG for 3 days. The CD47 antibody decreased the number of round non-adherent bCSCs cells (arrows) but had no effect on differentiated MDA-MB-231 cells (FIG. 9A-9B). B6H12 reduced size of mammosphere when bCSCs were cultured for 10 days using cancer stem cell medium (FIG. 26A-26C). Global microarray assessment of mRNA expression revealed that B6H12 altered the expression of 225 transcripts as compared to isotype control antibody (FIG. 10A, 27A). Principle component analysis showed that B6H12 antibody-treated bCSC showed distinct gene expression relative to control antibody-treated and differentiated MDA-MB-231 cells (FIG. 19B). Representative genes identified in the arrays were validated by qPCR (FIG. 27C-G). B6H12-treated bCSCs showed an up-regulation of thioredoxin-interacting protein (TXNIP) and LOX (lysyl oxidase), which are known tumor suppressors (Shin et al., *Biochem Biophys Res Commun*, 372(4): 880-5, 2008; Min et al., *A Cancer Res*, 69(16):6685-93, 2009). Altered TXNIP mRNA expression was previously reported following CD47 knockdown in hepatocellular carcinoma stem cells (Lee et al., *Hepatology*, 60(1):179-91, 2014). Similarly, B6H12 treatment selectively increased bCSC expression of plastin-3 (PLS3), which is associated with actin and calcium ion binding (Lin et al., *Mol Cell Biol*, 10(4):1818-21, 1990; Lin et al., *J Biol Chem*, 268(4):2781-92, 1993), PMAIP1 (phorbol-12-myristate-13-acetate-induced protein-11), which promotes activation of caspases and apoptosis (Bertin-Ciftci et al., *Cell Death Differ*, 20(5): 755-64, 2013), cysteine-rich secretory protein LCCL domain-containing-1 (CRISPLD1), which is released into extracellular vesicles, and CD14, which activates cell adhesion and NFκB (Palma et al., *Mol Cancer*, 13:79, 2014).

Figure 28A:
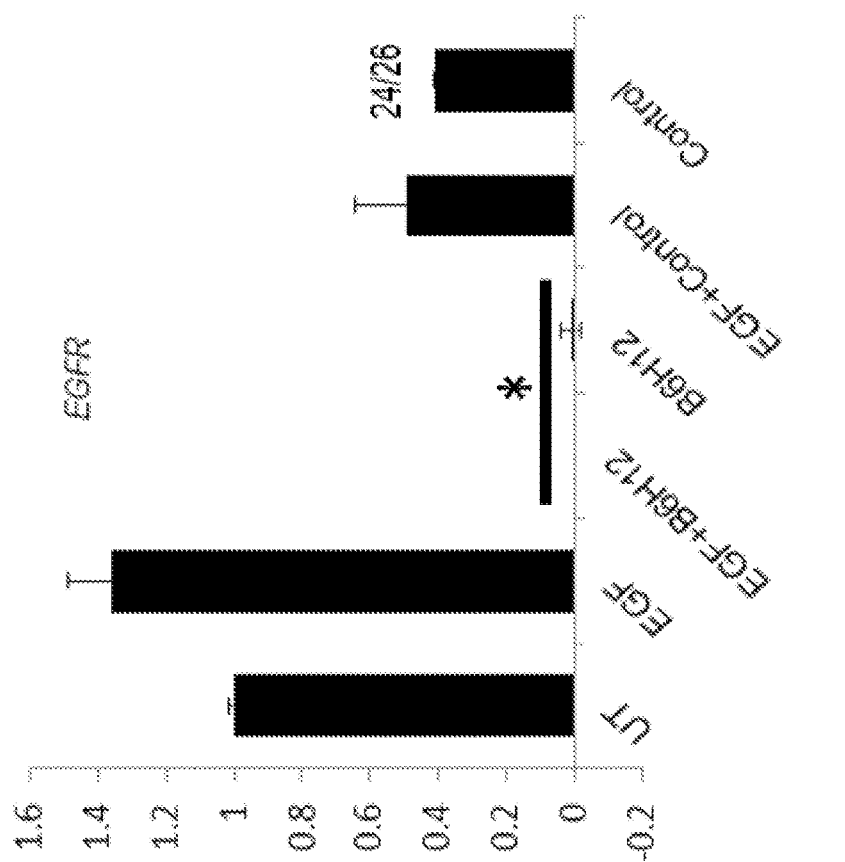
FIG. 28A-28H illustrates that EGF and EGFR mRNA expression is up-regulated in bCSCs, and down-regulated by B6H12 antibody treatment.
Figure 28B:
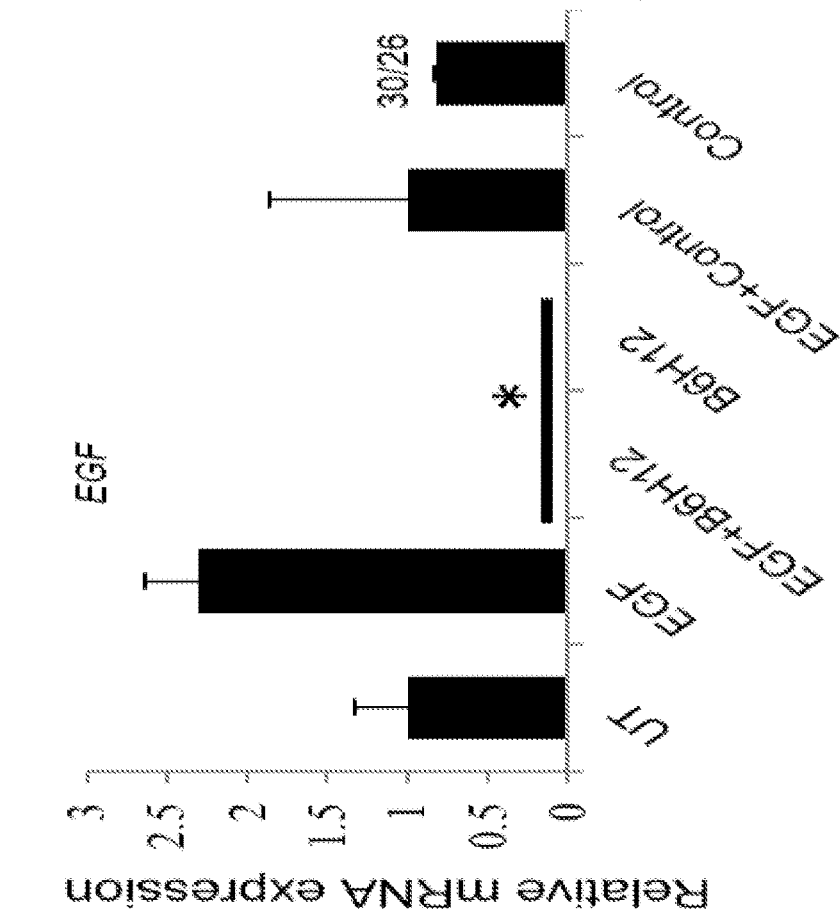

B6H12 Down-Regulates EGFR mRNA Expression and $Tyrosine^{1068}$ Phosphorylation in bCSCs High expression of EGFR is characteristic of ER⁻ breast tumors and has been linked to poor prognosis (Foley et al., *Semin Cell Dev Biol*, 21(9):951-60, 2010; Wang et al., *Lancet*, 365(9460):671-9, 2005; Bos et al., *Nature*, 459 (7249):1005-9, 2009). $ER^-/HER21^{low}$ cancers with a $EGFR^{high}$ phenotype were reported to have a higher number of stem/progenitor cells (Foley et al., *Semin Cell Dev Biol*, 21(9):951-60, 2010; Dontu et al., *Trends Endocrinol Metab*, 15(5):193-7, 2004; Zhu et al., *J Theor Biol*, 269(1): 138-49, 2011). Treatment of bCSCs with B6H12 for 3 days down-regulated EGFR at the mRNA level on microarray analysis (FIG. 27A). Real time PCR confirmed that treatment with B6H12 alone or in the presence of EGF completely blocked detectable EGF and EGFR transcript expression (FIG. 28A-28B), whereas treatment with isotype control antibody in the presence or absence of EGF did not significantly alter mRNA expression of EGF and EGFR.

Figure 28C:
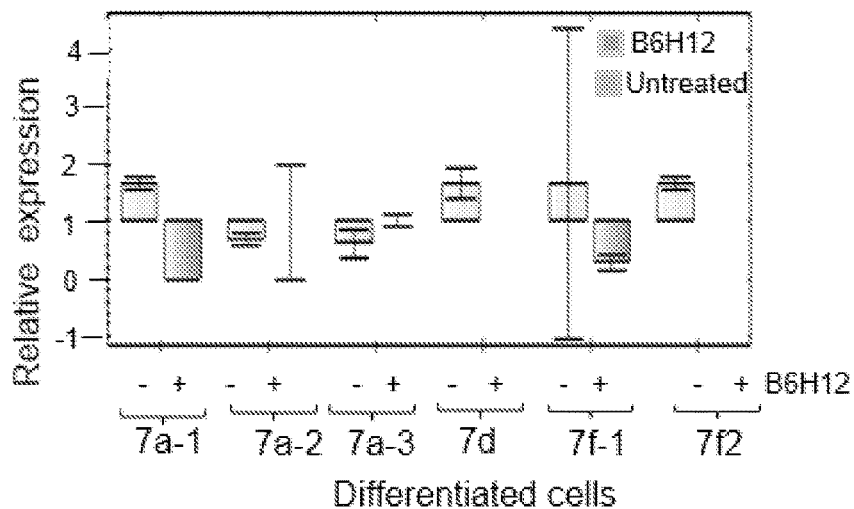
Figure 28D:
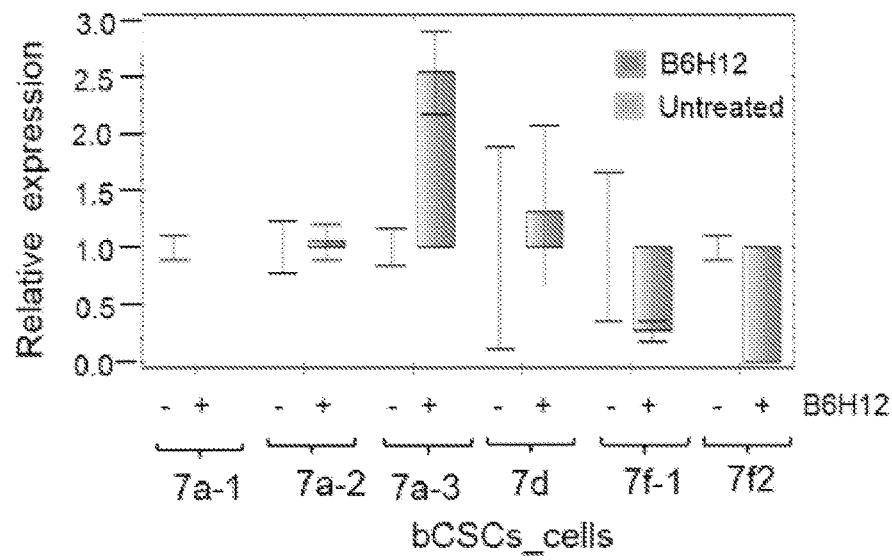
Figure 28E:
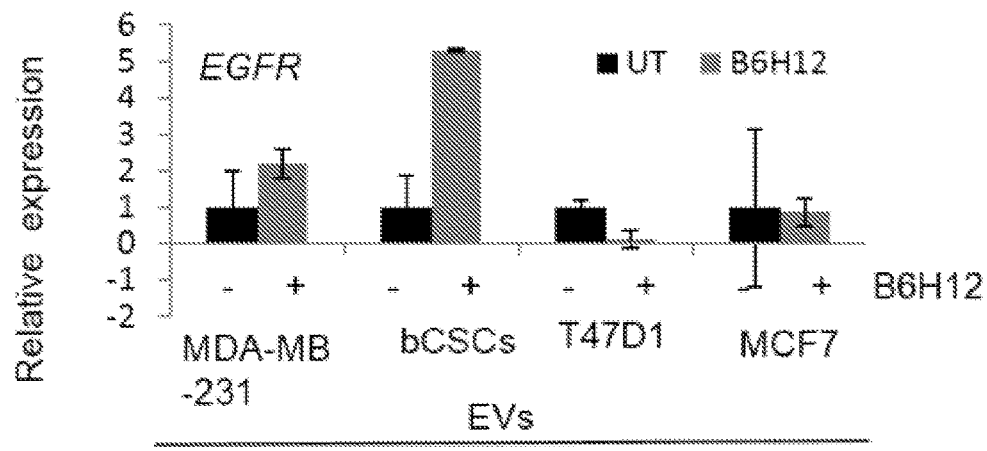
Figure 28F:
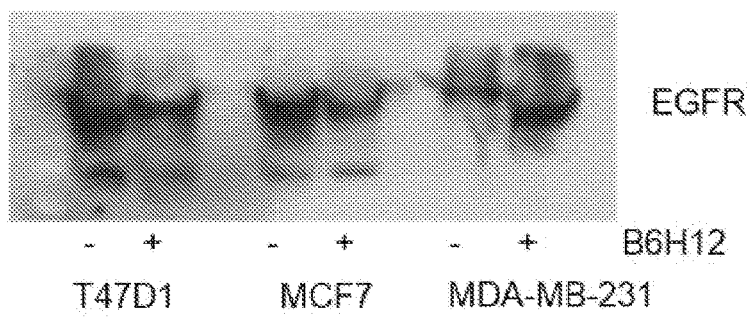
Figure 28G:
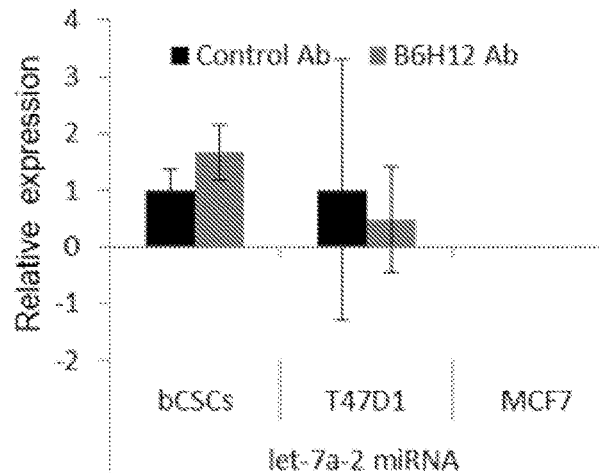
Figure 28H:
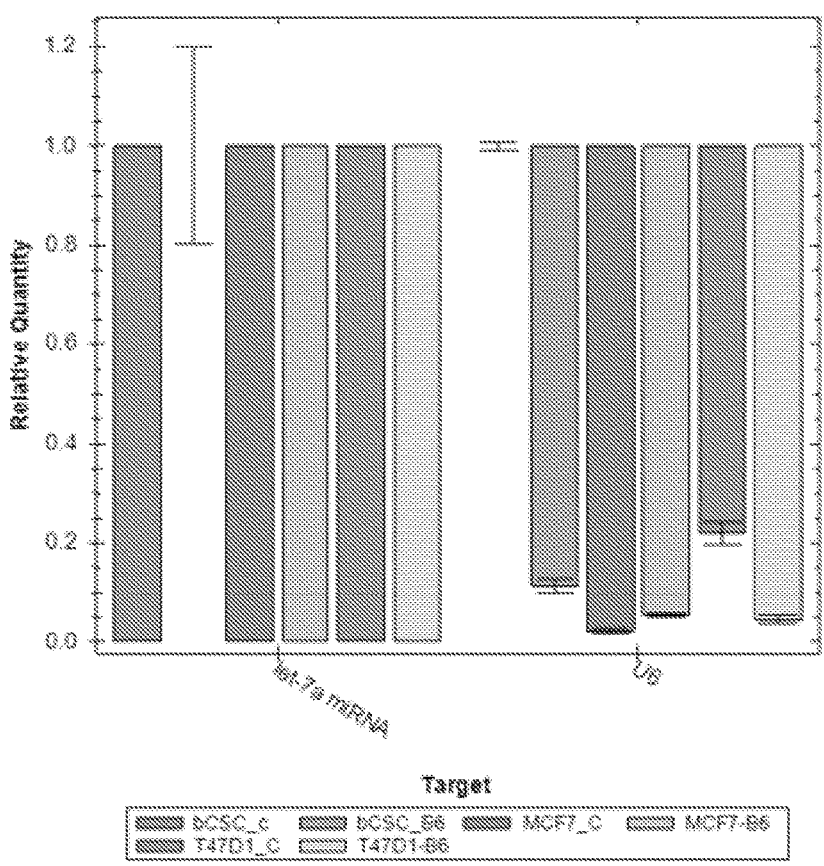
Figure 29:
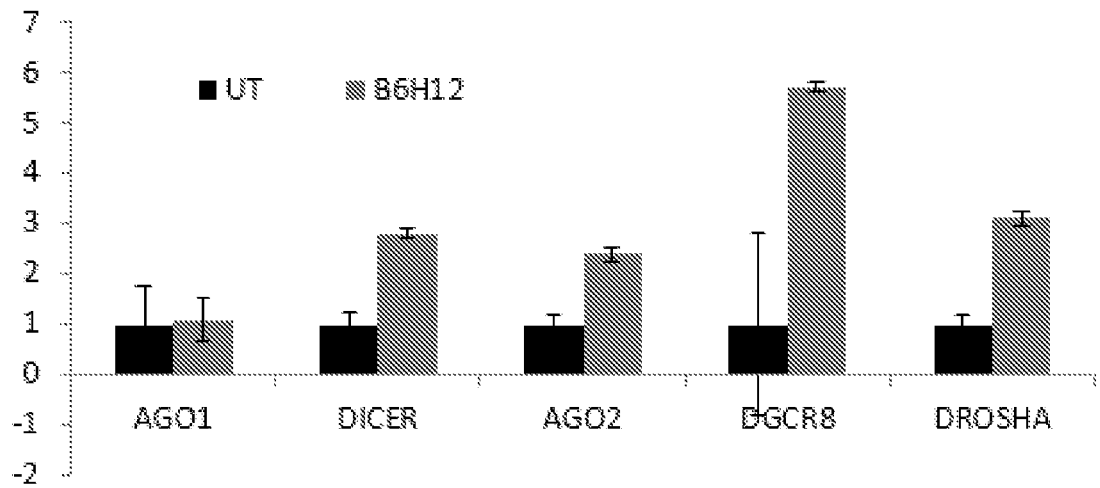
FIG. 29 is a graph illustrating that Dicer was also upregulated in Control Vs B6H12 treated bCSCs in microarray. We asked if B6H12 has alter expression of RNA-induced silencing complex (RISC) genes. We found that B6H12 increased mRNA expression of Ago2, DICER, DGCR8 and Drosha, but not Ago1.
Figure 30A:
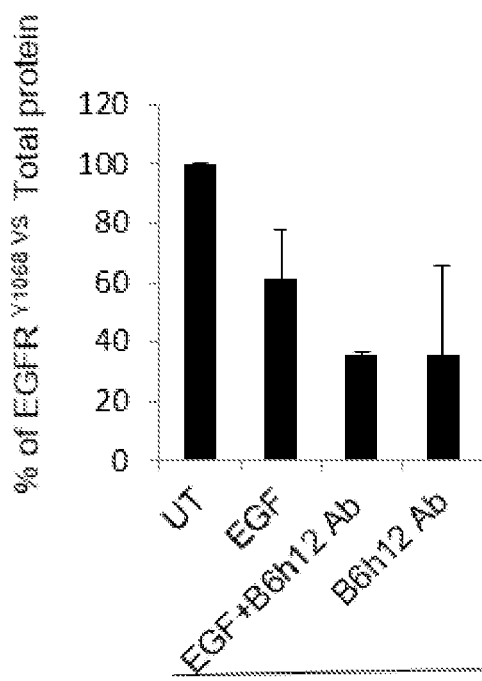
FIG. 30A-30B shows.
Figure 30B:
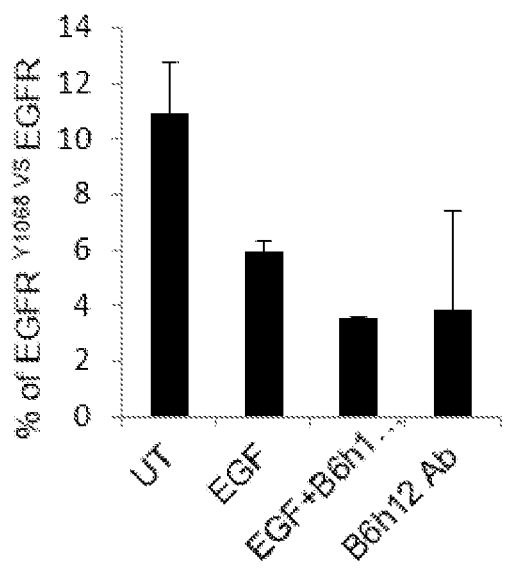
Figure 31A:
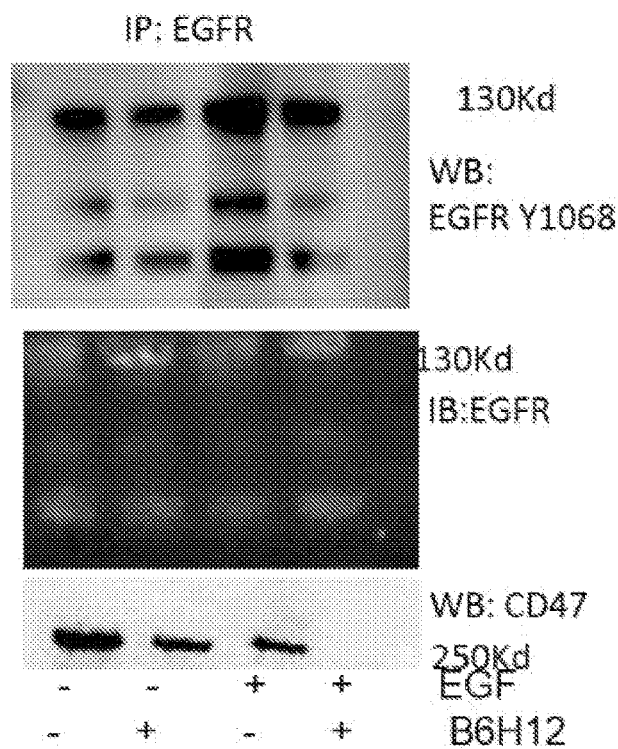
FIG. 31A-31F is a series of images.
Figure 31B:
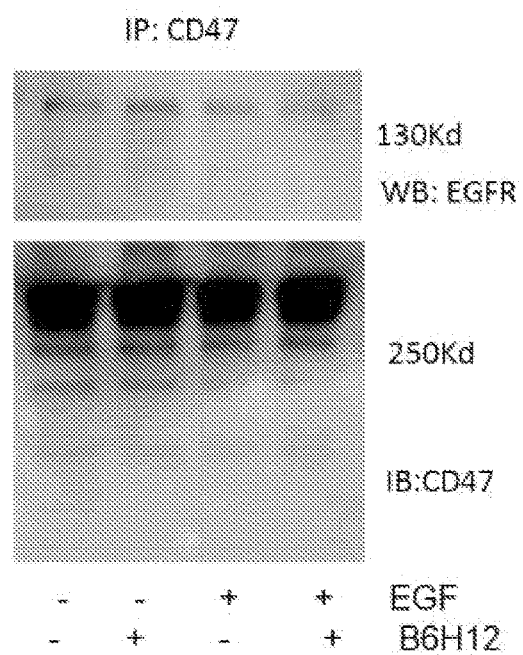
Figure 31C:
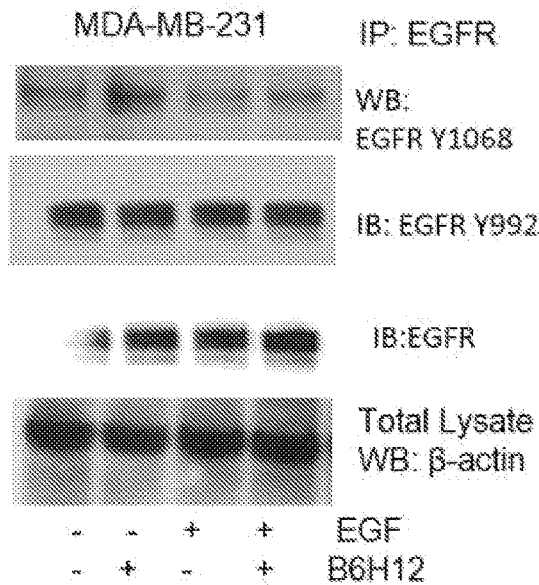
Figure 31D:
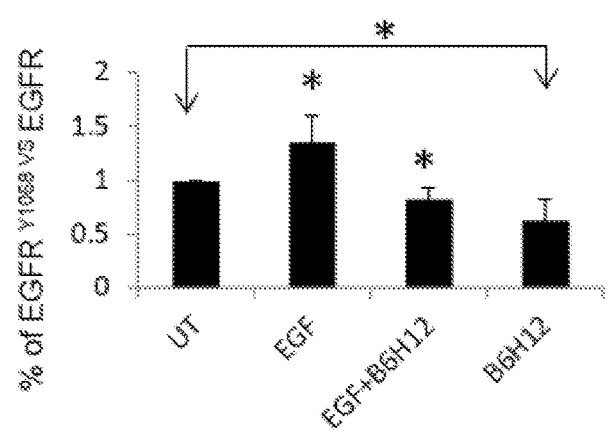

CD47 regulates the release of mRNA into exosomes in T cells, which suggested that the loss of EGFR mRNA induced by B6H12 treatment could result from export of this mRNA. We isolated exosomes from conditioned medium of MDA-MB-231 cells and derived bCSCs, T47D1 cells, and MCF7 cells in the presence or absence of B6H12 for 6 h. Treatment with B6H12 increased EGFR mRNA levels in EVs 2-fold in MDA-MB-231 cells, 5-fold in bCSCs. HPRT1, actin and 18S have different Ct levels in B6H12 treated samples as compared to untreated. U6 was used for this analysis, which is more appropriate for miRNA but less so for mRNA expression; but not in T47D1 and MCF7 cells (FIG. 28C). In contrast to EGFR mRNA, EGF mRNA was not detected in the EVs, and levels of other mRNAs were not significantly changed FACS sorted bCSCs_MDA-MB-231 showed increase in EGFR protein level expression on EVs but not bCSCs derived from T47D1 and MCF7 (FIG. 28D). To test exosomes secretion, we transfected EGFR-GFP in MDA-MB-231 cells were transfected with EGFR-GFP and confocal microscopy analysis showed that B6H12 stimulated EGFR release in the form of vesicles. We further isolated a pure population of CD44$^{high}$/CD24$^{low}$ from MDA-MB-231, T47D1 and MCF7 cell lines and treated with B6H12 for 24 hours. The exosomes were extracted and protein expression of EGFR was analyzed by western blot. B6H12 treatment specifically upregulate EGFR level only in bCSCs derived from MDA-MB-231 but not from T47D1 and MCF7 cells which could play role as decoy receptor for EGFR (available online at grantome.com/grant/NIH/R01-CA163563-03). We further found that B6H12 treatment increase MicroRNA-7a-2 and 7a-3 expression (Table 4). Down-regulation of EGFR has been reported by MicroRNA-7 (miR-7) in human cancer cells (Webster et al., *J Biol. Chem.* 284:5731-5741, 2009). MiR-7 has been underexpressed in lung, breast and glioblastoma cancer cells and an emerging cancer therapeutic target (Barh et al., *Curr Oncol* 17:70-80, 2010). This could be a potential mechanism by which B6H12 decrease EGFR expression in Triple negative breast cancer (TNBC).

cipitation revealed that EGFR and CD47 very small fraction of CD47 and EGFR co-immunoprecipitate, and pretreatment with B6H12 antibody disrupted this interaction and inhibit EGFR Y$^{1068}$ phosphorylation (FIG. 31A-31B). To determine whether B6H12 treatment acutely altered EGFR tyrosine phosphorylation, we pre-treated MDA-MB-231 cells, for 15 min with B6H12. EGF stimulation for 5 min significantly increased EGFR Y$^{1068}$. B6H12 treatment in the presence or absence of EGF inhibited EGFR phosphorylation at Y$^{1068}$ but not Y$^{992}$. B6H12 treatment alone inhibited basal EGFR Y$^{1068}$ phosphorylation as compared to untreated (FIG. 28C-28D). Similarly, differentiated cells and bCSCs derived from MDA-MB-231 cells were treated with either EGF alone or in combination with B6H12. B6H12 treatment inhibited basal and EGF-stimulated EGFR phosphorylation in bCSCs but not in differentiated cells (FIG. 28E). We also examined Y$^{998}$ phosphorylation but did not observe any change (FIG. 29B) which is consistent with (FIG. 28C). To further validate these results, we isolated a pure population of CD44$^{high}$/CD24$^{low}$ MDA-MB-231 cells by cell sorting. Stimulation of FACS-sorted bCSCs with EGF did not further increase EGFR Y$^{1068}$ phosphorylation, but B6H12 strongly inhibited EGFR Y$^{1068}$ phosphorylation in the absence and presence of co-stimulation with EGF (FIG. 28F). These data demonstrate that B6H12 selectively targets EGFR signaling in bCSCs by down-regulating EGFR phosphorylation.

B6H12 Inhibits Asymmetric Cell Division and Expression of KLF4

Figure 32A:
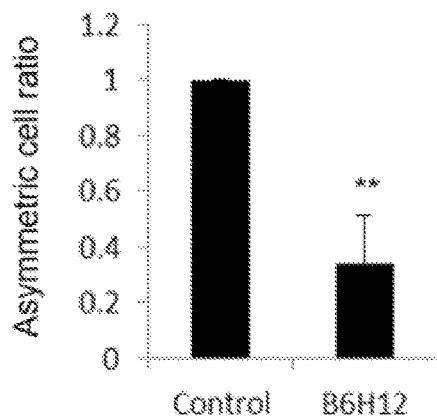
FIG. 32A-32G illustrates B6H12-Ab inhibits Asymmetric cell division and cell proliferation and increase caspase 7.

To observe the effect of B6H12 on asymmetric cell division, we labeled bCSCs with BrdU and chased using BrdU-free medium in the presence of B6H12 or control antibody. The cells were immunostained using anti-BrdU and quantified using confocal microscopy imaging (FIG. 32A). The fraction of cells exhibiting asymmetric division significantly decreased after B6H12 treatment.

Figure 32B:
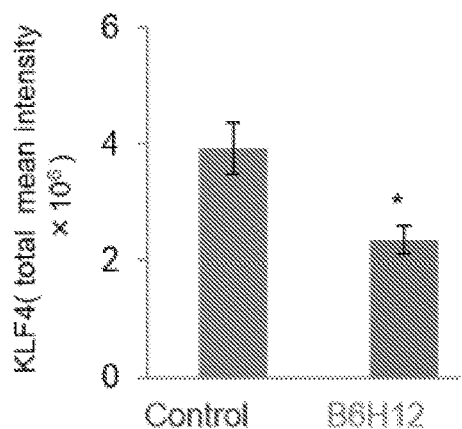
Figure 32C:
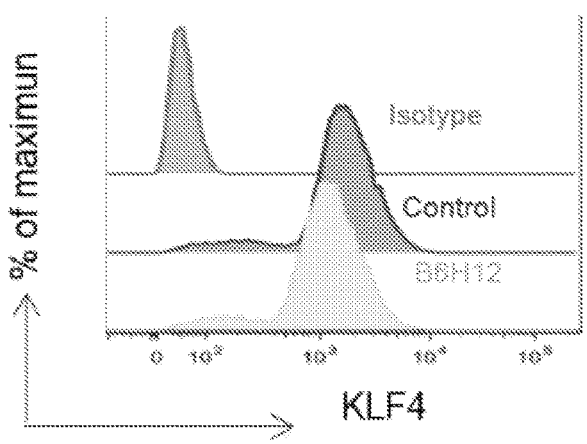
Figure 33A:
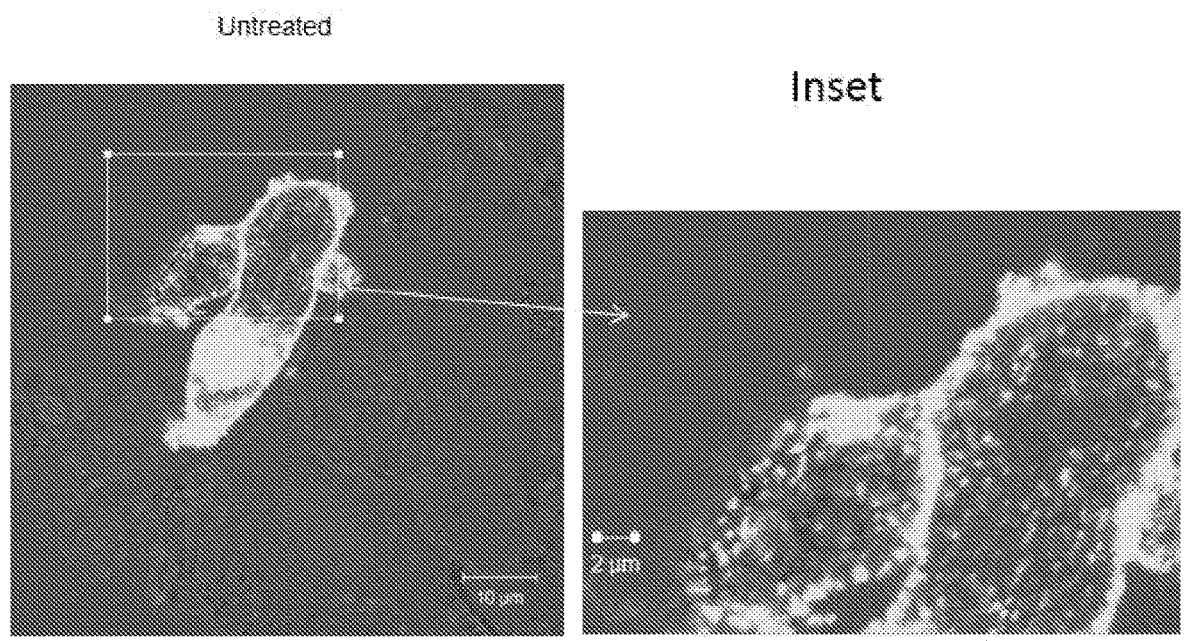
FIG. 33A-33B are a series of fluorescence microscopy images showing that MDA-MB-231 cells transfected with EGFR-GFP in the presence of B6H12 Ab exhibit increase in exosomes secretion as compared to untreated cells.
Figure 33B:
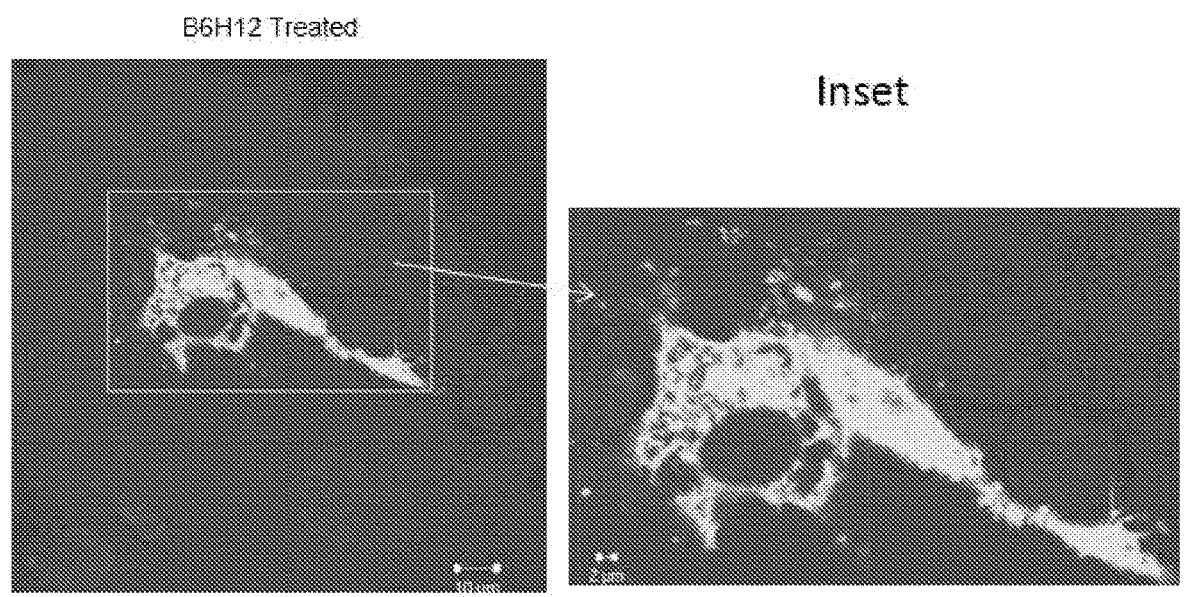
Figure 34A:
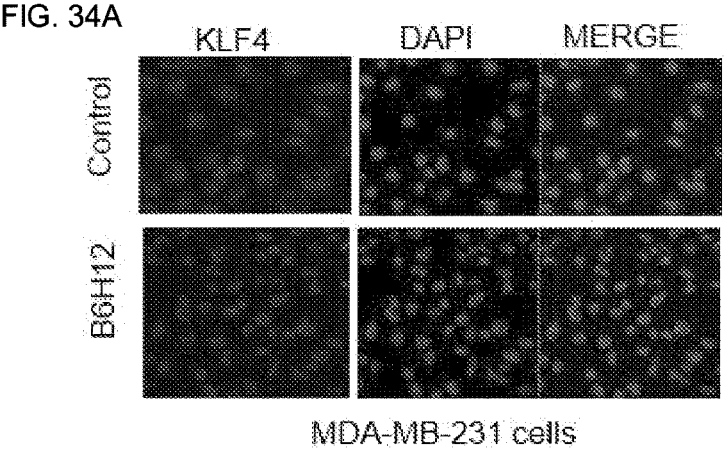
FIG. 34A-34C show that B6H12 treatment of bCSC reduces expression of KLF4.
Figure 34B:
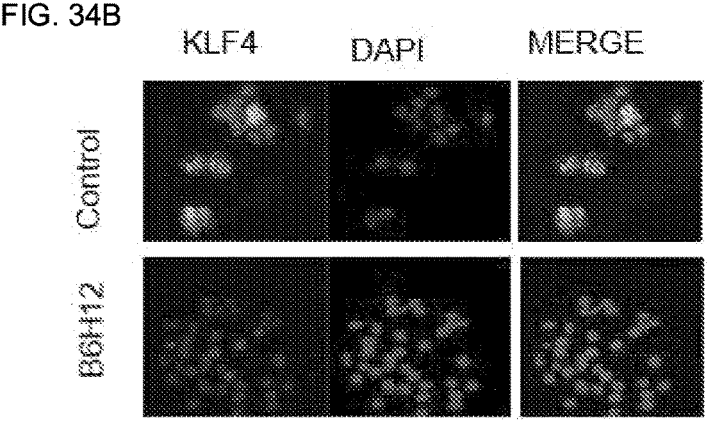

We further analyzed the effect of B6H12 on the embryonic stem cell markers OCT4, SOX2, NANOG and KLF4 using differentiated cells and bCSCs. OCT4, SOX2, and NANOG immunostaining did not change between isotype control and B6H12 treatments as well as in microarray analysis, KLF4 decreased moderately in differentiated cells (FIGS. 33A and 33C), but a statistically significant reduction of KLF4 was observed in bCSCs (FIG. 32B and FIG. 34B). Decreased KLF4 expressing was confirmed using flow cytometry (FIG. 32C). Because KLF4 is an essential gene for breast cancer stem cell maintenance and it's decrease

TABLE 4

Ct value of miR let7-family from cellular RNA of MDA-MB-231

|  | 18S RNA | 7a-2 | 7a-3 | 7d | 7f-2 |
| --- | --- | --- | --- | --- | --- |
| UT | 18.81 ± 0.46 | 25.94 ± 0.06 | 28.29 ± 0.13 | 27.12 ± 0.16 | 32.88 ± 0.18 |
| B6H12 | 22.27 ± 0.02 | 32.41 ± 0.23 | 31.66 ± 0.44 | 29.27 ± 0.03 | 38.50 ± 0.50 |
| B6H12 + EGF | 22.03 ± 0.03 | 29.63 ± 0.04 | 32.99 ± 0.05 | 32.60 ± 0.14 | 34.40 ± 0.07 |
| EGF | 17.65 ± 0.35 | 26.09 ± 0.50 | 28.88 ± 0.71 | 27.38 ± 0.18 | 33.24 ± 0.05 |
| EGF + Control Ab | 17.60 ± 0.02 | 25.63 ± 0.66 | 28.94 ± 0.47 | 27.18 ± 0.44 | 32.67 ± 0.43 |
| Control Ab | 17.43 ± 0.03 | 24.10 ± 0.01 | 28.99 ± 0.26 | 26.51 ± 0.18 | 31.78 ± 0.07 |

Based on our previous finding that CD47 laterally associates with the tyrosine kinase receptor VEGFR2 (Kaur et al., *J Biol Chem*, 285(50):38923-32, 2010), we asked whether CD47 similarly interacts with EGFR. Immunopreleads to decreased proportion of stem/progenitor cells (Yu et al., *Oncogene*, 30(18):2161-72, 2011), B6H12 treatment may reduce the number of bCSC by down-regulation of KLF4 and inhibition of asymmetric cell division.

B6H12 Inhibits Proliferation of bCSCs and Induces Caspase 3/7 Activity

Figure 31E:
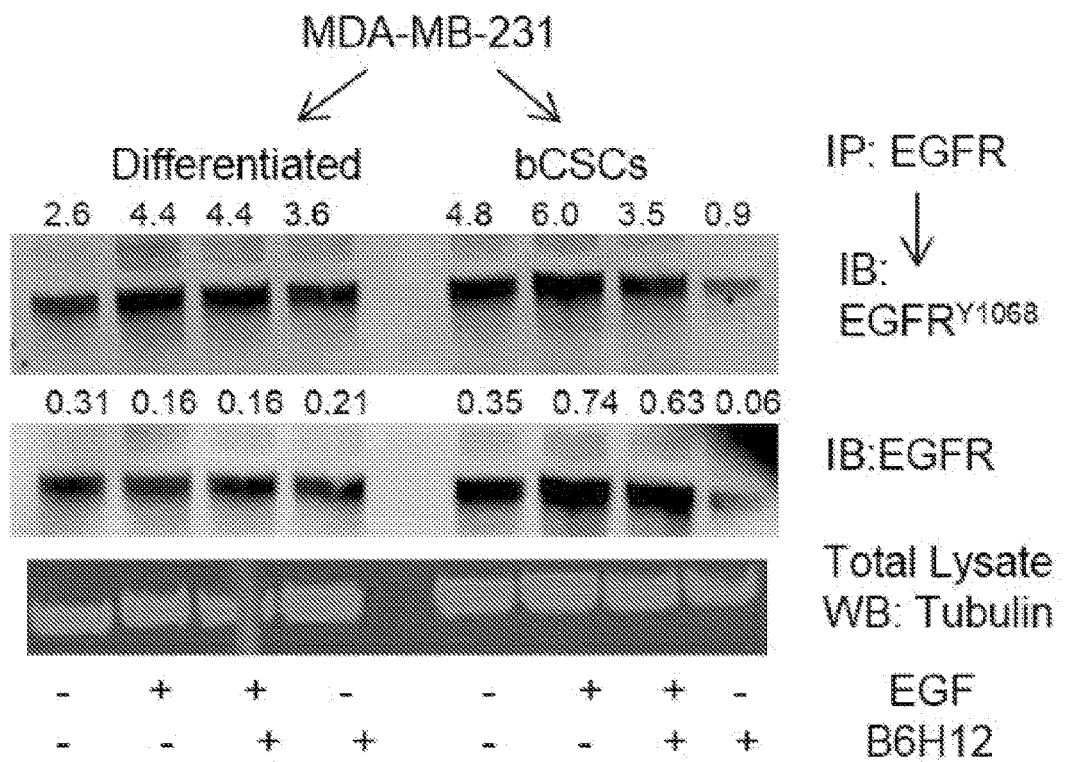
Figure 31F:
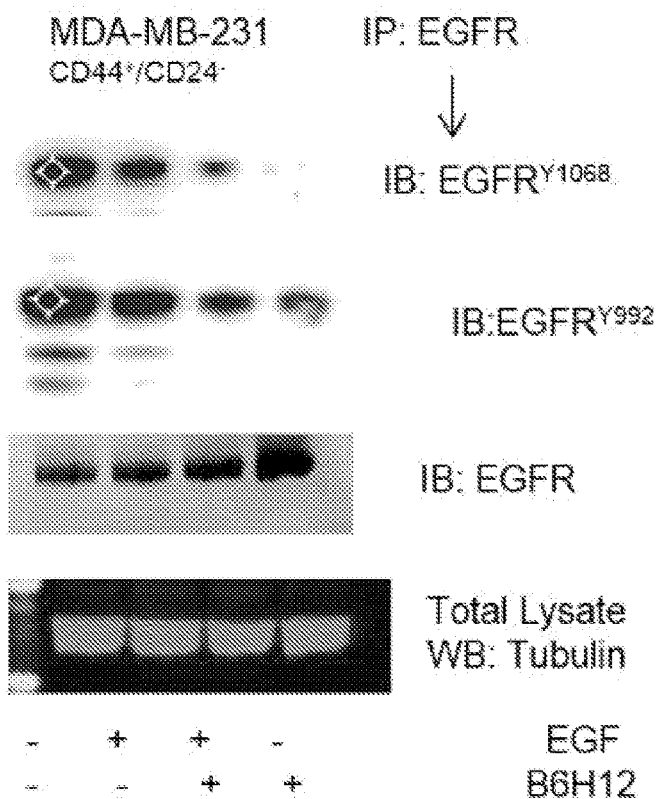
Figure 32D:
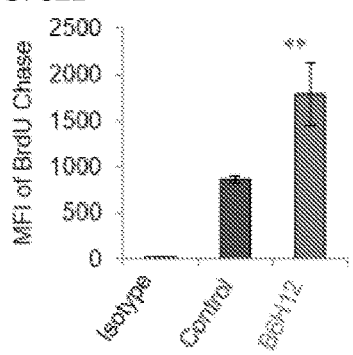
Figure 32E:
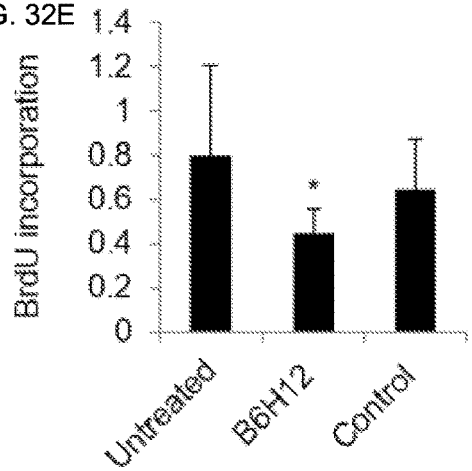
Figure 35A:
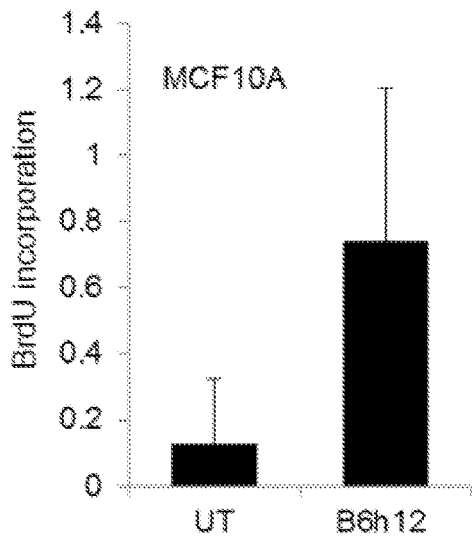
FIG. 35A-35E illustrate that B6H12 specifically targets breast carcinoma cells that have high number of bCSCs/tumor initiating cells. The following cell lines were treated with 1 μg/ml B6H12, and DNA synthesis was quantified by BrdU incorporation.
Figure 35B:
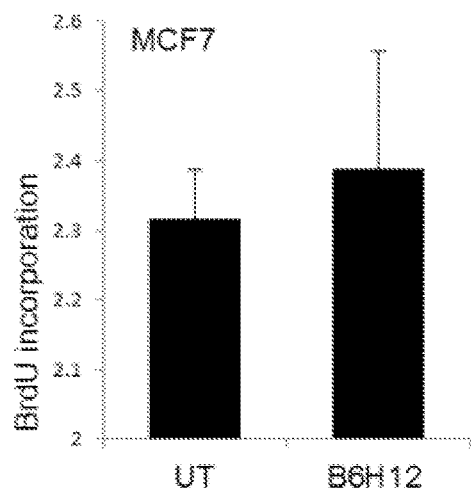
Figure 35C:
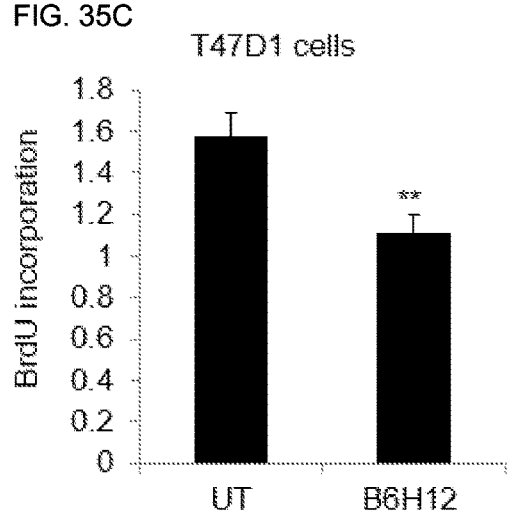
Figure 35D:
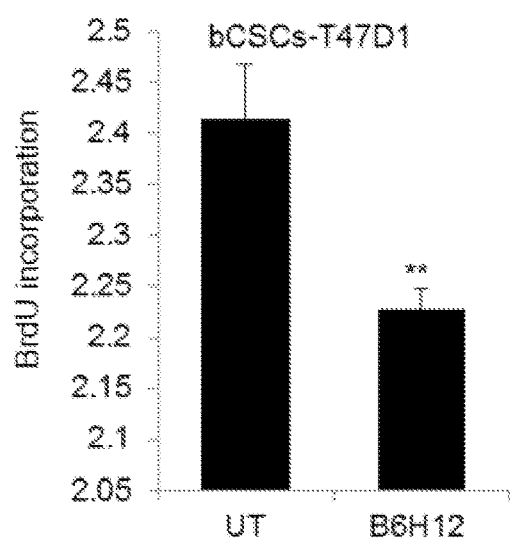
Figure 35E:
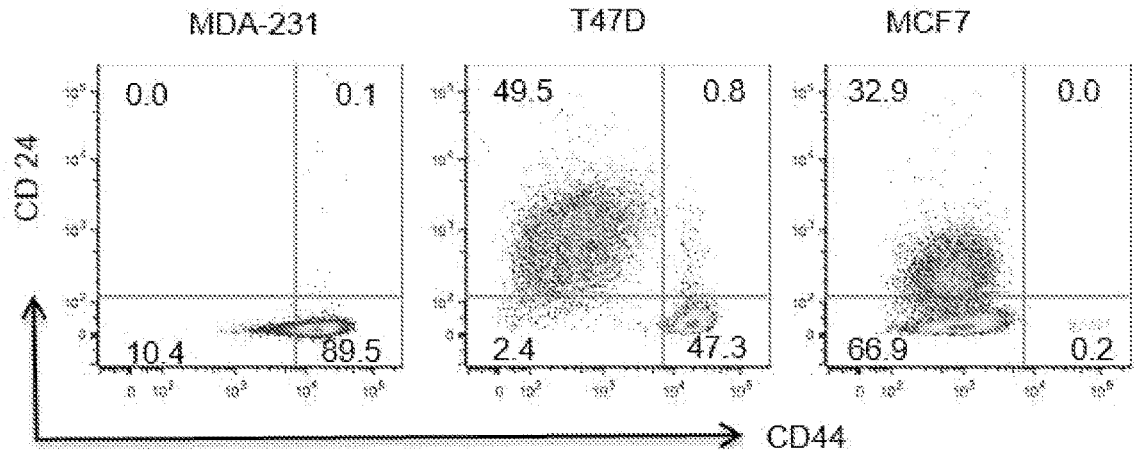

Flow cytometric analysis of equilibrium BrdU-labeled bCSCs chased with unlabeled BrdU showed that B6H12 treatment significantly limited the mean dilution of BrdU compared to isotype control antibody (FIG. 32D). This indicated that ligation of CD47 by B6H12 initiates an anti-proliferative signal in bCSC, we examined the specificity of B6H12 for TNBC by testing two ER+ breast cancer cell lines (MCF7 and T47D) and a normal immortalized breast epithelial cell line (MCF10A). Consistent with our published studies using lung endothelial and T cells, the CD47 blocking antibody B6H12 increased DNA synthesis in MCF10A cells (FIG. 35B). MCF7, a well-differentiated ER+ breast carcinoma cell line with limited malignant potential, also exhibited a positive response to B6H12 (FIG. 34A). However, the breast carcinoma cell line T47D and sorted bCSC showed a similar inhibition of proliferation by B6H12 as MDA-MB-231-sorted bCSC (FIG. 35C-35D). To verify the sensitivity of bSCS derived from MDA-MB-231 and T47D, we sorted $CD44^{high}/CD24^{low}$ cells and assessed BrdU incorporation. B6H12 significantly inhibited cell proliferation of bCSCs derived from MDA-MB-231 and T47D (FIGS. 31E and 35D). This data indicates that B6H12 specifically targets $CD44^{high}$ and $CD24^{low}$ subsets of cells in triple negative and certain ER+ breast cancers that have more tumor initiating cells but is not effective on other ER positive breast cancers or normal breast epithelial cells (FIG. 35E).

It was previously reported that ligation CD47 on several breast cancer cell lines by thrombospondin-1, a CD47-binding peptide, or the CD47 antibody 1F7 induce programmed cell death (Manna & Frazier, Cancer Res, 64(3): 1026-36, 2004). One potential mechanism for the decrease in cell proliferation following B6H12 treatment is increased programmed cell death. Although a CD47-binding peptide induced mitochondrial-independent death of MDA-MB-231 and three additional breast cancer cell lines without caspase activation, such effects of the 4N1K peptide may be independent of CD47 (Barazi et al., J Biol Chem, 277(45): 42859-66, 2002; Leclair & Lim, PLoS One, 9(5): e98358, 2014).

Figure 32F:
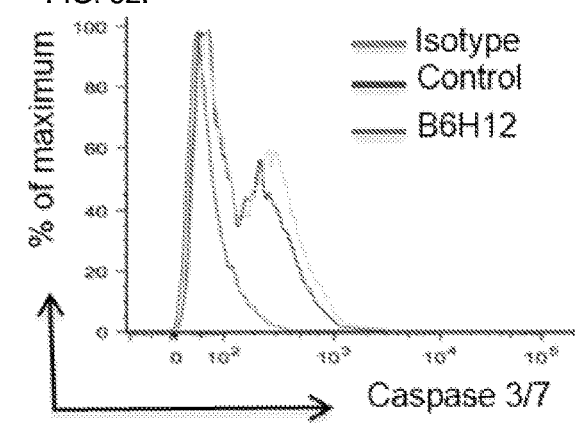
Figure 32G:
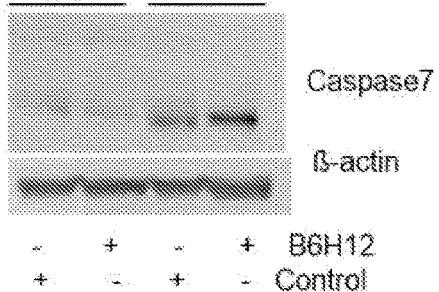

We treated MDA-MB-231 cells with B6H12 or isotype control for 36 hours and found that levels of the initiator caspases-2, 3, 9 and 8 were upregulated as compared to isotype control and untreated cells, but cleavage of these caspases were not observed in any treatments. However, flow cytometry demonstrated that B6H12 increased executioner caspase 3/7 activity (FIGS. 32F and 32G). Consistent with previous reports (Pettersen et al., J Immunol, 166(8): 4931-42, 2001), B6H12 treatment did not induce binding of the apoptosis indicator annexin V. Thus, B6H12-induced cell death does not occur by the canonical apoptosis pathway.

Figure 34C:
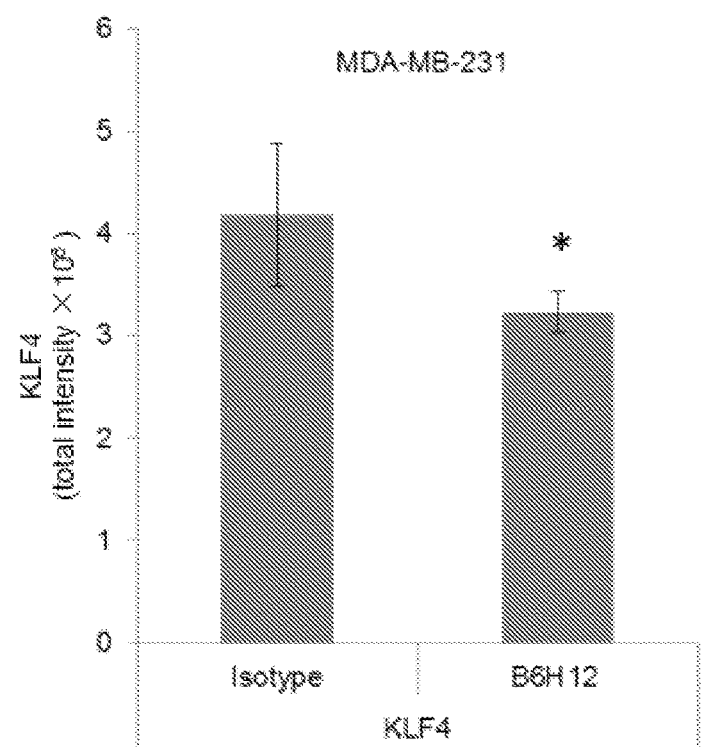
Figure 36C:
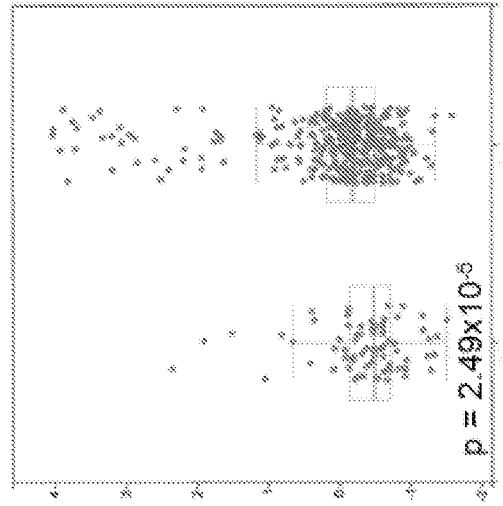

Stem Cell and Cell Death Markers Correlate with CD47 Expression in Human Breast Cancers The relevance of this in vitro data to human breast cancers was examined using cBioPortal tools to analyze The Cancer Genome Atlas (TCGA) mRNA and protein expression data for invasive breast carcinoma (Cancer Genome Atlas Network, Nature, 490(7418):61-70, 2012; Gao et al., Sci Signal, 6(269): p 11, 2013; Cerami et al., Cancer Discov, 2(5):401-4, 2012). CD47 mRNA expression>1 SD higher than the mean by RNAseq analysis was associated with significantly decreased overall survival (median survival 93.7 versus 114.7 months, log rank p-value 0.029, FIG. 36A). Consistent with the diminished sensitivity of ER+ breast cancer cells to B6H12 observed here and a previous report that basal breast carcinomas express higher CD47 (Zhao et al., Proc Natl Acad Sci USA, 108(45):18342-7, 2011), CD47 mRNA expression in the TCGA dataset was negatively correlated with ER and with HER2 protein expression (p=$1.7×10^{-6}$ and $2.5×10^{-5}$, respectively, FIG. 34B-34C). In contrast to HER2 but consistent with our in vitro data, EGFR protein expression in the tumors positively correlated with CD47 mRNA expression (p=0.009, FIG. 32D)

Figure 36E:
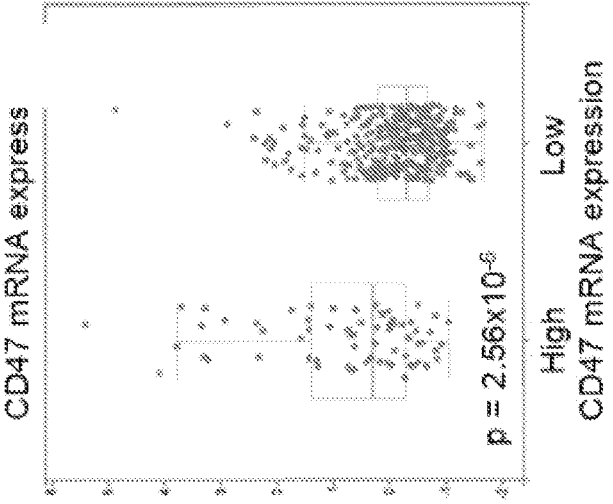
Figure 36B:
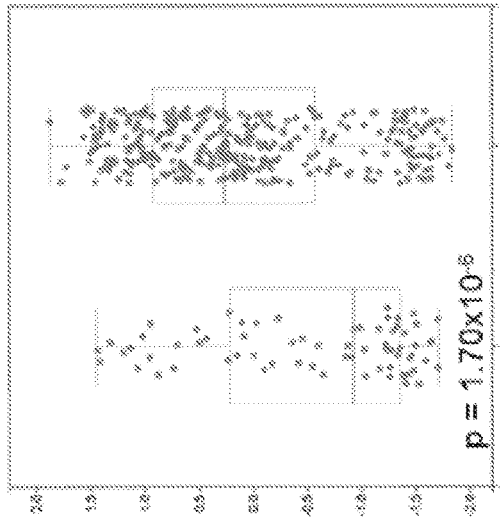
Figure 36D:
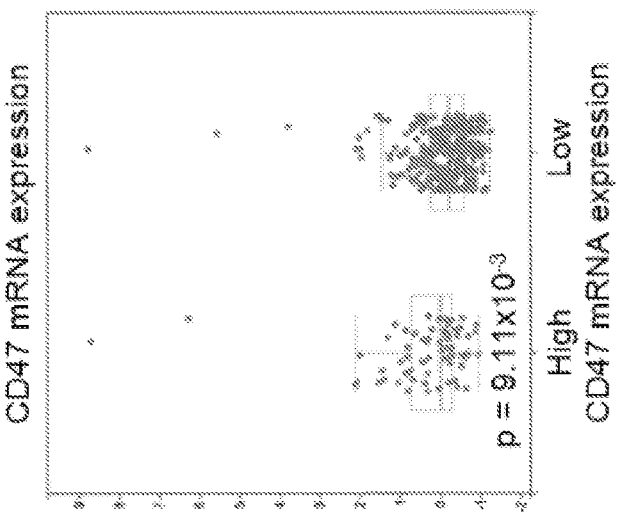

CD47 mRNA expression data showed a strong positive correlation with levels of caspases-7 protein cleaved at $Asp^{198}$ (FIG. 32F, G, p=$2.6×10^{-6}$, FIG. 36E). This was the fifth most significant change in protein levels associated with CD47 mRNA expression in the breast cancer dataset. In contrast, levels of the anti-apoptotic protein Bcl2 were significantly lower in breast cancers with elevated CD47 mRNA (p=0.001). Similar positive correlations between CD47 mRNA and caspase-7 cleavage were found in TCGA melanoma (p=$1×10^{-3}$) and bladder carcinoma (p=$9.7×10^{-5}$) datasets. These results are consistent with a recent study showing that long term blocking of CD47 using B6H12 directly induced apoptosis of pancreatic cancer stem cells in the absence of macrophages (Cioffi et al., Clin Cancer Res, 21:2325, 2015). This suggests that high CD47 expression in cancer stem cells may generally increase caspase-7 cleavage and be a liability for their survival.

Figure 37A:
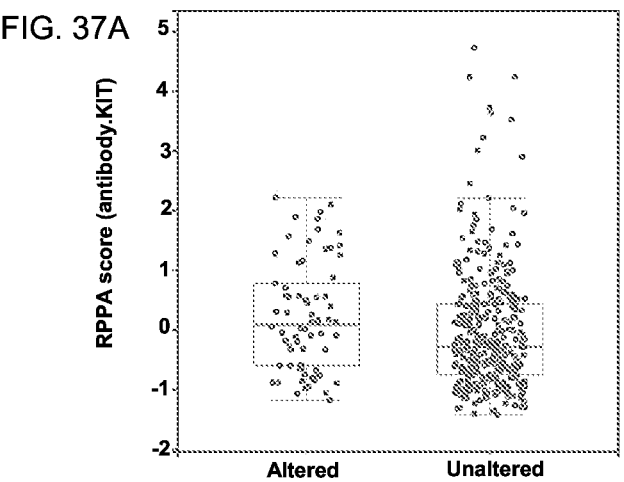
FIG. 37A-37C are a series of plots illustrating.
Figure 37B:
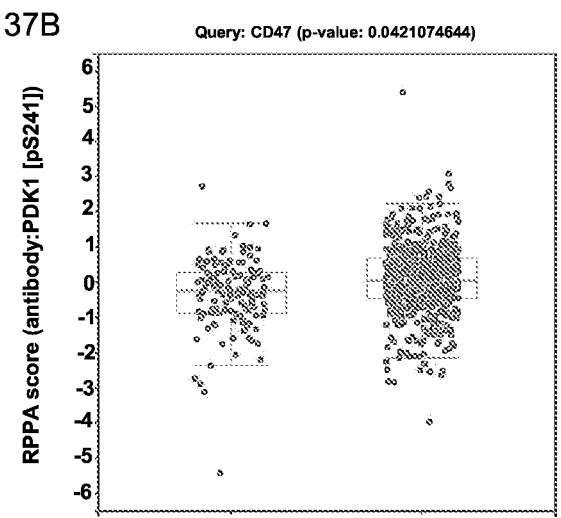
Figure 37C:
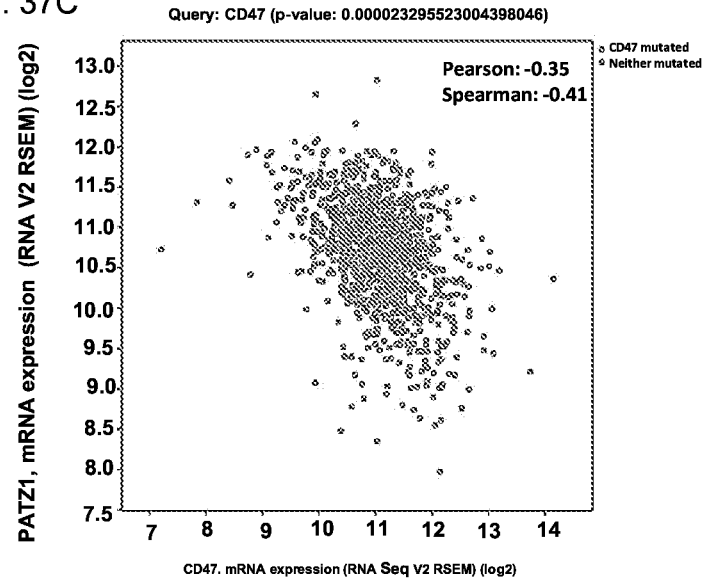

Several known stem cell markers correlated with CD47 mRNA expression in the TCGA breast carcinoma dataset including a positive correlation with cKit protein expression (p=0.042). In contrast, phosphorylation of PDK1 at Ser241, which induces a cancer stem cell gene expression signature (Tan et al., Cancer Discov, 3(10):1156-71, 2013; Casamayor et al., Biochem J, 342 (Pt 2): 287-92, 1999), was negatively correlated with CD47 mRNA expression and was the fourth most significant change in protein phosphorylation in the breast cancer dataset (p=0.0015). The transcription factor PATZ1 maintains stem cells by its regulation of Pou5f1 and Nanog (Ow et al., Stem Cells Dev, 23(10):1062-73, 2014). PATZ1 mRNA expression in breast cancers negatively correlated with CD47 mRNA expression (Spearman correlation=-0.41, FIG. 37C). Similar negative correlations between PATZ1 and CD47 mRNA expression were found in TCGA datasets for melanoma (-0.41), head and neck squamous cell carcinoma (-0.45), and bladder carcinoma (-0.50). Therefore, elevated CD47 expression correlates with known markers and regulators of stem cell maintenance in breast tumors, but CD47 expression may have both positive and negative effects on bCSC differentiation.

We examined the specificity of B6H12 for TNBC by testing two ER+ breast cancer cell lines (MCF7 and T47D) and a normal immortalized breast epithelial cell line (MCF10A). Consistent with our published studies using lung endothelial and T cells, the CD47 blocking antibody B6H12 increased DNA synthesis in MCF10A cells. However, the breast carcinoma cell line T47D and sorted bCSC showed a similar inhibition of proliferation by B6H12 as MDA-MB-231-sorted bCSC. This data indicates that B6H12 specifically targets CD44high and CD24low subsets of cells in triple negative and certain ER+ breast cancers that have more tumor initiating cells but is not effective on other ER positive breast cancers or normal breast epithelial cells. Our results indicate that bCSC express both high levels of CD47 and characteristic stem cell genes. Treatment with B6H12 down regulates KLF4 and inhibits asymmetric cell division of bCSCs. The treated cells resemble differentiated MDA-MB-231 cells and have limited proliferative capacity. This suggests that CD47 expression supports bCSC maintenance.

DISCUSSION

The premise for developing therapeutic antibodies that target CD47 was that high expression of this cell surface protein protects tumor cells from host innate immune surveillance (Jaiswal et al., Cell, 138(2):271-85, 2009). However, we recently reported that expression of CD47 in non-transformed cells plays a critical role in regulating stem cell homeostasis. Specifically, CD47 signaling inhibits the expression of cMyc, SOX2, OCT3/4 and KLF4 (Kaur et al., Sci Rep, 3:1673, 2013). Decreasing CD47 in non-transformed cells increases their self-renewal, asymmetric division and ability to reprogram into other differentiated cell types. Because, high CD47 expression limits the stem cell character of non-transformed cells, the high expression of CD47 on cancer stem cells appeared paradoxical, suggesting that the CD47 expressed on CSC may lack the signaling activity to control stem cell self-renewal, either due to alterations in the CD47 or inactivation of pathways that mediate its signaling in CSC. A recent study in hepatocarcinoma stem cells demonstrated that reducing CD47 expression resulted in loss of stem cell character (Lee et al., Hepatology, 60(1):179-91, 2014), suggesting that CD47 signaling differentially regulates normal versus malignant stem cells. Conversely, treatment with the CD47 ligand thrombospondin-1 was recently reported to inhibit proliferation, sphere formation, and expression of stem cell transcription factors in Lewis lung carcinoma cells, and CD47 shRNA knockdown blocked this activity (Zheng et al., J Biol Chem, 290(14):8975-86, 2015). Our results indicate that bCSC express both high levels of CD47 and characteristic stem cell genes. Treatment with B6H12 down regulates KLF4 and inhibits asymmetric cell division of bCSCs. The treated cells resemble differentiated MDA-MB-231 cells and have limited proliferative capacity. This suggests that CD47 expression supports bCSC maintenance. However, increased CD47 expression in human breast cancers correlates with increased cleavage of the executioner caspase-7 and loss of Bcl2. Therefore, maintaining high CD47 expression to evade host immunity and support CSC may have an associated cost in terms of tumor cell viability.

From a therapeutic perspective, our data indicates that the prototypical CD47 "blocking" antibody B6H12 has a second activity that could provide therapeutic benefit by suppressing stem cell character in bCSC. B6H12 down regulates EGFR expression at the mRNA and protein levels and inhibits $Tyr^{1068}$ phosphorylation of EGFR. CD47 and EGFR co-immunoprecipitation and their interaction are disturbed by B6H12, but only a small fraction of these proteins interact and co-localize at the cell surface however B6H12 alone enhance EGFR release on exosomes only in TNBC. Currently EGFR inhibitors are in phase II clinical trials and show efficacy to inhibit tumor growth in xenograft models (Gluz et al., Ann Oncol, 20(12):1913-27, 2009; Zhang et al., Clin Cancer Res, 15(21):6639-48, 2009; Friess et al., Clin Cancer Res, 11(14):5300-9, 2005; Sohn et al., J Cancer, 5(9):745-53, 2014). The correlation between CD47 and EGFR expression in human breast tumors suggests that therapeutic CD47 antibodies may be effective against tumors with high EGFR expression alone or in combination with EGFR inhibitors.

B6H12 may also limit tumor growth by inhibiting asymmetric division of CSCs. This activity was observed in a TNBC line, but not in the less aggressive MCF7 cell line or MCF10 immortalized mammary epithelial cells, which showed increased proliferation consistent with our primary endothelial cell data (Kaur et al., Sci Rep, 3:1673, 2013). Based on our data and a recent report that shRNA knockdown of CD47 suppressed cancer stem cells of hepatocyte carcinoma cells (Lee et al., Hepatology, 60(1):179-91, 2014), suggesting that a direct cell-autonomous effects of therapeutic CD47 antibodies to suppress CSC may extend to additional cancers.

Others have shown that certain CD47 antibodies, but not B6H12, directly induce apoptosis of B-cell chronic lymphocytic leukemia associated with cell shrinkage, decreased mitochondrial transmembrane potential, and phosphatidylserine externalization, but independent of apoptotic caspase activation (Pettersen et al., J Immunol, 166(8):4931-42, 2001). These studies suggest that each CD47 antibody may have different effects on CD47 signaling, which may involve direct agonist activities of a given antibody as well as antagonism of the signaling induced by SIRPα or TSP1 binding.

In summary, these data demonstrate that CD47 is an active signaling receptor in triple negative human breast cancer. The CD47 antibody B6H12 directly inhibits cell growth and CSC maintenance in an aggressive subset of the breast cancer cell lines we have tested, whereas stimulation of proliferation was also observed in cell lines with less malignant potential, which is consistent with known CD47 signaling in non-transformed cells. The EGFR phosphorylation data presented here reveals a novel lateral signaling mechanism through which B6H12 inhibits proliferation of aggressive cancer cells.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

TABLE 1

| Col # | Column ID | Entrez Gene | Gene Symbol | Gene Title |
| --- | --- | --- | --- | --- |
| 7865 | 1565483_at | 1956 | EGFR | epidermal growth factor receptor |
| 7866 | 1565484_x_at | 1956 | EGFR | epidermal growth factor receptor |
| 50111 | 240854_x_at | — | — | — |
| 43862 | 234605_at | 8555 | CDC14B | CDC14 cell division cycle 14 homolog B (S. cerevisiae) |
| 49205 | 239948_at | 9972 | NUP153 | nucleoporin 153 kDa |
| 13503 | 204048_s_at | 9749 | PHACTR2 | phosphatase and actin regulator 2 |

TABLE 1-continued

| | | | | |
|---|---|---|---|---|
| 53002 | 243745_at | — | — | — |
| 52905 | 243648_at | 100381270 | ZBED6 | zinc finger, BED-type containing 6 |
| 31907 | 222620_s_at | 64215 | DNAJC1 | DnaJ (Hsp40) homolog, subfamily C, member 1 |
| 33266 | 223984_s_at | 9818 | NUPL1 | nucleoporin like 1 |
| 4385 | 1558733_at | 253461 | ZBTB38 | zinc finger and BTB domain containing 38 |
| 10370 | 200914_x_at | 3895 | KTN1 | kinectin 1 (kinesin receptor) |
| 48863 | 239606_at | — | — | — |
| 49561 | 240304_s_at | 79838 | TMC5 | transmembrane channel-like 5 |
| 38782 | 229520_s_at | 55668 | C14orf118 | chromosome 14 open reading frame 118 |
| 30846 | 221555_x_at | 8555 | CDC14B | CDC14 cell division cycle 14 homolog B (*S. cerevisiae*) |
| 17149 | 207700_s_at | 8202 | NCOA3 | nuclear receptor coactivator 3 |
| 44682 | 235425_at | 151246 | SGOL2 | shogoshin-like 2 (*S. pombe*) |
| 28863 | 219571_s_at | 7559 | ZNF12 | zinc finger protein 12 |
| 41357 | 232095_at | 100509683 | LOC100509683 | uncharacterized LOC100509683 |
| 14770 | 205315_s_at | 6645 | SNTB2 | sytrophin, beta 2 (dystrophin-associated protein A1, 59 kDa, basic component 2) |
| 46009 | 236752_at | — | — | — |
| 42339 | 233078_at | 8539 | API5 | apoptosis inhibitor 5 |
| 54032 | 244774_at | 9749 | PHACTR2 | phosphatase and actin regulator 2 |
| 33528 | 224250_s_at | 79048 | SECISBP2 | SECIS binding protein 2 |
| 11373 | 201917_s_at | 55186 | SLC25A36 | solute carrier family 25 (pyrimidine nucleotide carrier), member 36 |
| 49912 | 240655_at | — | — | — |
| 21534 | 212220_at | 23198 | PSME4 | proteasome (prosome, macropain) activator subunit 4 |
| 2498 | 1555677_s_at | 8243 | SMC1A | structural maintenance of chromosomes 1A |
| 27814 | 218521_s_at | 55284 | UBE2W | ubiquitin-conjugating enzyme E2W (putative) |
| 1390 | 1554178_a_at | 285172 | FAM126B | family with sequence similarity 126, member B |
| 5111 | 1559993_at | 81855 | SFXN3 | Sideroflexin 3 |
| 21427 | 212113_at | 552889 | ATXN7L3B | ataxin 7-like 3B |
| 31975 | 222688_at | 55331 | ACER3 | alkaline ceramidase 3 |
| 48650 | 239393_at | — | — | — |
| 29867 | 220575_at | 80039 | FAM106A | family with sequence similarity 106, member A |
| 37002 | 227740_at | 127933 | UHMK1 | U2AF homology motif (UHM) kinase 1 |
| 12428 | 202971_s_at | 8445 | DYRK2 | dual-specificity tyrosine-(Y)-phosphorylation regulated kinase 2 |
| 48649 | 239392_s_at | 57645 | POGK | pogo transposable element with KRAB domain |
| 13502 | 204047_s_at | 9749 | PHACTR2 | phosphatase and actin regulator 2 |
| 50648 | 241391_at | — | — | — |
| 12432 | 202975_s_at | 22836 | RHOBTB3 | Rho-related BTB domain contaning 3 |
| 35318 | 226054_at | 23476 | BRD4 | bromodomain containing 4 |
| 47598 | 238341_at | — | — | — |
| 39892 | 230630_at | 1000507855 /// 205 | AK4 /// LOC100507855 | adenylate kinase 4 /// adenylate kinase isoenzyme 4, mitochondrial-like |
| 36646 | 227383_at | 727820 | LOC727820 | uncharacterized LOC727820 |
| 53599 | 244341_at | — | — | — |
| 45781 | 236524_at | — | — | — |
| 48999 | 239742_at | 56995 | TULP4 | Tubby like protein 4 |

TABLE 1-continued

| | | | | |
|---|---|---|---|---|
| 38295 | 229033_s_at | 84939 | MUM1 | melanoma associated antigen (mutated) 1 |
| 11439 | 201983_s_at | 1956 | EGFR | epidermal growth factor receptor |
| 37193 | 227931_at | 54891 | INO80D | INO80 complex subunit D |
| 30232 | 220940_at | 57730 | ANKRD36B | ankyrin repeat domain 36B |
| 9181 | 1569362_at | 214 | ALCAM | activated leukocyte cell adhesion molecule |
| 38848 | 229586_at | 80205 | CHD9 | chromodomain helicase DNA binding protein 9 |
| 40665 | 231403_at | 7204 | TRIO | triple functional domain (PTPRF interacting) |
| 2044 | 1555058_a_at | 9926 | LPGAT1 | lysophosphatidyl-glycerol acyltransferase 1 |
| 19548 | 210136_at | 4155 | MBP | myelin basic protein |
| 17407 | 207966_s_at | 2734 | GLG1 | golgi glycoprotein 1 |
| 44314 | 235057_at | 83737 | ITCH | itchy E3 ubiquitin protein ligase |
| 24526 | 215224_at | 619505 | SNORA21 | small nucleolar RNA, H/ACA box 2.1 |
| 22539 | 213229_at | 23405 | DICER1 | dicer 1, ribonuclease type III |
| 11835 | 202379_s_at | 4820 | NKTR | natural killer-tumor recognition sequence |
| 15515 | 206061_s_at | 23405 | DICER1 | dicer 1, ribonuclease type III |
| 41270 | 232008_s_at | 56987 | BBX | bobby sox homolog (Drosophila) |
| 46640 | 237383_at | — | — | — |
| 52270 | 243013_at | — | — | — |
| 5295 | 1560318_at | 9411 | ARHGAP29 | Rho GTPase activating protein 29 |
| 10755 | 201299_s_at | 55233 | MOB1A | MOB kinase activator 1A |
| 45257 | 236000_s_at | — | — | — |
| 36520 | 227257_s_at | 143384 | CACUL1 | CDK2-associated, cullin domain 1 |
| 37391 | 228129_at | 26135 | SERBP1 | SERPINE1 mRNA binding protein 1 |
| 38615 | 229353_s_at | 64710 | NUCKS1 | nuclear casein kinase and cyclin-dependent kinase substrate 1 |
| 31827 | 222540_s_at | 51773 | RSF1 | remodeling and spacing factor 1 |
| 48044 | 238787_at | 163486 | DENND1B | DENN/MADD domain containing 1B |
| 53443 | 244185_at | — | — | — |
| 18679 | 209257_s_at | 9126 | SMC3 | structural maintenance of chromosomes 3 |
| 52846 | 243589_at | 284058 | KANSL1 | KATB regulatory NSL complex subunit 1 |
| 31831 | 222544_s_at | 54904 | WHSC1L1 | Wolf-Hirschhorn syndrome canidiate 1-like 1 |
| 4581 | 1559060_a_at | 96459 | FNIP1 | Folliculin interacting protein 1 |
| 34354 | 225089_at | 55230 | USP40 | ubiquitin specific peptidase 40 |
| 16511 | 207057_at | 9194 | SLC16A7 | solute carrier family 16, member 7 (monocarboxylic acid transporter 2) |
| 9247 | 1569472_s_at | 286495 /// 7267 | TTC3 /// TTC3P1 | tetratricopeptide repeat domain 3 /// tetratricopeptide repeat domain 3 pseudogene 1 |
| 13083 | 203628_at | 3480 | IGF1R | insulin-like growth factor 1 receptor |
| 34199 | 224933_s_at | 221037 | JMJD1C | jumonji domain containing 1C |
| 13258 | 203803_at | 51449 | PCYOX1 | prenylcysteine oxidase 1 |
| 29364 | 220072_at | 79848 | CSPP1 | centrosome and spindle pole associated protein 1 |
| 45729 | 235388_at | — | — | — |
| 44645 | 235388_at | 80205 | CHD9 | chromodomain helicase DNA binding protein 9 |

TABLE 1-continued

| | | | | |
|---|---|---|---|---|
| 30972 | 221683_s_at | 80184 | CEP290 | centrosomal protein 290 kDa |
| 43290 | 234032_at | — | — | — |
| 37146 | 227884_at | 8148 | TAF15 | TAF15 RNA polymerase II, TATA box binding protein (TBP)-associated factor, 68 kDa |
| 45613 | 236356_at | 4719 | NDUFS1 | NADH dehydrogenase (ubiquinone)Fe-S protein 1, 75 kDa (NADH-coenzyme Q reductase) |
| 34755 | 225490_at | 196528 | ARID2 | AT rich interactive domain 2 (ARID, RFX-like) |
| 48588 | 239331_at | — | — | — |
| 20457 | 211085_s_at | 6789 | STK4 | serine/threonine kinase 4 |
| 30794 | 221503_s_at | 3839 | KPNA3 | karyopherin alpha 3 (importin alpha 4) |
| 38569 | 229307_at | 23243 | ANKRD28 | ankyrin repeat domain 28 |
| 18353 | 208930_s_at | 3609 | ILF3 | interleukin enhancer binding factor 3, 90 kDa |
| 45060 | 235803_at | — | — | — |
| 48279 | 239022_at | — | — | — |
| 22887 | 213579_s_at | 2033 | EP300 | E1A binding protein p300 |
| 46098 | 236841_at | 100134445 | LOC100134445 | uncharacterized LOC100134445 |
| 36717 | 227454_at | 57551 | TAOK1 | TAO kinase 1 |
| 12671 | 203215_s_at | 4646 | MYO6 | myosin VI |
| 34836 | 225571_at | 3977 | LIFR | leukemia inhibitory factor receptor alpha |
| 28450 | 219158_s_at | 80155 | NAA15 | N(alpha)-acetyltransferase 15, NatA auxiliary subunit |
| 52940 | 243683_at | 9643 | MORF4L2 | Mortality factor 4 like 2 |
| 18680 | 209258_s_at | 9126 | SMC3 | structural maintenance of chromosomes 3 |
| 7160 | 1563321_s_at | 8028 | MLLT10 | myeloid/lymphoid or mixed-lineage leukemia (trithorax homolog, Drosophila); translocate |
| 44783 | 235526_at | 55553 | SOX6 | SRY (sex-determining region Y)-box 6 |
| 36776 | 227514_at | 162073 | ITPRIPL2 | inositol 1,4,5-trisphosphate receptor interacting protein-like 2 |
| 38661 | 229399_at | 55088 | C10orf118 | chromosome 10 open reading frame 118 |
| 33223 | 223940_x_at | 100507645 /// 378938 | LOC100507645 /// MALAT1 | uncharacterized LOC100507645 /// metastasis associated lung adenocarcinoma transcript 1 |
| 51077 | 241820_at | 55183 | RIF1 | RAP1 interacting factor homolog (yeast) |
| 3442 | 1557100_s_at | 25831 | HECTD1 | HECT domain containg E3 ubiquitin protein ligase 1 |
| 28513 | 219221_at | 253461 | ZBTB38 | zinc finger and BTB domain containing 38 |
| 10638 | 201182_s_at | 1108 | CHD4 | chromodomain helicase DNA binding protein 4 |
| 51967 | 242710_at | — | — | — |
| 11452 | 201996_s_at | 23013 | SPEN | spen homolog, transcriptional regulator (Drosophila) |
| 36647 | 227384_s_at | 727820 /// 728855 /// 728875 | LOC727820 /// LOC728855 /// LOC728875 | uncharacterized LOC727820 /// uncharacterized LOC728855 /// uncharacterized LOC728875 |
| 5267 | 1560271_at | — | — | — |
| 42186 | 232925_at | — | — | — |
| 27244 | 217951_s_at | 23469 | PHF3 | PHD finger protein 3 |
| 51490 | 242233_at | — | — | — |

TABLE 1-continued

| | | | | |
|---|---|---|---|---|
| 3544 | 1557267_s_at | 348654 | GEN1 | Gen endonuclease homolog 1 (Drosophila) |
| 41128 | 231866_at | 4012 | LNPEP | leucyl/cystinyl aminopeptidase |
| 4048 | 1558080_s_at | 5611 | DNAJC3 | DnaJ (Hsp40) homolog, subfamily C, member 3 |
| 34685 | 225420_at | 57678 | GPAM | glycerol-3-phosphate acyltransferase, mitochondrial |
| 45525 | 236268_at | 9117 | SEC22C | SEC22 vesicle trafficking protein homolog C (S. cerevisiae) |
| 39120 | 229858_at | — | — | — |
| 49564 | 240307_at | — | — | |
| 44523 | 235266_at | 29028 | ATAD2 | ATPase family, AAA domain containing 2 |
| 32861 | 223577_x_at | 378938 | MALAT1 | metastasis associated lung adenocarcinoma transcript 1 (non-protein coding) |
| 17459 | 208022_s_at | 8555 | CDC14B | CDC14 cell division cycle 14 homolog B (S. cerevisiae) |
| 10796 | 201340_s_at | 8507 | ENC1 | ectodermal-neural cortex 1 (with BTB-like domain) |
| 44979 | 235722_at | 55333 | SYNJ2BP | synaptojanin 2 binding protein |
| 37418 | 228156_at | — | — | |
| 24924 | 215623_x_at | 10051 | SMC4 | structural maintenance of chromosomes 4 |
| 31920 | 222633_at | 79718 | TBL1XR1 | tranducin (beta)-like 1 x-linked receptor 1 |
| 33102 | 223818_s_at | 51773 | RSF1 | remodeling and spacing factor 1 |
| 27106 | 217813_s_at | 10927 | SPIN1 | spindlin 1 |
| 19166 | 209750_at | 9975 | NR1D2 | nuclear receptor subfamily 1, group D, member 2 |
| 18302 | 208879_x_at | 24148 | PRPF6 | PRP6 pre-mRNA processing factor 6 homolog (S. cerevisiae) |
| 33898 | 224631_at | 80829 | ZFP91 | zinc finger protein 91 homolog (mouse) |
| 48018 | 238761_at | 2005 | ELK4 | ELK4, ETS-domain protein (SRF accessory protein 1) |
| 17440 | 208003_s_at | 10725 | NFAT5 | nuclear factor of activated T-cells 5, tonicity-responsive |
| 256 | 1552611_a_at | 3716 | JAK1 | Janus kinase 1 |
| 33835 | 224568_x_at | 100507645 /// 378938 | LOC100507645 /// MALAT1 | uncharacterized LOC100507645 /// metastasis associated lung adenocarcinoma transcript 1 |
| 10541 | 201085_s_at | 6651 | SON | SON DNA binding protein |
| 21392 | 212078_s_at | 4297 | MLL | myeloid/lymphoid or mixed-lineage leukemia (trithorax homolog, Drosophila) |
| 43958 | 234701_at | 29123 | ANKRD11 | ankyrin repeat domain 11 |
| 11323 | 201867_s_at | 6907 | TBL1X | transducin (beta)-like 1X-linked |
| 49947 | 240690_at | — | — | |
| 15954 | 206500_s_at | 55320 | MIS18BP1 | MIS18 binding protein 1 |
| 44316 | 235059_at | 201475 | RAB12 | RAB12, member RAS oncogene family |
| 44266 | 235009_at | 259282 | BOD1L1 | biorientation of chromosomes in cell division 1-like 1 |
| 10291 | 200835_s_at | 4134 | MAP4 | microtubule-associated protein 4 |
| 44966 | 235709_at | 283431 | GAS2L3 | growth arrest-specific 2 like 3 |

TABLE 1-continued

| | | | | |
|---|---|---|---|---|
| 4392 | 1558747_at | 23347 | SMCHD1 | structural maintenance of chromosomes flexible hinge domain containing 1 |
| 37740 | 228478_at | — | — | — |
| 27171 | 217878_s_at | 996 | CDC27 | cell division cycle 27 homolog (*S. cerevisiae*) |
| 39756 | 230494_at | 6574 | SLC20A1 | solute carrier family 20 (phosphate transporter), member 1 |
| 38534 | 229272_at | 23360 | FNBP4 | formin binding protein 4 |
| 48303 | 239046_at | — | — | — |
| 31700 | 222413_s_at | 58508 | MLL3 | myeloid/lymphoid or mixed-lineage leukemia 3 |
| 24288 | 214985_at | 2131 | EXT1 | exostosin 1 |
| 24640 | 215338_s_at | 4820 | NKTR | natural killer-tumor recognition sequence |
| 4092 | 1558173_a_at | 7798 | LUZP1 | leucine zipper protein 1 |
| 18088 | 208663_s_at | 286495 /// 7267 | TTC3 /// TTC3P1 | tetratricopeptide repeat domain 3 /// tetratricopeptide repeat domain 3 pseudogene 1 |
| 12125 | 202669_s_at | 1948 | EFNB2 | ephrin-B2 |
| 18134 | 208711_s_at | 595 | CCND1 | cyclin D1 |
| 25237 | 215936_s_at | 23325 | KIAA1033 | KIAA1033 |
| 24508 | 215206_at | — | — | — |
| 7608 | 1564378_a_at | — | — | — |
| 25861 | 216563_at | 23253 | ANKRD12 | ankyrin repeat domain 12 |
| 38377 | 229115_at | 1778 | DYNC1H1 | dynein, cytoplasmic 1, heavy chain 1 |
| 20396 | 211022_s_at | 546 | ATRX | alpha thalassemia/mental retardation syndrome X-linked |
| 14295 | 204840_s_at | 8411 | EEA1 | early endosome antigen 1 |
| 21963 | 212650_at | 23301 | EHBP1 | EH domain binding protein 1 |
| 10297 | 200841_s_at | 2058 | EPRS | glutamyl-prolyl-tRNA synthase |
| 21781 | 212468_at | 9043 | SPAG9 | sperm associated antigen 9 |
| 22107 | 212794_s_at | 23325 | KIAA1033 | KIAA1033 |
| 22378 | 213067_at | 4628 | MYH10 | myosin, heavy chain 10, non-muscle |
| 2764 | 1556054_at | — | — | — |
| 40997 | 231735_s_at | 378938 | MALAT1 | metastasis associated lung adenocarcinoma transcript 1 (non-protein coding) |
| 51325 | 242068_at | — | — | — |
| 39027 | 229765_at | 7756 | ZNF207 | zinc finger protein 207 |
| 51517 | 242260_at | 9782 | MATR3 | Matrin 3 |
| 23659 | 214352_s_at | 3845 | KRAS | v-Ki-ras2 Kirsten rat sarcoma viral oncogene homolog |
| 18049 | 208624_s_at | 1981 | EIF4G1 | eukaryotic translation initiation factor 4 gamma, 1 |
| 29377 | 220085_at | 3070 | HELLS | helicase, lymphoid-specific |
| 51212 | 241955_at | 25831 | HECTD1 | HECT domain containing E3 ubiquitin protein ligase 1 |
| 50030 | 240773_at | — | — | — |
| 31726 | 222439_s_at | 9967 | THRAP3 | thyroid hormone receptor associated protein 3 |
| 3461 | 1557129_a_at | 374393 | FAM111B | family with sequence similarity 111, member B |
| 28679 | 219387_at | 55704 | CCDC88A | coiled-coil domain containing 88A |
| 4502 | 1558924_s_at | 6249 | CLIP1 | CAP-GLY domain containing linker protein 1 |
| 53114 | 243857_at | 9643 | MORF4L2 | Mortality factor 4 like 2 |
| 18323 | 208900_s_at | 7150 | TOP1 | topoisomerase (DNA) 1 |

TABLE 1-continued

| | | | | |
|---|---|---|---|---|
| 49893 | 240636_at | — | — | — |
| 40398 | 231136_at | 407032 | MIR30C2 | microRNA 30c-2 |
| 309 | 1552680_a_at | 57082 | CASC5 | cancer susceptibility candidate 5 |
| 18036 | 208610_s_at | 23524 | SRRM2 | serine/arginine repetitive matrix 2 |
| 20375 | 211000_s_at | 3572 | IL6ST | interleukin 6 signal transducer (gp130, oncostatin M receptor) |
| 18510 | 209088_s_at | 29855 | UBN1 | ubinuclein 1 |
| 14318 | 204863_s_at | 3572 | IL6ST | interleukin 6 signal transducer (gp130, oncostatin M receptor) |
| 21393 | 212079_s_at | 4297 | MLL | myeloid/lymphoid or mixed-lineage leukemia (trithorax homolog, Drosophila) |
| 38248 | 228986_at | 114882 | OSBPL8 | oxysterol binding protein-like 8 |
| 23771 | 214464_at | 8476 | CDC42BPA | CDC42 binding protein kinase alpha (DMPK-like) |
| 4349 | 1558678_s_at | 100507645 /// 378938 | LOC100507645 /// MALAT1 | uncharacterized LOC100507645 /// metastasis associated lung adenocarcinoma transcript 1 |
| 33834 | 224567_x_at | 100507645 /// 378938 | LOC100507645 /// MALAT1 | uncharacterized LOC100507645 /// metastasis associated lung adenocarcinoma transcript 1 |
| 18282 | 208859_s_at | 546 | ATRX | alpha thalassemia/mental retardation syndrome X-linked |
| 33830 | 224563_at | 10163 | WASF2 | WAS protein family, member 2 |
| 45877 | 236620_at | 55183 | RIF1 | RAP1 interacting factor homolog (yeast) |
| 3521 | 1557227_s_at | 7175 | TPR | translocated promoter region, nuclear basket protein |
| 11186 | 201730_s_at | 7175 | TPR | translocated promoter region, nuclear basket protein |
| 35938 | 226675_s_at | 100507645 /// 378938 | LOC100507645 /// MALAT1 | uncharacterized LOC100507645 /// metastasis associated lung adenocarcinoma transcript 1 |
| 22755 | 213446_s_at | 8826 | IQGAP1 | IQ motif containing GTPase activating protein 1 |
| 52175 | 242918_at | 4678 | NASP | Nuclear autoantigenetic sperm protein (histone-binding) |
| 15264 | 205809_s_at | 8976 | WASL | Wiskott-Aldrich syndrome-like |
| 41500 | 232238_at | 259266 | ASPM | asp (abnormal spindle) homolog, microcephaly associated (Drosophila) |
| 51609 | 242352_at | 25836 | NIPBL | Nipped-B homolog (Drodophila) |

| Col # | RefSeq Transcript ID | p-value (Attribute) | Fold-Change (B6H12_Ab vs. Ctrl_Ab) |
|---|---|---|---|
| 7865 | NM_055228 /// NM_201282 /// NM_201283 /// NM_201284 | 0.00758284 | −1.9058 |
| 7866 | NM_055228 /// NM_201282 /// NM_201283 /// NM_201284 | 0.00929699 | −1.69678 |
| 50111 | — | 0.00716955 | −1.55596 |

TABLE 1-continued

| | | | |
|---|---|---|---|
| 43862 | NM_001077181 /// NM_003671 /// NM_033331 /// NM_033332 | 0.00145854 | 1.50173 |
| 49205 | NM_005124 | 0.00537521 | 1.50258 |
| 13503 | NM_001100164 /// NM_001100165 /// NM_001100166 /// NM_014721 | 0.0141831 | 1.50419 |
| 53002 | — | 0.00180785 | 1.50472 |
| 52905 | NM_001174108 | 0.0219142 | 1.50648 |
| 31907 | NM_022365 | 0.000177968 | 1.50759 |
| 33266 | NM_001008564 /// NM_001008565 /// NM_014089 | 0.0426645 | 1.50852 |
| 4385 | NM_001080412 /// NM_152535 | 0.037835 | 1.50948 |
| 10370 | NM_001079521 /// NM_001079522 /// NM_004986 /// NM_182926 | 0.00536708 | 1.50981 |
| 48863 | — | 0.00109509 | 1.51 |
| 49561 | NM_001105248 /// NM_001105249 /// NM_001261841 /// NM_024780 | 0.0212464 | 1.51049 |
| 38782 | NM_017926 /// NM_017972 | 0.0000662047 | 1.51135 |
| 30846 | NM_001077181 /// NM_003671 /// NM_033331 /// NM_033332 | 0.0488715 | 1.5127 |
| 17149 | NM_001174087 /// NM_001174088 /// NM_006534 /// NM_181659 | 0.0104055 | 1.51282 |
| 44682 | NM_001160033 /// NM_001160046 /// NM_152524 | 0.00247415 | 1.51305 |
| 28863 | NM_006956 /// NM_016265 | 0.00148539 | 1.5166 |
| 41357 | XR_112004 | 0.00460052 | 1.51713 |
| 14770 | NM_006750 /// NM_130845 | 0.000695291 | 1.51732 |
| 46009 | — | 0.0108735 | 1.51862 |
| 42339 | NM_001142930 /// NM_001142931 /// NM_001243747 /// NM_006595 /// NR_024625 | 0.0074819 | 1.5193 |
| 54032 | NM_001100164 /// NM_001100165 /// NM_001100166 /// NM_014721 | 0.0216076 | 1.52175 |
| 33528 | NM_024077 | 0.000168024 | 1.52234 |
| 11373 | NM_001104647 /// NM_018155 | 0.00462846 | 1.52367 |
| 49912 | — | 0.0345829 | 1.52775 |
| 21534 | NM_014614 | 0.0146262 | 1.52807 |
| 2498 | NM_006306 | 0.0096529 | 1.52887 |
| 27814 | NM_001001481 /// NM_001001482 /// NM_018299 | 0.0214975 | 1.53094 |
| 1390 | NM_173822 | 0.00140223 | 1.53106 |
| 5111 | NM_030971 | 0.0256685 | 1.53147 |
| 21427 | NM_001136262 | 0.0092876 | 1.53278 |
| 31975 | NM_018367 | 0.00568208 | 1.53322 |
| 48650 | — | 0.0333635 | 1.53379 |
| 29867 | NM_024974 /// NR_26809 | 0.0473866 | 1.53439 |
| 37002 | NM_001184763 /// NM_144624 /// NM_175866 | 0.00366961 | 1.5347 |
| 12428 | NM_003583 /// NM_006482 | 0.0135754 | 1.53583 |
| 48649 | NM_017542 | 0.000501282 | 1.53627 |
| 13502 | NM_001100164 /// NM_001100165 /// NM_001100166 /// NM_014721 | 0.00411187 | 1.53867 |

TABLE 1-continued

| | | | |
|---|---|---|---|
| 50648 | — | 0.00027805 | 1.53944 |
| 12432 | NM_014899 | 0.000538566 | 1.5403 |
| 35318 | NM_014299 /// NM_058243 | 0.00748653 | 1.5403 |
| 47598 | — | 0.00349413 | 1.54212 |
| 39892 | NM_001005353 /// NM_013410 /// NM_203464 /// XM_003119530 | 0.0236654 | 1.54404 |
| 36646 | XR_041980 | 0.00982574 | 1.54717 |
| 53599 | — | 0.00832358 | 1.54938 |
| 45781 | — | 0.00272043 | 1.54964 |
| 48999 | NM_001007466 /// NM_020245 | 0.0419099 | 1.55012 |
| 38295 | NM_032853 /// NR_024247 | 0.0350633 | 1.55263 |
| 11439 | NM_005228 /// NM_201282 /// NM_201283 /// NM_201284 | 0.0160253 | 1.55342 |
| 37193 | NM_017759 | 0.00144066 | 1.55524 |
| 30232 | NM_020970 /// NM_025190 | 0.00169712 | 1.55578 |
| 9181 | NM_001243280 /// NM_001243281 /// NM_001243283 /// NM_001627 | 0.00991597 | 1.55629 |
| 38848 | NM_025134 | 0.000565799 | 1.55647 |
| 40665 | NM_007118 | 0.000351701 | 1.55759 |
| 2044 | NM_014873 | 0.0246991 | 1.55787 |
| 19548 | NM_001025081 /// NM_001025090 /// NM_001025092 /// NM_001025094 /// NM_001025098 /// NM | 0.00513611 | 1.55807 |
| 17407 | NM_001145666 /// NM_001145667 /// NM_012201 /// NR_027264 /// NR_027265 | 0.0150821 | 1.56042 |
| 44314 | NM_001257137 /// NM_001257138 /// NM_031483 | 0.0267355 | 1.56109 |
| 24526 | NR_002576 | 0.000536919 | 1.56208 |
| 22539 | NM_001195573 /// NM_030621 /// NM_177438 | 0.0200868 | 1.56391 |
| 11835 | NM_001012651 /// NM_005385 | 0.00469482 | 1.56815 |
| 15515 | NM_001195573 /// NM_030621 /// NM_177438 | 0.0255576 | 1.5686 |
| 41270 | NM_001142568 /// NM_020235 | 0.00092687 | 1.56873 |
| 46640 | — | 0.00131189 | 1.57192 |
| 52270 | — | 0.00115308 | 1.57343 |
| 5295 | NM_004815 | 0.000103225 | 1.57462 |
| 10755 | NM_018221 | 0.0102216 | 1.57694 |
| 45257 | — | 0.0120607 | 1.57749 |
| 36520 | NM_153810 | 0.00322839 | 1.57983 |
| 37391 | NM_001018067 /// NM_001018068 /// NM_001018069 /// NM_015640 | 0.00444628 | 1.58016 |
| 38615 | NM_022731 | 0.00527112 | 1.58045 |
| 31827 | NM_016578 | 0.00134395 | 1.58096 |
| 48044 | NM_001142795 /// NM_001195215 /// NM_001195216 /// NM_019049 /// NM_144977 | 0.00337621 | 1.58315 |
| 53443 | — | 0.00109565 | 1.58432 |
| 18679 | NM_005445 | 0.00218202 | 1.58551 |
| 52846 | NM_001193465 /// NM_001193466 /// NM_015443 /// XM_003403598 /// XM_003403599 /// XM_00 | 0.0109478 | 1.58729 |

TABLE 1-continued

| | | | |
|---|---|---|---|
| 31831 | NM_017778 /// NM_023034 | 0.0105939 | 1.59152 |
| 4581 | NM_001008738 /// NM_133372 | 0.017307 | 1.59165 |
| 34354 | NM_018218 | 0.000538702 | 1.592 |
| 16511 | NM_004731 | 0.000510397 | 1.59641 |
| 9247 | NM_001001894 /// NM_003316 /// NR_030737 | 0.00421749 | 1.59679 |
| 13083 | NM_000875 /// NM_152452 | 0.006082 | 1.59853 |
| 34199 | NM_004241 /// NM_032776 | 0.00521599 | 1.59926 |
| 13258 | NM_016297 | 0.00020689 | 1.59966 |
| 29364 | NM_001077204 /// NM_024790 | 0.00731063 | 1.60277 |
| 45729 | — | 0.00720356 | 1.603 |
| 44645 | NM_025134 | 0.00343612 | 1.60332 |
| 30972 | NM_025114 | 0.0430594 | 1.60434 |
| 43290 | — | 0.0136508 | 1.60619 |
| 37146 | NM_003487 /// NM_139215 | 0.015747 | 1.60873 |
| 45613 | NM_001199981 /// NM_001199982 /// NM_001199983 /// NM_001199984 /// NM_005006 | 0.0240567 | 1.61047 |
| 34755 | NM_152641 | 0.00224833 | 1.61096 |
| 48588 | — | 0.00275564 | 1.6118 |
| 20457 | NM_006282 | 0.0235459 | 1.61205 |
| 30794 | NM_002267 | 0.0205337 | 1.61663 |
| 38569 | NM_001195098 /// NM_001195099 /// NM_015199 | 0.00139142 | 1.61668 |
| 18353 | NM_001137673 /// NM_004516 /// NM_012218 /// NM_017620 /// NM_153464 | 0.0182301 | 1.61859 |
| 45060 | — | 0.0225123 | 1.62271 |
| 48279 | — | 0.0334072 | 1.62429 |
| 22887 | NM_001429 | 0.0036532 | 1.62606 |
| 46098 | XM_001720526 | 0.00243628 | 1.62736 |
| 36717 | NM_020791 /// NM_025142 | 0.00720828 | 1.62742 |
| 12671 | NM_004999 | 0.0126125 | 1.62761 |
| 34836 | NM_001127671 /// NM_002310 | 0.0161661 | 1.62983 |
| 28450 | NM_057175 | 0.00232713 | 1.63131 |
| 52940 | NM_001142418 /// NM_001142419 /// NM_001142420 /// NM_001142421 /// NM_001142422 /// NM | 0.0205152 | 1.63181 |
| 18680 | NM_005445 | 0.00172564 | 1.63185 |
| 7160 | NM_001009569 /// NM_001195626 /// NM_001195627 /// NM_001195628 /// NM_001195630 /// NM | 0.0176147 | 1.63255 |
| 44783 | NM_001145811 /// NM_001145819 /// NM_017508 /// NM_033326 | 0.0330642 | 1.63454 |
| 36776 | NM_001034841 /// NR_028028 | 0.0145369 | 1.63576 |
| 38661 | NM_018017 | 0.0413405 | 1.63704 |
| 33223 | NR_002819 /// XR_110915 /// XR_110916 /// XR_110917 /// XR_111190 /// XR_111191 /// XR_ | 0.0292591 | 1.64434 |
| 51077 | NM_001177663 /// NM_001177664 /// NM_001177665 /// NM_018151 | 0.0245286 | 1.64497 |

TABLE 1-continued

| | | | |
|---|---|---|---|
| 3442 | NM_015382 | 0.0252237 | 1.64535 |
| 28513 | NM_001080412 /// NM_152535 | 0.0011571 | 1.64824 |
| 10638 | NM_001273 | 0.0058932 | 1.64852 |
| 51967 | — | 0.0327547 | 1.64964 |
| 11452 | NM_015001 | 0.0171906 | 1.65008 |
| 36647 | NR_024510 /// NR_024511 /// NR_024584 /// XR_041980 | 0.0255387 | 1.65063 |
| 5267 | — | 0.00391521 | 1.65177 |
| 42186 | — | 0.038837 | 1.65236 |
| 27244 | NM_015153 | 0.00244501 | 1.65357 |
| 51490 | — | 0.00271001 | 1.65646 |
| 3544 | NM_001130009 /// NM_182625 | 0.0228586 | 1.66227 |
| 41128 | NM_005575 /// NM_175920 | 0.00429813 | 1.66515 |
| 4048 | NM_006260 | 0.00438813 | 1.66648 |
| 34685 | NM_001244949 /// NM_020918 | 0.00679399 | 1.66814 |
| 45525 | NM_001201572 /// NM_001201584 /// NM_004206 /// NM_032970 | 0.00208389 | 1.67104 |
| 39120 | — | 0.0386334 | 1.68237 |
| 49564 | — | 0.0282523 | 1.68804 |
| 44523 | NM_014109 | 0.0040998 | 1.69135 |
| 32861 | NR_002819 | 0.0152794 | 1.69738 |
| 17459 | NM_001077181 /// NM_003671 /// NM_033331 /// NM_033332 | 0.00142907 | 1.69967 |
| 10796 | NM_001256574 /// NM_001256575 /// NM_001256576 /// NM_003633 /// NR_046318 | 0.0138129 | 1.70015 |
| 44979 | NM_018373 | 0.0217892 | 1.70451 |
| 37418 | — | 0.00856184 | 1.70602 |
| 24924 | NM_001002799 /// NM_001002800 /// NM_005496 | 0.000631502 | 1.70906 |
| 31920 | NM_024665 | 0.00298632 | 1.71649 |
| 33102 | NM_016578 | 0.00129842 | 1.72008 |
| 27106 | NM_006717 | 0.00939252 | 1.72364 |
| 19166 | NM_001145425 /// NM_005126 | 0.00030303 | 1.72724 |
| 18302 | NM_012469 | 0.00561885 | 1.73723 |
| 33898 | NM_001197051 /// NM_053023 | 0.00241181 | 1.73771 |
| 48018 | NM_001973 /// NM_021795 | 0.0162532 | 1.74057 |
| 17440 | NM_001113178 /// NM_006599 /// NM_138713 /// NM_138714 /// NM_173214 /// NM_173215 | 0.00457515 | 1.74202 |
| 256 | NM_002227 | 0.0186674 | 1.74617 |
| 33835 | NR_002819 /// XR_110915 /// XR_110916 /// XR_110917 /// XR_111190 /// XR_111191 /// XR_ | 0.0404992 | 1.75208 |
| 10541 | NM_003103 /// NM_032195 /// NM_058183 /// NM_138925 /// NM_138926 /// NM_138927 | 0.00303166 | 1.75255 |
| 21392 | NM_001197104 /// NM_005933 /// NM_024891 | 0.00635272 | 1.75681 |
| 43958 | NM_001256182 /// NM_001256183 /// NM_013275 /// NR_045839 | 0.000238534 | 1.75952 |

TABLE 1-continued

| | | | |
|---|---|---|---|
| 11323 | NM_001139466 /// NM_001139467 /// NM_001139468 /// NM_005647 | 0.00368541 | 1.76902 |
| 49947 | — | 0.00198799 | 1.76926 |
| 15954 | NM_018353 | 0.0259793 | 1.7749 |
| 44316 | NM_001025300 | 0.00165136 | 1.77978 |
| 44266 | NM_148894 | 0.0241619 | 1.77982 |
| 10291 | NM_001134364 /// NM_001134365 /// NM_002375 /// NM_030884 /// NM_030885 | 0.00250008 | 1.78104 |
| 44966 | NM_174942 | 0.0256883 | 1.78185 |
| 4392 | NM_015295 | 0.0330839 | 1.78271 |
| 37740 | — | 0.0192989 | 1.78339 |
| 27171 | NM_001114091 /// NM_001256 | 0.039132 | 1.78366 |
| 39756 | NM_005415 | 0.00670771 | 1.78563 |
| 38534 | NM_015308 | 0.00528746 | 1.78906 |
| 48303 | — | 0.00250028 | 1.78979 |
| 31700 | NM_021230 /// NM_170606 | 0.0276727 | 1.79679 |
| 24288 | NM_000127 | 0.0112472 | 1.80175 |
| 24640 | NM_001012651 /// NM_005385 | 0.00360133 | 1.80846 |
| 4092 | NM_001142546 /// NM_033631 | 0.0100121 | 1.81185 |
| 18088 | NM_001001894 /// NM_003316 /// NR_030737 | 0.00674795 | 1.81703 |
| 12125 | NM_004093 | 0.0226477 | 1.82888 |
| 18134 | NM_053056 | 0.0115323 | 1.83042 |
| 25237 | NM_015275 | 0.0166419 | 1.83448 |
| 24508 | — | 0.00376487 | 1.8582 |
| 7608 | — | 0.0045512 | 1.85918 |
| 25861 | NM_001083625 /// NM_001204056 /// NM_015208 | 0.00786514 | 1.87083 |
| 38377 | NM_001376 | 0.00311892 | 1.87432 |
| 20396 | NM_000489 /// NM_138270 /// NM_138271 | 0.0304891 | 1.87675 |
| 14295 | NM_003566 | 0.00819668 | 1.88274 |
| 21963 | NM_001142614 /// NM_001142615 /// NM_001142616 /// NM_015252 | 0.009319 | 1.88314 |
| 10297 | NM_004446 | 0.00258631 | 1.93041 |
| 21781 | NM_001130527 /// NM_001130528 /// NM_001251971 /// NM_003971 /// NM_172345 | 0.00362449 | 1.93517 |
| 22107 | NM_015275 | 0.00765823 | 1.94138 |
| 22378 | NM_001256012 /// NM_001256095 NM_005964 | 0.00759319 | 1.94171 |
| 2764 | — | 0.00387442 | 1.98692 |
| 40997 | NR_002819 | 0.00182841 | 1.99074 |
| 51325 | — | 0.0197402 | 1.99077 |
| 39027 | NM_001032293 /// NM_001095807 /// NM_003457 | 0.000769356 | 1.99093 |
| 51517 | NM_001194954 /// NM_001194955 /// NM_001194956 /// NM_018834 /// NM_199189 /// NR_03653 | 0.018593 | 2.00734 |
| 23659 | NM_004985 /// NM_033360 | 0.0262788 | 2.03062 |
| 18049 | NM_001194946 /// NM_001194947 /// NM_004953 /// NM_182917 /// NM_198241 /// NM_198242 / | 0.0119994 | 2.03273 |
| 29377 | NM_018063 | 0.00839666 | 2.03541 |
| 51212 | NM_015382 | 0.000788387 | 2.03696 |

TABLE 1-continued

| | | | |
|---|---|---|---|
| 50030 | — | 0.0137585 | 2.04324 |
| 31726 | NM_005119 | 0.00504398 | 2.05116 |
| 3461 | NM_001142703 /// NM_001142704 /// NM_198947 | 0.0287632 | 2.0535 |
| 28679 | NM_001195597 /// NM_001254943 /// NM_018084 | 0.00365158 | 2.0778 |
| 4502 | NM_001247997 /// NM_002956 /// NM_198240 | 0.0267528 | 2.09463 |
| 53114 | NM_001142418 /// NM_001142419 /// NM_001142420 /// NM_001142421 /// NM_001142422 /// NM | 0.0074179 | 2.13027 |
| 18323 | NM_003286 | 0.0365807 | 2.13487 |
| 49893 | — | 0.0377752 | 2.14111 |
| 40398 | NR_029598 | 0.00328686 | 2.15034 |
| 309 | NM_144508 /// NM_170589 | 0.00799316 | 2.15456 |
| 18036 | NM_016333 | 0.00110455 | 2.16673 |
| 20375 | NM_001190981 /// NM_002184 /// NM_175767 | 0.0136659 | 2.2082 |
| 18510 | NM_001079514 /// NM_016936 | 0.00669916 | 2.22201 |
| 14318 | NM_001190981 /// NM_002184 /// NM_175767 | 0.00704479 | 2.24897 |
| 21393 | NM_001197104 /// NM_005933 /// NM_024891 | 0.00889717 | 2.25754 |
| 38248 | NM_001003712 /// NM_020841 | 0.0161915 | 2.26479 |
| 23771 | NM_003607 /// NM_014826 | 0.00114942 | 2.27563 |
| 4349 | NR_002819 /// XR_110915 /// XR_110916 /// XR_110917 /// XR_111190 /// XR_111191 /// XR_ | 0.00592243 | 2.28297 |
| 33834 | NR_002819 /// XR_110915 /// XR_110916 /// XR_110917 /// XR_111190 /// XR_111191 /// XR_ | 0.00410374 | 2.29298 |
| 18282 | NM_000489 /// NM_138270 /// NM_138271 | 0.000865449 | 2.31098 |
| 33830 | NM_001201404 /// NM_006990 | 0.00632155 | 2.36071 |
| 45877 | NM_001177663 /// NM_001177664 /// NM_001177665 /// NM_018151 | 0.00480654 | 2.46908 |
| 3521 | NM_003292 | 0.0185624 | 2.56223 |
| 11186 | NM_003292 | 0.0023957 | 2.62456 |
| 35938 | NR_002819 /// XR_110915 /// XR_110916 /// XR_110917 /// XR_111190 /// XR_111191 /// XR_ | 0.0061131 | 2.63183 |
| 22755 | NM_003870 | 0.0118332 | 2.68542 |
| 52175 | NM_001195193 /// NM_002482 /// NM_152298 /// NM_172164 | 0.017061 | 2.75136 |
| 15264 | NM_003941 | 0.0252923 | 2.82213 |
| 41500 | NM_001206846 /// NM_018136 | 0.00155378 | 2.83547 |

TABLE 1-continued

| | | | |
|---|---|---|---|
| 51609 | NM_015384 /// NM_133433 | 0.0177762 | 2.92333 |

TABLE 3

Part 1 (on 3 pages)

| Column # | Column ID | Entrez Gene | Gene Symbol | Gene Title |
|---|---|---|---|---|
| 18582 | 209160_at | 8644 | AKR1C3 | aldo-keto reductase family 1, member C3 (3-alpha hydroxysteroid dehydrogenase, type II) |
| 20985 | 211653_x_at | 100653286 /// 1646 | AKR1C2 /// LOC100653286 | aldo-keto reductase family 1, member C2 (dihydrodiol dehydrogenase 2; bile acid binding |
| 13606 | 204151_x_at | 1645 | AKR1C1 | aldo-keto reductase family 1, member C1 (dihydrodiol dehydrogenase 1; 20-alpha (3-alpha |
| 13026 | 203571_s_at | 10974 | C10orf116 | chromosome 10 open reading frame 116 |
| 25892 | 216594_x_at | 1645 | AKR1C1 | aldo-keto reductase family 1, member C1 (dihydrodiol dehydrogenase 1; 20-alpha (3-alpha |
| 13796 | 204341_at | 10626 | TRIM16 | tripartite motif containing 16 |
| 18317 | 208894_at | 3122 | HLA-DRA | major histocompatibility complex, class II, DR alpha |
| 19115 | 209699_x_at | 100653286 /// 1646 | AKR1C2 /// LOC100653286 | aldo-keto reductase family 1, member C2 (dihydrodiol dehydrogenase 2; bile acid binding |
| 25005 | 215704_at | 2312 | FLG | filaggrin |
| 13753 | 204298_s_at | 4015 | LOX | lysyl oxidase |
| 41497 | 232235_at | 92126 | DSEL | dermatan sulfate epimerase-like |
| 11693 | 202237_at | 4837 | NNMT | nicotinamide N-methyltransferase |
| 19171 | 209755_at | 23057 | NMNAT2 | nicotinamide nucleotide adenylyltransferase 2 |
| 13743 | 204288_s_at | 8470 | SORBS2 | sorbin and SH3 domain containing 2 |
| 3439 | 1557094_at | 100652762 | LOC100652762 | uncharacterized LOC100652762 |
| 22738 | 213429_at | 80114 | BICC1 | bicaudal C homolog 1 (Drosophila) |
| 19707 | 210299_s_at | 2273 | FHL1 | four and a half LIM domains 1 |
| 19154 | 209738_x_at | 5675 | PSG6 | pregnancy specific beta-1-glycoprotein 6 |
| 21468 | 212154_at | 6383 | SDC2 | syndecan 2 |
| 17182 | 207733_x_at | 5678 | PSG9 | pregnancy specific beta-1-glycoprotein 9 |
| 28341 | 219049_at | 55790 | CSGALNACT1 | chondroitin sulfate N-acetylgalactosaminyltransferase 1 |
| 14713 | 205258_at | 3625 | INHBB | inhibin, beta B |
| 28501 | 219209_at | 64135 | IFIH1 | interferon induced with helicase C domain 1 |
| 37497 | 228235_at | 84848 | MGC16121 | uncharacterized protein MGC16121 |
| 12959 | 203504_s_at | 19 | ABCA1 | ATP-binding cassette, sub-family A (ABC1), member 1 |
| 10996 | 201540_at | 2273 | FHL1 | four and a half LIM domains 1 |
| 21802 | 212489_at | 1289 | COL5A1 | collagen, type V, alpha 1 |
| 11606 | 202150_s_at | 4739 | NEDD9 | neural precursor cell expressed, developmentally down-regulated 9 |
| 22054 | 212741_at | 4128 | MAOA | monoamine oxidase A |
| 13087 | 203632_s_at | 51704 | GPRC5B | G protein-coupled receptor, family C, group 5, member B |
| 37712 | 228450_at | 144100 | PLEKHA7 | pleckstrin homology domain containing, family A member 7 |
| 33112 | 223828_s_at | 85329 | LGALS12 | lectin, galactoside-binding, soluble, 12 |
| 14862 | 205407_at | 8434 | RECK | reversion-inducing-cysteine-rich protein with kazal motifs |
| 11694 | 202238_s_at | 4837 | NNMT | nicotinamide N-methyltransferase |
| 13279 | 203824_at | 7103 | TSPAN8 | tetraspanin 8 |
| 36110 | 226847_at | 10468 | FST | follistatin |
| 10962 | 201506_at | 100652886 /// 100653157 /// 7045 | LOC100652886 /// LOC100653157 /// TGFBI | uncharacterized LOC100652886 /// uncharacterized LOC100653157 /// transforming growth f |
| 19322 | 209908_s_at | 7042 | TGFB2 | transforming growth factor, beta 2 |
| 28815 | 219523_s_at | 55714 | ODZ3 | odz, odd Oz/ten-m homolog 3 (Drosophila) |
| 32994 | 223710_at | 10344 | CCL26 | chemokine (C-C motif) ligand 26 |
| 46044 | 236787_at | 100507286 | LOC100507286 | uncharacterized LOC100507286 |

TABLE 3-continued

| | | | | |
|---|---|---|---|---|
| 28959 | 219667_s_at | 55024 | BANK1 | B-cell scaffold protein with ankyrin repeats 1 |
| 14403 | 204948_s_at | 10468 | FST | follistatin |
| 35482 | 226218_at | 3575 | IL7R | interleukin 7 receptor |
| 13844 | 204389_at | 4128 | MAOA | monoamine oxidase A |
| 38147 | 228885_at | 256691 | MAMDC2 | MAM domain containing 2 |
| 45055 | 235798_at | 100113407 | TMEM170B | transmembrane protein 170B |
| 9315 | 1569582_at | 201651 | LOC201651 | arylacetamide deacetylase (esterase) pseudogene |
| 12222 | 202766_s_at | 2200 | FBN1 | fibrillin 1 |
| 37233 | 227971_at | 203447 | NRK | Nik related kinase |
| 28821 | 219529_at | 9022 | CLIC3 | chloride intracellular channel 3 |
| 12531 | 203074_at | 244 /// 653145 /// 728113 | ANXA8 /// ANXA8L1 /// ANXA8L2 | annexin A8 /// annexin A8-like 1 /// annexin A8-like 2 |
| 15749 | 206295_at | 3606 | IL18 | interleukin 18 (interferon-gamma-inducing factor) |
| 41330 | 232068_s_at | 7099 | TLR4 | toll-like receptor 4 |
| 20711 | 211367_s_at | 834 | CASP1 | caspase 1, apoptosis-related cysteine peptidase |
| 14388 | 204933_s_at | 4982 | TNFRSF11B | tumor necrosis factor receptor superfamily, member 11b |
| 11806 | 202350_s_at | 100506558 /// 4147 | LOC100506558 /// MATN2 | uncharacterized LOC100506558 /// matrilin 2 |
| 20252 | 210869_s_at | 4162 | MCAM | melanoma cell adhesion molecule |
| 32680 | 223395_at | 25890 | ABI3BP | ABI family, member 3 (NESH) binding protein |
| 33059 | 223775_at | 64399 | HHIP | hedgehog interacting protein |
| 46723 | 237466_s_at | 64399 | HHIP | hedgehog interacting protein |
| 12221 | 202765_s_at | 2200 | FBN1 | fibrillin 1 |
| 21472 | 212158_at | 6383 | SDC2 | syndecan 2 |
| 14285 | 204830_x_at | 5673 | PSG5 | pregnancy specific beta-1-glycoprotein 5 |
| 39409 | 230147_at | 2151 | F2RL2 | coagulation factor II (thrombin) receptor-like 2 |
| 21949 | 212636_at | 9444 | QKI | QKI, KH domain containing, RNA binding |
| 20712 | 211368_s_at | 834 | CASP1 | caspase 1, apoptosis-related cysteine peptidase |
| 12595 | 203139_at | 1612 | DAPK1 | death-associated protein kinase 1 |
| 16378 | 206924_at | 3589 | IL11 | interleukin 11 |
| 19012 | 209594_x_at | 5678 | PSG9 | pregnancy specific beta-1-glycoprotein 9 |
| 46692 | 237435_at | — | — | — |
| 21048 | 211719_x_at | 2335 | FN1 | fibronectin 1 |
| 12144 | 202688_at | 8743 | TNFSF10 | tumor necrosis factor (ligand) superfamily, member 10 |
| 19894 | 210495_x_at | 2335 | FN1 | fibronectin 1 |
| 21777 | 212464_s_at | 2335 | FN1 | fibronectin 1 |
| 25741 | 216442_x_at | 2335 | FN1 | fibronectin 1 |
| 11605 | 202149_at | 4739 | NEDD9 | neural precursor cell expressed, developmentally down-regulated 9 |
| 39397 | 230135_at | 64399 | HHIP | hedgehog interacting protein |
| 16667 | 207214_at | 27290 | SPINK4 | serine peptidase inhibitor, Kazal type 4 |
| 29306 | 220014_at | 51334 | PRR16 | proline rich 16 |
| 25678 | 216379_x_at | 100133941 | CD24 | CD24 molecule |
| 22421 | 213110_s_at | 1287 | COL4A5 | collagen, type IV, alpha 5 |
| 36662 | 227399_at | 389136 | VGLL3 | vestigial like 3 (Drosophila) |
| 19187 | 209771_x_at | 100133941 | CD24 | CD24 molecule |
| 324 | 1552703_s_at | 114769 /// 834 | CARD16 /// CASP1 | caspase recruitment domain family, member 16 /// caspase 1, apoptosis-related cysteine |
| 54150 | 266_s_at | 100133941 | CD24 | CD24 molecule |
| 18075 | 208650_s_at | 100133941 | CD24 | CD24 molecule |
| 323 | 1552701_a_at | 114769 | CARD16 | caspase recruitment domain family, member 16 |
| 23636 | 214329_x_at | 8743 | TNFSF10 | tumor necrosis factor (ligand) superfamily, member 10 |
| 15018 | 205563_at | 3814 | KISS1 | KiSS-1 metastasis-suppressor |
| 22253 | 212942_s_at | 57214 | KIAA1199 | KIAA1199 |
| 19909 | 210511_s_at | 3624 | INHBA | inhibin, beta A |
| 12143 | 202687_s_at | 8743 | TNFSF10 | tumor necrosis factor (ligand) superfamily, member 10 |
| 34993 | 225728_at | 8470 | SORBS2 | sorbin and SH3 domain containing 2 |
| 36403 | 227140_at | 3624 | INHBA | inhibin, beta A |
| 19363 | 209949_at | 4688 | NCF2 | neutrophil cytosolic factor 2 |
| 14464 | 205009_at | 7031 | TFF1 | trefoil factor 1 |

TABLE 3-continued

Part 2 (on 5 pages)

| Column # | RefSeq Transcript ID | p-value (Attribute) | p-value (Suspended vs. Attached) | Ratio (Suspended vs. Attached) | Fold-Change (Suspended vs. Attached) |
|---|---|---|---|---|---|
| 18582 | NM_001253908 /// NM_001253909 /// NM_003739 | 0.000170367 | 0.000170367 | 1.81864 | 1.81864 |
| 20985 | NM_001135241 /// NM_001354 /// NM_205845 /// XM_003403856 | 0.000143927 | 0.000143927 | 1.67318 | 1.67318 |
| 13606 | NM_001353 | 0.000659841 | 0.000659841 | 1.65919 | 1.65919 |
| 13026 | NM_006829 | 0.000387207 | 0.000387207 | 1.65068 | 1.65068 |
| 25892 | NM_001353 | 0.000756883 | 0.000756883 | 1.60532 | 1.60532 |
| 13796 | NM_006470 | 1.72E−05 | 1.72E−05 | 1.51663 | 1.51663 |
| 18317 | NM_019111 | 0.00512881 | 0.00512881 | 1.51385 | 1.51385 |
| 19115 | NM_001135241 /// NM_001354 /// NM_205845 /// XM_003403856 | 0.00033636 | 0.00033636 | 1.50424 | 1.50424 |
| 25005 | NM_002016 | 0.00218557 | 0.00218557 | 0.665474 | −1.50269 |
| 13753 | NM_001178102 /// NM_002317 | 6.59E−05 | 6.59E−05 | 0.664062 | −1.50588 |
| 41497 | NM_032160 | 0.00226259 | 0.00226259 | 0.66251 | −1.50941 |
| 11693 | NM_006169 | 0.000462864 | 0.000462864 | 0.662281 | −1.50993 |
| 19171 | NM_015039 /// NM_170706 | 0.020548 | 0.020548 | 0.661458 | −1.51181 |
| 13743 | NM_001145670 /// NM_001145671 /// NM_001145672 /// NM_001145673 /// NM_001145674 /// NM | 0.0112829 | 0.0112829 | 0.660839 | −1.51323 |
| 3439 | XM_003403544 | 0.00309358 | 0.00309358 | 0.660605 | −1.51376 |
| 22738 | NM_001080512 | 0.0062046 | 0.0062046 | 0.659525 | −1.51624 |
| 19707 | NM_001159699 /// NM_001159700 /// NM_001159701 /// NM_001159702 /// NM_001159703 /// NM | 0.025324 | 0.025324 | 0.659366 | −1.51661 |
| 19154 | NM_001031850 /// NM_002782 | 0.000207499 | 0.000207499 | 0.657119 | −1.52179 |
| 21468 | NM_002998 | 0.000566015 | 0.000566015 | 0.656899 | −1.5223 |
| 17182 | NM_002784 | 0.00758296 | 0.00758296 | 0.6558 | −1.52486 |
| 28341 | NM_001130518 /// NM_018371 /// NR_024040 | 0.000369511 | 0.000369511 | 0.654509 | −1.52786 |
| 14713 | NM_002193 | 0.00235168 | 0.00235168 | 0.654085 | −1.52885 |
| 28501 | NM_022168 | 0.00655627 | 0.00655627 | 0.65325 | −1.53081 |
| 37497 | NM_032762 /// NR_024607 | 0.00968185 | 0.00968185 | 0.652485 | −1.5326 |
| 12959 | NM_005502 | 0.00392514 | 0.00392514 | 0.651694 | −1.53446 |
| 10996 | NM_001159699 /// NM_001159700 /// NM_001159701 /// NM_001159702 /// NM_001159703 /// NM | 0.00223441 | 0.00223441 | 0.650122 | −1.53817 |
| 21802 | NM_000093 | 0.000341289 | 0.000341289 | 0.649968 | −1.53854 |
| 11606 | NM_001142393 /// NM_006403 /// NM_182966 | 0.0280295 | 0.0280295 | 0.645034 | −1.55031 |
| 22054 | NM_000240 | 0.00100831 | 0.00100831 | 0.643901 | −1.55303 |
| 13087 | NM_016235 | 0.00133541 | 0.00133541 | 0.642282 | −1.55695 |
| 37712 | NM_175058 | 0.000419231 | 0.000419231 | 0.64162 | −1.55855 |
| 33112 | NM_001142535 /// NM_001142536 /// NM_001142537 /// NM_001142538 /// NM_033101 | 0.0390828 | 0.0390828 | 0.641364 | −1.55918 |
| 14862 | NM_021111 | 0.00695804 | 0.00695804 | 0.639083 | −1.56474 |
| 11694 | NM_006169 | 0.000173649 | 0.000173649 | 0.638349 | −1.56654 |
| 13279 | NM_004616 | 0.000799162 | 0.000799162 | 0.63719 | −1.56939 |
| 36110 | NM_006350 /// NM_013409 | 0.0030227 | 0.0030227 | 0.636925 | −1.57004 |

TABLE 3-continued

| | | | | | |
|---|---|---|---|---|---|
| 10962 | NM_000358 /// XR_132813 /// XR_133407 | 0.000241245 | 0.000241245 | 0.635083 | −1.5746 |
| 19322 | NM_001135599 /// NM_003238 | 0.0300973 | 0.0300973 | 0.634683 | −1.57559 |
| 28815 | NM_001080477 | 0.016908 | 0.016908 | 0.633668 | −1.57811 |
| 32994 | NM_006072 | 0.0445369 | 0.0445369 | 0.632818 | −1.58023 |
| 46044 | XR_109951 | 0.00634762 | 0.00634762 | 0.631059 | −1.58464 |
| 28959 | NM_001083907 /// NM_001127507 /// NM_017935 | 0.00600733 | 0.00600733 | 0.630334 | −1.58646 |
| 14403 | NM_006350 /// NM_013409 | 0.000425631 | 0.000425631 | 0.629981 | −1.58735 |
| 35482 | NM_002185 | 0.000443453 | 0.000443453 | 0.629004 | −1.58981 |
| 13844 | NM_000240 | 0.00104301 | 0.00104301 | 0.627119 | −1.59459 |
| 38147 | NM_153267 | 0.000232264 | 0.000232264 | 0.626074 | −1.59725 |
| 45055 | NM_001100829 | 0.00992984 | 0.00992984 | 0.622005 | −1.6077 |
| 9315 | NR_026915 | 0.00258393 | 0.00258393 | 0.618288 | −1.61737 |
| 12222 | NM_000138 | 0.00176066 | 0.00176066 | 0.618179 | −1.61765 |
| 37233 | NM_198465 | 0.0138066 | 0.0138066 | 0.61709 | −1.62051 |
| 28821 | NM_004669 | 0.000316266 | 0.000316266 | 0.614298 | −1.62787 |
| 12531 | NM_001039801 /// NM_001040084 /// NM_001098845 /// NM_001630 | 0.00261053 | 0.00261053 | 0.613273 | −1.6306 |
| 15749 | NM_001243211 /// NM_001562 | 0.00789586 | 0.00789586 | 0.612172 | −1.63353 |
| 41330 | NM_003266 /// NM_138554 /// NM_138556 /// NM_138557 /// NR_024168 /// NR_024169 | 0.00707246 | 0.00707246 | 0.610647 | −1.63761 |
| 20711 | NM_001223 /// NM_001257118 /// NM_001257119 /// NM_033292 /// NM_033293 /// NM_033294 / | 0.00177852 | 0.00177852 | 0.609003 | −1.64203 |
| 14388 | NM_002546 | 0.0034562 | 0.0034562 | 0.608783 | −1.64262 |
| 11806 | NM_002380 /// NM_030583 /// XR_108869 /// XR_133494 | 0.00269868 | 0.00269868 | 0.603891 | −1.65593 |
| 20252 | NM_006500 | 0.00214434 | 0.00214434 | 0.603836 | −1.65608 |
| 32680 | NM_015429 | 0.0154958 | 0.0154958 | 0.602208 | −1.66056 |
| 33059 | NM_022475 | 0.000751578 | 0.000751578 | 0.600994 | −1.66391 |
| 46723 | NM_022475 | 0.000230794 | 0.000230794 | 0.5999 | −1.66695 |
| 12221 | NM_000138 | 0.0112647 | 0.0112647 | 0.598516 | −1.6708 |
| 21472 | NM_002998 | 0.000137552 | 0.000137552 | 0.595021 | −1.68061 |
| 14285 | NM_001130014 /// NM_002781 | 0.00469336 | 0.00469336 | 0.593415 | −1.68516 |
| 39409 | NM_001256566 /// NM_004101 | 0.00262479 | 0.00262479 | 0.592707 | −1.68717 |
| 21949 | NM_006775 /// NM_206853 /// NM_206854 /// NM_206855 | 0.0109828 | 0.0109828 | 0.588126 | −1.70032 |
| 20712 | NM_001223 /// NM_001257118 /// NM_001257119 /// NM_033292 /// NM_033293 /// NM_033294 / | 0.00544332 | 0.00544332 | 0.586424 | −1.70525 |
| 12595 | NM_004938 | 0.00070315 | 0.00070315 | 0.583547 | −1.71366 |
| 16378 | NM_000641 /// NM_001267718 | 0.00206342 | 0.00206342 | 0.575597 | −1.73733 |
| 19012 | NM_002784 | 0.000350804 | 0.000350804 | 0.567073 | −1.76344 |
| 46692 | — | 0.00486443 | 0.00486443 | 0.565559 | −1.76816 |
| 21048 | NM_002026 /// NM_054034 /// NM_212474 /// NM_212475 /// NM_212476 /// NM_212478 /// NM_ | 0.000320581 | 0.000320581 | 0.56548 | −1.76841 |
| 12144 | NM_001190942 /// NM_001190943 /// NM_003810 /// NR_033994 | 0.00322745 | 0.00322745 | 0.563625 | −1.77423 |

TABLE 3-continued

| | | | | | |
|---|---|---|---|---|---|
| 19894 | NM_002026 /// NM_054034 /// NM_212474 /// NM_212475 /// NM_212476 /// NM_212478 /// NM_ | 0.000274524 | 0.000274524 | 0.563315 | −1.77521 |
| 21777 | NM_002026 /// NM_054034 /// NM_212474 /// NM_212475 /// NM_212476 /// NM_212478 /// NM_ | 0.000185237 | 0.000185237 | 0.560338 | −1.78464 |
| 25741 | NM_002026 /// NM_054034 /// NM_212474 /// NM_212475 /// NM_212476 /// NM_212478 /// NM_ | 0.000355233 | 0.000355233 | 0.558125 | −1.79171 |
| 11605 | NM_001142393 /// NM_006403 /// NM_182966 | 5.75E−05 | 5.75E−05 | 0.557276 | −1.79444 |
| 39397 | NM_022475 | 0.00081091 | 0.00081091 | 0.556999 | −1.79534 |
| 16667 | NM_014471 | 0.00379337 | 0.00379337 | 0.556208 | −1.79789 |
| 29306 | NM_016644 | 0.000373382 | 0.000373382 | 0.551386 | −1.81361 |
| 25678 | NM_013230 | 0.000831434 | 0.000831434 | 0.550468 | −1.81664 |
| 22421 | NM_000495 /// NM_033380 /// NM_033381 | 0.000153119 | 0.000153119 | 0.550254 | −1.81734 |
| 36662 | NM_016206 | 0.00145565 | 0.00145565 | 0.545624 | −1.83276 |
| 19187 | NM_013230 | 0.00103971 | 0.00103971 | 0.542121 | −1.84461 |
| 324 | NM_001017534 /// NM_001223 /// NM_001257118 /// NM_001257119 /// NM_033292 /// NM_03329 | 0.0012893 | 0.0012893 | 0.535819 | −1.8663 |
| 54150 | NM_013230 | 0.000136369 | 0.000136369 | 0.535661 | −1.86685 |
| 18075 | NM_013230 | 9.53E−05 | 9.53E−05 | 0.528598 | −1.8918 |
| 323 | NM_001017534 /// NM_052889 | 0.0112715 | 0.0112715 | 0.526508 | −1.89931 |
| 23636 | NM_001190942 /// NM_001190943 /// NM_003810 /// NR_033994 | 6.44E−05 | 6.44E−05 | 0.52413 | −1.90792 |
| 15018 | NM_002256 | 3.43E−05 | 3.43E−05 | 0.510055 | −1.96057 |
| 22253 | NM_018689 | 4.12E−05 | 4.12E−05 | 0.491527 | −2.03448 |
| 19909 | NM_002192 | 0.000271854 | 0.000271854 | 0.484229 | −2.06514 |
| 12143 | NM_001190942 /// NM_001190943 /// NM_003810 /// NR_033994 | 0.00371971 | 0.00371971 | 0.480021 | −2.08324 |
| 34993 | NM_001145670 /// NM_001145671 /// NM_001145672 /// NM_001145673 /// NM_001145674 /// NM | 0.00394697 | 0.00394697 | 0.477446 | −2.09448 |
| 36403 | NM_002192 | 0.00472489 | 0.00472489 | 0.469154 | −2.13149 |
| 19363 | NM_000433 /// NM_001127651 /// NM_001190789 /// NM_001190794 | 0.00011872 | 0.00011872 | 0.464326 | −2.15366 |
| 14464 | NM_003225 | 9.43E−06 | 9.43E−06 | 0.246286 | −4.06032 |

We claim:

1. A method for inducing differentiation of a cancer stem cell (CSC) that expresses CD47, comprising:
contacting a breast cancer stem cell, a lung cancer stem cell, a prostate cancer stem cell, or a melanoma stem cell with an anti-CD47 monoclonal antibody B6H12, a humanized antibody B6H12, or a peptide consisting of the amino acid sequence of SEQ ID NO: 1 for at least 3 days, wherein the contacting comprises administering the anti-CD47 monoclonal antibody B6H12, humanized antibody B6H12, or peptide consisting of the amino acid sequence of SEQ ID NO: 1, to a subject with breast cancer, lung cancer, prostate cancer, or melanoma; and inducing macrophage SIRPα-independent terminal differentiation of CSCs, thereby producing differentiated CSCs.

2. The method of claim 1, wherein the subject has a primary tumor, has a tumor in regression, has or is suspected of having a metastatic tumor, or a combination thereof.

3. The method of claim 1, further comprising administering a therapeutically effective amount of an anti-cancer treatment to the subject.

4. The method of claim 1, comprising contacting the breast cancer stem cell, the lung cancer stem cell, the prostate cancer stem cell, or the melanoma stem cell with the anti-CD47 monoclonal antibody B6H12, the humanized antibody B6H12, or the peptide consisting of the amino acid sequence of SEQ ID NO: 1 for at least 10 days.

5. A method for inducing differentiation of a cancer stem cell (CSC) that expresses CD47, comprising:
   contacting a CSC in vitro with an anti-CD47 monoclonal antibody B6H12, a humanized antibody B6H12, a peptide consisting of the amino acid sequence of SEQ ID NO: 1 for at least 3 days; and inducing SIRPα-independent terminal differentiation of CSCs, thereby producing differentiated CSCs.

6. The method of claim 5, wherein the CSC is a breast cancer stem cell, a lung cancer stem cell, a prostate cancer stem cell, or a melanoma stem cell.

7. A method for inducing differentiation of a cancer stem cell (CSC) that expresses CD47, comprising:
   contacting a breast cancer stem cell, a lung cancer stem cell, a prostate cancer stem cell, or a melanoma stem cell with a CD47-targeted CRISPR construct, wherein the contacting comprises administering the CD47-targeted CRISPR construct to a subject with breast cancer, lung cancer, prostate cancer, or melanoma; wherein the CD47-targeted CRISPR construct is targeted using SEQ ID NO: 2 as a targeting sequence; and inducing macrophage SIRPα-independent terminal differentiation of CSCs, thereby producing differentiated CSCs.

8. A method for inducing differentiation of a cancer stem cell (CSC) that expresses CD47, comprising:
   contacting a CSC in vitro with a CD47-targeted CRISPR construct; wherein the CD47-targeted CRISPR construct is targeted using SEQ ID NO: 2 as a targeting sequence; and inducing SIRPα-independent terminal differentiation of CSCs, thereby producing differentiated CSCs.

* * * * *